US008614197B2

(12) United States Patent
Chan et al.

(10) Patent No.: US 8,614,197 B2
(45) Date of Patent: *Dec. 24, 2013

(54) ANTI-TUMOR COMPOUNDS WITH ANGELOYL GROUPS

(75) Inventors: Pui-Kwong Chan, Sugar Land, TX (US); May Sung Mak, Kowloon Hong Kong (CN); Yun Wang, Dunedin (NZ)

(73) Assignee: Pacific Arrow Limited (CN)

( * ) Notice: Subject to any disclaimer, the term of this patent is extended or adjusted under 35 U.S.C. 154(b) by 372 days.

This patent is subject to a terminal disclaimer.

(21) Appl. No.: 11/683,198

(22) Filed: Mar. 7, 2007

(65) Prior Publication Data

US 2007/0161580 A1    Jul. 12, 2007

Related U.S. Application Data

(63) Continuation-in-part of application No. 10/906,303, filed on Feb. 14, 2005, now Pat. No. 7,524,824, which is a continuation-in-part of application No. PCT/US2004/043465, filed on Dec. 23, 2004, which is a continuation-in-part of application No. PCT/US2004/033359, filed on Oct. 8, 2004.

(60) Provisional application No. 60/795,417, filed on Apr. 27, 2006, provisional application No. 60/841,727, filed on Sep. 1, 2006, provisional application No. 60/890,380, filed on Feb. 16, 2007, provisional application No. 60/532,101, filed on Dec. 23, 2003, provisional application No. 60/509,851, filed on Oct. 9, 2003, provisional application No. 60/617,379, filed on Oct. 8, 2004, provisional application No. 60/613,811, filed on Sep. 27, 2004, provisional application No. 60/607,858, filed on Sep. 7, 2004.

(51) Int. Cl.
| A61K 31/7012 | (2006.01) |
| A61K 31/7032 | (2006.01) |
| A61K 31/704 | (2006.01) |
| A61K 31/231 | (2006.01) |
| A61K 31/22 | (2006.01) |
| C07H 15/256 | (2006.01) |
| C07C 69/013 | (2006.01) |
| C07C 69/03 | (2006.01) |
| C07C 69/33 | (2006.01) |
| C07C 69/608 | (2006.01) |

(52) U.S. Cl.
USPC ............. 514/33; 514/548; 514/549; 536/4.4; 536/18.1; 560/128; 560/220

(58) Field of Classification Search
None
See application file for complete search history.

(56) References Cited

U.S. PATENT DOCUMENTS

| 6,197,306 B1 | 3/2001 | Murali et al. | |
| 6,231,859 B1 | 5/2001 | Kensil | |
| 6,444,233 B1 | 9/2002 | Arntzen et al. | |
| 6,616,943 B2 * | 9/2003 | Wang | 424/451 |
| 6,689,398 B2 | 2/2004 | Haridas et al. | |
| 6,746,696 B2 | 6/2004 | Arntzen et al. | |
| 6,962,720 B2 | 11/2005 | Haridas et al. | |
| 7,105,186 B2 | 9/2006 | Arntzen et al. | |
| 7,189,420 B2 | 3/2007 | Wang et al. | |
| 7,262,285 B2 * | 8/2007 | Chan et al. | 536/18.1 |
| 7,488,753 B2 | 2/2009 | Chan et al. | |
| 7,514,412 B2 | 4/2009 | Chan et al. | |
| 7,524,824 B2 | 4/2009 | Chan et al. | |
| 7,670,632 B2 | 3/2010 | Arntzen et al. | |
| 7,727,561 B2 * | 6/2010 | Chan et al. | 424/725 |
| 7,780,974 B2 | 8/2010 | Gutterman | |
| 8,334,269 B2 | 12/2012 | Chan et al. | |
| 2003/0082293 A1 * | 5/2003 | Wang et al. | 426/655 |
| 2003/0096030 A1 | 5/2003 | Wang et al. | |
| 2004/0138151 A1 | 7/2004 | Maes et al. | |
| 2005/0209445 A1 | 9/2005 | Gokaraju et al. | |
| 2005/0220910 A1 | 10/2005 | Chan et al. | |
| 2005/0245470 A1 | 11/2005 | Chan et al. | |
| 2005/0276872 A1 | 12/2005 | Chan et al. | |
| 2005/0277601 A1 | 12/2005 | Chan et al. | |
| 2006/0111310 A1 * | 5/2006 | Chan et al. | 514/33 |
| 2006/0122129 A1 | 6/2006 | Chan et al. | |
| 2006/0183687 A1 | 8/2006 | Cory | |

(Continued)

FOREIGN PATENT DOCUMENTS

| AU | 2002348988 | 1/2004 |
| AU | 2004281707 | 9/2011 |

(Continued)

OTHER PUBLICATIONS

2006 Chemical Abstracts Catalog, published 2006 by Chemical Abstracts Service, p. 52.*
Koike et al., "New Triterpenoid Saponins from *Maesa japonica*" Journal of Natural Products (1999) vol. 62, pp. 228-232.*
Apers et al., New acylated triterpenoid saponins from *Maesa lanceolata* Phytochemistry (1999) vol. 52, pp. 1121-1131.*
Lu et al., "Triterpenoid saponins from the roots of tea plant" Phytochemistry (2000) vol. 53, pp. 941-946.*
Seo et al., "A New Triterpene Saponin from *Pittosporum viridiflorum* from the Madagascar Rainforest" Journal of Natural Products (2002) vol. 65 pp. 65-68.*

(Continued)

Primary Examiner — Eric S Olson
(74) Attorney, Agent, or Firm — Law Offices of Albert Wai-Kit Chan, PLLC

(57) ABSTRACT

This invention provides a method for treating cancer by blocking the migration, metastasis of cancer cells, growth of cancers wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. This invention provides uses of compositions comprising a triterpenoidal saponin, triterpenoid, triterpenoidal compound or sapongenin, comprising at least two side groups selected from the group consisting of angeloyl groups, tigloyl groups and senecioyl groups, wherein the side groups are attached to carbon 21, 22 or/and 28 of triterpenoidal sapogenin, triterpenoid, triterpenoidal compound or other sapongenin backbones.

59 Claims, 47 Drawing Sheets

(56) References Cited

U.S. PATENT DOCUMENTS

Figure 1:
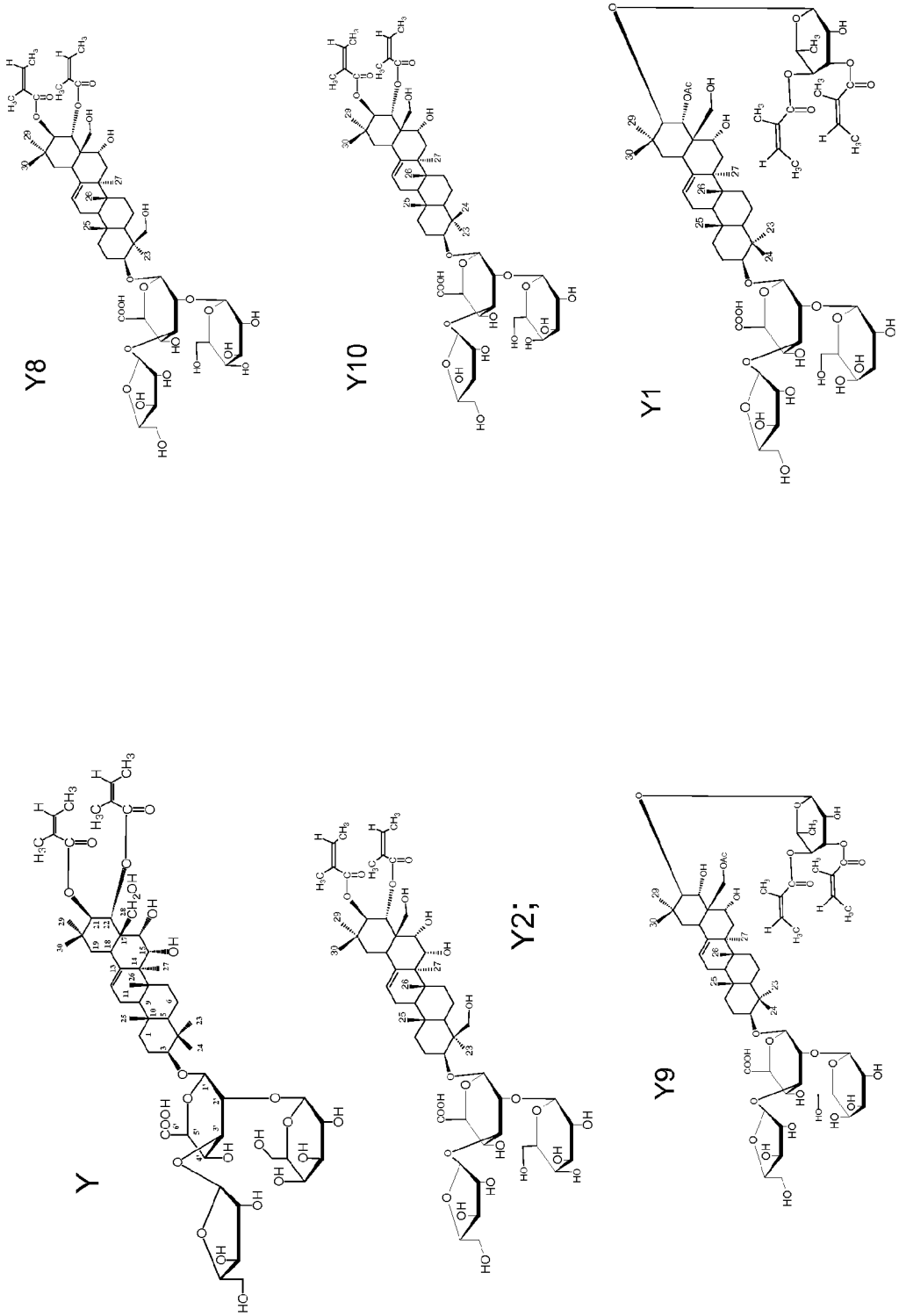

| | | | |
|---|---|---|---|
| 2006/0263458 | A1 | 11/2006 | Mak et al. |
| 2007/0196517 | A1 | 8/2007 | San Martin |
| 2007/0212329 | A1 | 9/2007 | Bruck et al. |
| 2007/0243269 | A1 | 10/2007 | McNeff et al. |
| 2007/0245470 | A1* | 10/2007 | Nguyen et al. ............ 4/223 |
| 2007/0249711 | A1 | 10/2007 | Choi et al. |
| 2007/0254847 | A1 | 11/2007 | Liu et al. |
| 2008/0058273 | A1 | 3/2008 | Yang et al. |
| 2008/0064762 | A1 | 3/2008 | Fuchs et al. |
| 2008/0096938 | A1 | 4/2008 | Evindar et al. |
| 2008/0112925 | A1 | 5/2008 | Hancock |
| 2008/0119420 | A1 | 5/2008 | Liu et al. |
| 2009/0041877 | A1 | 2/2009 | Mak et al. |
| 2009/0156515 | A1* | 6/2009 | Chan et al. ............ 514/33 |
| 2010/0004190 | A1 | 1/2010 | Chan et al. |
| 2010/0204167 | A1 | 8/2010 | Chan et al. |
| 2010/0204169 | A1 | 8/2010 | Chan et al. |
| 2010/0317606 | A1 | 12/2010 | Chan et al. |

FOREIGN PATENT DOCUMENTS

| | | |
|---|---|---|
| AU | 2009200988 | 3/2013 |
| CA | 2451740 | 12/2003 |
| CA | 2541425 | 1/2013 |
| CN | 93111010.6 | 5/1994 |
| CN | 1092991 A | 10/1994 |
| CN | 1092992 A | 10/1994 |
| CN | ZL02142258.3 | 8/2002 |
| CN | 1236792 C | 1/2006 |
| EP | 02781502.6 | 2/2004 |
| HK | 05102536.2 | 3/2005 |
| JP | 61-007285 | 1/1986 |
| JP | 61-130232 | 6/1986 |
| JP | 02-247196 | 10/1990 |
| JP | P2002-515430 A | 5/2002 |
| JP | 2003-522442 | 2/2004 |
| JP | 2006-070018 | 3/2006 |
| JP | 4815558 | 9/2011 |
| JP | 4880479 B2 | 2/2012 |
| JP | 5087400 | 9/2012 |
| KR | 10-2004-7002889 | 2/2004 |
| KR | 10-1135824 | 4/2012 |
| NZ | 530449 | 1/2004 |
| NZ | 546138 | 4/2010 |
| NZ | 554037 | 8/2011 |
| SG | 102310 | 3/2006 |
| SG | 120666 | 12/2008 |
| SG | 130542 | 1/2010 |
| TW | 09111947 | 8/2002 |
| TW | 93140030 | 12/2004 |
| TW | 94130519 | 9/2005 |
| WO | 200038700 A1 | 7/2000 |
| WO | WO/03/017919 | 3/2003 |
| WO | WO/2005/037200 | 4/2005 |
| WO | WO/2005/063273 | 7/2005 |
| WO | WO 2006/029221 | 3/2006 |
| WO | WO 2006/116656 | 11/2006 |
| WO | PCT/US2007/077273 | 8/2007 |
| WO | PCT/US08/02086 | 2/2008 |
| WO | WO 2008/028060 A2 | 3/2008 |
| WO | WO 2008/028060 A3 | 3/2008 |
| WO | 2011009032 | 1/2011 |

OTHER PUBLICATIONS

Tuntiwachwuttikul et al., "A Triterpenoid Saponin from *Maesa ramentacea*" Phytochemistry (1997) vol. 44 No. 3, pp. 491-495.*
Sirtori, "Aescin: Pharmacology, Pharmacokinetics, and Therapeutic Profile" Pharmacological Research vol. 44 No. 3, pp. 183-193.*
Sirtori, "Aescin: Pharmacology, Pharmacokinetics, and Therapeutic Profile" Pharmacological Research (2001) vol. 44 No. 3, pp. 183-193.*
D'Acquarica, et al., "Isolation and Structure Elucidation of Four New Triterpenoid Estersaponins from Fruits of Pittosporum Tobira AIT", Tetrahedron vol. 58, pp. 10127-10136 (2002).
PCT International Search Report for Pacific Arrow Limited, International Application No. PCT/US2005/031900, filed Sep. 7, 2005, Dated Feb. 6, 2007.
PCT Written Opinion of the International Searching Authority for Pacific Arrow Limited, International Application No. PCT/US2005/031900, filed Sep. 7, 2005, Dated Feb. 6, 2007.
Li et al., "Two New Triterpenes From the Husks of *Xanthoceras sorbifolis*", Planta Med, vol. 71, pp. 1068-1070 (2005).
The Oxford Textbook of Oncology, 1995, Oxford University Press, pp. 447-456.
The Merk Manual of Diagnosis and Therapy, seventeenth edition, 1999, Merck Research Laboratories, pp. 397-398, 948-949, 1916, and 1979-1981.
U.S. Appl. No. 60/617,379, filed Oct. 8, 2004, May Sung Mak.
U.S. Appl. No. 60/613,811, filed Sep. 27, 2004, Mak, et al.
U.S. Appl. No. 60/607,858, filed Sep. 7, 2004, May Sung Mak.
U.S. Appl. No. 60/532,101, filed Dec. 23, 2003, Wang, et al.
U.S. Appl. No. 60/509,851, filed Oct. 9, 2003, Wang, et al.
U.S. Appl. No. 60/675,807, filed Apr. 27, 2005, Chan, et al.
U.S. Appl. No. 60/841,727, filed Sep. 1, 2006, May Sung Mak.
U.S. Appl. No. 60/675,282, filed Apr. 27, 2005, Chan, et al.
U.S. Appl. No. 60/795,417, filed Apr. 27, 2006, Mak, et al.
U.S. Appl. No. 60/890,380, filed Feb. 16, 2007, Chan, et al.
U.S. Appl. No. 60/947,705, filed Jul. 3, 2007, Chan, et al.
U.S. Office Action for Mak, et al., U.S. Appl. No. 11/412,659, filed Apr. 27, 2006, Dated Mar. 8, 2007.
U.S. Final Office Action for Mak, et al., U.S. Appl. No. 11/412,659, filed Apr. 27, 2006, Dated Sep. 5, 2007.
U.S. Office Action for Chan, et al., U.S. Appl. No. 11/131,551, filed May 17, 2005, Dated Jan. 22, 2007.
U.S. Notice of Allowability for Chan, et al., U.S. Appl. No. 11/131,551, filed May 17, 2005, Dated May 11, 2007.
U.S. Office Action for Chan, et al., U.S. Appl. No. 11/289,142, filed Nov. 28, 2005, Dated Sep. 27, 2007.
U.S. Office Action for Chan, et al., U.S. Appl. No. 11/267,523, filed Nov. 4, 2005, Dated Sep. 27, 2007.
U.S. Office Action for Chan, et al., U.S. Appl. No. 10/906,303, filed Feb. 14, 2005, Dated Feb. 12, 2007.
U.S. Office Action for Chan, et al., U.S. Appl. No. 10/906,303, filed Feb. 14, 2005, Dated Jul. 27, 2007.
U.S. Office Action for Chan, et al., U.S. Appl. No. 11/117,760, filed Apr. 27, 2005, Dated Jun. 29, 2007.
U.S. Office Action for Chan, et al., U.S. Appl. No. 11/117,760, filed Apr. 27, 2005, Dated Aug. 20, 2007.
U.S. Office Action for Chan, et al., U.S. Appl. No. 11/117,745, filed Apr. 27, 2005, Dated Jan. 25, 2008.
U.S. Office Communication for Chan, et al., U.S. Appl. No. 11/117,760, filed Apr. 27, 2005, Dated Feb. 8, 2008.
U.S. Office Action for Mak, et al., U.S. Appl. No. 11/412,659, filed Apr. 27, 2006, Dated Feb. 20, 2008.
U.S. Office Action for Chan, et al., U.S. Appl. No. 11/289,142, filed Nov. 28, 2005, Dated Apr. 14, 2008.
U.S. Office Action for Chan, et al., U.S. Appl. No. 11/117,745, filed Apr. 27, 2005, Dated Mar. 12, 2007.
U.S. Office Action for Chan, et al., U.S. Appl. No. 11/117,745, filed Apr. 27, 2005, Dated Aug. 22, 2007.
U.S. Office Action for Chan, et al., U.S. Appl. No. 10/906,303, filed Feb. 14, 2005, Dated Jan. 4, 2008.
U.S. Advisory Action for Chan, et al., U.S. Appl. No. 11/289,142, filed Nov. 28, 2005, Dated Jul. 28, 2008.
Notice of Allowability for Chan et al.,U.S. Appl. No. 10/906,303, filed Feb. 14, 2005, dated Nov. 26, 2008.
Notice of Allowability for Chan et al., U.S. Appl. No. 11/117,745, filed Apr. 27, 2005, dated Dec. 2, 2008.
Notice of Allowability for Chan et al., U.S. Appl. No. 11/289,142, filed Nov. 28, 2005, dated No. Oct. 1,2008.
PCT Written Opinion of the International Searching Authority for PCT/US04/33359, filed Oct. 8, 2004 for Pacific Arrow Limited et al., dated Apr. 12, 2005.
PCT International Search Report for PCT/US04/33359, filed Oct. 8, 2004 for Pacific Arrow Limited et al., dated Apr. 12, 2005.

(56) References Cited

OTHER PUBLICATIONS

PCT Written Opinion of the International Searching Authority for PCT/US04/43465, filed Dec. 23, 2004 for Pacific Arrow Limited et al., dated May 17, 2005.
PCT International Search Report for PCT/US04/43465, filed Dec. 23, 2004 for Pacific Arrow Limited et al., dated May 17, 2005.
PCT International Preliminary Report on Patentability issued on Mar. 22, 2007 for Pacific Arrow Limited, International App'l No. PCT/US2005/031900.
PCT International Search Report issued on Nov. 13, 2006 for Pacific Arrow Limited, International App'l No. PCT/US2006/016158.
PCT Written Opinion of the International Searching Authority issued on Nov. 13, 2006 for Pacific Arrow Limited, International App'l No. PCT/US2006/016158.
PCT International Preliminary Report on Patentability for Pacific Arrow Limited, et al., International Application No. PCT/US2006/016158, filed Apr. 27, 2006, Dated Oct. 30, 2007.
PCT International Preliminary Report on Patentability issued on Feb. 7, 2006 for Pacific Arrow Limited, International App'l No. PCT/US2004/043465.
PCT International Preliminary Report on Patentability for Pacific Arrow Limited et al., Int'l App'l No. PCT/US2004/033359, filed Oct. 8, 2004, Dated Apr. 11, 2006.
PCT International Search Report issued on Jul. 7, 2008 for Pacific Arrow Limited, International App'l No. PCT/US08/02086.
PCT Written Opinion of the International Searching Authority issued on Jul. 7, 2008 for Pacific Arrow Limited, International App'l No. PCT/US US08/02086.
PCT International Search Report for Pacific Arrow Limited et al., International App'l No. PCT/US07/77273, filed Aug. 30, 2007, Dated Aug. 4, 2008.
PCT Written Opinion of the International Searching Authority for Pacific Arrow Limited et al., International App'l No. PCT/US07/77273, filed Aug. 30, 2007, Dated Aug. 4, 2008.
PCT Notification Concerning Availability of the Publication of the International Application for PCT/US2008/002086, filed Feb. 15,2008 for Pacific Arrow Limited et al., dated Nov. 6, 2008.
PCT First Notice Informing the Applicant of the Communication of the International Application for PCT/LIS2008/002086, filed Feb. 15, 2008 for Pacific Arrow Limited et al., dated Nov. 13, 2008.
PCT Notification Concerning Availability of the Publication of the International Application for PCT/US2007/077273, filed Aug. 30, 2007 for Pacific Arrow Limited et al., dated Nov. 20, 2008.
Supplementary European Search Report issued on Jul. 6, 2005 for Fountain Silver Limited et al., European Patent Application No. 02781502.6.
Australian Letters Patent No. 2002348988, Nov. 8, 2007, Wang, Yun, "Composition comprising Wenguanguo Extracts, Methods for Preparing Same and Uses Thereof".
New Zealand Letters Patent No. 530449, Oct. 11, 2007, Wang, Yun, "Composition comprising Wenguanguo Extracts, Methods for Preparing Same and Uses Thereof".
Notice of Acceptance for Wang, Yun, Australia Patent App'l No. 2002348988, filed Jan. 21, 2004, Dated Jul. 26, 2007.
Notice of Acceptance for Wang, Yun, New Zealand Patent No. App'l No. 530449, filed Jan. 6, 2004, Dated Jun. 29, 2007.
European Office Communication for Wang, Yun, European App'l No. EP 02781502.6, filed Feb. 25, 2004, Dated Jul. 20, 2007.
European Office Communication for Wang, Yun, European App'l No. EP 02781502.6, filed Feb. 25, 2004, Dated Oct. 12, 2005.
European Supplementary Search Report for Wang, Yun, European App'l No. EP 02781502.6, filed Feb. 25, 2004, Dated Jul. 6, 2005.
New Zealand Examination Report for Wang, Yun, New Zealand Patent No. App'l No. 530449, filed Jan. 6, 2004, Dated Feb. 15, 2006.
New Zealand Examination Report for Wang, Yun, New Zealand Patent No. App'l No. 530449, filed Jan. 6, 2004, Dated Apr. 10, 2007.
Chinese Office Action for Wang, Yun, Chinese Publication No. CN 1236792C, filed Jan. 18, 2006, Dated Aug. 27, 2004.
Chinese Office Action for Wang, Yun, Chinese Publication No. CN 1236792C, filed Jan. 18, 2006, Dated May 27, 2005.
Taiwan Office Action for Wang, Yun, Taiwan Application No. 091119471, filed Aug. 28, 2002, Dated Sep. 14, 2004.
Taiwan Office Action for Wang, Yun, Taiwan Application No. 091119471, filed Aug. 28, 2002, Dated Apr. 26, 2005.
Japan Office Action for Japan Patent Application No. 2003-522442, Nov. 4, 2008, International No. PCT/IB02/04750, filed Aug. 28,2002, Fountain Silver Limited, "Composition Comprising Wenguanoguo Extracts, Methods for Perparing Same and Uses Thereof".
Korean Office Action for Korean Application No. 10-2004-7002889, Nov. 21, 2008, International Application No. PCT/IB02/04750, filed Aug. 28,2002, Fountain Silver Limited, "Composition Comprising Wenguanoguo Extracts, Methods for Perparing Same and Uses Thereof".
Canadian Office Communication for Application No. 2,451,740, Dec. 18, 2003, Wang, Yun, "Composition comprising Wenguanguo Extracts, Methods for Preparing Same and Uses Thereof", Dated Nov. 7, 2008.
Arda, Nazly. "Saniculoside N from *Sanicula europaea* L." Journal of Natural Products (1997), 60(11), 1170-1173.
Azam, Amir. "A triterpenoidal sapogenin from the seeds of *Dodonaea viscosa* Linn." Indian Journal of Chemistry, Section B: Organic Chemistry Including Medicinal Chemistry (1993), 32B(4), 513-14.
Barre, Juanita T. "A bioactive triterpene from *Lantana camara*." Phytochemistry (1997), 45(2), 321-324.
Barua, Arun K. "Triterpenoids. XXIX. Structure of barringtogenol B—a new triterpenoid sapogenin from *Barringtonia acutangula*." Tetrahedron (1968), 24(3), 1113-17.
Beeby, Philip J. "Angeloyl chloride: synthesis and utilization in the partial synthesis of lantadene A (rehmannic acid)." Tetrahedron Letters (1977), (38), 3379-82.
Brown, J. M. M. "The relation of chemical structure to the icterogenic and photosensitizing action of some naturally occurring and synthetic triterpene acids." South African Journal of Laboratory and Clinical Medicine (1963), 9 262-72.
Brown, J. M. M. "Biliary excretion in the rabbit. II. The relation between the chemical structure of certain natural or synthetic pentacyclic triterpenes and their icterogenic activity. 2. The substituents on carbon atoms 17, 29, 20, and 22." Proc. Roy. Soc. (London) Ser. B (1964), 160(979), 246-57.
Chen, Y J. "Studies on the constituents of *Xanthoceras sorbifolia* Bunge. (I)." Shoyakugaku Zasshi (1984), 38(2), 203-6.
Chen, Y J. "Studies on the constituents of *Xanthoceras sorbifolia* Bunge. II." Chemical & pharmaceutical bulletin (Sep. 1984), 32(9), 3378-83.
Chen, Y J. "Studies on the constituents of *Xanthoceras sorbifolia* Bunge. III." Chemical & Pharmaceutical Bulletin (1985), 33(1), 127-34.
Chen, et al. "Studies on the constituents of *Xanthoceras sorbifolia* Bunge. IV. Structures of the minor prosapogenins." Chemical & Pharmaceutical Bulletin (1985), 33(3), 1043-8.
Chen, et al. "Studies on the constituents of *Xanthoceras sorbifolia* Bunge. V. Major saponins from the fruits of *Xanthoceras sorbifolia* Bunge." Chemical & Pharmaceutical Bulletin (1985), 33(4), 1387-94.
Cheng, et al. "Two new sterols in husk of *Xanthoceras sorbifolia*." Zhongcaoyao (2001), 32(3), 199-201.
Chakravarty, et al. "Triterpenoid prosaponins from leaves of *Maesa chisia* var. *Angustifolia*." Phytochemistry (1987), 26(8), 2345-9.
Cui, et al. "2D NMR structure determination of five flavonoids from the wood of *Xanthoceras sorbifolia* Bunge." Shenyang Yaoxueyuan Xuebao (1991), 8(1), 36-8, 57.
Cui, et al. "Blood-activating constituents of Wenguanmu (*Xanthoceras sorbifolia*)." Zhongcaoyao (1987), 18(7), 297-8, 296.
Cui, et al. "The application of the microcomputer in the study of Chinese herb and natural drugs. 1. The BASIC program used for the design of liquid-liquid extraction and forecasting the results of extraction and separation." Shenyang Yaoxueyuan Xuebao (1986), 3(2), 79-84.
Eakins, et al. "The effect of three triterpene acids and sporidesmin on the enzyme activities of rat liver plasma membranes." Chemico-Biological Interactions (1978), 21(1), 117-24.

(56) References Cited

OTHER PUBLICATIONS

Eakins, et al. "Studies on bile secretion with the aid of the isolated perfused rat liver. II. The effect of two further pentacyclic triterpenes, asiatic acid and 22-angeloyloxyoleanolicacid." Chemico-Biological Interactions (1978), 21(1), 79-87.

Hart, et al. "New triterpenes of Lantana cemara. A comparative study of the constituents of several taxa." Australian Journal of Chemistry (1976), 29(3), 655-71.

Hopkins, et al. "Eicosenoic acid and other fatty acids of Sapindaceae seed oils." Lipids (1967), 2(3), 258-60.

Hu, et al. "Preparation of high-heating value synthetic liquid fuels." Faming Zhuanli Shenqing Gongkai Shuomingshu (1999), 4 pp.

Hu, et al. "Preparation of liquid fuels having high caloric value." Faming Zhuanli Shenqing Gongkai Shuomingshu (1994), 5 pp.

Huang, et al. "Chemical constituents of Wenguanmu (Xanthoceras sorbifolia) (I)." Zhongcaoyao (1987), 18(5), 199-202.

Huang, et al. "Preliminary studies on absorption and accumulation of atmospheric lead and cadmium by woody plants." Linye Kexue (1982), 18(1), 93-7.

Kim, et al. "Fatty-acid composition of vegetable oils." Choson Minjujuui Inmin Konghwaguk Kwahagwon Tongbo (1985), (3), 43-6.

Koike, et al. "New triterpenoid saponins from Maese japonica." Journal of Natural Products (1999), 62(2), 228-232.

Kuang, et al. "Anti-inflammatory effects of n-butanol extract of Xanthoceras sorbifolia Bunge." Shenyang Yaoke Daxue Xuebao (2001), 18(1), 53-50.

Li, et al. "Medicine for enhancing mental activity." Faming Zhuanli Shenqing Gongkai Shuomingshu (1994), 7 pp.

Li, et al. "Xanthoceras sorbifolia fruit extracts for enhancing mental activity." Faming Zhuanli Shenqing Gongkai Shuomingshu (1994), 6 pp.

Li, et al. "Identification of fatty acids in the kernel oil of Xanthoceras sorbifolia Bge. with GC-MS." Zhiwu Ziyuan Yu Huanjing (1993), 2(2), 28-32.

Ll, et al. "Isolation and structural determination of triterpene alcohols and 4-methylsterols in unsaponifiable fraction of the oil from Xanthoceras sorbifolia Bge." Linye Kexue (1984), 20(4), 397-402.

Li, et al. "Eremophilenolides and other constituents from the roots of Ligularia sagitta." Planta Medica (2003), 69(4), 356-360.

Li, et al. "New guaianolides and xanthine oxidase inhibitory flavonols from Ajania fruticulosa." Journal of Natural Products (1999), 62(7), 1053-1055.

Liu, et al. "The components of Cacelia tangutica," Bulletin of the Korean Chemical Society (2004), 25(7), 1078-1080.

Ma, et al. "A novel protoilludane sesquiterpene from the wood of Xanthoceras sorbifolia." Chinese Chemical Letters (2004), 15(1), 65-67.

Ma, et al. "Screening of Chinese and Mongolian herbal drugs for anti-human immunodeficiency virus type 1 (HIV-1) activity." Phytotherapy Research (2002), 16(S1), 186-189.

Ma, et al. "Inhibitory effects on HIV-1 protease of constituents from the wood of Xanthoceras sorbifolia." Journal of natural products (Feb. 2000), 63(2), 238-42.

Mahato, et al. "New triterpenoids from Lantana camara: Isomerisation of the angeloyl moiety of lantadene a during catalytic hydrogenation." Journal of the Indian Chemical Society (1999), 76(11-12), 723-726.

Meng, et al. "Antifungal highly oxygenated guaianolides and other constituents from Ajania fruticulosa." Phytochemistry (2001), 58(7), 1141-1145.

Nakamura, et al. "Inhibitory effects of some traditional medicines on proliferation of HIV-1 and its protease." Yakugaku Zasshi (2004), 124(8), 519-529.

Nethaji et al. "Molecular structure of lantadene-B&C, triterpenoids of Lantana camara, red variety: lantadene-B, 22β-angeloyloxy-3-oxoolean-12-en-28-oic acid; lantadene-C, 22 β-(S)-2'-methyl butanoyloxy-3-oxoolean-12-en-28-oic acid." Journal of Crystallographic and Spectroscopic Research (1993), 23(6), 469-72. (Abstract only).

Plouvier, et al. "Fraxoside and coumarin heterosides occurring in various botanical groups." Comptes Rendus des Seances de l'Academie des Sciences, Serie D: Sciences Naturelles (1968), 267 (22), 1883-5.

Plouvier, et al. "Flavone heterosides: kaempferol 3-rhamnoglucoside, myricitrin, linarin, and saponarin." Comptes Rendus des Seances de l'Academie des Sciences, Serie D: Sciences Naturelles (1966), 262(12), 1368-71.

Plouvier, et al. "Oil of the seeds of Xanthoceras sorbifolia Bunge and of Koelreuteria paniculata Laxm." Compt. rend. (1946), 222 916-17.

Sakurai, et al. "Assamicin I and II, novel triterpenoid saponins with insulin-like activity from Aesculus assamica Griff." Bioorganic & Medicinal Chemistry Letters (2002), 12(5), 807-810.

Semikhov, et al. "Comparative study of the amino acid composition of the embryo in grasses (Poaceae) and other flowering plants." Botanicheskii Zhurnal (Sankt-Peterburg, Russian Federation) (1994), 79(3), 83-92.

Sharma, et al. "Molecular structure, polymorphism, and toxicity of lantadene A, the pentacyclic triterpenoid from the hepatotoxic plant Lantana camara." Journal of biochemical toxicology (1991 Spring), 6(1), 57-63.

Shang-Jiang, et al. "Constituents of Shashen (Adenophora axilliflora)." Planta Medica (1986), (4), 317-20.

Sindambiwe, et al. "Triterpenoid saponins from Maesa lanceolate." Phytochemistry (1996), 41(1), 269-77.

Singh, et al. "Biotransformation of lantadene A (22•-angeloyloxy-3-oxoolean-12-en-28-oic acid), the pentacyclic triterpenoid, by Alcaligenes faecalis." Biodegradation (1999), 10(5), 373-381.

Tian, et al. "Study on the vegetative storage proteins in temperate hardwoods of fifteen families." Xibei Zhiwu Xuebao (2000), 20(5), 835-841.

"Triterpenoids. XVI. The constitution of rehmannic acid." Journal of the Chemical Society, Abstracts (1954), 900-3.

Tuntiwachwuttikul, et al. "A triterpenoid saponin from Maesa ramentacea." Phytochemistry (1997), 44(3), 491-495.

Voutquenne, et al. "Triterpenoid saponins and acylated prosapogenins from Harpullia austro-caledonica." Phytochemistry (2002), 59(8), 825-832.

Wang, et al. "Chemical constituents of the oil and kernels of Xanthoceras sorbifolia Bunge." Zhiwu Xuebao (1981), 23(4), 331-3.

Waechter, et al. "Antitubercular Activity of Triterpenoids from Lippia turbinata." Journal of Natural Products (2001), 64(1), 37-41.

Yan, et al. "Separation, identification and determination of the unsaponifiable matters in vegetable oils." Beijing Shifan Daxue Xuebao, Ziran Kexueban (1985), (1), 53-8.

Yan, et al. "Isolation, content analysis and structural determination of sterols in unsaponifiable fraction of the oil from Xanthoceras sorbifolia Bge." Linye Kexue (1984), 20(4), 389-96.

Yang, et al. "Extraction of total saponin, fat, protein, and saccharide from Xanthoceras sorbifolia." Faming Zhuanli Shenqing Gongkai Shuomingshu (2002), 4 pp.

Yang, et al. "Application of the extract of Xanthoceras sorbifolia shell in preparing the food and medicine for improving brain functions." Faming Zhuanli Shenqing Gongkai Shuomingshu (2002), 6 pp.

Yang, et al. "Two new triterpenoid saponins from the seeds of Aesculus chinensis." Chinese Chemical Letters (2000), 11(2), 139-142.

Zhang, et al. "Quantitative determination of myricetin and quercetin in Xanthoceras sorbifolia Bunge by HPLC." Shenyang Yaoke Daxue Xuebao (2000), 17(3), 194-196.

Zhang, et al. "Studies on chemical constituents of Xanthoceras sorbifolia Bunge." Yaoxue Xuebao (2000), 35(2), 124-127.

Zhao, et al. "Four new triterpene saponins from the seeds of Aesculus chinensis." Journal of Asian Natural Products Research (2003), 5(3), 197-203.

Zhao, et al. "Three new triterpene saponins from the seeds of Aesculus chinensis." Chemical & Pharmaceutical Bulletin (2001), 49(5), 626-628.

Zheng, et al. "Triterpenoids from Mosla chinensis." Indian Journal of Chemistry, Section B: Organic Chemistry Including Medicinal Chemistry (2000), 39B(11), 875-878.

(56) References Cited

OTHER PUBLICATIONS

Apers, et al. "New acylated triterpenoid saponins from *Maesa lanceolata*." Phytochemistry 52 (1999) 1121-1131.
Jiang, et al. "Six Triterpenoid Saponins from *Maesa laxiflora*." J. Nat. Prod. 1999, 62, 873 876.
Lu, at al. "Triterpenoid saponins from the roots of tea plants (*Camellia sinensis* var. *Assamica*)." Phytochemistry 53 (2000) 941-946.
Seo, et al. "A New Triterpene Saponin from *Pittosporum viridiflorum* from the Madagascar Rainforest." J. Nat. Prod. 2002, 65, 65-68.
Yang, et al. "Anti-HIV-1 Protease Triterpenoid Saponins from the Seeds of *Aesculus chinensis*." J. Nat. Prod. 1999, 62, 1510-1513.
Voutquenne, et al. "Structure-Activity Relationships of Haemolytic Saponins" Pharmaceutical Biology (2002), vol. 40, No. 4, pp. 253-262.
Sirtori, C., "Aescin: Pharmacology, Pharmacokinetic Profile" Pharmacological Research(2001) vol. 44, No. 3, pp. 183-193.
Oda, K. et al., "Adjuvant and Haemolytic Activities of 47 Saponins Derived from Medicinal and Food Plants" Biol. Chem. (2000) vol. 381, pp. 67-74.
Chan, Pui-Kwong, 2007, "Acylation with diangeloyl groups at C21-22 positions in triterpenoid saponins is essential for cytotoxcity towards tumor cells", Biochemical Pharmacology 73(2007): 341-350.
Lavaud, et al., 1992, "Saponins from *Steganotaenia araliacea*", Phycochemistry, 31(9):3177-3181.
Zhang, et al., 2007, "Cytotoxic triterpenoid saponins from the fruits of *Aesculus pavia* L", Phytochemistry 68(2007): 2075-2086.
Voutquenne, et al., 2005, "Haemolytic Acylated Triterpenoid saponins from Harpullia austro-caledonica". Phytochemistry, vol. 66: 825-826.
Ma, et al, 2008, "Cytotoxic Triterpenoid Saponins Acylated with Monoterpenic Acid from *Pithecellobium lucidum*",Journal of Natural Products, vol. 71(1): 41-46.
Ushijima, et al, 2008, "Triterpene Glycosides from the Roots of *Codonopsis lanceolata*", Chemical & Pharmaceutical Bulletin, vol. 56(3) 308-314.
Yadava, et al., 2008, "New antibacterial triterpenoid saponin from *Lactuca scariola*", Fitoterapia, vol. 1:1-5.
Wang, et al., 2008, "Bioactive Triterpene Saponins from the Roots of *Phytolacca americana*", Journal of Natural Products, vol. 71(1): 35-40.
Chang, et al, 2007, "Biologically Active Triterpenoid Saponins from *Ardisia japonica*", Journal of Natural Products, vol. 70(2): 179-187.
Akihisa et al, 2006, "Cancer Chemopreventive Effects and Cytotoxic Activities of the Triterpene Acids from the Resin of *Boswellia carteri*", Biological & Pharmaceutical Bulletin, vol. 29(9):1976-1979.
Liang, et al., 2006, "Triterpenoid Saponins from *Lysimachia davurica*", Chemical & Pharmaceutical Bulletin, vol. 54 (10):1380-1383.
Fujioka, et al., 2006, "Antiproliferative Constituents from Umbelliferae Plants. New Triterpenoid Glycosides from the Fruits of *Bupleurum rotundifolium*", Chemical & Pharmaceutical Bulletin, vol. 54 (12):1694-1704.
Rabi, et al., 2007, "Novel triterpenoid 25-hydroxy-3-oxoolean-12-en-28-oic acid induces growth arrest and apoptosis in breast cancer cells", Breast Cancer Research & Treatment, vol. 101:27-36.
Sporn, et al., 2007, "Platforms and Networks in Triterpenoid Pharmacology", Drug Development Research, vol. 68:174-182 (2007).
Puiffe, et al., 2007, "Characterization of Ovarian Cancer Ascites on Cell Invasion, Proliferation, Spheroid Formation, and Gene Expression in an In Vitro Model of Epithelial Ovarian Cancer" Neoplasia, vol. 9(10):820-829.
Ricciardelli, et al., 2006, "Extracellular Matrix of Ovarian Tumors", Seminars in Reproductive Medicine, vol. 24(4): 270-282.
Bang, et al., 2007, "Facile Synthesis of Trisaccharide Moiety Corresponding to Antitumor Activity in Triterpenoid Saponins Isolated from Pullsatila Roots", Chemical & Pharmaceutical Bulletin, vol. 55(12): 1734-1739.

Talmadge, James E., 2008, "Follistatin as an Inhibitor of Experimental Metastasis", Clinical Cancer Research, vol. 14(3) 624-626.
Wei, et al., 2004, "Anti-inflammatory Triterpenoid Saponins from the Seeds of *Aesculus chinensis*", Chemical & Pharmaceutical Bulletin, vol. 52(10): 1246-1248.
Zhu et al, "Preliminary test of chemical constituents of wenguanguo and its multipurpose utilization", Research of Land and Natural Resources (1): 69-71, 1997.
Konoshima, et al. "Antitumor Agents, 82. Cytotoxic Sapogenols from *Aesculus hippocastanum*", Journal of Natural Products vol. 49, No. 4, pp. 650-656, Jul.-Aug. 1986.
U.S. Appl. No. 12/392,795, filed Mar. 20, 2009, Chan et al.
U.S. Office Action, Mar. 18, 2009, U.S. Appl. No. 11/117,760, filed Apr. 27, 2005.
U.S. Office Action, May 19, 2009, U.S. Appl. No. 12/195,112, filed Aug. 20, 2008, Dated May 19, 2009.
New Zealand Office Action, May 8, 2009, for New Zealand Application No. 554037, filed Mar. 22, 2007.
New Zealand Office Action, Aug. 12, 2009, New Zealand Application No. 546138, filed Mar. 27, 2006.
New Zealand Office Action, Sep. 22, 2009, New Zealand Application No. 546138, filed Mar. 27, 2006.
Supplementary European Search Report, Oct. 13, 2009, European Patent Application No. 04815530.3, filed Jul. 19, 2006.
Supplementary European Search Report, Oct. 13, 2009, European Patent Application No. 04809909.7, filed Mar. 27, 2005.
PCT Written Opinion of the International Searching Authority, Jun. 2, 2009, International App'l No. PCT/US09/34115, filed Feb. 13, 2009.
PCT Written Opinion of the International Searching Authority, Aug. 4, 2008, International App'l No. PCT/US07/77273, filed Aug. 30, 2007.
PCT International Preliminary Report on Patentability, Mar. 12, 2009, International App'l No. PCT/US07/77273, filed Aug. 30, 2007.
Maes, et al. Jan. 2004, "In vitro and in vivo activities of a triterpenoid saponin extract (px-6518) from the plant *Maesa balansae* against visceral leishmania species." Antimicrobial agents and chemotherapy, vol. 48 (1): 130-136.
Murakami, et al. 1996, "New hypoglycemic constituents in "gymnemic acid" from gymnema sylvestre." Chem. Pharm. Bull., vol. 44(2) 469-471.
Na, et al. 2006, "Protein tryoshine phosphatase 1B inhibitory activity of triterpenes isolated from astilbe koreana." Bioorg Med Chem Lett., vol. 16(12):3273-6.
Zhou, et al. 2001, "The first naturally occurring tie2 kinase inhibitor." Org Lett., vol. 3(25): 4047-9.
Zhou, et al. "The first naturally occuring tie2 kinase inhibitor" Org. Lett. Dec. 13, 2001;3(25): 4047-9.
Apers Sandra et al., Aug. 2001, "Antiviral, haemolytic and molluscicidal activities of triterpenoid saponins from *Maesa lanceolata*: Establishment of structure-activity relationships", Planta Medica, vol. 67(6): %28-532.
Dizes C et al., 1998, "Harpuloside a triterpenoid saponin from *Harpullia ramiflora*", Phytochemistry, Pergamon Press, GB, vol. 48(7): 1229-1232.
Chinese Office Action, Mar. 27, 2009 for Pacific Arrow Limited, Chinese application No. 2005800375247, filed Jul. 26, 2007.
Chinese Office Action Apr. 21, 2010 for Pacific Arrow Limited, Chinese application No. 2005800375247, filed Jul. 26, 2007.
U.S. Office Action, Feb. 18, 2010, for Chan et al., U.S. Appl. No. 12/195,112, filed Aug. 20, 2008.
PCT International Preliminary Examination Report, Jun. 3, 2003, for Pacific Arrow Limited et al., Int'l App'l No. PCT/IB02/04750, filed Aug. 28, 2002.
PCT International Search Report, Jun. 2, 2009, for Pacific Arrow Limited et al., Int'l App'l No. PCT/US2009/034115, filed Feb. 13, 2009.
Supplementary European Search Report, Oct. 22, 2009, for Mak et al., European Patent Application No. 05810263.3, PCT/US2005031900.
Australian Office Action, Feb. 19, 2010, for Pacific Arrow Limited et al., for Australian Patent No. 2004281707, filed Oct. 8, 2004.

(56) References Cited

OTHER PUBLICATIONS

European Office Communication, Jan. 15, 2010, for Pacific Arrow Limited, et al., European App'l No. EP 06751723.5-2123, filed Nov. 14, 2007.
European Office Communication, Dec. 29, 2009, for Mak et al., European App'l No. EP 0581026.3-2123, filed Mar. 30, 2007.
China Office Action, Jan. 15, 2010, for Pacific Arrow Limited, et al., Chinese App'l No. 200480036717, filed Jun. 8, 2006.
European Office Communication, Apr. 19, 2010, for Pacific Arrow Limited, et al., European App'l No. EP 04809909.7-2123, filed Mar. 26, 2007.
European Office Communication, Apr. 19, 2010, for Pacific Arrow Limited, et al., European App'l No. EP 04815530.3-2123, filed Jul. 19, 2006.
European Office Communication, Apr. 19, 2010, for Mak May Sung, et al., European App'l No. EP 05810263.3-2123, filed Mar. 30, 2007.
European Office Communication, Apr. 19, 2010, for Pacific Arrow Limited, et al., European App'l No. EP 07841638.5-2123, filed Mar. 27, 2009.
Cheng, et al. "Two new sterols in the husk of *Xanthoceras sorbifolia*." Chinese Traditional and Herbal Drugs (2001), 32(3), 199-201.
Japan Final Office Action, Feb. 23, 2009, for Fountain Silver Limited et al., Japan App'l No. 2003-522442, filed Feb. 5, 2004. (w/English translation).
Japan Office Action, Jan. 14, 2011, for Pacific Arrow Limited et al., Japan App'l No. 2006-534419, filed Mar. 22, 2006. (w/English translation).
U.S. Office Action, Jan. 19, 2011, for Chan et al., U.S. Appl. No. 12/344,682, filed Dec. 29, 2008.
Japan Office Action, Feb. 2, 2011, for Pacific Arrow Limited et al., Japan App'l No. 2006-534419, filed Mar. 22, 2006. (w/English translation).
Japan Office Action, Mar. 18, 2011, for Pacific Arrow Limited et al., Japan App'l No. 2006-547422, filed Jun. 16, 2006. (w/English translation).
Australian Office Action, Mar. 18, 2011 for Pacific Arrow Limited et al., Australian Patent Application No. 2004281707, filed Oct. 8, 2004.
US Office Action, May 12, 2011, for Chan et al., U.S. Appl. No. 12/714,598, filed Mar. 1, 2010.
Korean Office Action, Jun. 3, 2011 for Pacific Arrow Limited et al., Korean App'l No. 10-2006-7008896, filed May 8, 2000. (w/English translation).
New Zealand Office Action, Mar. 7, 2011 for Pacific Arrow Limited et al., New Zealand App'l No. 587973, filed Sep. 14, 2010.
Australian Notice of Acceptance, May 26, 2011, for Pacific Arrow Limited et al., Australian Patent App'l No. 2004281707, filed Mar. 23, 2006.
New Zealand Office Action, Apr. 12, 2011 for Pacific Arrow Limited et al., New Zealand App'l No. 554037, filed Mar. 19, 2007.
Japan Office Action, Jun. 3, 2011 for Pacific Arrow Limited at al., Japan App'l No. 2006-534419, filed Mar. 22, 2006. (w/English translation).
Chinese Office Action, Jun. 3, 2011 for Pacific Arrow Limited, Chinese application No. 200880012065.0, filed Oct. 14, 2009. (w/English translation).
U.S. Office Action, May 20, 2011, for Chan et al., U.S. Appl. No. 12/392,795, filed Feb. 25. 2009.
New Zealand Office Action, Sep. 24, 2010 for Pacific Arrow Limited, New Zealand App'l No. 579194, filed Aug. 21, 2009.
PCT International Search Report, Dec. 6, 2011, for Pacific Arrow Limited et al., Int'l App'l No. PCT/US2011/044233, filed Jul. 15, 2011.
PCT Written Opinion of the International Searching Authority, Dec. 6, 2011, for Pacific Arrow Limited et al., Int'l App'l No. PCT/US2011/044233, filed Jul. 15, 2011.
U.S. Office Action, Oct. 27, 2011, for Chan et al., U.S. Appl. No. 12/344,682, filed Dec. 29, 2008.
Canadian Office Action, Sep. 8, 2011, for Fountain Silver Limited et al., Canadian App'l No. 2,451,740, filed Dec. 18, 2003.
Canadian Notice of Allowance, Oct. 5, 2011, for Pacific Arrow Limited et al., Canadian App'l No. 2541425, filed Oct. 8, 2004.
China Office Action, Mar. 23, 2011, for Pacific Arrow Limited, China App'l No. 200780040744.4, Filed Apr. 30, 2009. (w/English translation).
Chinese Office Action, Jun. 14, 2011, for Pacific Arrow Limited et al., Chinese App'l No. 200480036761.7, filed Jun. 8, 2006. (w/English translation).
Chinese Office Action, Sep. 28, 2011 for Pacific Arrow Limited et al., Chinese App'l No. 200480036761.7, Filed Jun. 8, 2006. (w/English translation).
Chinese Office Action, Oct. 28, 2011 for Pacific Arrow Limited et al., Chinese App'l No. 200480038698.0, Filed Jun. 23, 2006. (w/English translation).
Chinese Notice of Allowance, Feb. 1, 2011, for Pacific Arrow Limited, China app'l No. 200580037524.7, filed Apr. 30, 2007. (w/English translation).
Japanese Notice of Allowance, Nov. 15, 2011, for Pacific Arrow Limited et al., Japan App'l No. 2006-547422, filed Jun. 16, 2006.
Japanese Office Action, Nov. 21, 2011, for Pacific Arrow Limited, Japanese app'l No. 2007-530484, filed Mar. 2, 2007. (w/English translation).
Taiwan Office Action, Mar. 3, 2011, for Pacific Arrow Limited et al., Taiwan App'l No. 093140030, filed Dec. 22, 2004. (w/English translation).
Taiwan Office Action, Mar. 12, 2010 for Pacific Arrow Limited et al., Taiwan App'l No. 093140030, filed Dec. 22, 2004. (w/English translation).
U.S. Office Action, Dec. 21, 2011, for Chan et al., U.S. Appl. No. 12/541,713, filed Aug. 14, 2009.
U.S. Office Action, Dec. 28, 2011, for Chan et al., U.S. Appl. No. 12/714,598, filed Mar. 1, 2010.
U.S. Office Action, Mar. 20, 2012, for Chan et al., U.S. Appl. No. 12/344,682, filed Dec. 29, 2008.
U.S. Office Action, Apr. 17, 2012, for Chan et al., U.S. Appl. No. 12/392,795, filed Feb. 25, 2009.
New Zealand Office Action, Jan. 11, 2012, for Pacific Arrow Limited, New Zealand App'l No. 579194, filed Aug. 21, 2009.
Canadian Office Action, Jan. 31, 2012, for Pacific Arrow Limited, Canadian Application No. 2,579,231, filed Mar. 6, 2007.
European Office Communication, Feb. 13, 2012, for Pacific Arrow Limited, European App'l No. EP 07841638.5-2123, filed Mar. 27, 2009.
European Office Communication, Feb. 13, 2012 for Pacific Arrow Limited, European App'l No. EP 05810263.3-2123, filed Mar. 30, 2007.
European Office Communication, Feb. 13, 2012, for Pacific Arrow Limited, European App'l No. EP 04815530.3-2123, filed Jul. 19, 2006.
European Office Communication, Mar. 3, 2012 for Pacific Arrow Limited, European App'l No. EP 04809909.7-2123, filed Mar. 27, 2006.
Australian Office Action, Feb. 6, 2012 for Pacific Arrow Limited, Australian App'l No. 2009208069, filed Aug. 7, 2009.
Australian Office Action, Feb. 6, 2012 for Pacific Arrow Limited, Australian App'l No. 2005282437, filed Mar. 19, 2007.
Australian Office Action, Feb. 6, 2012 for Pacific Arrow Limited, Australian App'l No. 2009200988, filed Mar. 10, 2009.
Taiwan Office Action, Jan. 18, 2012 for Pacific Arrow Limited, Taiwan App'l No. 094130519, filed Sep. 6, 2005.
Yang et al. "The Influence of aquaporin -1 and microvessel density on ovarian carcinogenesis and ascites formation", International Journal of Gynecological Cancer, vol. 16, No. S1, Feb. 1, 2006, pp. 400-405.
U.S. Office Action, Jun. 26, 2012, for Chan et al., U.S. Appl. No. 12/541,713, filed Aug. 14, 2009.
European Office Communication, Apr. 26, 2012 for Pacific Arrow Limited, European App'l No. EP 09721583.4-2123, filed Sep. 7, 2010.
European Office Communication, Jun. 4, 2012 for Pacific Arrow Limited, European App'l No. EP 02781502.6-2112, filed Feb. 25, 2004.
New Zealand Office Action, Mar. 26, 2012, for Pacific Arrow Limited, New Zealand App'l No. 598934, filed Mar. 21, 2012.

(56) References Cited

OTHER PUBLICATIONS

Chinese Office Action, Apr. 9, 2012, for Pacific Arrow Limited, Chinese App'l No. 200780040744.4, filed Apr. 30, 2009.
Japanese Office Action, May 8, 2012, for Pacific Arrow Limited, Japanese app'l No. 2007-530484, filed Mar. 2, 2007.
Germonprez, N. et al., 2005, "In vitro and in vivo anti-leishmanial activity of triterpenoid saponins isolated from *Maesa balansae* and some chemical derivatives", J. Med. Chem., 48(1):32-37.
Germonprez, N. et al., 2003, "Antileishmanial saponins from *Maesa balansae*", Tap Chi Hoa Hoc, 41(spec.), 125-130. From Chemical Abstracts Service, Columbus, Ohio, US.
Australian Office Action, Jun. 21, 2012 for Pacific Arrow Limited, Australian App'l No. 2008244648, filed Aug. 21, 2009.
Korean Office Action, Jun. 22, 2012 for Pacific Arrow Limited, Korean App'l No. 10-2007-7007902, filed Apr. 6, 2007 (w/English Translation).
Canadian Office Action, Jul. 5, 2012, for Fountain Silver Limited et al., Canadian App'l No. 2,451,740, filed Dec. 18, 2003.
Notice of Allowability, Aug. 15, 2012, for Chan et al., U.S. Appl. No. 12/392,795, filed Feb. 25, 2009.
PCT International Search Report, Oct. 2, 2012, for Pacific Arrow Limited, Int'l App'l No. PCT/US12/46716, filed Jul. 13, 2012.
PCT Written Opinion of the International Searching Authority, Oct. 2, 2012, for Pacific Arrow Limited, Int'l App'l No. PCT/US12/46716, filed Jul. 13, 2012.
U.S. Notice of Allowance, Sep. 12, 2012, for U.S. Appl. No. 12/541,713, filed Aug. 14, 2009.
U.S. Office Action, Oct. 15, 2012, for Chan et al., U.S. Appl. No. 13/259,480, filed Sep. 23, 2011.
Peer et al., 2007, "Nanocarriers as an emerging platform for cancer therapy." Nature Publishing Group, vol. 2: 751-760.
Mahato et al., 1991, "Structure Elucidation of Four New Triterpenoid Oligoglycosides From *Anagallis Arvensis*", Tetrahedron, vol. 47(28): 5215-5230.
Sheng-Xiang et al., 1993, "A Triterpene From *Marsdenia Globifera*", Phytochemistry, vol. 34(5):1385-1387.
PCT International Preliminary Report on Patentability, Jun. 25, 2013, for Pacific Arrow Limited, Int'l App'l No. PCT/US2011/044233, filed Jul. 15, 2011.
PCT Notification Concerning Transmittal of International Preliminary Report on Patentability, Jul. 4, 2013, for Pacific Arrow Limited, Int'l App'l No. PCT/US2011/044233, filed Jul. 15, 2011.
European Office Communication, Jun. 26, 2013, for Pacific Arrow Limited, European App'l No. EP 04815530.3-1464, filed Jul. 19, 2006.
U.S. Office Action, Mar. 21, 2013, for Chan et al., U.S. Appl. No. 12/856,322, filed Aug. 13, 2010.
U.S. Office Action, Feb. 1, 2013, for Chan et al., U.S. Appl. No. 13/259,480, filed Sep. 23, 2011.
U.S. Office Action, Jun. 6, 2013, for Chan et al., U.S. Appl. No. 13/259,480, filed Sep. 23, 2011.
Canadian Office Action, May 21, 2013, for Fountain Silver Limited et al., Canadian App'l No. 2,451,740, filed Dec. 18, 2003.
Canadian Office Action, Feb. 26, 2013, for Pacific Arrow Limited, Canadian App'l No. 2,579,231, filed Mar. 6, 2007.
European Office Communication, May 13, 2013 for Pacific Arrow Limited, European App'l No. EP 10800596.8-1462, filed Mar. 30, 2012.
Ohtsuki et al. "Acylated triterpenoid saponins from *Schima noronhae* and their cell growth inhibitory activity", Journal of Natural Products, vol. 71, No. 5, Mar. 20, 2008, pp. 918-921, XP002694762.
Sharma et al. "Lanthadenes and their esters as potential antitumor agents", Journal of Natural Products, vol. 71, No. 7, Jun. 14, 2008, pp. 1222-1227, XP002694763.

* cited by examiner

Structure of saponin

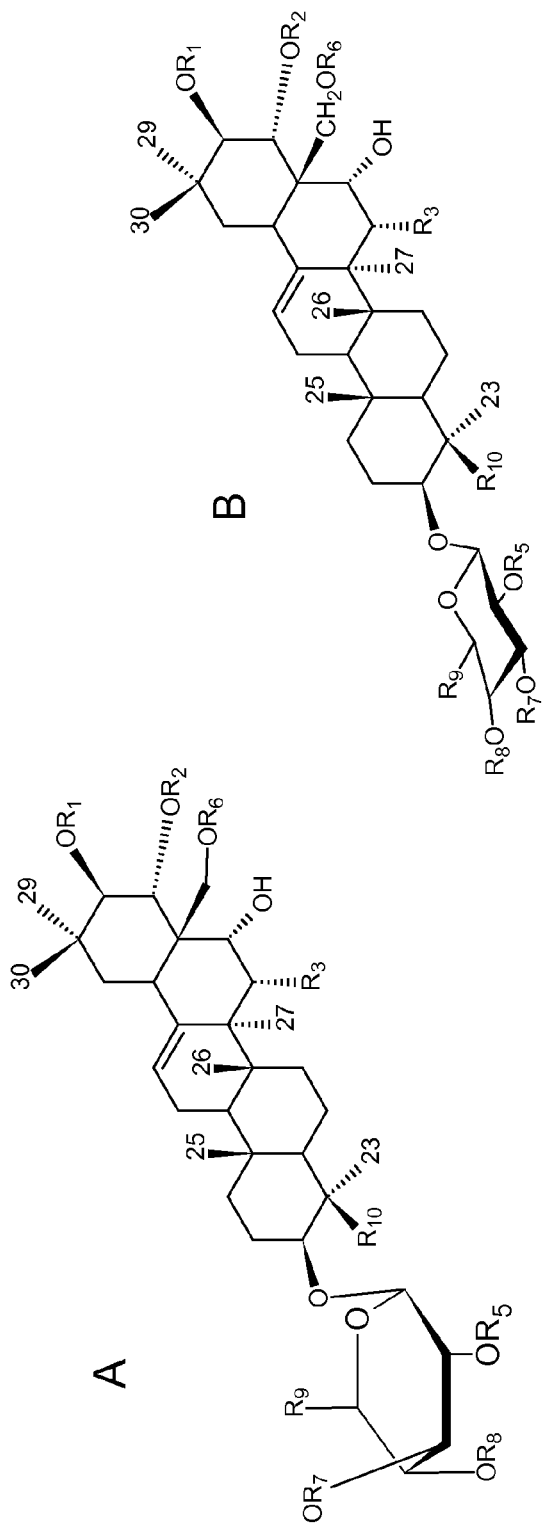

Figure 2

R1= angeloyl or Tigloyl or Senecioyl or acetyl or H or a sugar moiety comprising angeloyl, Tigloyl, Senecioyl or acetyl
R2= angeloyl or Tigloyl or Senecioyl or acetyl or H or a sugar moiety comprising angeloyl, Tigloyl, senecioyl or acetyl
R6= angeloyl or Tigloyl or Senecioyl or acetyl or H or a sugar moiety comprising angeloyl, Tigloyl, senecioyl or acetyl Wherein R1, R2 are not in combination of acetyl with one of angeloyl, Tigloyl and Senecioyl
R3=H or OH
R10=CH3 or CH2OH or CHO
R5= D- glucose or D-galactose or L-rhamnose or L-arabinose or, D-xylose or alduronic acid or, D- glucuronic acid or D-galacturonic acid or H
R7=D- glucose or D-galactose or L-rhamnose or L-arabinose or, D-xylose or alduronic acid or D- glucuronic acid or D-galacturonic acid or H
R8=D- glucose or D-galactose or L-rhamnose or L-arabinose or, D-xylose or alduronic acid or, D- glucuronic acid or D-galacturonic acid or H
R9= COOH or CH2OH Figure 4
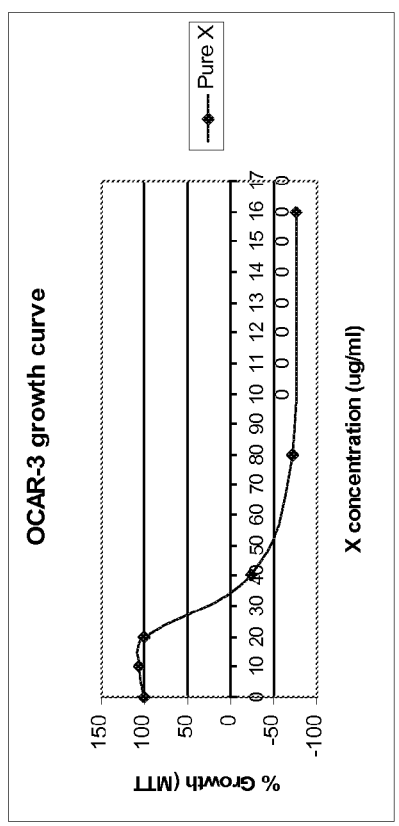
B
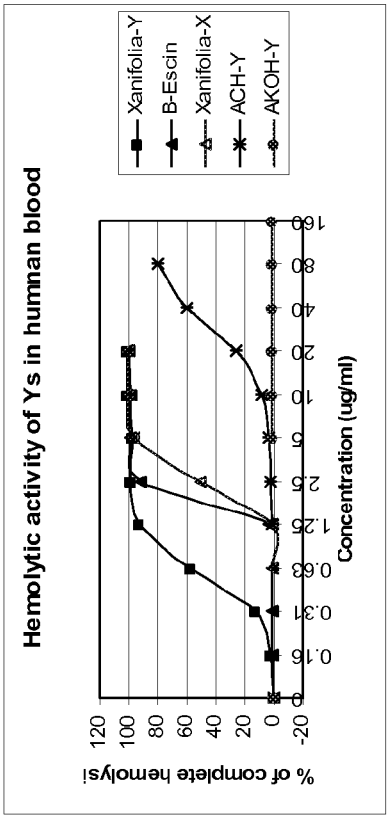
D
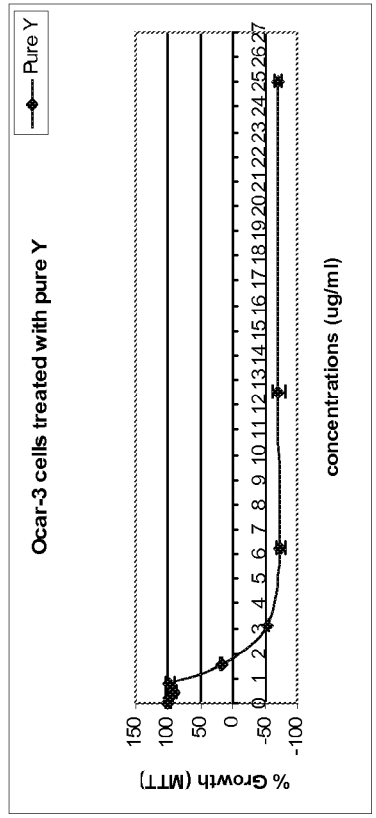
A
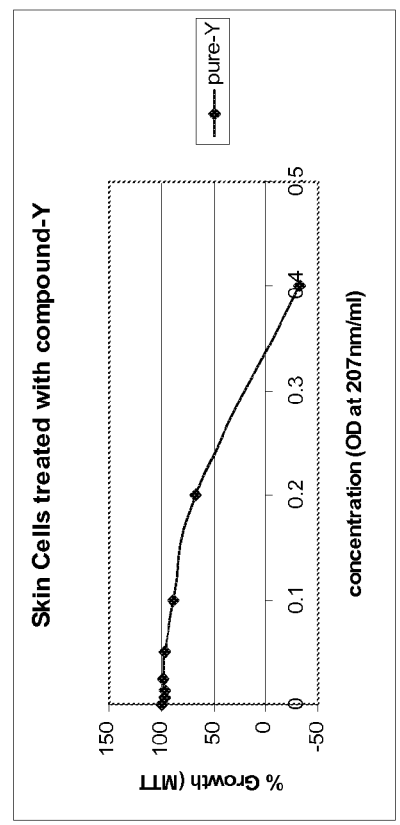
C Figure 5
Anticancer activity of Compounds Y, Y1, Y2, Y8, Y9 and Y10.
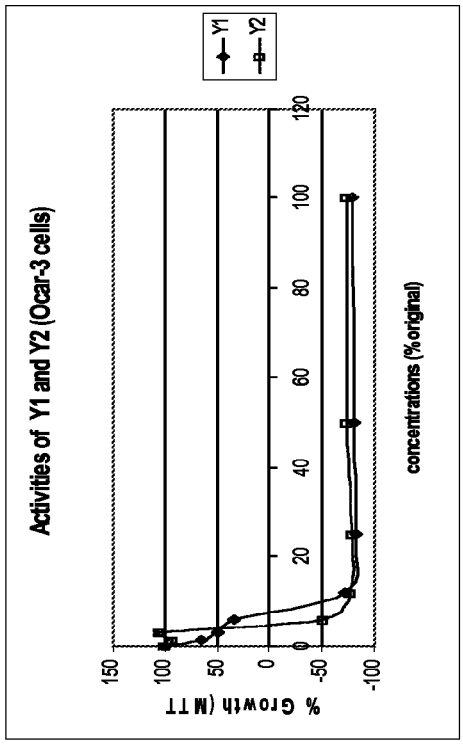
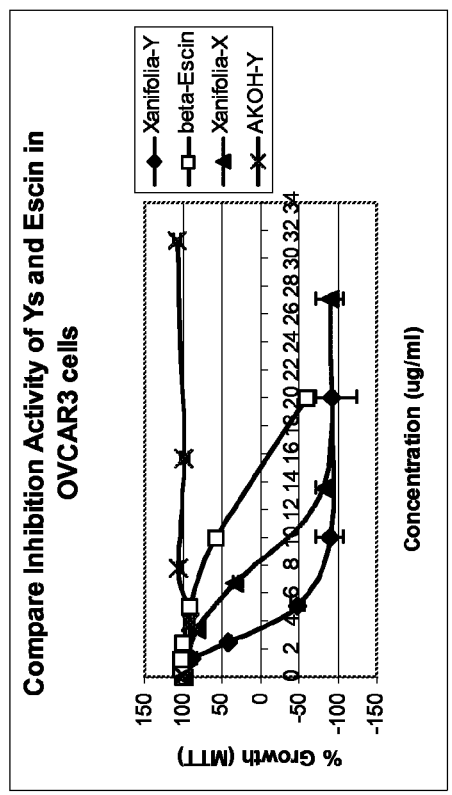
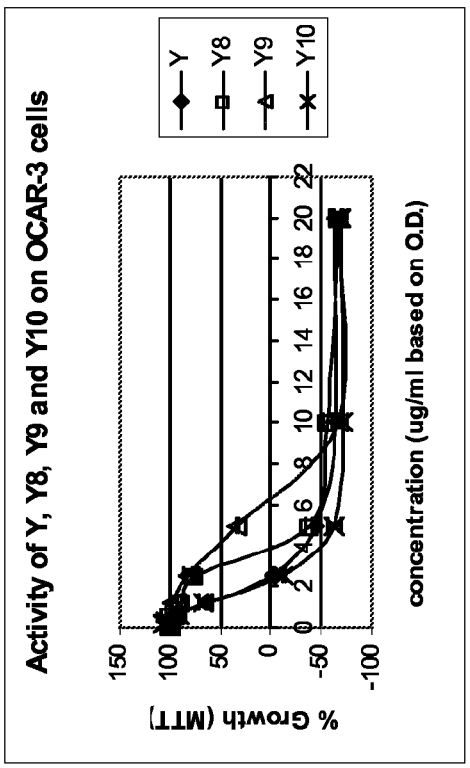
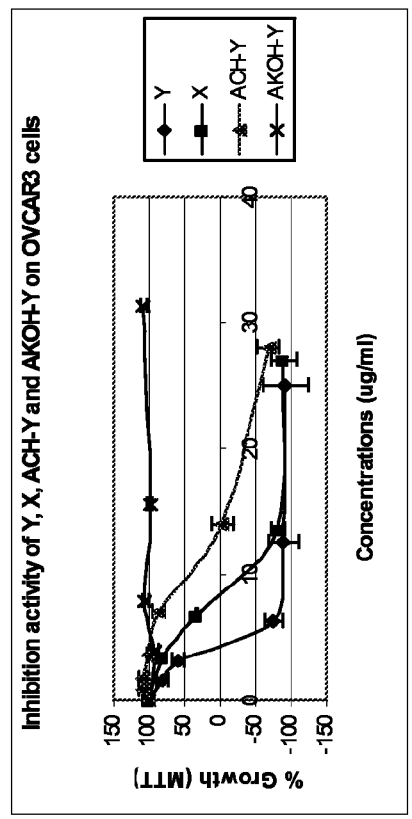

Figure 6
Haemolytic and Mtt activities of Compound Y
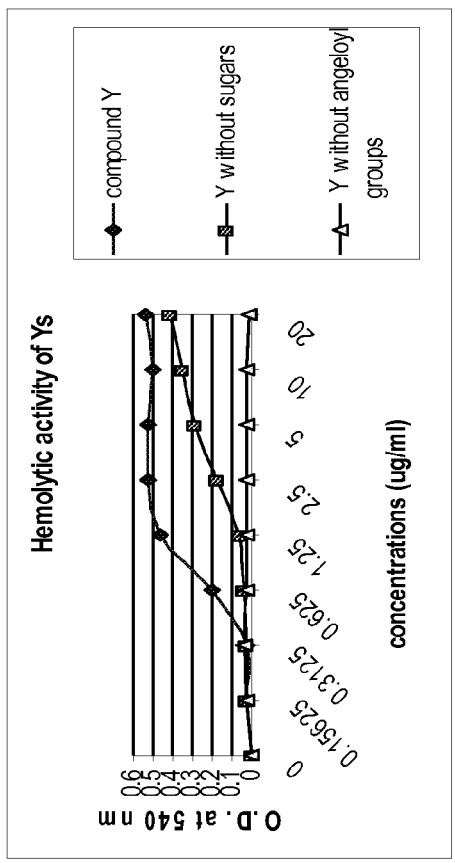
B
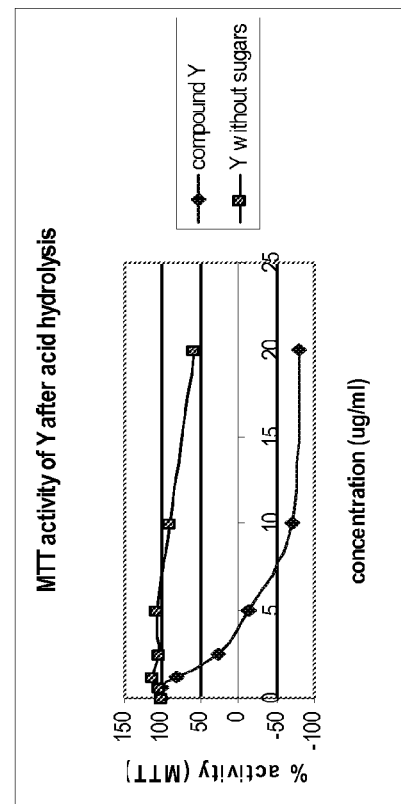
D
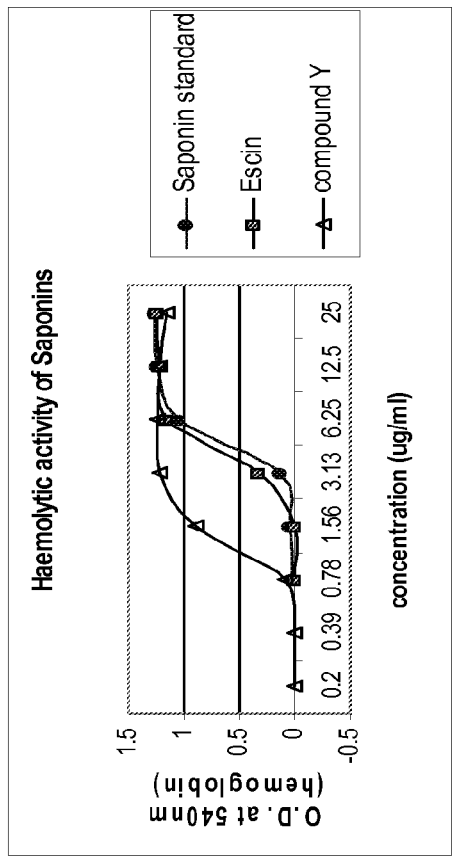
A
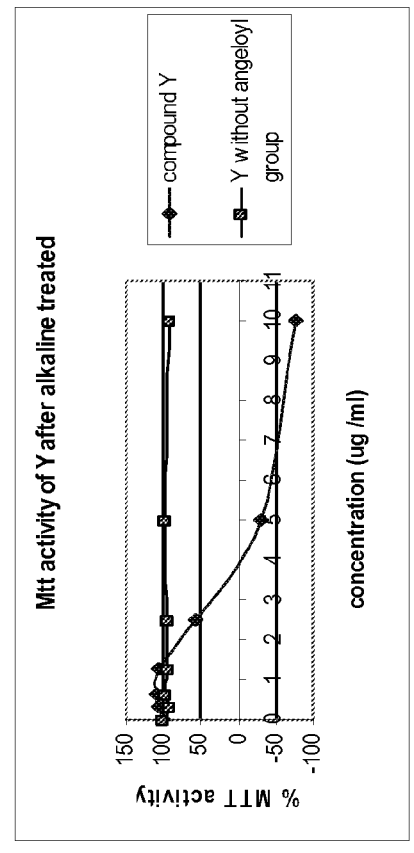
C Structures of Y, X, ACH-Y, AKOH-Y and B-Escin Figure 9
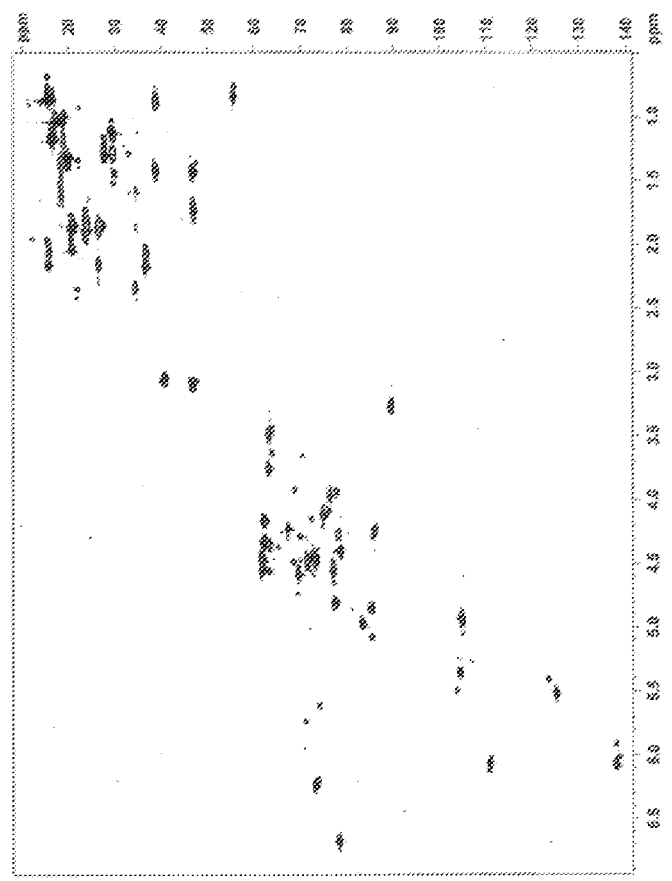
B
Y0 HMQC
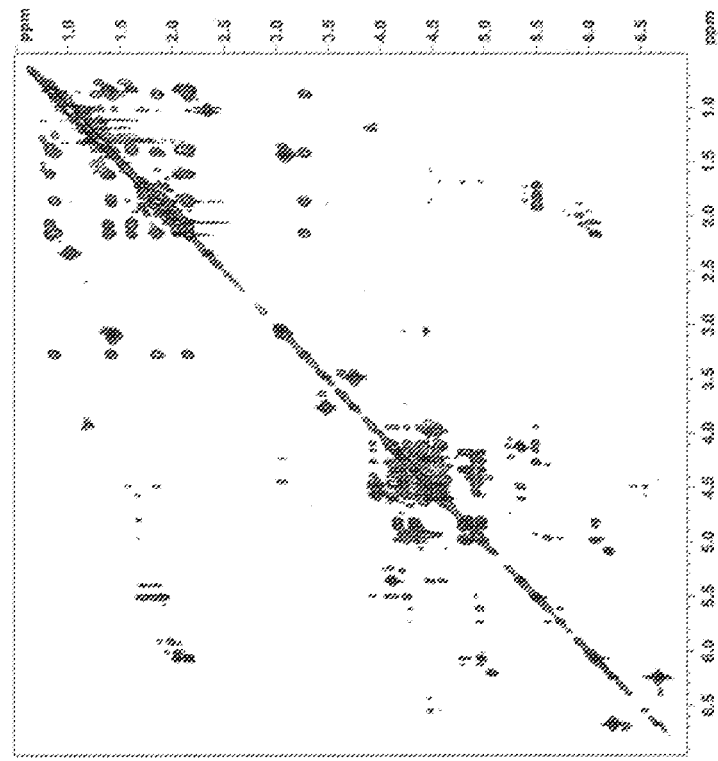
A
Y0 TOCSY MS of Y0

Formula: C56H88O23
FW: 1129.28
Theoretical mass: 1128.572
M+Na: 1151.561
Experimental result: 1151.556
Accuracy: -4.962827 ppm

Y0

3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene, Figure 13
Y1 activities 1

Figure 14

Y1 activities 2

Y1 activities 3

Y1 activities 4

Y1 activities 5

Y1 activities 6

Y1 activities 7

Y1 activities 8

Figure 21
Y2 activities 1

Figure 22
Y2 activities 2

Y2 activities 3

Y2 activities 4

Y2 activities 5

Y2 activities 6

Y2 activities 7

Y2 activities 8

Animal Studies

Group A Mice - Implanted tumor and no drug
Group B Mice - Implanted tumor and with drug
Group C Mice - No tumor and with drug Group A Mice – Died on day 19-22
Group B Mice – Survived over 50 days
Group C Mice – Survived over 50 days Survival Test (AS-3)

Result:
Group A Mice implanted with tumor and no drug. All died within 24 days
Group D Mice implanted with tumor and were given drug 9 times from 4th day.
All survived
Group E Mice implanted with tumor and were given drug 10 times from 10th day.
Half the number of mice survived Animal experiment of solid tumor Apoptosis of xanifolia EM study the effect of Xanifolia on membrane Inhibition effect of Xanifolia and Paclitaxel on cancer cell Activity of Ys Animal survival experiment NMR of Y7

Y7 NMR

Determination of Aquaporin

Y0 Activities(1)

Y0 Activities(2)

Y0 Activities (3)

Y9 activities (1)

Y9 Activities (2)

Y9 Activities(3)

ANTI-TUMOR COMPOUNDS WITH ANGELOYL GROUPS

This application claims the benefit of priority of U.S. Ser. Nos. 60/795,417, filed on Apr. 27, 2006, 60/841,727, filed on Sep. 1, 2006, 60/890,380, filed on Feb. 16, 2007, and International Application No. PCT/US2006/016158, filed Apr. 27, 2006, which claims the benefit of the priority of the following applications: (1) U.S. Ser. Nos. 11/289,142, filed Nov. 28, 2005, and Ser. No. 11/267,523, filed Nov. 4, 2005; (2) International Application No. PCT/US05/31900, filed Sep. 7, 2005 (which claims the priority of U.S. Ser. Nos. 60/617,379, filed Oct. 8, 2004, 60/613,811, filed Sep. 27, 2004, and 60/607,858, filed Sep. 7, 2004); (3) U.S. Ser. No. 11/131,551, filed May 17, 2005; and (4) U.S. Ser. No. 11/117,760, filed Apr. 27, 2005. This application also is a Continuation-In-Part of U.S. Ser. No. 10/906,303, filed Feb. 14, 2005, now U.S. Pat. No. 7,524,824 which is a Continuation-In-Part of International Application No. PCT/US04/43465, filed Dec. 23, 2004, which is a Continuation-In-Part of International Application No. PCT/US04/33359, filed Oct. 8, 2004, which claims the benefit of U.S. Ser. Nos. 60/532,101, filed Dec. 23, 2003, and 60/509,851, filed Oct. 9, 2003. The contents of these preceding applications are hereby incorporated in their entireties by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention identifies Xanifolia-Y's cellular target(s). Xanifolia-Y is an alternate or supplemental anticancer agent to other DNA-inhibition or microtubule-targeting drugs.

In an embodiment, Xanifolia-Y binds adhesion proteins to blocks the migration, metastasis angiogenesis of cancer cells. It inhibits the growth of cancers. The compounds in this application have effects on cell membrane structure and cell's adhesion process.

This invention relates to the mechanism of inhibiting cancer through regulating aquaporin in cancer cells and/or interacting with aquaporin with compounds comprise of a triterpene with two angeloyl groups. In an embodiment, the compound may be a saponin wherein comprises at least one angeloyl, preferable two angeloyl groups. In an embodiment, the compound may comprise more than two angeloyl groups, acetyl group, tigloyl group, senecioyl group, or an acid having two to five carbons or combination thereof.

This invention relates to saponins and compounds with angeloyl groups isolated from plants, their uses and functions. A composition comprises a diangeloyl group compound for inhibiting hemorrhoids, venous insufficiency and swelling. The compounds and compositions in this invention inhibit tumor or cancer growth.

BACKGROUND OF THE INVENTION

We have identified an herbal extract from *Xanthoceras sorbifolia* that inhibits cancer cell's growth. The active compounds were purified and their structures identified to be novel triterpenoid saponins. We named them as Xanifolia-Y and family.

Varicose veins are swollen and knotted veins that can occur in any part of the body, especially in the calf, inside leg or around the anus. Escin has been satisfactorily used for treating Varicose veins and chronic venous insufficiency for many years. Escin is a mixture of saponins found in the seed of the horse chestnut tree, *Aesculus hippocastanum* L., Hippocastanaceae. Escin is the major active ingredient prepared from *Aesculus hippocastanum* (Hippocastanaceae), the horse chestnut tree. In one controlled trial study, aescin was shown to be as effective as compression therapy as an alternative to medical treatment for CVI. The therapeutic benefit is well supported by a number of experimental investigations in different animal models. See Department of Pharmacological Sciences, University of Milano, Via Balzaretti 9, 20133 Milano, Italy. New saponin compounds with two angeloyls have been provided in International PCT Application No. PCT/US04/33359, filed Oct. 8, 2004, and U.S. Ser. No. 10/906, 303. Yingjie Chen, Tadahiro Takeda and Yukio Ogihara reported four new saponin compounds that were isolated from the fruits of *Xanthoceras sorbifolia* Bunge in Chem. Pharm. Bull., 33(1) 127-134, 1985; 33(3) 1043-1048, 1985 and 33(4) 1387-1394, 1985. Other related studies on saponin compounds include: triterpenoid saponins and acylated prosapogenins from *Harpullia austro-calcdonica* (Voutquenne et al. 2002); six triterpennoid saponins from *Maesa laxiflora* (Zhong et al. 1999); new triterpene saponin from *Pittosporum viridiflorum* from the Madagascar rainforest (Young et al. 2002); anti-HIV-1 protease triterpenoid saponins from the seeds of *Aesculus chinensis* (Yang et al. 1999); triterpenoid saponins from the roots of *Camellia sinensis* var. *assamica* (Lu et al. 2000); new acylated triterpenoid saponins from *Maesa laceceolata* (Apers et al. 1999); isolation and structure elucidation of four new triterpenoid estersaponins from fruits of the *Pittosporumtobira AIT* (D'Acquarica et al. 2002) and method for the prevention and treatment of chronic venous insufficiency (U.S. Pat. No. 6,210,680). The contents of the above-mentioned references are hereby incorporated by reference.

This invention shows that the saponins with two angeloyl groups have a strong activity for inhibiting cancers cells, anti-angiogenisis, inhibiting chronic venous insufficiency (CVI), shrinking hemorrhoids, inhibiting post-operative edema, rheumatism and cancerous cell growth.

This invention discloses saponin compounds having the specific structures that are capable of inhibiting cancer or tumor cell growth.

Human cells are surrounded by aquatic environments. Aquaporins is a family of transmembrane water-channel transporting proteins that play a major role in transcellular and transepithelial water movement. This invention shows that the triterpene saponins with two angeloyls have stronger activity for inhibiting cancer cell growth by affecting membrane functions. In an embodiment they affect the aquaporin and permeability of cell membrane.

SUMMARY OF THE INVENTION

In accordance with these and other objects of the invention, a brief summary of the present invention is presented. Some simplifications and omissions may be made in the following summary, which is intended to highlight and introduce some aspects of the present invention, but not to limit its scope. Detailed descriptions of a preferred exemplary embodiment adequate to allow those of ordinary skill in the art to make and use the invention's concepts will follow in later sections.

This invention provides the uses of compounds comprising a triterpene or other sapongenin with two angeloyl groups, or at least two side groups selected from the following groups: angeloyl, tigloyl and/or senecioyl groups, wherein the side groups are attached to carbon 21, 22 or/and 28 of triterpenoidal saponin, triterpenoid, triterpenoidal compounds or other sapongenin backbones. The methods of purification and determination of structures of the compounds are detailed in the International Application No. PCT/US05/31900, filed Sep. 7, 2005, U.S. Ser. No. 11/289,142, filed Nov. 28, 2005 and U.S. Ser. No. 11/131,551, filed May 17, 2005, the contents of which are incorporated herein by reference.

We have identified an herbal extract from *Xanthoceras sorbifolia* that inhibits cancer cell's growth. The active compounds were purified and their structures identified to be a novel triterpenoid saponin. We named them as Xanifolia-Y and family. Details are in U.S. Ser. No. 10/906,303 and Int'l App'l No. PCT/US04/33359 In vivo studies with Xanifolia-Y employing human ovarian carcinoma xenografts in mouse indicate that Xanifolia-Y is capable of extending the life span of animals bearing human tumors. These results show that it can be useful in treating cancers in mammal. In an embodiment it can be use in treating human cancers, preferably ovarian cancer.

Xanifolia-Y prolongs the life span of mice bearing of human tumor. It blocks the migration or metastasis of cancer cells. In an embodiment it binds with adhesion proteins or interferes with the function of molecules on carcinoma cells or on the mesothelial cells. It inhibits the tumor growth in mammal. It is useful in cancer therapy. See Experiment 7, 8, 9

Xanifolia-Y binds with adhesion proteins or signaling proteins in cancer cells. Xanifolia-Y is radioactive labeled with $^3$H and use it as ligand to search for target molecules. With the labeled Xanifolia-Y, we study the cellular binding location with autoradiography; determine binding affinity to adhesion proteins or target protein with RIA, investigate its associated proteins with co-IP and verify them with competition assay.

In an embodiment, Xanifolia-Y binds to adhesion proteins comprising integrins family, CD44, fibronectin, Myosin VI or FAK. We identify the target proteins by 2D gel blotting and MALDI-TOF peptide mapping techniques.

Xanifolia-Y is inhibiting nodule formation and/or growth in the peritoneal cavity of mouse. Cancer cell is inoculated into the peritoneal cavity of nude mice. Drug treatment starts at different stages of tumor progression. At the end of the drug-treatment, the change in the number and weight of tumor nodules are measured. Xanifolia-Y is inhibiting solid tumor growth.

Xanifolia-Y has effects on cell membrane structure and adhesion process. This invention identifies Xanifolia-Y's cellular target(s). It is an alternate or supplemental anticancer agent to other DNA-inhibition or microtubule-targeting drugs. In an embodiment, this invention provides a method of binding with adhesion proteins to blocks the migration, metastasis of cancer cells, anti-angiogenesis and inhibits the growth of cancers.

This invention discloses saponin compounds having the specific structures are capable of inhibiting cancer or tumor cell growth and anti-angiogenesis.

This invention provides a method for treating cancer wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention provides a method for treating cancer by binding with adhesion proteins to blocks the migration, metastasis of cancer cells, growth of cancers wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention relates to the mechanism of inhibiting cancer by regulating aquaporin in cancer cell and the interacting of aquaporin with compounds comprise a triterpene and two angeloyl groups. In an embodiment, the compound may be a saponin wherein comprises at least one angeloyl, preferable two angeloyl groups.

This invention relates to the aquaporin pathway that is influenced by saponins with angeloyl groups in inhibiting cancer.

This invention relates to a method for curing enuresis, frequent micturition, and urinary incontinence by regulating the aquaporin with a compound wherein comprise a triterpene, angeloyl group(s) and sugar moiety.

Varicose veins are enlarged veins that can be flesh colored, dark purple or blue. They often look like cords and appear twisted and bulging. They are swollen and raised above the surface of the skin. Varicose veins are commonly found on the backs of the calves or on the inside of the leg. During pregnancy, varicose veins called hemorrhoids can form in the vagina or around the anus. See http://www.4woman.gov/faq/varicose.htm (April 2006).

This invention provides the uses of compositions for treating or preventing chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thromophlebitis and for treating or preventing gastric ulcers or use for antispasmotic. This invention also provides a composition for inhibiting tumor cell growth. This invention further provides a composition for preventing tumor formation or killing tumor cells. This invention further comprises the composition of an effective amount of compound used for manufacture of a medicament for the treatment of varicose vein disease, chronic venous insufficiency, hemorrhoids or inhibition of leg swelling.

DETAILED DESCRIPTION OF THE FIGURES

FIG. 1. Structure of saponin comprising two angeloyl groups.

FIG. 2 A, 2 B. Structures of saponins

R1=angeloyl, tigloyl, senecioyl, H, or a sugar moiety comprising angeloyls, tigloyl or senecioyl. R2=angeloyl, tigloyl, senecioyl, H, or a sugar moiety comprising angeloyls, tigloyl or senecioyl. R6=angeloyl, tigloyl, senecioyl, acetyl, H, or a sugar moiety comprising angeloyls, tigloyl or snecioyl. Wherein R1, R2 are not in combination of acetyl with one of angeloyl, Tigloyl and Senecioyl R3=H or OH. R10=CH$_3$, CH$_2$OH, or CHO.

R5=D-glucose, D-galactose, L-rhamnose, L-arabinose, D-xylose, alduronic acid, D-glucuronic acid, D-galacturonic acid or H. R7=D-glucose, D-galactose, L-rhamnose, L-arabinose, D-xylose, alduronic acid, D-glucuronic acid, D-galacturonic acid or H. R8=D-glucose, D-galactose, L-rhamnose, L-arabinose, D-xylose, alduronic acid, D-glucuronic acid, D-galacturonic acid or H. R9=COOH or CH$_2$OH FIG. 3. Structures of saponins FIGS. 4 A and B. Comparison of potency of compound Y (saponin with 2 angeloyl groups) and compound X (saponin with 1 angeloyl) in inhibiting growth of ovarian cancer cells. The IC50 for Compound Y is about 1.5 µg/ml while 30 µg/ml for compound X.

FIG. 4 C. Inhibition of growth of skin cancer cells by the purified compound Y. The IC50 is 0.23 µg/ml.

FIG. 4 D. Hemolytic activity of Xanifolia-Y, B-Escin, Xanifolia-X, ACH—Y and AKOH—Y FIG. 5. A. Anticancer activities of Y, Y8, Y9 and Y10, determined by MTT assay on ovarian cancer cells. B. The purified compound Y1 and compound Y2 show inhibition of growth of ovarian cancer cells. C. Compound Y inhibits tumor growth (IC50=4 µg/ml). Compound X which has a similar structure to Y but with only one angeloyl group at C22, has less anticancer activity (IC50=6 µg/ml). Removal of sugars from Y (ACH—Y) but retaining the diangeloyl group retains 40% of the anticancer activity (IC50=9.5 µg/ml). However, removal of both angeloyl groups from Y (AKOH—Y) completely abolishes its anticancer activity (even at 120 µg/ml). The results indicate that diangeloyl groups in compound Ys are important for anti-tumor activity.

FIG. 5 D Compare inhibition activity of Xanifolia-Y, B-Escin, Xanifolia-X and AKOH—Y FIG. 6. Comparison of MTT and hemolytic activities of saponin compound and compound Ys. (A) and (B). Hemolytic activities; (C) and (D). MTT activities.

Figure 7:
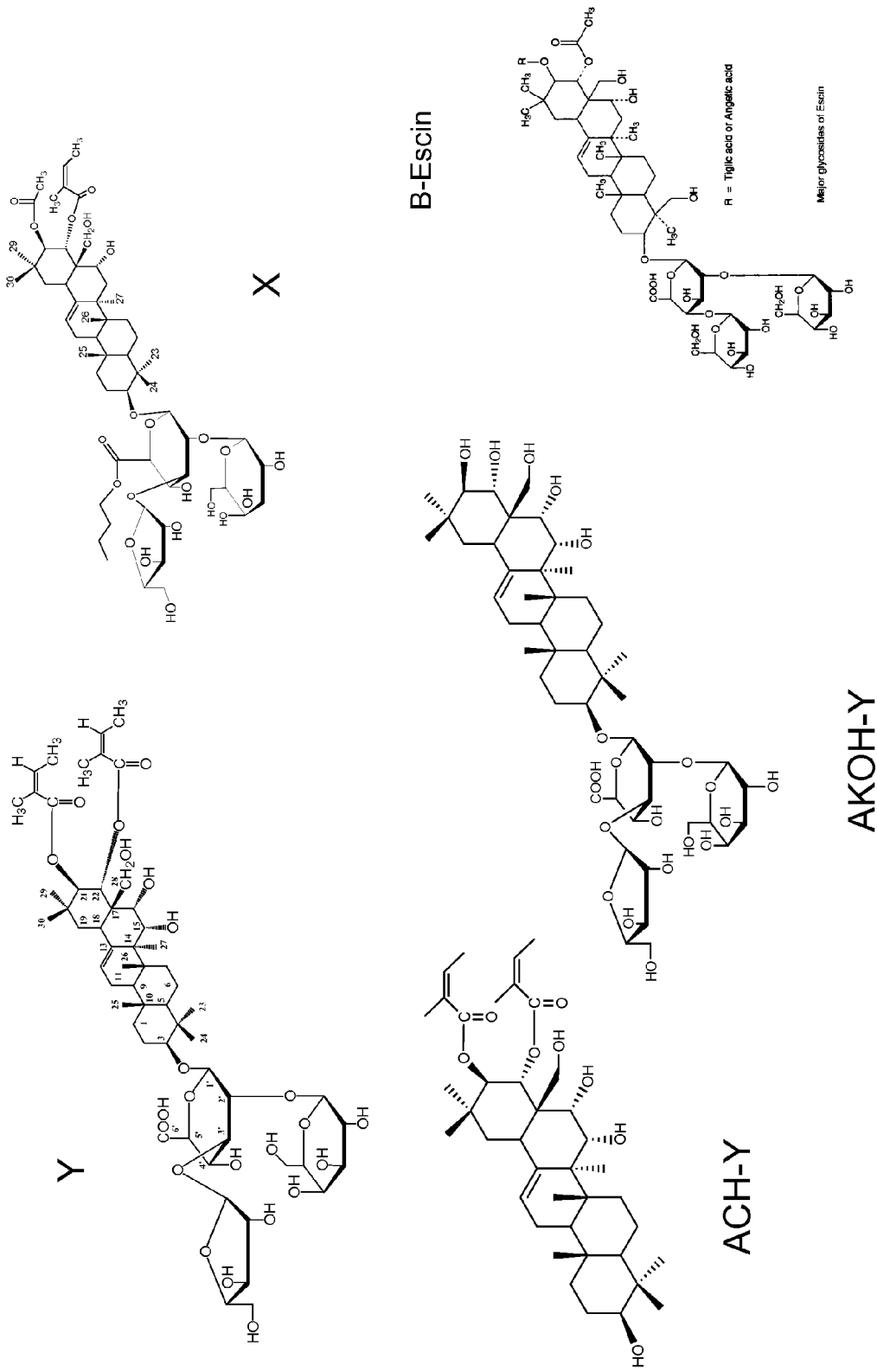

FIG. 7. Saponin compound Y, X, ACH—Y, AKOH—Y and B-Escin

These compounds are purified and their structures were verified by NMR and MS. These compounds are then used for MTT test.

Figure 8:
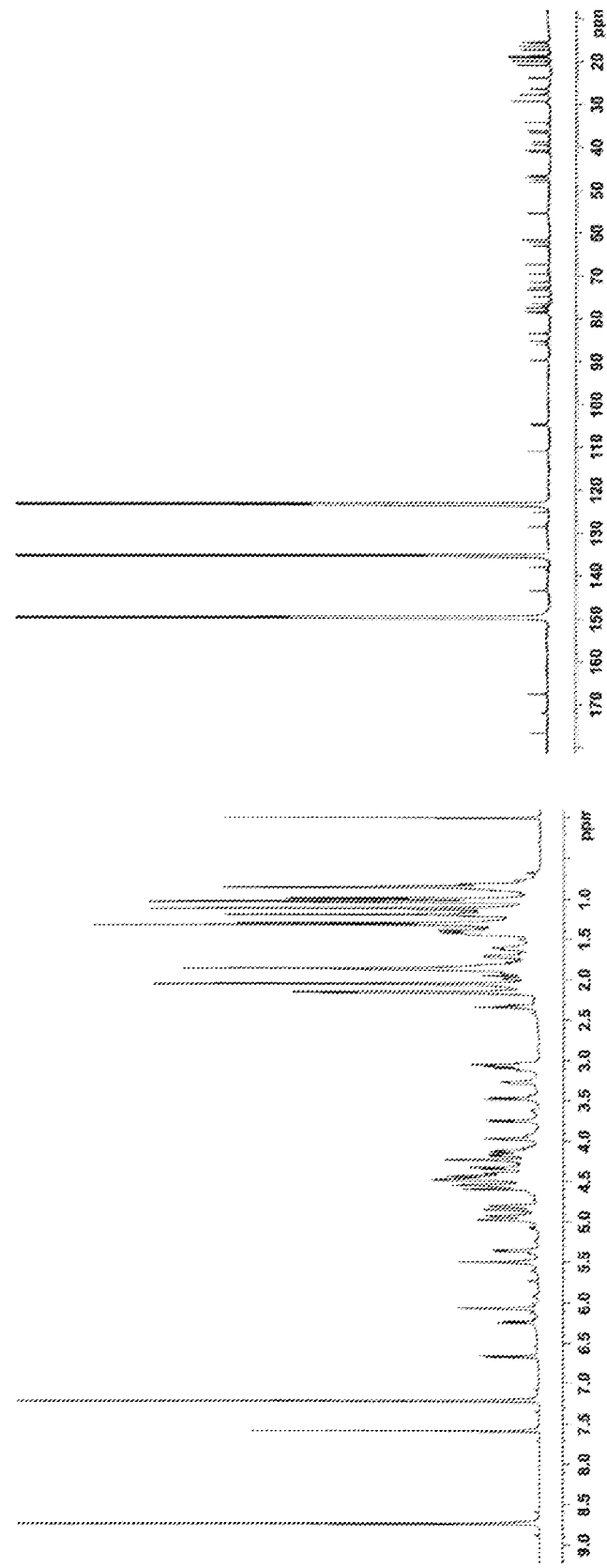
Figure 10:
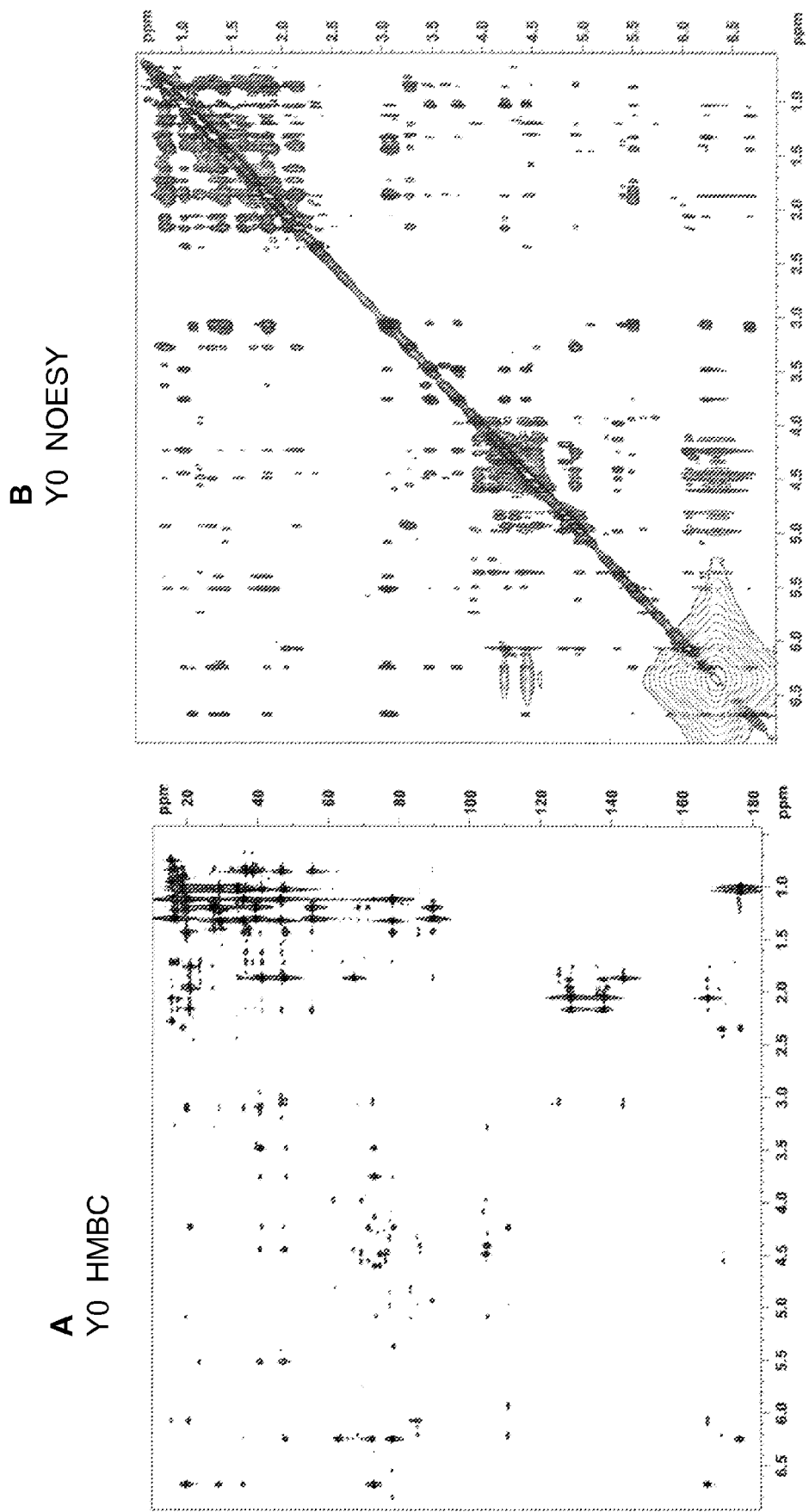

FIG. 8 A: NMR 1H of Y0. B: NMR 13C of Y0
FIG. 9 A: TOCSY of Y0. B: HMQC of Y0
FIG. 10 A: HNBC of Y0. B: NOESY of Y0
FIG. 11 MS of Y0
FIG. 12 Structure of Y0

Figure 28:
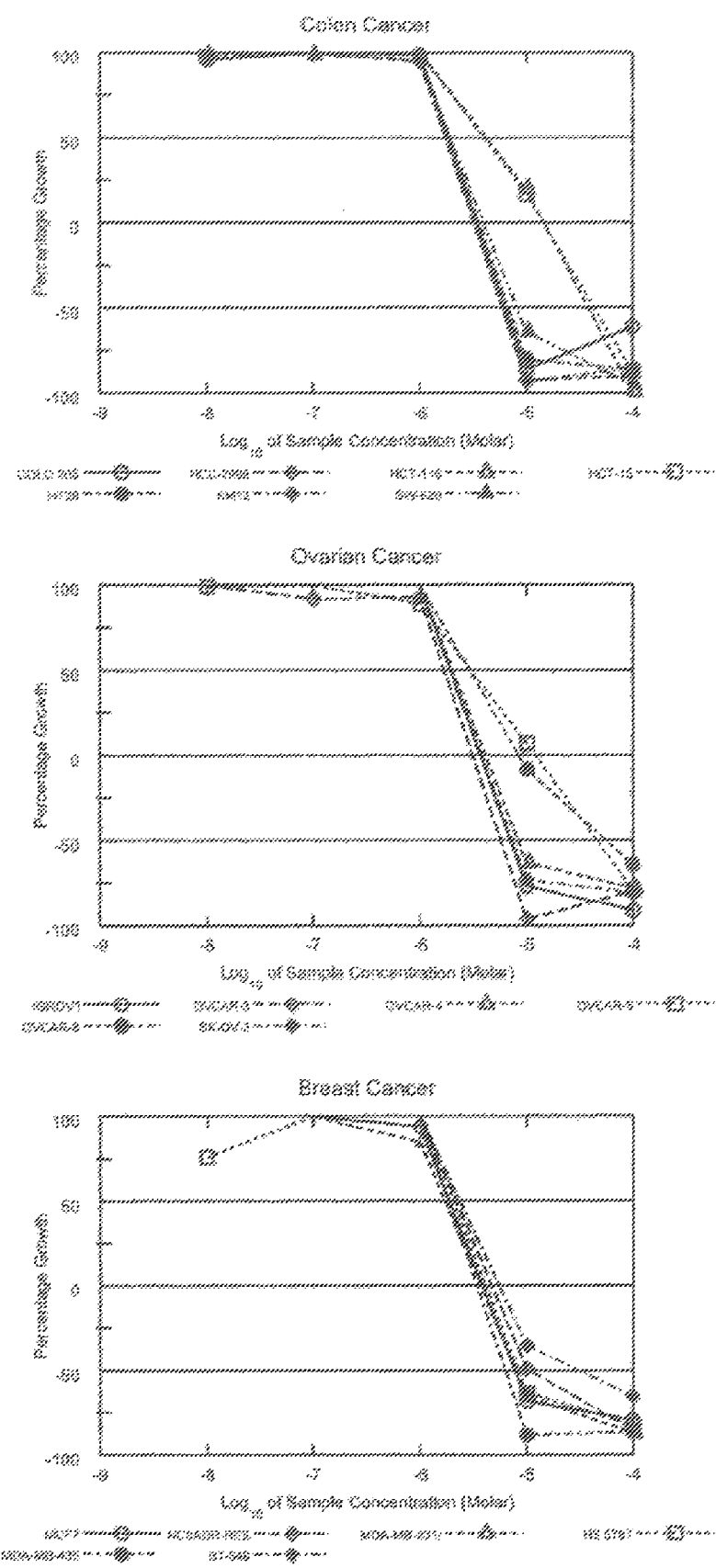
Figure 29:
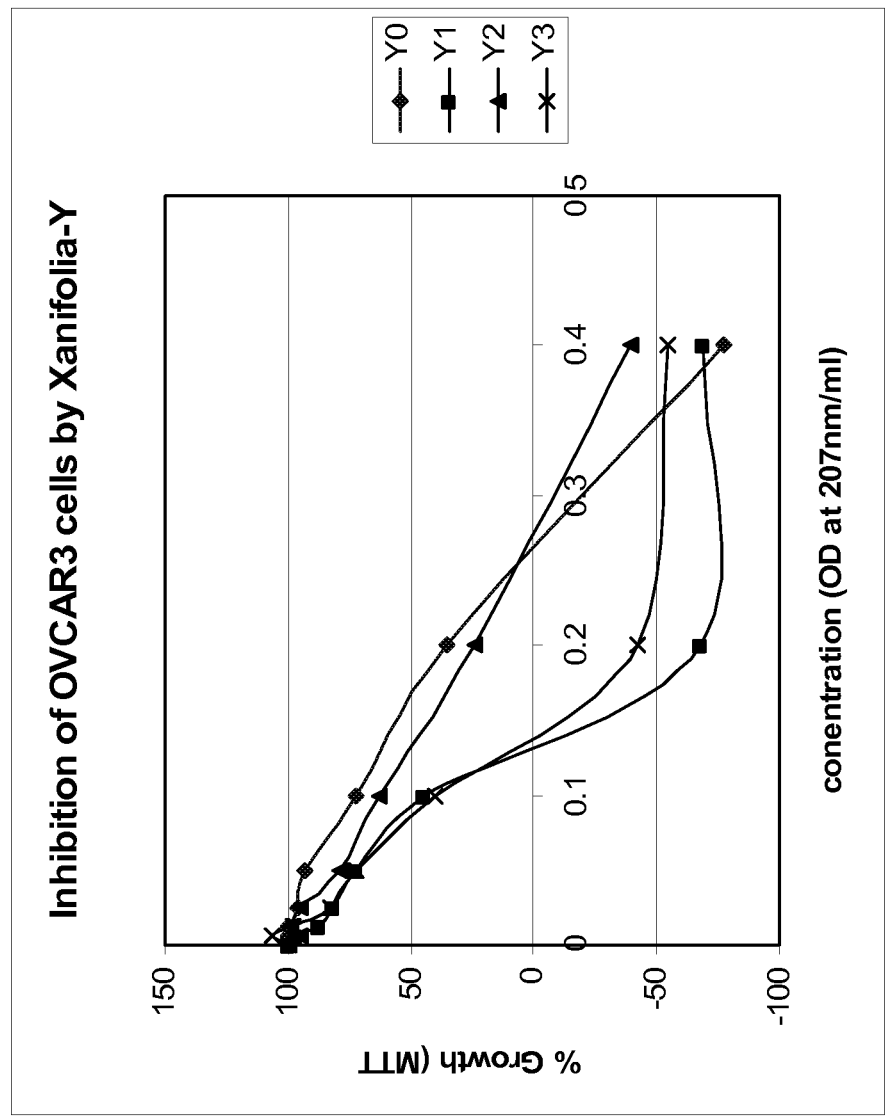

FIG. 13-20 show Xanifolia Y1 inhibits Leukemia cancer, Lung cancer, Colon cancer, CNS cancer, Melanoma Ovarian cancer, Renal cancer, Prostate cancer and Breast cancer activities FIG. 21-28 show Xanifolia Y2 inhibits Leukemia cancer, Lung cancer, Colon cancer, CNS cancer, Melanoma Ovarian cancer, Renal cancer, Prostate cancer and Breast cancer activities FIG. 29 Anticancer activities of Y0, Y1, Y2 and Y3

Figure 30:
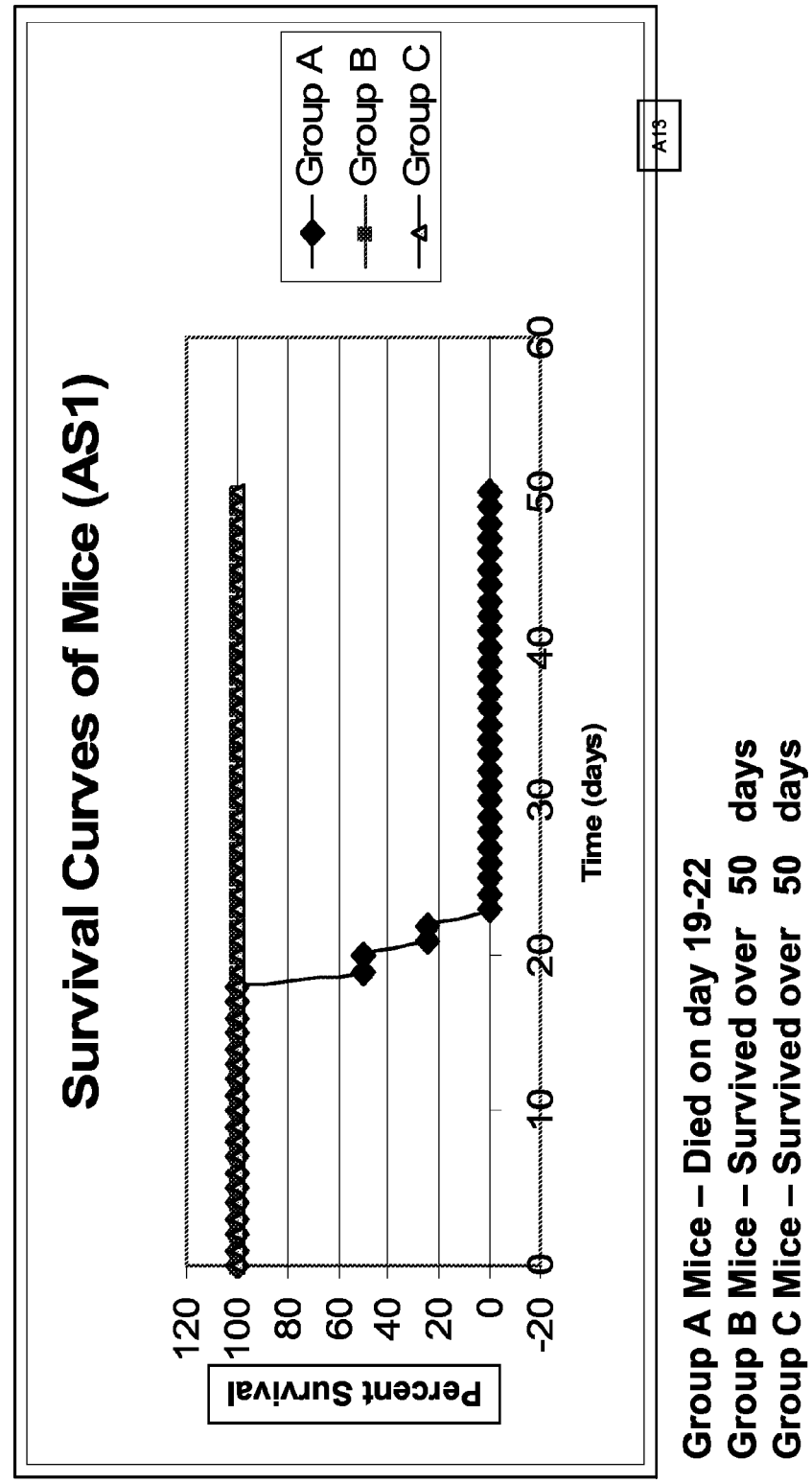

FIG. 30 Animal study result shows Group A Mice—Implanted tumor and no drug, Died on day 19-22; Group B Mice—Implanted tumor and with drug, survived over 50 days; Group C Mice—No tumor and with drug, survived over 50 days.

Figure 31:
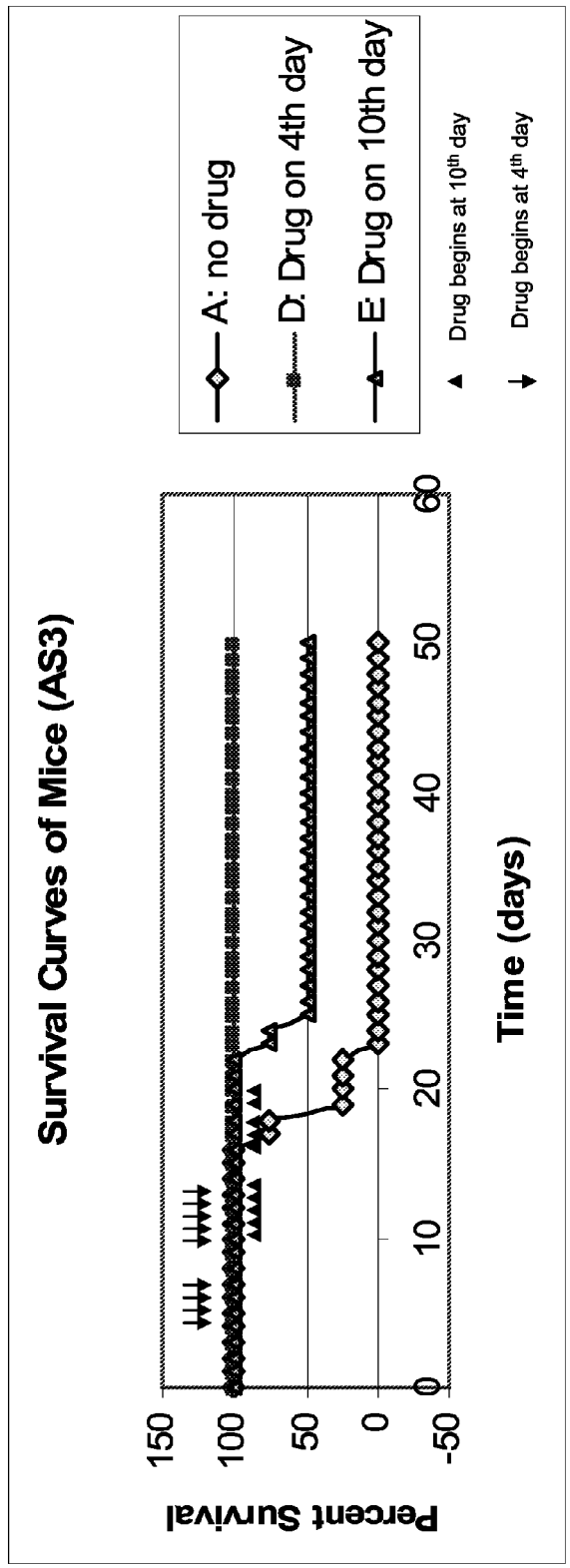

FIG. 31 Animal study result shows Group A Mice implanted with tumor and no drug, all died within 24 days; Group D Mice implanted with tumor and were given drug 9 times from 4th day, all survived; Group E Mice implanted with tumor and were given drug 10 times from 10th day, half the number of mice survived.

Figure 32:
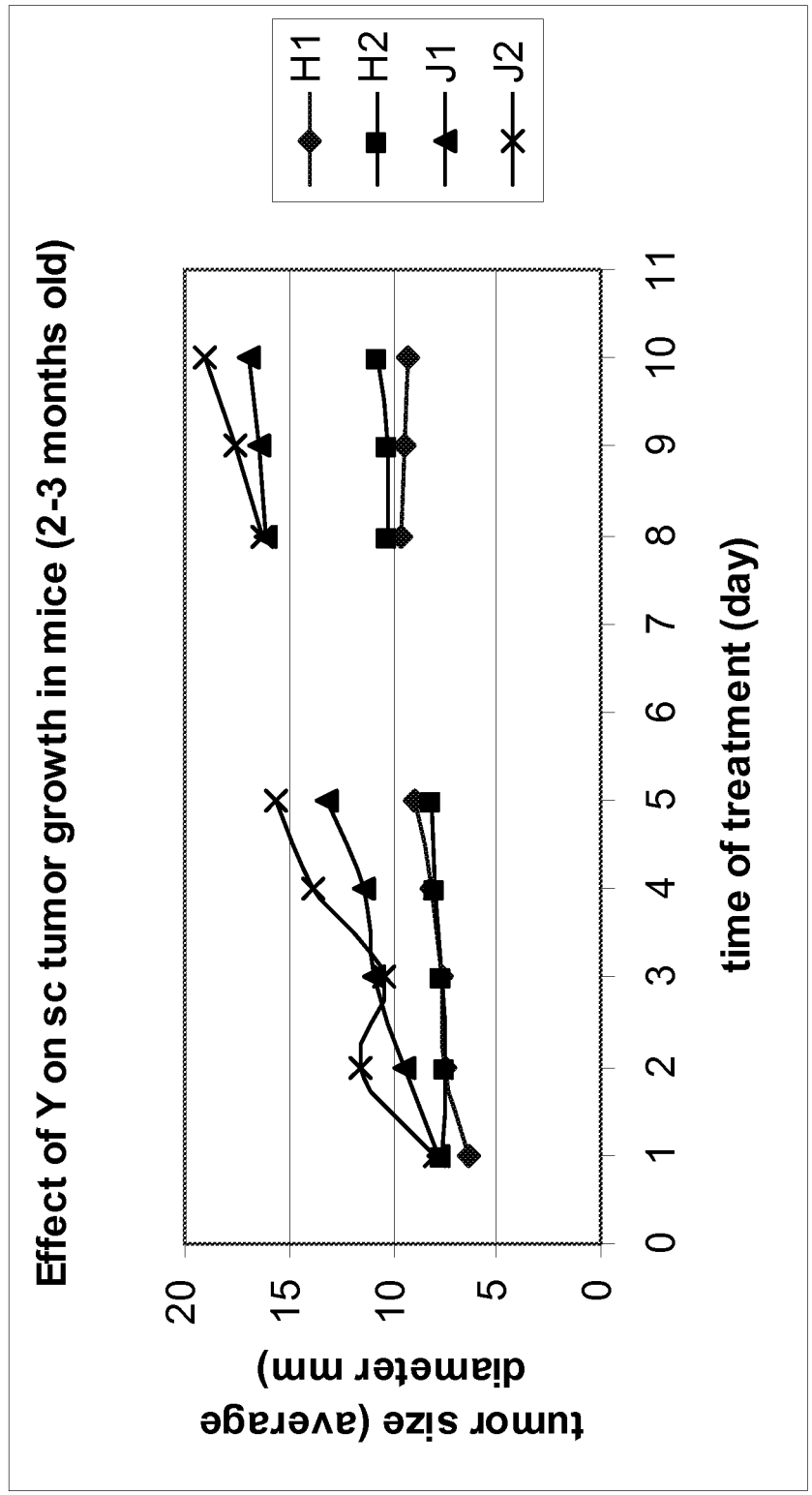

FIG. 32 Animal study shows that the tumor size is 45% smaller in mice with drug than the mice with no drug in 10 days period.

Figure 33:
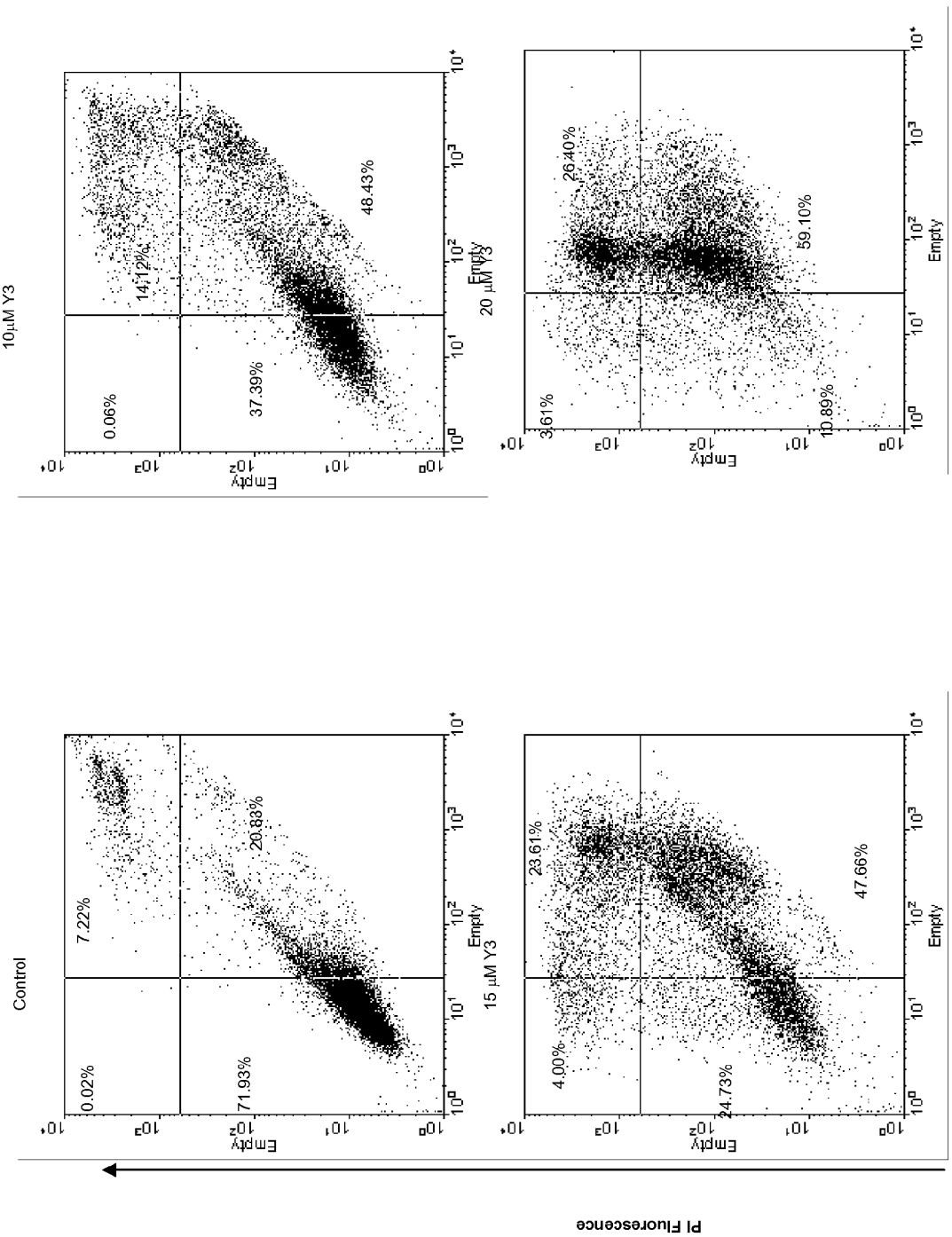

FIG. 33 Study apoptosis induced by Xanifolia-Y that apoptosis is a major form of cell death induced by Xanifolia-Y.

Figure 34:
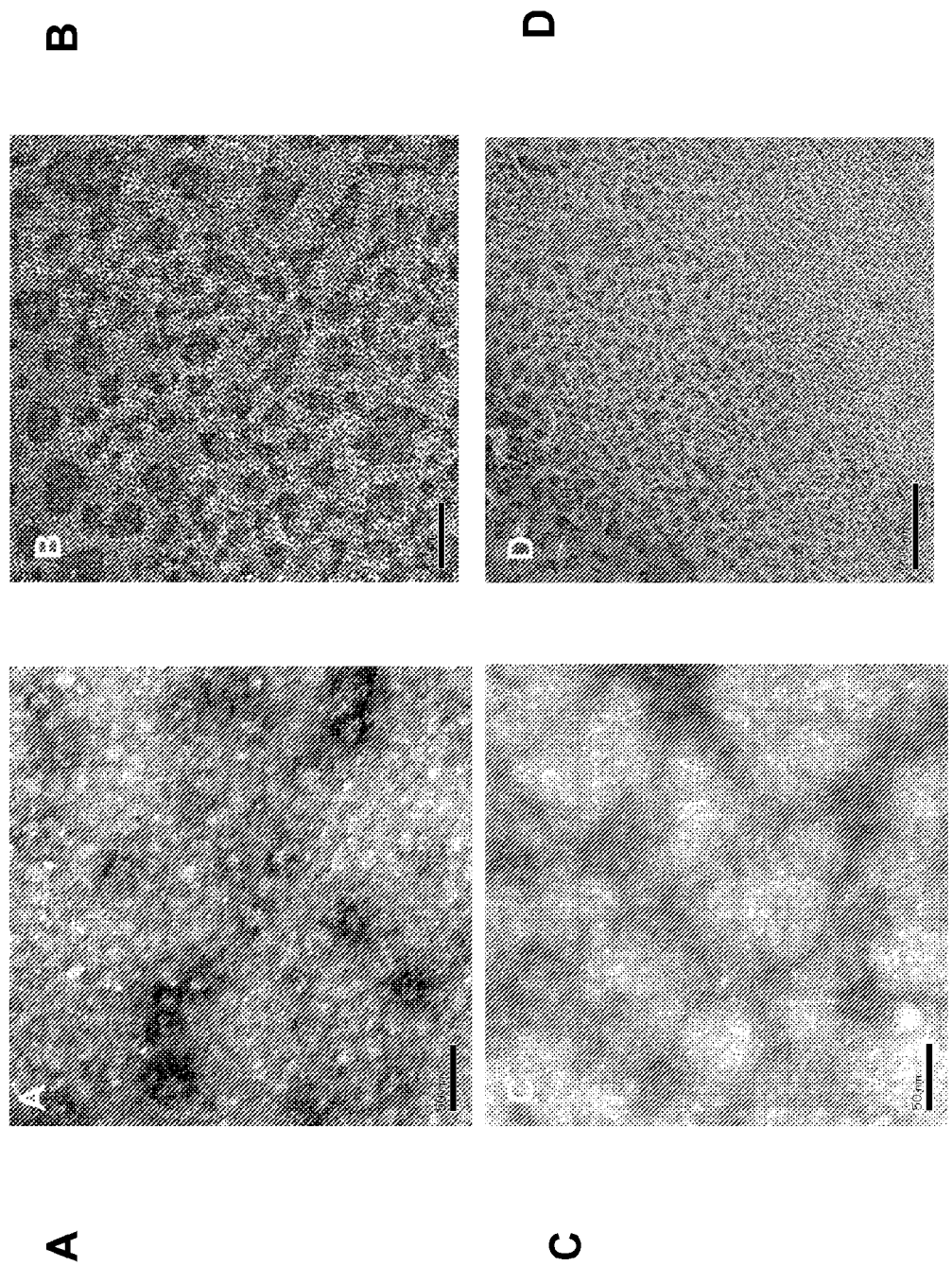

FIG. 34 EM study the effect of Xanifolia on membrane show that patches of pits were found in the membrane of Xanifolia-Y treated cells (FIG. 34B) but not in cells treated with the DMSO (FIG. 34A) or AKOH—Y (FIG. 34C) controls. These pits have the size from 80 A to 500 A (in diameter). The pits represent holes formed in the membrane. The pits are arranged in a characteristic pattern with smaller pits (80 A in diameter) located in the periphery and the bigger ones (500 A in diameter) in the center. The bigger holes are resulted from fusing of the smaller holes (FIG. 34D). Membrane image of cells treated with A: DMSO solvent control, 60 min (magnification: ×60,000); B: Xanifolia-Y 5 uM, 60 min. (×60000); C: AKOH—Y, 20 uM, 60 min. (×60000); D: Xanifolia-Y 5 uM, 60 min. (×20000)

Figure 35:
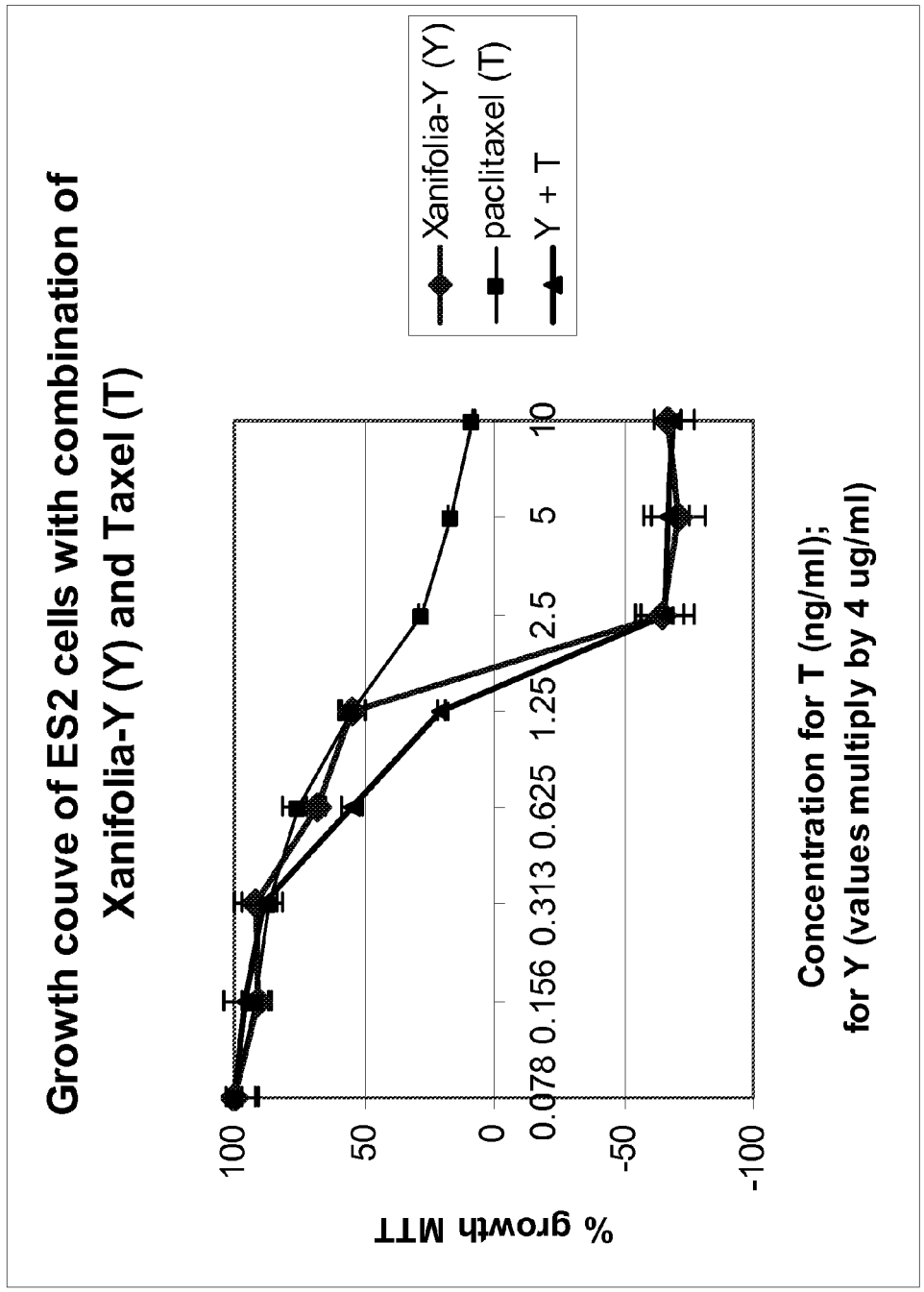

FIG. 35 Inhibition effect of Xanifolia and Paclitaxel on cancer cell

Figure 36:
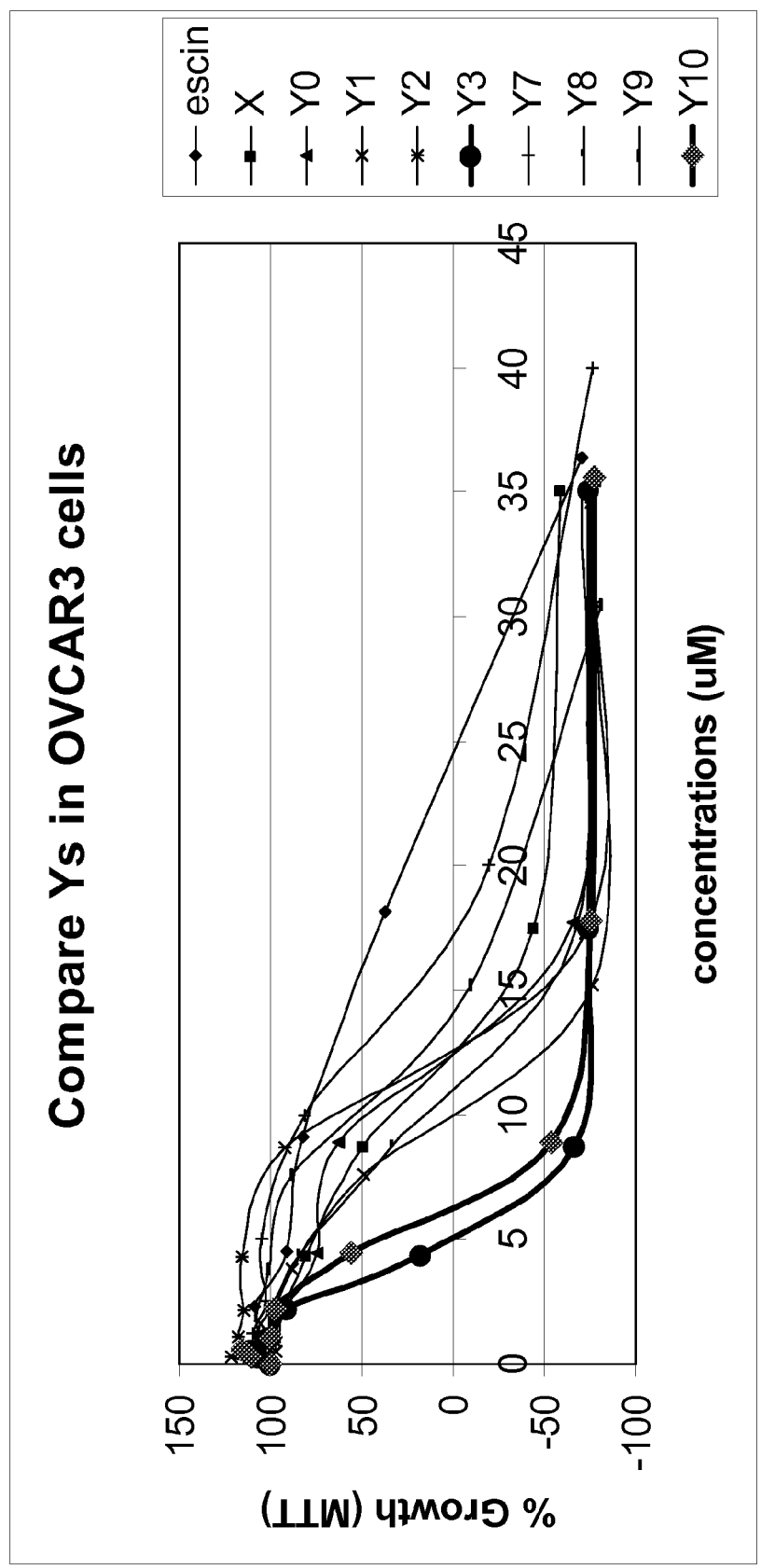
Figure 37:
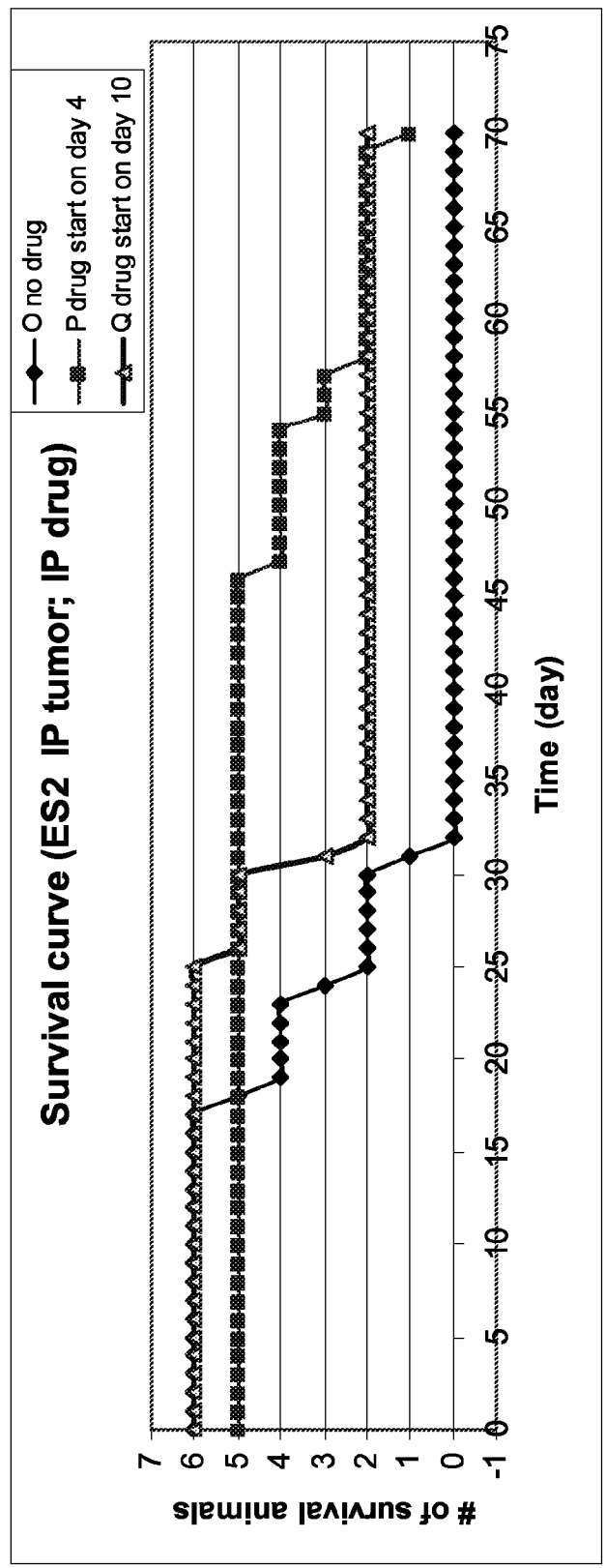
Figure 38:
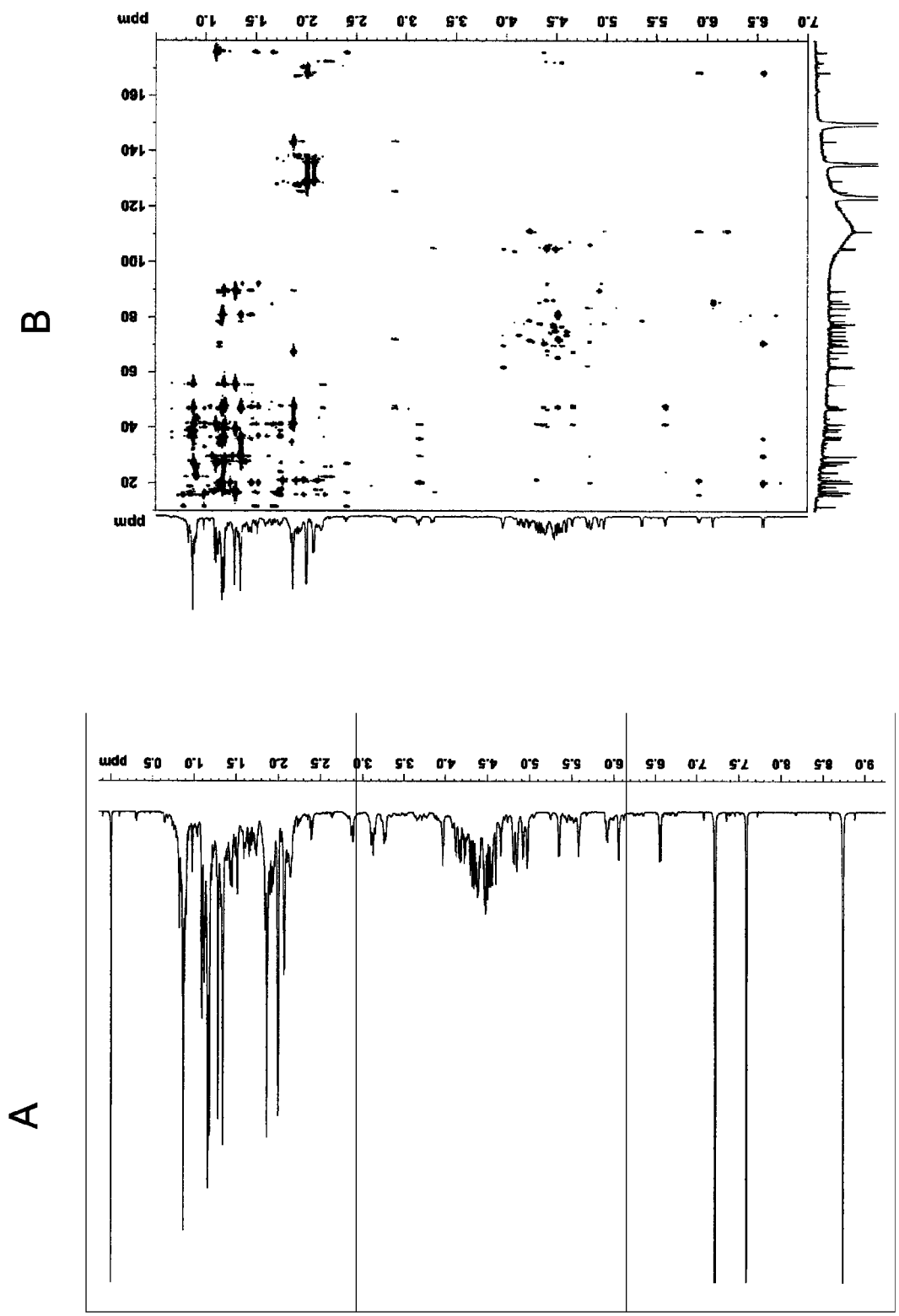
Figure 39:
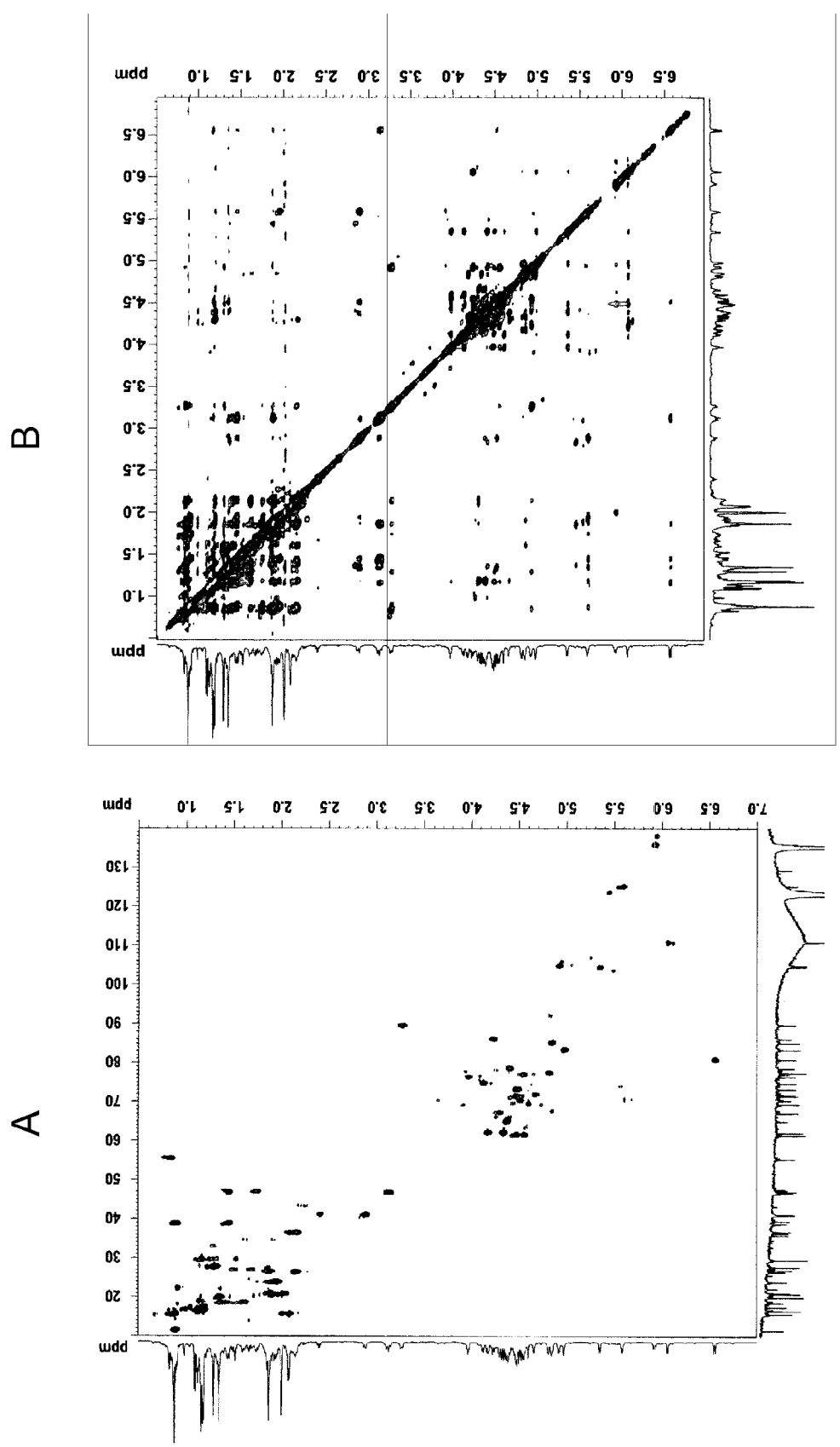

FIG. 36 Activities of Ys
FIG. 37 Animal survival experiment
FIG. 38 Y7 NMR profile, A: HNMR, B: HMBC
FIG. 39 Y7 NMR profile, A: HMQC, B: NOESY
FIG. 40 Determination of Aquaporin FIG. 41 Compare the potency of Xanifolia Y in ovary and cervix cell.

Figure 42:
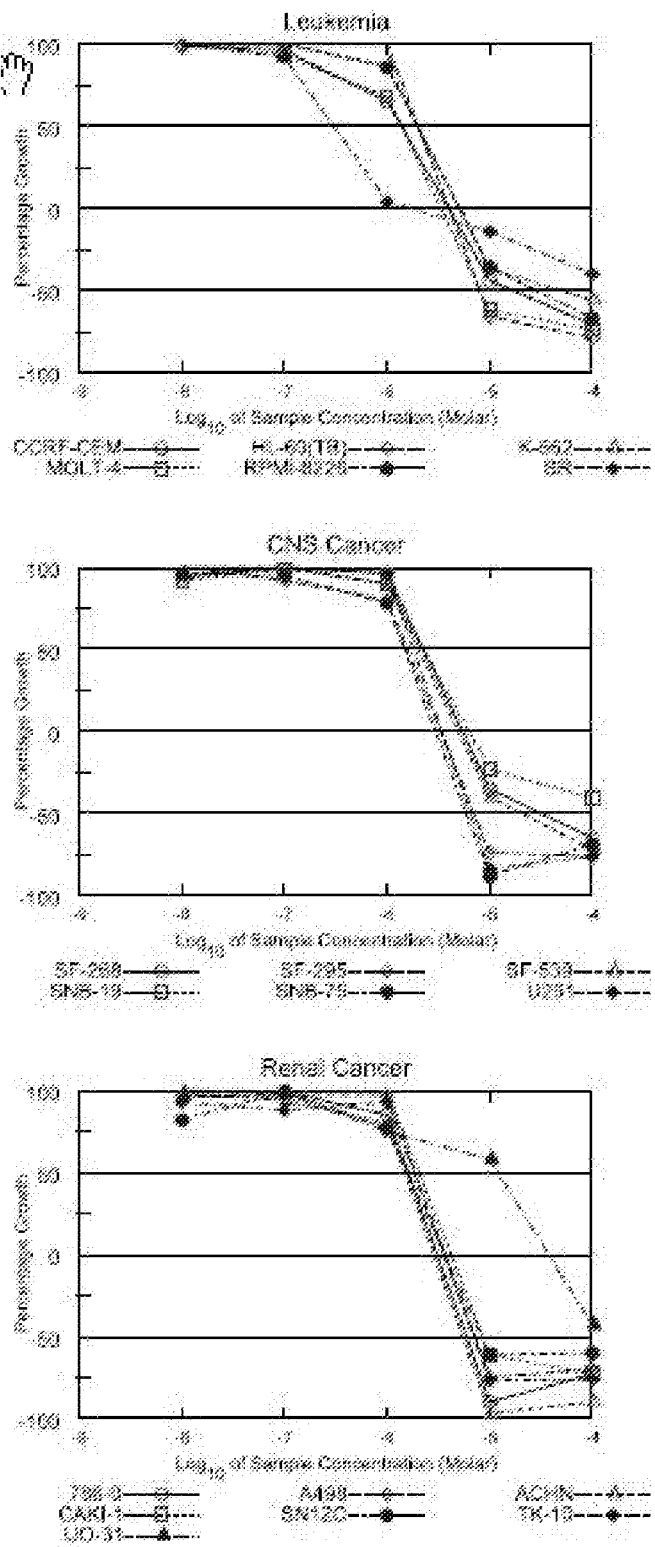
Figure 43:
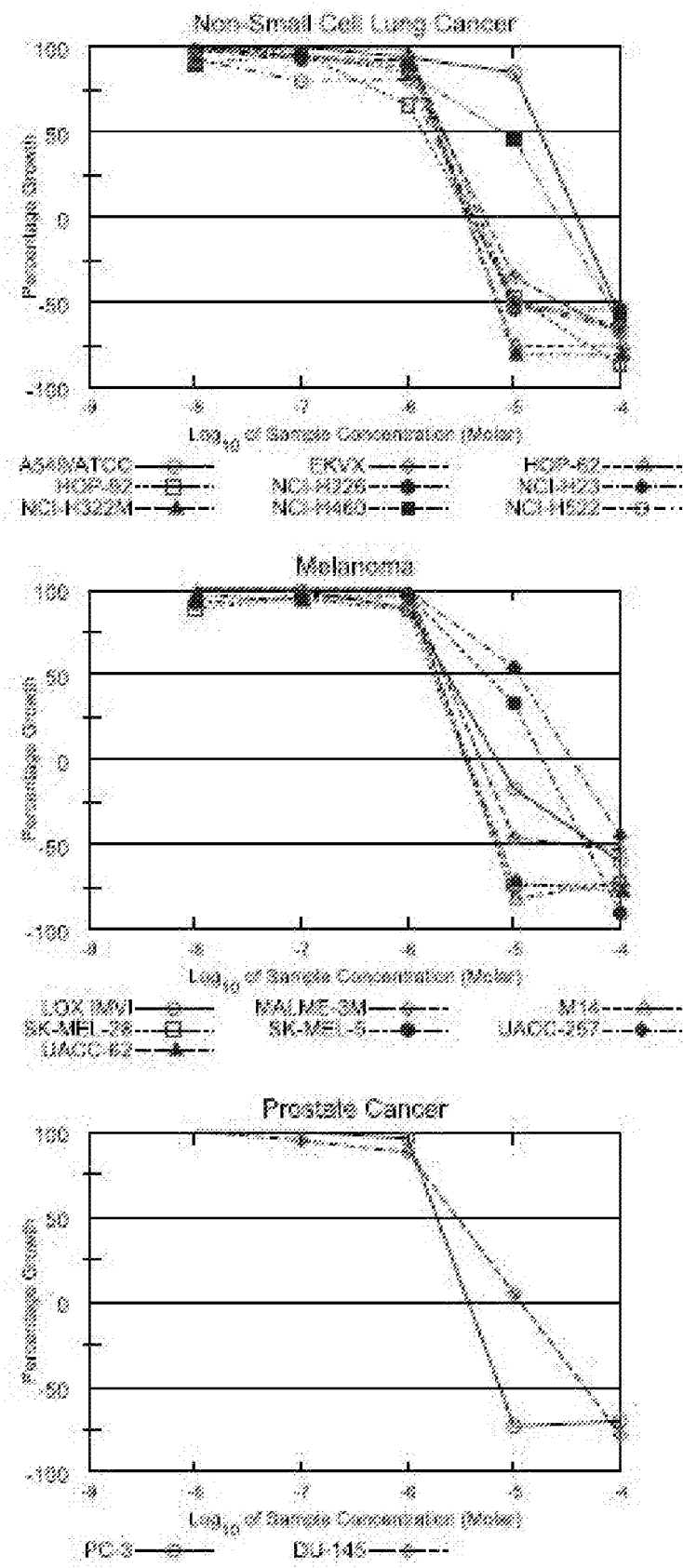
Figure 44:
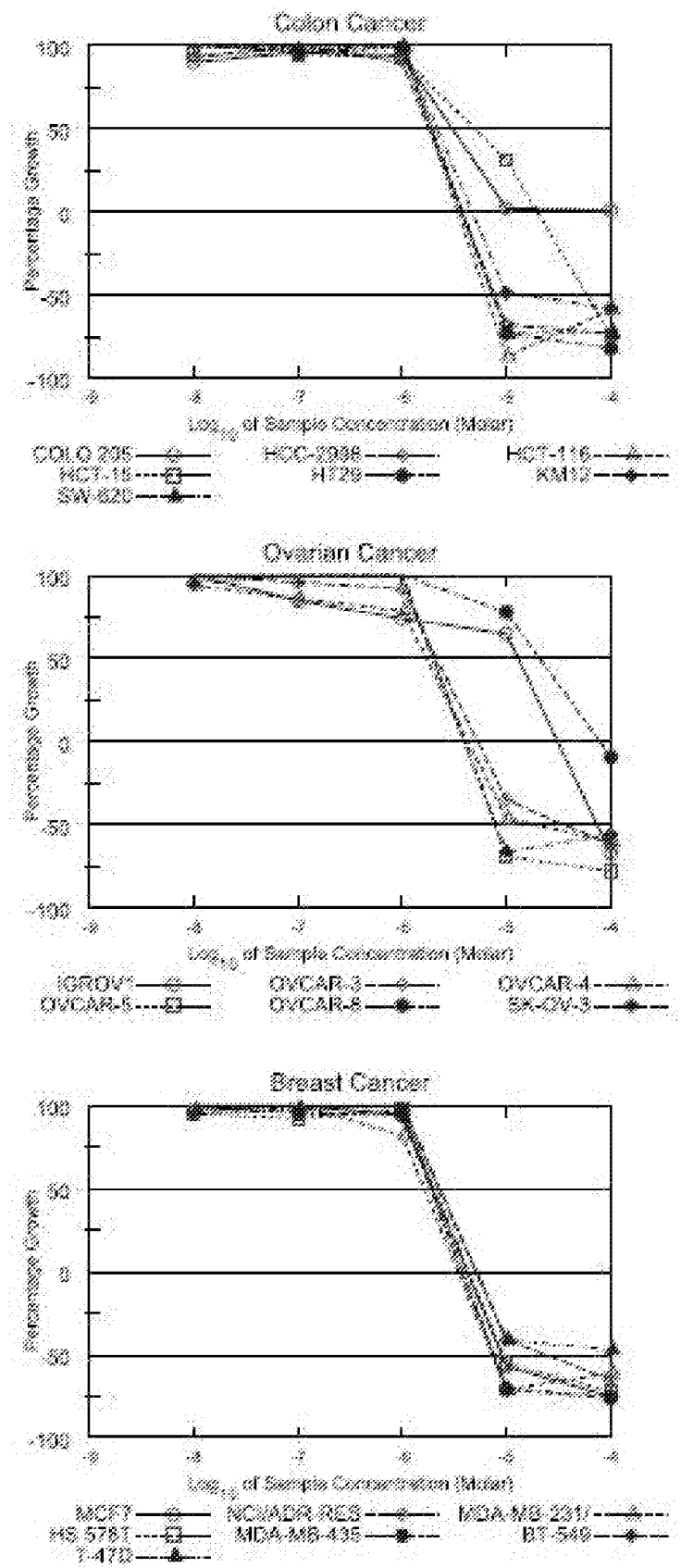
Figure 45:
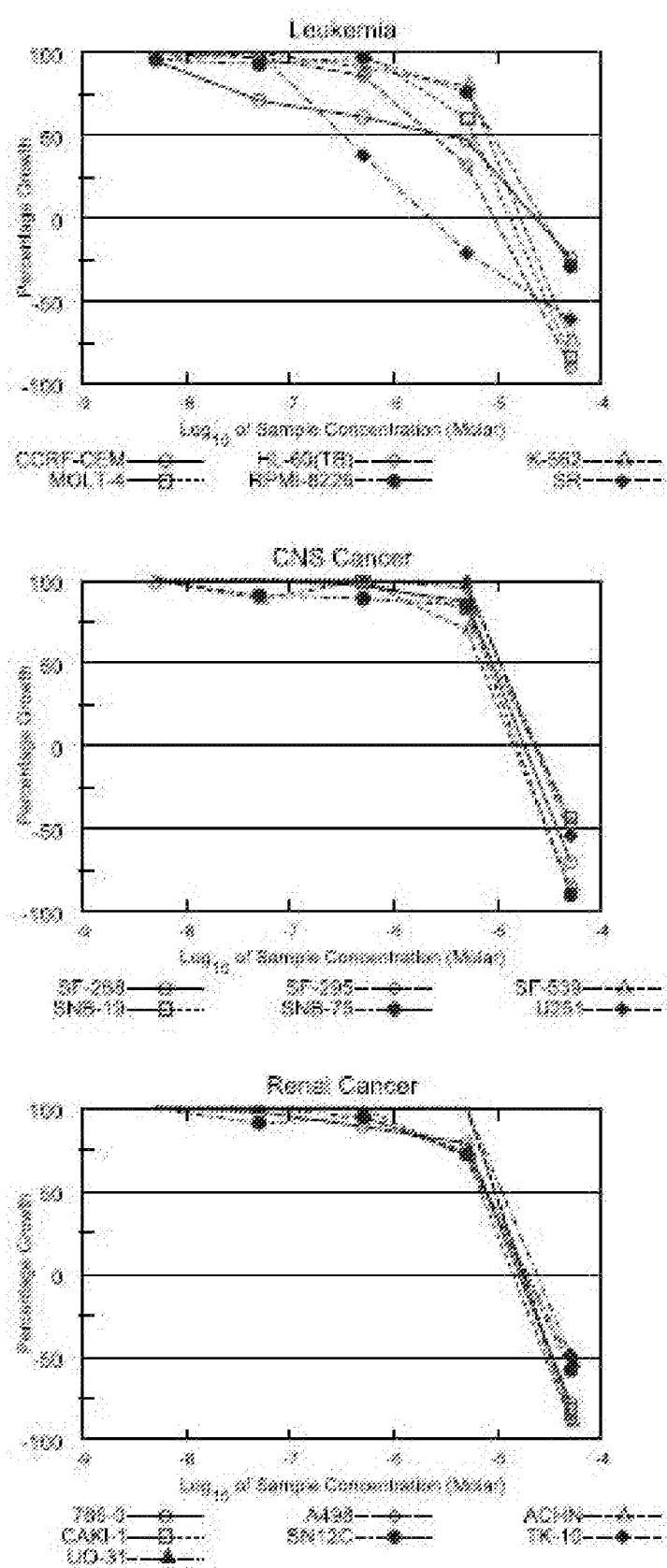
Figure 46:
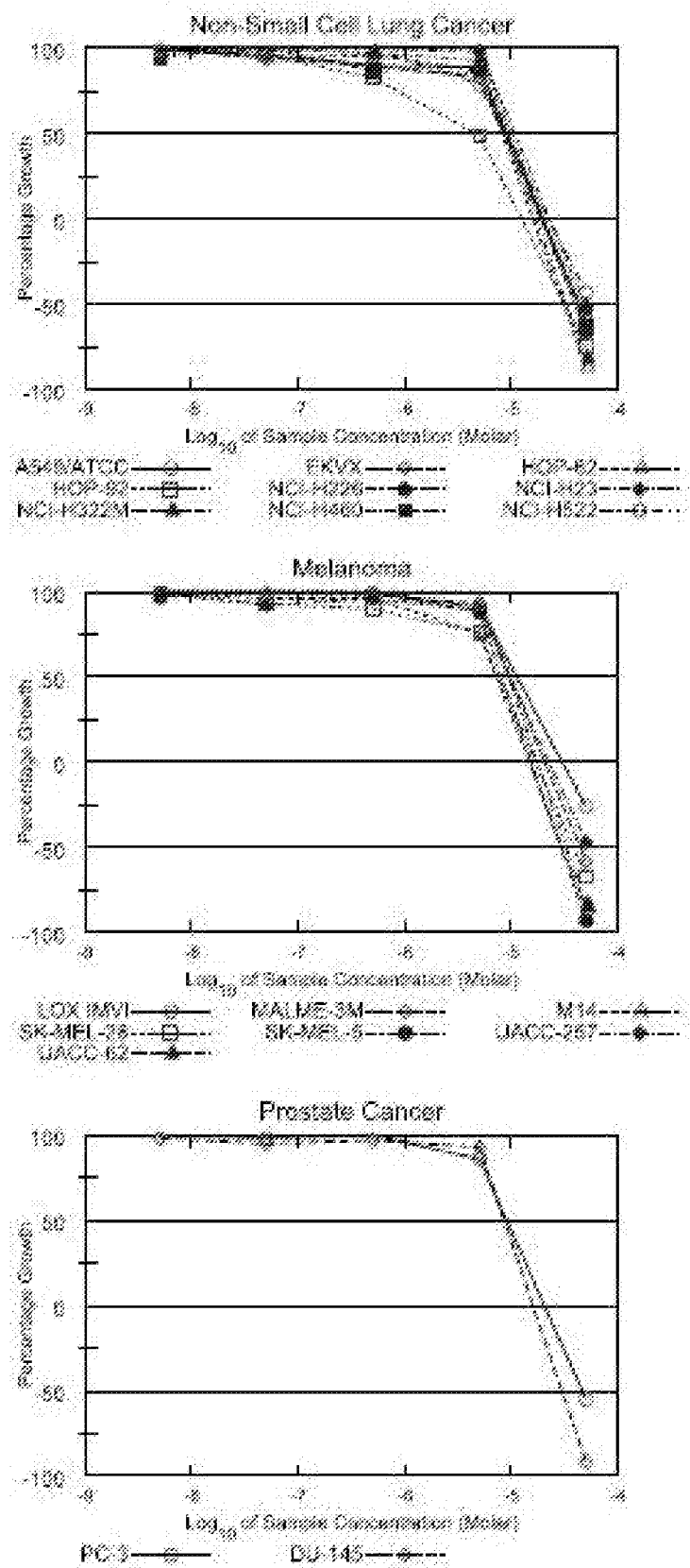
Figure 47:
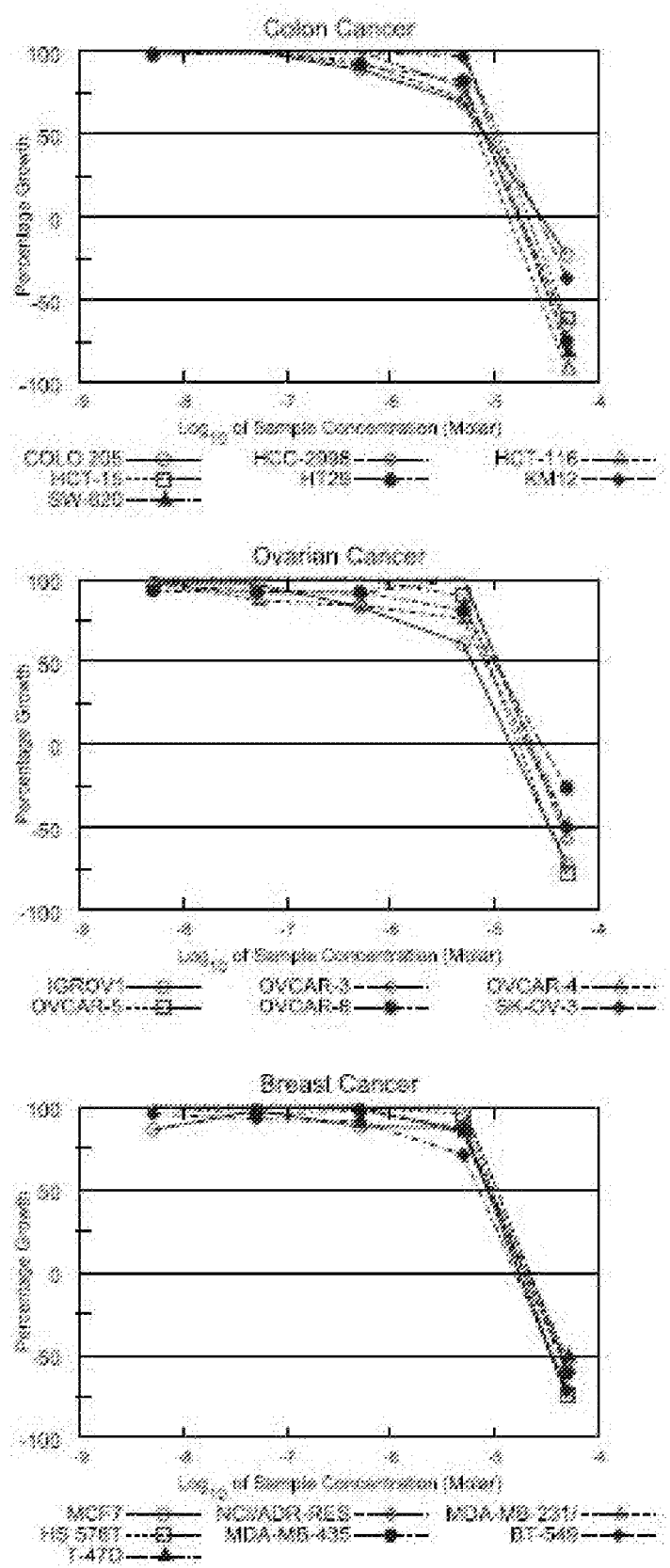

FIG. 42-44 show Xanifolia Y0 inhibits Leukemia cancer, Lung cancer, Colon cancer, CNS cancer, Melanoma Ovarian cancer, Renal cancer, Prostate cancer and Breast cancer activities FIG. 45-47 show Xanifolia Y9 inhibits Leukemia cancer, Lung cancer, Colon cancer, CNS cancer, Melanoma Ovarian cancer, Renal cancer, Prostate cancer and Breast cancer activities

DETAILED DESCRIPTION OF THE INVENTION

This invention provides the results of a program for screening the bioactive compounds from natural plants. The majority of the plants are from the Sapindaceae family, which has 140-150 genera with 1400-2000 species. The program is based on our purification methods and biological assays including the MTT assay See International Application No. PCT/US05/31900, filed Sep. 7, 2005, U.S. Ser. No. 11/289,142, filed Nov. 28, 2005, and U.S. Ser. No. 11/131,551, filed May 17, 2005, the contents of which are incorporated herein by reference The invention provides compositions comprising triterpenoidal saponins may be isolated from plants in the following genus:

Acer, Aesculus, Alectryon, Allophylus, Allosanthus, Amesiodendron, Aphania, Aporrhiza, Arfeuillea, Arytera, Atalaya, Athyana, Averrhoidium, Blighia, Boniodendron, Camellia, Camptolepis, Cardiospermum, Castanospora, Chonopetalum, Chouxia, Chytranthus, Conchopetalum, Cossinia, Cubilia, Cupania, Cupaniopsis, Deinbollia, Delavaya, Diatenopteryx, Dictyoneura, Dilodendron, Dimocarpus, Diploglottis, Diplokelepa, Diplopeltis, Dipteronia, Distichostemon, Dodonaea, Doratoxylon, Elattostachys, Eriocoelum, Erioglossum, Erythrophysa, Euchorium, Euphorianthus, Eurycorymbus, Exothea, Filicium, Ganophyllum, Glenniea, Gloeocarpus, Gongrodiscus, Gongrospermum, Guindilia, Guioa, Handeliodendron, Haplocoelum, Harpullia, Hippobromus, Hornea, Houssayanthus, Hypelate, Hypseloderma, Jagera, Koelreuteria, Laccodiscus, Lecaniodiscus, Lepiderema, Lepidopetalum, Lepisanthes, Litchi, Llagunoa, Lophostigma, Loxodiscus, Lychnodiscus, Macphersonia, Maesa, Magonia, Majidea, Matayba, Melicoccus, Mischocarpus, Molinaea, Negundo, Neotina, Nephelium, Otonephelium, Otophora, Pappea, Paranephelium, Paullinia, Pavieasia, Pentascyphus, Phyllotrichum, Pittosporum, Placodiscus, Plagioscyphus, Podonephelium, Pometia, Porocystis, Pseudima, Pseudopancovia, Pseudopteris, Ptelea, Radlkofera, Rhysotoechia, Sapindus, Sarcopteryx, Sarcotoechia, Scyphonychium, Serjania, Sisyrolepis, Smelophyllum, Stadmania, Stocksia, Storthocalyx, Synima, Talisia, Thinouia, Thouinia, Thouinidium, Tina, Tinopsis, Toechima, Toulicia, Trigonachras, Tripterodendron, Tristira, Tristiropsis, Tsingya, Ungnadia, Urvillea, Vouarana, Xanthoceras, Xerospermum, Zanha, Zollingeria.

This invention provides the uses of compositions comprising a triterpenoidal saponin. In an embodiment, the saponin has triterpenoid, triterpenoidal or other sapongenin, one or more sugar moieties and two angeloyl groups, or at least two side groups selected from the following groups: angeloyl groups, tigloyl groups or senecioyl groups, wherein the side groups are attached to the sapongenin backbone at carbon 21 and 22. In an embodiment, at least two of angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl attached to the side groups; wherein the sugar moiety in the saponin comprises at least one or more of the following sugars and alduronis acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose.

This invention further provides a composition comprising the structures comprising at least two side groups selected from the following groups: angeloyl, tigloyl or senecioyl groups, wherein the side groups are attached to a triterpenoidal, triterpenoid, triterpenoidal or other sapongenin backbone. These compositions are obtainable from the above-identified plants or synthesis.

This invention provides a method of preparing the saponins, comprising the steps of: (a) Extracting roots, kernels, leaves, bark, stem, husks, seeds, seed shells or fruits of the above plant, or combinations thereof with organic solvents such as ethanol or methanol to obtain an organic extract; (b) Collecting the organic extracts; (c) Refluxing the organic extract to obtain a second extract; (d) Removing the organic solvent from the second extract to obtain a third extract; (e) Drying and sterilizing the third extract to obtain a crude extract powder; (f) Fractionating the crude extract powder into fractions or components. Fractionation may be achieved by HPLC and FPLC chromatography with silica gel, C18 or other equivalent solid phase materials; (g) Monitoring the fractionating, if using HPLC or FPLC, the absorption wavelength at 207 nm to 500 nm may be used; (h) Identifying the bioactive components of the crude extract; (i) Purifying one or more bioactive components of the crude extract with FPLC to obtain one or more fractions of the bioactive component; and (j) isolating the bioactive components with chromatographic techniques that employ preparative columns and HPLC.

In an embodiment, this invention provides the method of MTT Assay to test the bioactivities of the saponins or other compounds.

Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), SK-MEL-5 (Skin) and OVCAR-3 (ovary). The cells were grown in following culture media: HeLa-S3, DU145, MCF-7, Hep-G2 and T98G are in MEN (Earle's salts); HTB-9, H460, K562 and OVCAR-3 in RPMI-1640; HCT-116 and U20S in McCoy-5A. They are supplemented with 10% fetal calf serum, glutamine and antibiotics, and incubated in an incubator with 5% $CO_2$ humidified at 37° C.

MTT Assay. The procedure for MTT assay followed the method described by Carmichael et al. (1987) with modifications. The cells were seeded into a 96-well plate at concentration of 10,000/well for HTB-9, HeLa, H460, HCT116, T98G and OVCAR-3), 15,000/well for DU145, MCF-7, HepG2 and U20S), and 40,000/well for K562 for 24 hours before drug-treatment. The cells were then exposed to the drugs for 48 hours (72 hours for HepG2 and U20S, and 96 hours for MCF-7). After the drug-treatment, MTT (0.5 mg/mL) was added to cultures and incubated for an hour. The formazan (product of the reduction of tetrazolium by viable cells) formed and was dissolved with DMSO and the O.D. at 490 nm, and was measured by an ELISA reader. The MTT level of the cells before drug-treatment was also measured (T0). The % cell-growth (% G) is calculated as: % G=(TD-T0/TC-T0)×100(1), where TC or TD represents O.D. readings of control or drug-treated cells.

When T0>TD, then the cytotoxicity (LC) expressed as % of the control is calculated as: % LC=(TD-T0/T0)×100(2).

This invention provides a composition that effectively reduced or inhibited the cancer cell growth, wherein the cancer includes but is not limited to bladder cancer, bone cancer and ovary cancer.

This invention provides a composition comprising an effective amount of triterpenoidal saponins named as Xanifolia Y1, Y2, Y, Y7, Y8, Y9, Y10, Y0 or their derivatives for treating chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thromophlebitis; for treating rheumatism; for preventing gastric ulcers antispasmotic and inhibiting tumor growth.

This invention provides a method of inhibiting cancer cell growth by affecting the aquaporin protein. This invention provides a method of inhibiting tumor growth in a subject comprising administering contracting an effective amount of compounds in this invention to the subject affecting or interacting the aquaporin protein at the surface of cancer cell. The compound comprises two angeloyl groups. In an embodiment the compound may be selected from formula (1), (1A), (1B), (1C) and (1D). In an embodiment, the compound comprises a triterpene backbone, two angeloyl groups and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application. This invention provides a method of inhibiting cancer cell growth by increasing the static charge of the cell, wherein increase water flow in the cell. In an embodiment the compounds open the channel protein or ion gates of the cells. The charged molecules or ions pass cell membrane through channel protein and kill cancer cell. As used herein, the term "inhibit" encompasses prevent, and killing of the said cancer or tumor cell This invention provides a method interacting with aquaporin protein for regulating the water channel, modulating the secretion, regulating the water metabolism of body, reducing the amount of urine, reducing urinate times, treating enuresis, treating frequent urination. The method comprises administering contracting an effective amount of compounds to the subject affecting or interacting with the aquaporin protein at the surface of cancer cell. The compound comprises two angeloyl groups. In an embodiment the compound may be selected from formula (1), (1A), (1B) and (1D). In an embodiment, the compound comprises a triterpene backbone, two angeloyl groups and sugar moiety. In an embodiment, the compound comprises a triterpene backbone, two acetyl groups with 2 or more carbon and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application.

This invention provides uses compound comprises a triterpene and angeloyl groups interacting with aquaporin protein for regulating the water channel, modulating the secretion, treating enuresis, inhibiting tumor growth, stopping cancer cell proliferate. In an embodiment, compound interacting with aquaporin protein for regulating the water channel, modulating the secretion, destroying the cancer cell.

This invention provides a composition interacting with aquaporin protein for regulating the water channel, modulating the secretion, treating enuresis, inhibiting tumor growth. A composition comprising an effective amount of the compound of any one of Y0, Y1, Y2, Y, Y7, Y8, Y9, Y10, or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

The aquaporins (AQPs) are a family of homologous water channels expressed in many epithelial and endothelial cell types involved in fluid transport. The family of mammalian AQPs consists of 11 members, AQP0-10, each with a distinct tissue. Functional measurements indicate that mammalian AQPs 1, 2, 4, 5, and 8 are probably water selective, whereas AQPs 3, 7, 9, and 10 also transport glycerol and other small solutes. They are expressed at part of membrane of cell. AQP1 protein is strongly expressed in most microvessel endothelia outside of the brain, as well as in endothelial cells in cornea, intestinal lacteals, and in other tissues AQP1 protein was strongly expressed in the membrane of microvessels and small vessels in all ovarian epithelial tumors, but less at the cytoplasm of tumor cells. In addition, AQP1 protein was also observed in the membrane of interstitial cells of ovarian carcinoma. Incorporated by reference of: The influence of aquaporin-1 and microvessel density on ovarian carcinogenesis and ascites formation, J. H. Yang et al., 2006 IGCS, International Journal of Gynecological Cancer 16 (suppl. 1)

Structural determinants of water permeation through aquaporin-1, by Kazuyoshi Murata, et al., Nature, Vol. 407, Oct. 5, 2000

The distribution amount of AQPs 1, 2, 3, 4, 5, 6, 7, 8, 9, 10 are varied at membrane of different cells. In different tumor cell, certain type of Aquaporin proteins is over-expressed. An increasing number of disturbances have been found associated to abnormal function of these proteins. The compounds Xanifolia can interact with the aquaporin and inhibit the tumor cell growth. We can use Western blot analysis and identified expression of aquaporin in cell lines. Detail of Xanifolia in PCT/US05/31900, filed Sep. 7, 2005, and U.S. Ser. No. 11/131,551, filed May 17, 2005.

A Western blot is a common method in molecular biology/biochemistry/immunogenetics to detect protein in a given sample of tissue homogenate or extract. It uses gel electrophoresis to separate proteins by mass. The proteins are then transferred out of the gel and onto a membrane, where they are "probed" using antibodies specific to the aquaporin protein. As a result, we can examine the amount of aquaporin protein in a given sample and compare levels between several groups. Other techniques which allow detection of proteins in tissues (immunohistochemistry) and cells (immunoctochemistry) are used. Other methods such as Bradford protein assay, UV spectroscopy, Biuret protein assay, Lowry protein assay, Bicinchonic acid protein assay may also be used.

There are many publications about the studies of the aquaporin as a maker for cancer cells but none of them mention the regulating or affecting the aquaporin as method to facilitate the blockage, inhibition or destroying the cancer cells.

This invention describes a method of destroying cancer cell or inhibiting the cancer cell proliferates by regulating or affecting the aquaporin. In an embodiment, the saponin with two angeloyl groups can interacts with the aquaporin in order inhibiting the cancer cell growth. In an embodiment the compound may be selected from formula (1), (1A), (1B) (1C) and (1D). In an embodiment, the compound comprises a triterpene backbone, two angeloyl groups and sugar moiety. In an embodiment, the compound comprises a triterpene backbone, two acetyl groups with 2 or more carbon and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application.

In embodiment the method is blocking the cancer cell proliferates by regulating, interacting or affecting the aquaporin. In embodiment, the method is increase the water permeability of the cell membrane by regulating or affecting the aquaporin in order to kill the cell. In an embodiment, the method is affecting the aquaporin permitting extra water into the cell to damage the cancer cell. In an embodiment, the method is affecting the aquaporin permitting Glycerol related solute into the cell to damage the cancer cell. In an embodiment, the method is affecting the aquaporin regulating water into the cell to damage the cancer cell, wherein the method comprise compound selecting from Xanifolia (Y0, Y1, Y2, Y, Y7, Y8, Y9, and Y10). In embodiment, the method is adjusting the fluid density outside the cell in order to damage the cancer cell by regulating the fluid pass in the cell wherein the aquaporin is overexpressed. In an embodiment this invention makes use of the change of cell membrane permeability to damage the cancer cells. The cell membrane permeability can be changed by the overexpression of some aquaporins.

The potency of Xanifolia (Y) is difference in different cancer cells of ovary, cervix, lung, skin and breast because they have variation of Aquaporin (AQPs 1, 2, 3, 4, 5, 6, 7, 8, 9, 10) at the membrane.

Amount of Aquarpoin (AQP 1, 2, 3, 4, 5, 6, 7, 8, 9, 10) at the membrane in various types of ovarian cancer cells such as OVCAR3, SKOV3, TOV21 G and ES2 is different, therefore they show different inhibition activity when treated with Xanifolia (Y). Xanifolia (Y) is a saponin comprises a triterpene, two angeloyl groups and sugar moiety. Xanifolia (Y) inhibits tumor growth (IC50=1.5-4.5 ug/ml). Xanifolia (X) which has a similar structure to Y but with only one angeloyl group at C22, has less anticancer activity (IC50=6 ug/ml). Removal of sugars from Y (ACH—Y) but retaining the diangeloyl group retains 40% of the anticancer activity (IC50=9.5 ug/ml).

However, removal of both angeloyl groups from Y (AKOH—Y) completely abolishes its anticancer activity (even at 120 ug/ml). The results indicate that diangeloyl groups in compound Ys are important for anti-tumor activity. The diangeloyl groups pay an important role in interacting with the aquaporin for inhibiting cancer growth.

The hemolytic activities of human red blood cells by Xanifolia-Y (#63Y), Escin and SIGMA saponin standard were compared. Y contains two angeloyl groups, Escin has one angeloyl group and SIGMA saponin standard is a mixture of saponins from *Quillaia* bark. The results show that #63Y (compound Y) has higher hemolytic activity (IC50=1 ug/ml) than Escin or SIGMA saponin standard (IC50=5 ug/ml). See application PCT/US2006/016158, filed Apr. 27, 2006, Dkt# 804-K-PCT, FIG. 6 A In embodiment, the compounds of this invention interact with cancer cells and increase the static charge of the cells. The static charge increase water flow into the cells. The cancer cells are collapsed.

This invention describes a method interacting or regulating the protein on the surface of a cell or altering the functional properties of intracellular membranes or regulating the fluid passage through the cell wall or softening the skin or improving the skin structure, comprising administering to a subject.

This invention describes a method of regulating or affecting the aquaporin, wherein the method comprising the uses of compositions comprising a triterpenoidal saponin. In an embodiment, the saponin has triterpenoid, triterpenoidal or other sapongenin, one or more sugar moieties and two angeloyl groups, or at least two side groups selected from the following groups: angeloyl groups, tigloyl groups or senecioyl groups, wherein the side groups are attached to the sapongenin backbone at carbon 21 and 22. Wherein the sugar moiety comprises at least one or more of the following sugars and alduronis acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose.

In an embodiment, the method comprise the use of a composition comprising the structures comprising at least two side groups selected from the following groups: angeloyl, tigloyl or senecioyl groups, wherein the side groups are attached to a triterpenoidal, triterpenoid, triterpenoidal or other sapongenin backbone. These compositions are obtainable from the above-identified plants or synthesis.

This invention provides the uses of composition comprising an effective amount of six novel saponin compounds with the diangeloyl groups (Y1, Y2, Y, Y8, Y9, Y10) and their structures are as follows. They have anti-cancer and hemotylic effect activies. These six compounds were determined in U.S. Serial 10/906,303, International Application No. PCT/US05/31900. and U.S. Ser. No. 11/131,551, the contents of which are incorporated herein by reference.

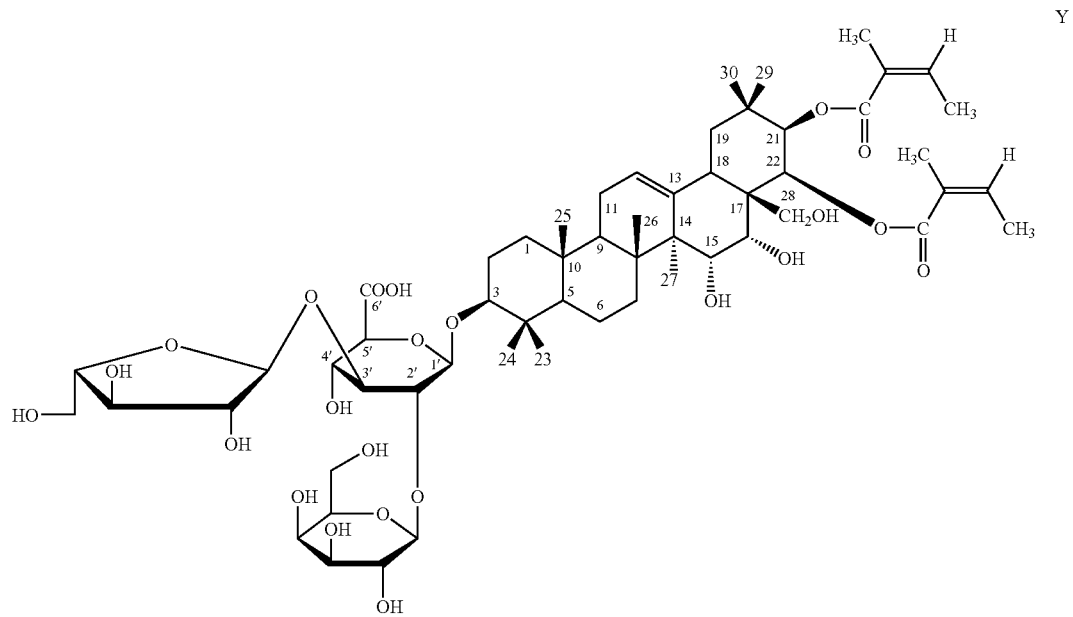

-continued
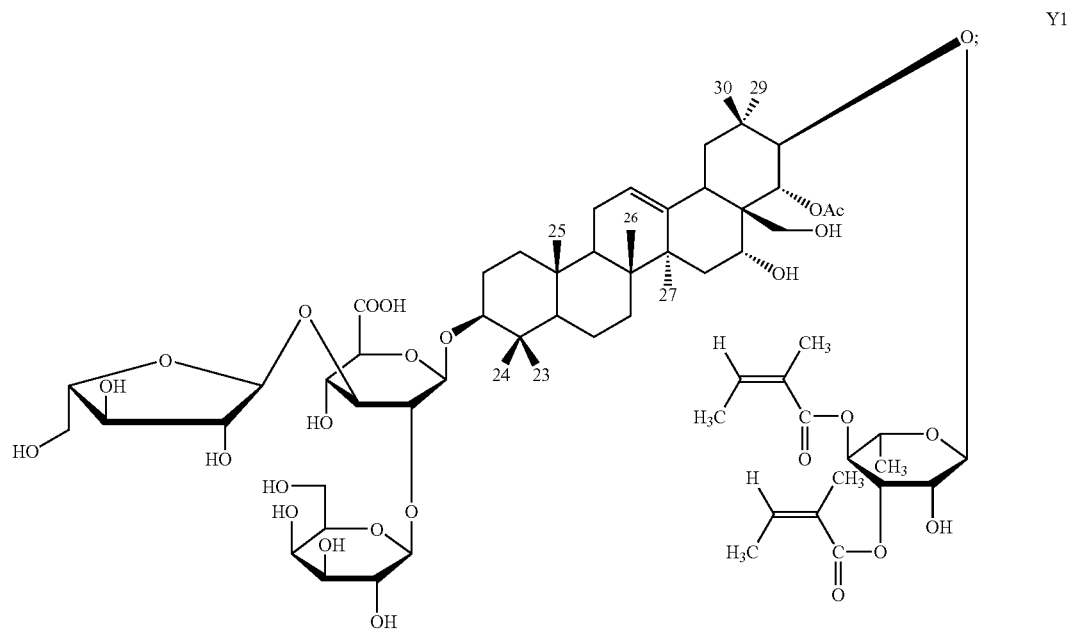
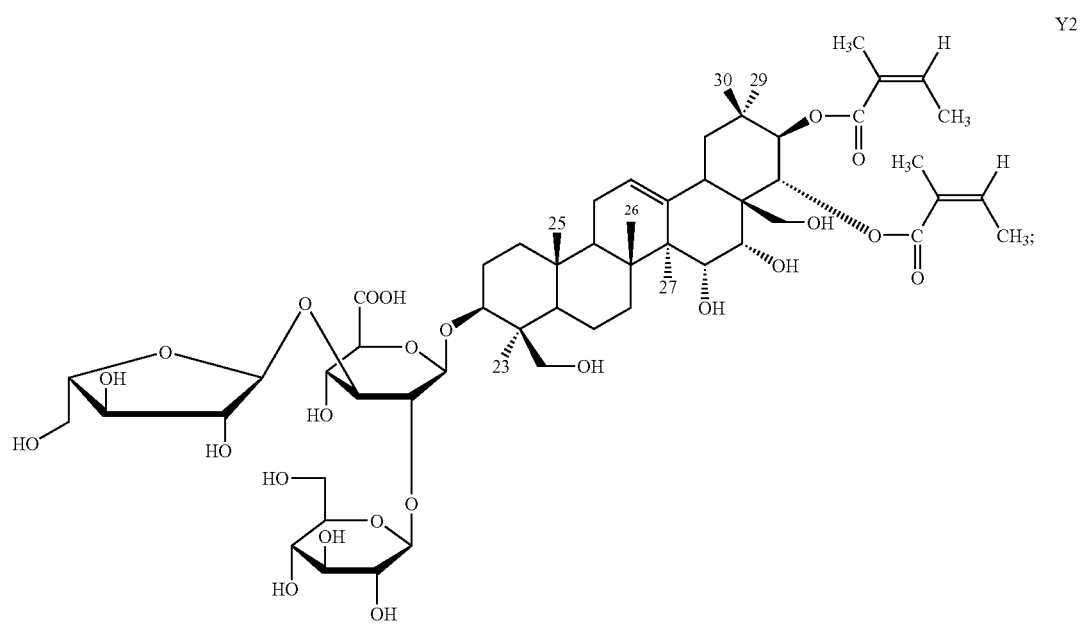

-continued
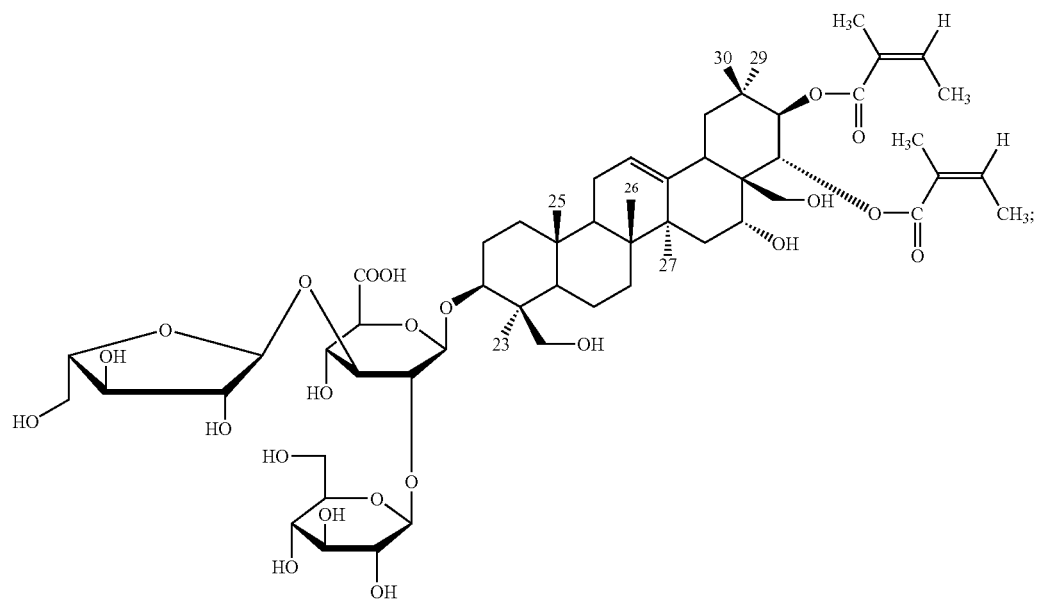
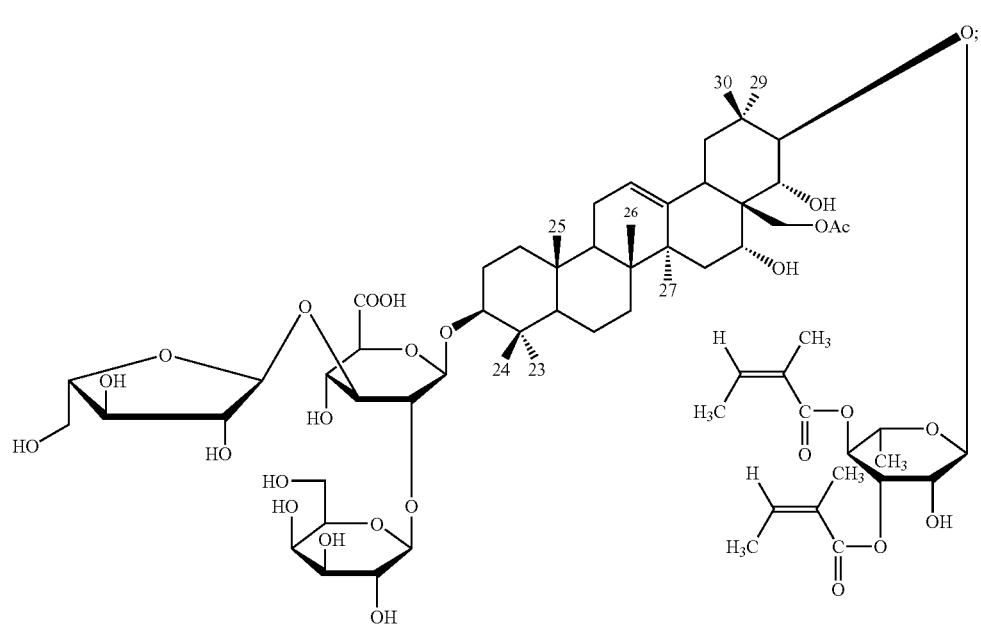

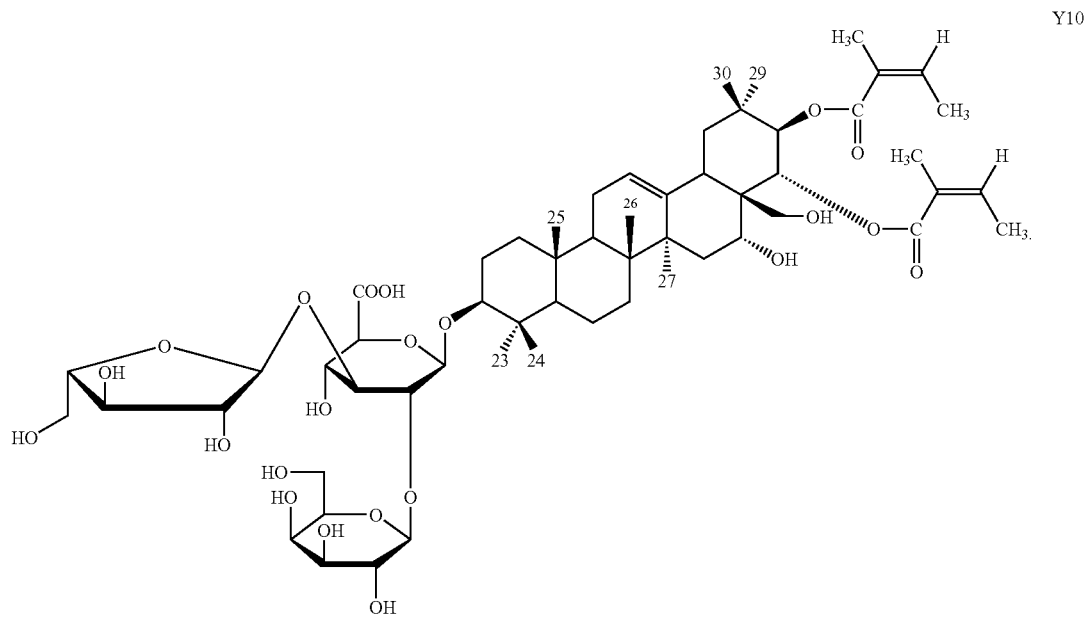

The formula, chemical name and common name of these compounds are presented in Table 1.

TABLE 1

Formula, Chemical Name and Common Name of Six Novel Compounds (Y, Y1, Y2, Y8, Y9, Y10).

| Common name | Formula | Chemical Name |
|---|---|---|
| Xanifolia-Y (Y3) | $C_{57}H_{88}O_{23}$ | 3-O-[β-D-galactopyranosyl(1→2)]-α-L-arabinofuranosyl(1→3)-β-D-glucuronopyranosyl-21,22-O-diangeloyl-3β,15α,16α,21β,22α,28-hexahydroxyolean-12-ene, |
| Xanifolia-Y1 | $C_{65}H_{100}O_{27}$ | 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α,21β,22α,28-pentahydroxyolean-12-ene |
| Xanifolia-Y2 | $C_{57}H_{88}O_{24}$ | 3-O-[β-D-glucopyranosyl-(1→2)]-α-L-arabinofuranosyl(1→3)-β-D-glucuronopyranosyl-21,22-O-diangeloyl-3β,15α,16α,21β,22α,24β,28-heptahydroxyolean-12-ene |
| Xanifolia-Y8 | $C_{57}H_{88}O_{23}$ | 3-O-[β-glucopyranosyl (1→2)]-α-arabinofuranosyl (1→3)-β-glucuronopyranosyl-21,22-O-diangeloyl-3β,16α,21β,22α,24β,28-hexahydroxyolean-12-ene |
| Xanifolia-Y9 | $C_{65}H_{100}O_{27}$ | 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β,16α,21β,22α,28-pentahydroxyolean-12-ene |
| Xanifolia-Y10 | $C_{57}H_{88}O_{22}$ | 3-O-[β-galactopyranosyl (1→2)]-α-arabinofuranosyl (1→3)-β-glucuronopyranosyl-21,22-O-diangeloyl-3β,16α,21β,22α,28-pentahydroxyolean-12-ene |

This invention provides a bioactive compound Xanifolia X, oleanene triterpenoidal saponin with a trisaccharide chain attached at C-3 and one angeloyl group acylated at C-22. The saponin is isolated from extract of *Xanthoceras sorbifolia*. The formula of X is $C_{58}H_{92}O_{22}$ and the chemical name is: 3-O-{[β-D-galactopyranosyl(1→2)]-[α-L-arabinofuranosyl(1→3)]-β-D-glucuronopyranoside butyl ester}-21-O-acetyl-22-O-angeloyl-3β,16α,21β,22α,28-pentahydroxyolean-12-ene. The chemical structure of compound X is presented in the following figure.

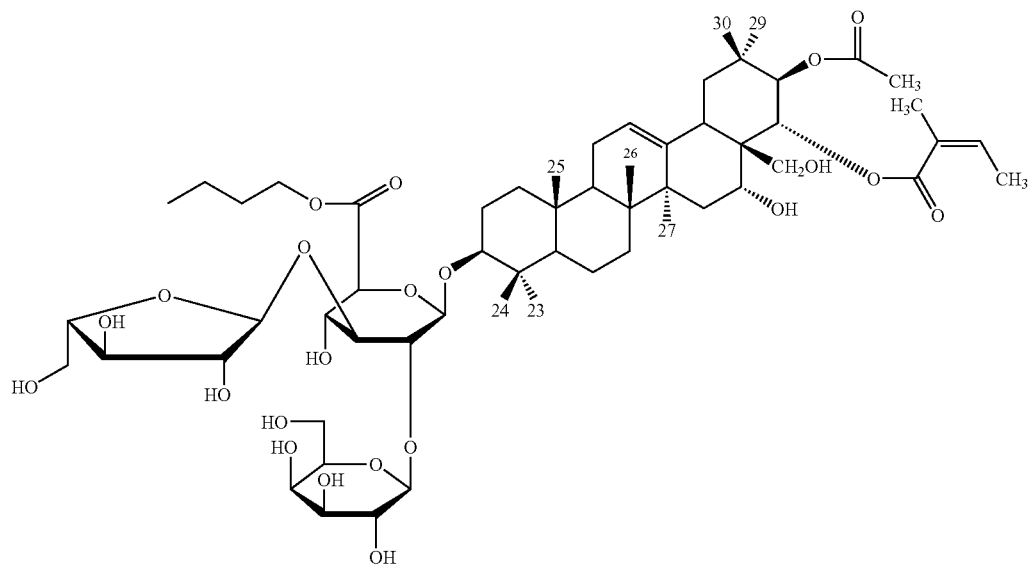
also named as Xanifolia X.
This invention provides a bioactive compound Xanifolia Y0 and the chemical name is: 3-O-[β-D-galactopyranosyl (1→2)]-α-L-arabinofuranosyl(1→3)-β-D-glucuronopyranosyl-21-O-angeloyl,22-O-(2-methylpropanoyl)-3β,15α,16α,21β, 22α,28-hexahydroxyolean-12-ene,
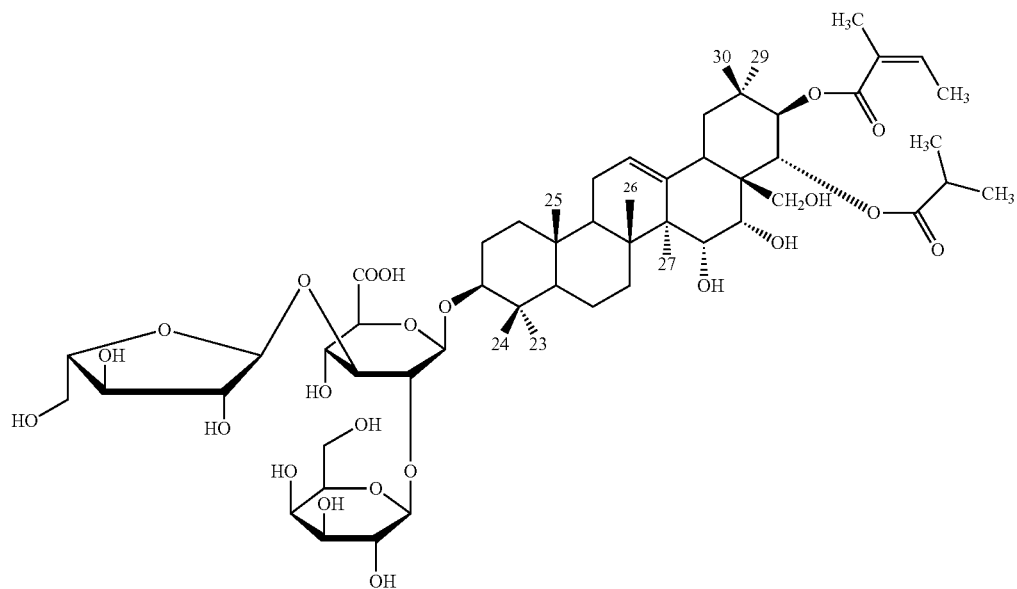
This invention provides a bioactive compound Xanifolia Y7 and the chemical name is:

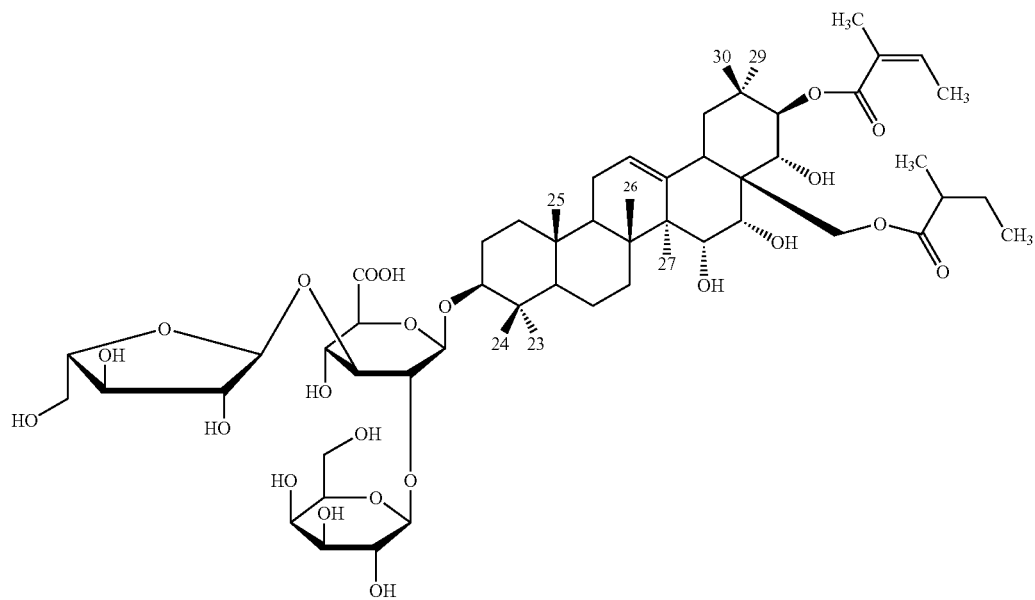

(a)

Compound Y$_7$: 3-O-[β-D-galactopyranosyl-(1→2)]-α-L-arabinofuranosyl-(1→3)-β-D-glucuronopyranosyl-21-O-angeloyl-28-O-2-methylbutanoyl-3β, 15α,16α,21β,22α, 28-hexahydroxyolean-12-ene This invention provides a method of treating a mammal for treating cancers comprising administering to said mammal a therapeutically effective amount of a pharmaceutical composition comprising a composition comprises the molecular formula or compound in this invention. The cancers comprise Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof. The compounds of this invention can be isolated from natural sources or synthesized.

See experiments results in FIG. 1-18 and see PCT/US05/31900, filed Sep. 7, 2006; U.S. Ser. No. 10/906,303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, the contents of which are incorporated herein by reference.

A salt of compound comprise sodium salt, potassium salt or calcium salt.

A salt of compounds comprise the following:

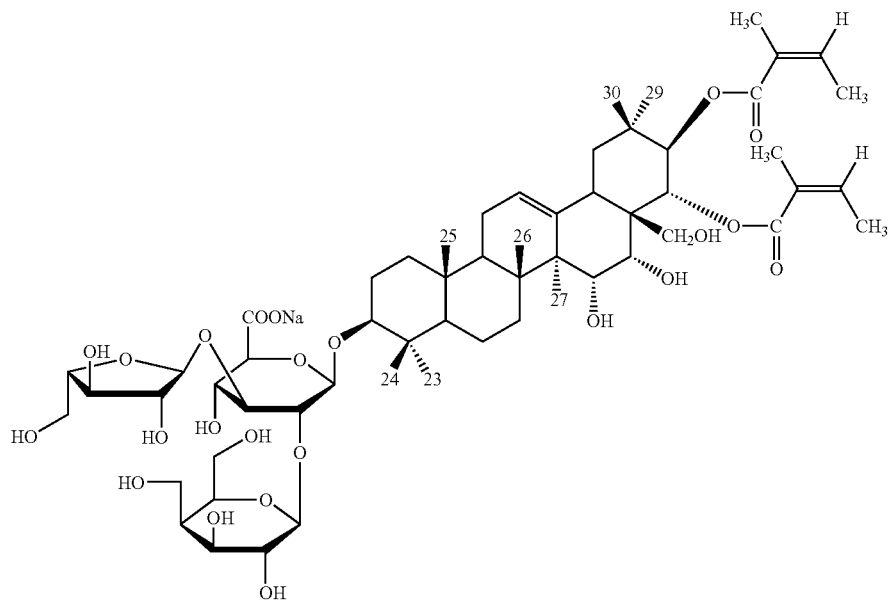

(b)
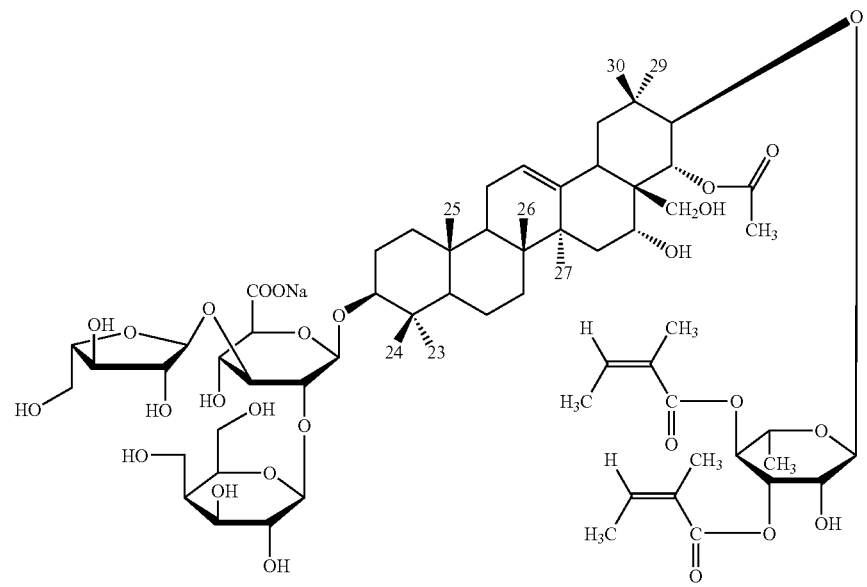
(c)
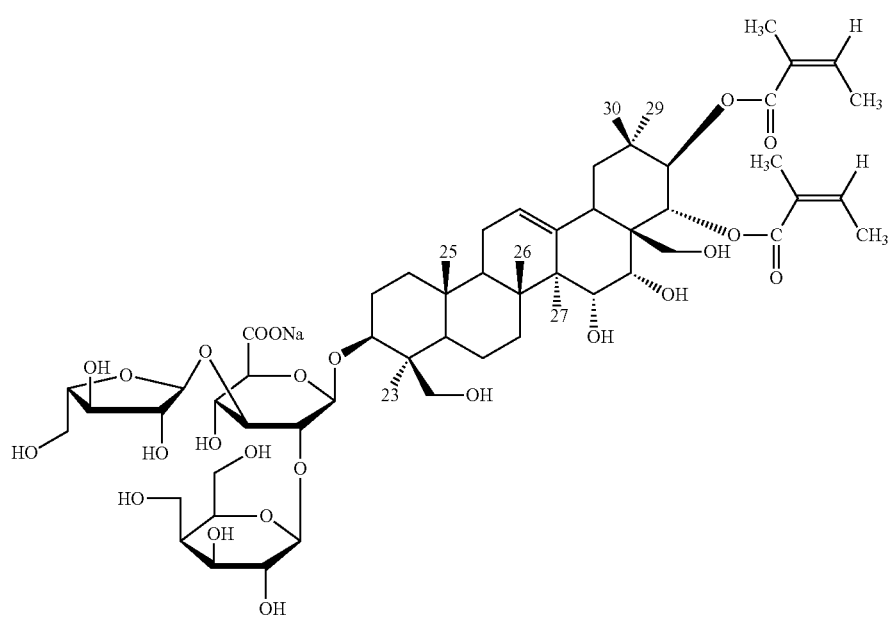

(d)
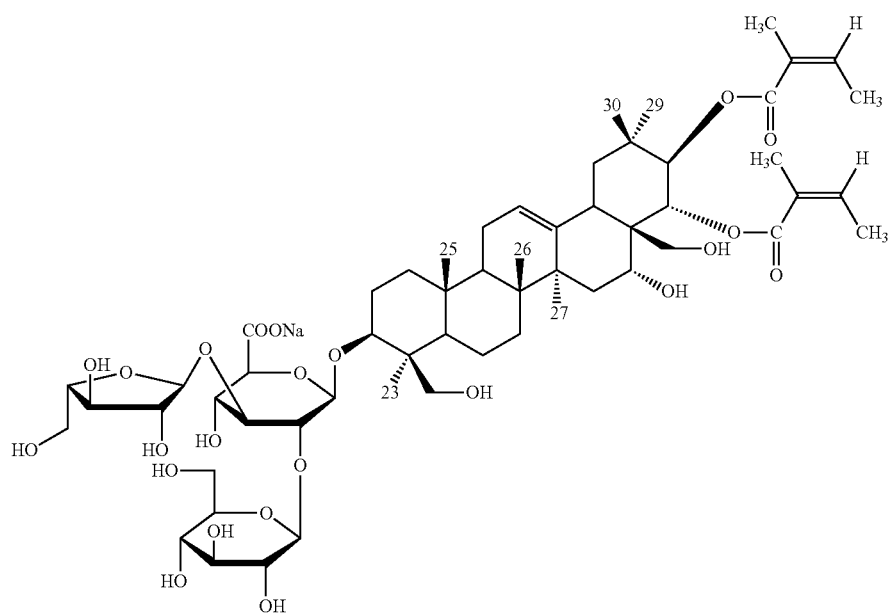
(e)
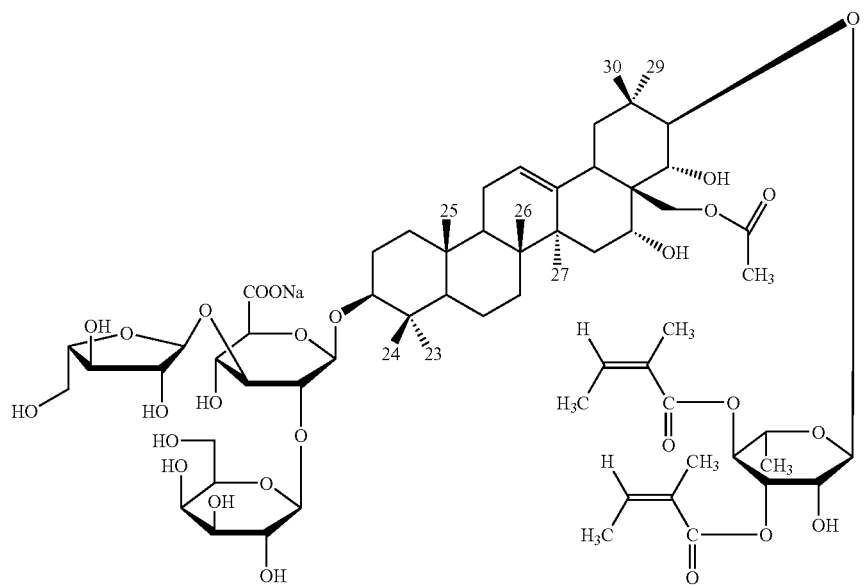

(f)
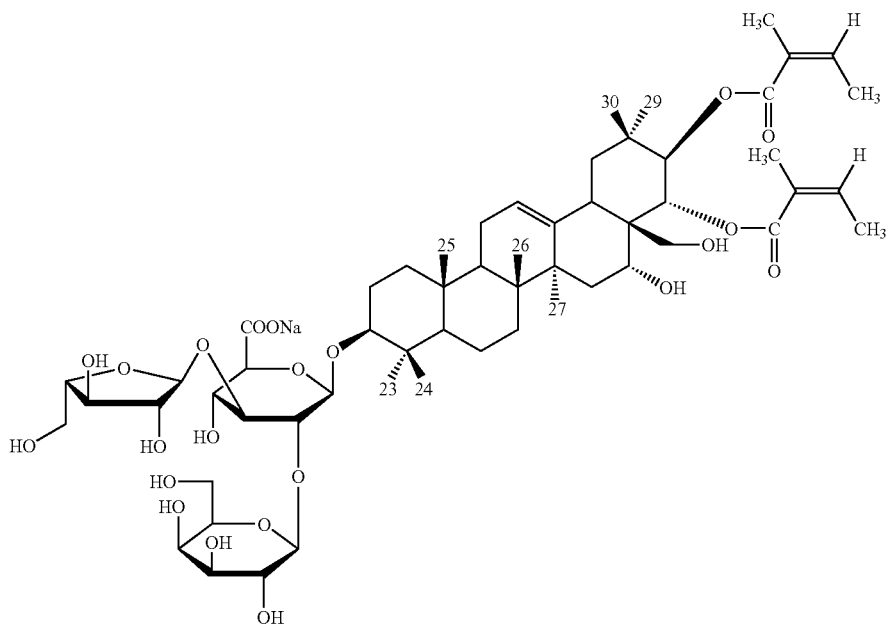
(g)
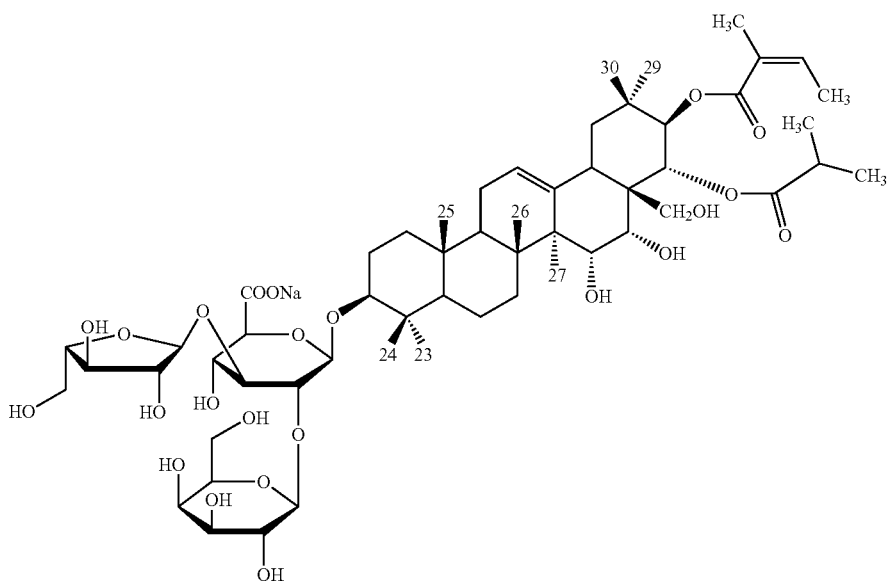

(h)

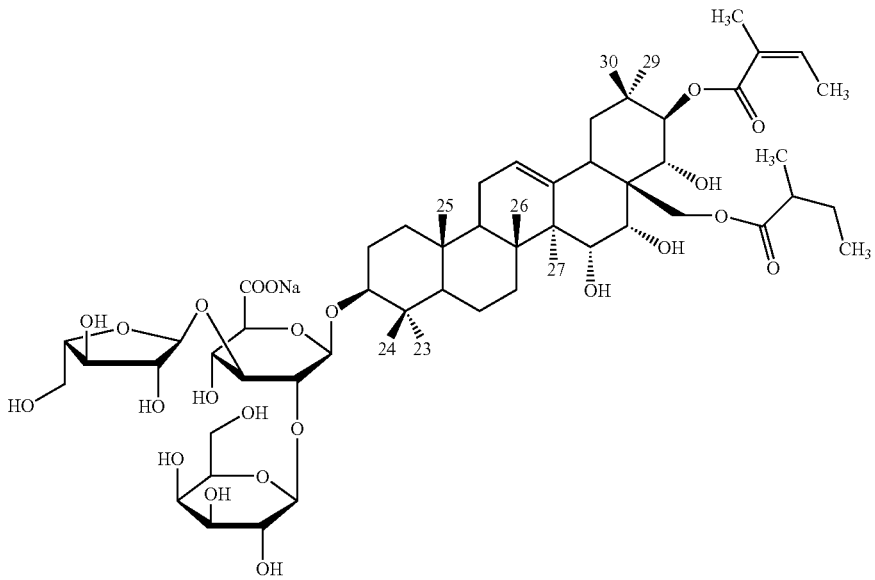

A salt of compounds for inhibiting venous insufficiency, particularly hemorrhoids or inhibiting leg swelling, or peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, hamonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic This invention provides the uses of composition comprising an effective amount of a compound selected from formula (1):

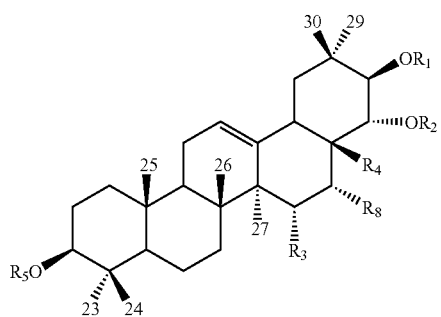

also named as (1)

or a salt, ester, metabolite or derivative thereof, wherein R1 and R2 comprises angeloyl group; R3 comprises H or OH; R4 comprises $CH_2OR6$, and wherein R6 is H; R5 comprises at least one sugar moiety comprising sugar or its derivatives; R8 may be OH.

In an embodiment, R1 and R2 comprise an angeloyl group; R3 comprises H or OH and R4 comprises COOR6 wherein R6 is H.

In an embodiment, R1 comprises H; R2 comprises an angeloyl group; R3 comprises H or OH; R4 comprises $CH_2OR6$ or COOR6; wherein R6 is an angeloyl group.

In another embodiment, R4 comprises $CH_2OR6$ or COOR6; at least two of R1, R2, and R6 comprise an angeloyl group or an acid having five carbons; R3 represents H or OH; and wherein R6 is an angeloyl group, H, acetyl group, tigloyl group, senecioly group, or an acid having two to five carbons.

In an embodiment, at least one angeloyl of R1 or R2 is replaced by an acetyl group, tigloyl group, senecioly group, or an acid having two to five carbons; R3 comprises H or OH; R4 comprises $CH_2OR6$ or COOR6; and wherein R6 is angeloyl group.

In an embodiment, the R4 comprises $CH_2OR6$ or COOR6; and wherein R6 is H or acetyl.

In an embodiment, at least one of R1, R2 and R4 comprises a sugar moiety or a side chain comprising sugar or its derivatives, wherein the sugar moiety comprises at least two angeloyl groups, acetyl group, tigloyl group, senecioly group, or an acid having two to five carbons or combination thereof.

In a further embodiment, position C23, C24, C25, C26, C29 and C30 independently comprises $CH_3$, $CH_2OH$, CHO, COOH, alkyls group, acetyl group or their derivatives thereof.

In a further embodiment, R5 comprises a sugar moiety, wherein the sugar moiety comprises one or more sugar of, but not limited to, glucose, galactose, rhamnose, arabinose, xylose, fucose, allose, altrose, gulose, idose, lyxose, mannose, psicose, ribose, sorbose, tagatose, talose, fructose, or alduronic acid: glucuronic acid, galacturonic acid, or derivatives thereof, or the combination thereof.

In an embodiment, R5 comprises a sugar moiety, wherein the sugar moiety comprises two sugars selected from D-glucose, D-galactose, L-rhamnose, L-arabinose, D-xylose, or their alduronic acids: D-glucuronic acid, D-galacturonic acid, and their derivatives thereof, and the combination thereof.

In an embodiment, R5 comprises a sugar moiety, wherein the sugar moiety comprises three sugars selected from D-glucose, D-galactose, L-rhamnose, L-arabinose, D-xylose, derivatives: alduronic acid, D-glucuronic acid, D-galacturonic acid, and their derivatives thereof, and the combination thereof.

In an embodiment, R5 comprises a sugar moiety, wherein the sugar moiety comprises three sugars selected from D-glucose, D-galactose, L-rhamnose, L-arabinose, D-xylose, and their derivatives thereof, and the combination thereof.

In an embodiment, R5 comprises a sugar moiety, wherein the sugar moiety comprises at least one sugar selected from D-glucose, D-galactose, L-rhamnose, L-arabinose, D-xylose, or alduronic acid: D-glucuronic acid, D-galacturonic acid or derivatives thereof, or the combination thereof.

In a further embodiment, R5 comprises a sugar moiety comprising glucose, galactose, arabinose or their aldironic acids thereof, or their combination thereof.

In an embodiment, R5 comprises a side chain capable of performing the function of the sugar moiety.

In an embodiment, the R5 represents H. In a further embodiment, R4 represents H, OH or $CH_3$. In a further embodiment, R1 or/and R2 is a functional group capable of performing the function of the angeloyl. R5 comprises a side chain capable of performing the function of the sugar moiety.

A sugar moiety is a side chain (segment of molecule) comprising one or more sugars or their aldironic acids thereof, or derivative thereof. Substitution, deletion and/or addition of any group or groups in the above-described compounds by other group or groups will be apparent to one of ordinary skill in the art based on the teaching of this application.

In a further embodiment, the substitution, deletion and/or addition of the group(s) in the compound of the invention does not substantially affect the biological function of the compound.

This invention provides uses of composition comprising effective amounts of compounds selected from formula (1A):

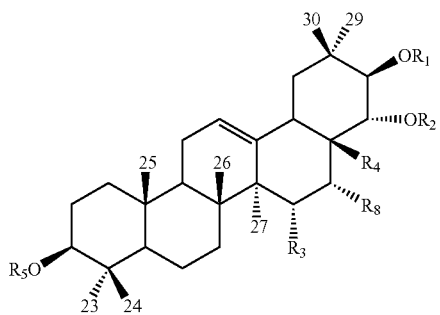

also named as (1A),
or a salt, acid, ester, metabolite or derivative thereof, wherein R1 and R2 independently comprise an angeloyl group; R3 comprises H or OH; R4 comprises $CH_2OR6$; and wherein R6 is H; R8 may be OH; R5 comprises at least one sugar moiety or its derivatives.

In an embodiment, R1 and R2 independently comprise an angeloyl group; R3 comprises H or OH; R4 comprises COOR6 wherein R6 is H; R5 comprises at least one sugar moiety or its derivatives.

In an embodiment, R1 comprises H; R2 comprises angeloyl group; R3 comprises H or OH; R4 comprises $CH_2OR6$ or COOR6; wherein R6 is an angeloyl group; and R5 comprises at least one sugar moiety or its derivatives.

In another embodiment, R3 comprises H or OH; R4 comprises $CH_2OR6$ or COOR6; and wherein R6 is an angeloyl group, H, acetyl group, tigloyl group, senecioyl group, or an acid having two to five carbons; at least two of R1, R2, and R6 comprise an angeloyl group or an acid having five carbons; R5 represents at least one sugar moiety or its derivatives.

In an embodiment, at least one angeloyl from R1 or R2 is replaced by an acetyl group, tigloyl group, senecioyl group, or an acid having two to five carbons; R3 represents H or OH; R4 comprises $CH_2OR6$ or COOR6 wherein R6 is angeloyl group; R5 comprises at least one sugar moiety or its derivatives.

In an embodiment, R4 comprises $CH_2OR6$ or COOR6; at least one of R1, R2, and R6 is a sugar moiety comprising at least two angeloyl groups, acetyl group, tigloyl group, senecioyl group, or an acid having two to five carbons or combination thereof. In an embodiment, position 24 of the compound comprises $CH_3$ or $CH_2OH$.

In a further embodiment, position C23, C24, C25, C26, C29, and C30 of the compound independently comprises $CH_3$ or $CH_2OH$.

In an embodiment, position C23, C24, C25, C26, C29 and C30 of the compound independently comprises $CH_3$, $CH_2OH$, CHO, COOH, COO-alkyl, COO-aryl, COO-heterocyclic, COO-heteroaryl, $CH_2O$-aryl, $CH_2O$-heterocyclic, $CH_2O$-heteroaryl, alkyls group, acetyl group or derivative thereof.

In an embodiment, R5 comprises a sugar moiety and alduronic acid selected from glucose, galactose, arabinose, glucuronic acid, galacturonic acid, or derivative thereof, or the combination thereof.

In an embodiment, R5 comprises a sugar moiety, wherein the sugar moiety comprises at least one sugar of, but is not limited, to D-glucose, D-galactose, L-rhamnose, L-arabinose or D-xylose, or alduronic acid: D-glucuronic acid, D-galacturonic acid, or derivatives thereof, or the combination thereof.

In an embodiment, R5 comprises a sugar moiety, wherein the sugar moiety comprises two sugars comprising but not limited to, D-glucose, D-galactose, L-rhamnose, L-arabinose or D-xylose, or alduronic acid: D-glucuronic acid, D-galacturonic acid, or derivative thereof, or the combination thereof.

In an embodiment, R5 comprises a sugar moiety, wherein the sugar moiety comprises at least three sugars selected from but not limited to, D-glucose, D-galactose, L-rhamnose, L-arabinose, D-xylose, or alduronic acid: D-glucuronic acid, D-galacturonic acid, or derivative thereof, or the combination thereof.

In an embodiment, R5 comprises a sugar moiety, wherein the sugar moiety comprises at least one sugar of, but is not limited to, glucose, galactose, rhamnose, arabinose, xylose, fucose, allose, altrose, gulose, idose, lyxose, mannose, psicose, ribose, sorbose, tagatose, talose or fructose, or alternatively alduronic acid, glucuronic acid, galacturonic acid, or derivative thereof, or the combination thereof.

In an embodiment, R5 comprises a sugar moiety, wherein the sugar moiety comprises three sugars selected from, but not limited to, glucose, galactose, rhamnose, arabinose, xylose, fucose, allose, altrose, gulose, idose, lyxose, mannose, psicose, ribose, sorbose, tagatose, talose or fructose, or alduronic acid: glucuronic acid and galacturonic acid, or/and derivative thereof, or/and the combination thereof. In an embodiment, R5 comprises a sugar moiety, wherein the sugar moiety comprises three sugars selected from, but not limited to, glucose, galactose, rhamnose, arabinose, xylose or fucose, or/and derivative thereof, or/and the combination thereof.

In an embodiment, R5 comprises a compound capable of performing the function of the sugar moiety. In a further embodiment, the R5 represents H. In a further embodiment, R4 represents H or OH or $CH_3$.

In a further embodiment, R1 or/and R2 is a functional group capable of performing the function of the angeloyl group. R5 represents a side chain capable of performing the function of the sugar moiety.

In an embodiment, R1 and R2 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl.

In a further embodiment, R1 and R2 comprise angeloyl, tigloyl, senecioyl, benzoyl or alkenoyl.

In an embodiment, R4 represents $CH_2OR6$; at least two of R1, R2 and R6 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl.

In an embodiment, R4 represents $CH_2OR6$; at least two of R1, R2 and R6 are selected from angeloyl, tigloyl, senecioyl, benzoyl or alkenoyl.

In an embodiment, R4 represents $CH_2OR6$; at least two of R1, R2 and R6 are selected from angeloyl, benzoyl or alkenoyl.

In an embodiment, R1 and R2 are selected from H, angeloyl, acetyl, tigloyl, senecioyl, alkyl, acyl, benzoyl, dibenzoyl, alkanoyl, alkenoyl, benzoyl alkyl substituted alkanoyl, aryl, heterocylic or heteroraryl; R4 represents $CH_2OR6$ or COOR6; wherein R6 is selected from H, $COCH_3$, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 represents $CH_2OR6$, COOR6 or $CH_2COOR6$; at least two of R1, R2 and R6 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, at least two of R1, R2 and R4 are comprising angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, at least two of R1, R2 and R4 comprise angeloyl, acetyl, tigloyl, senecioyl, benzoyl or alkenoyl, or a derivative thereof.

In an embodiment, at least two of R1, R2 and R4 comprise angeloyl, tigloyl, senecioyl, benzoyl or alkenoyl, or a derivative thereof.

In an embodiment, at least two of R1, R2 and R4 comprise a side chain capable of performing the function of the angeloyl group.

In an embodiment, at least two of R1, R2 and R4 comprise a side chain capable of performing the function of benzoyl.

In an embodiment, R4 represents $CH_2OR6$, COOR6 or $CH_2COOR6$; at least two of R1, R2 and R6 are selected from angeloyl, tigloyl, senecioyl, benzoyl, alkenoyl, benzoyl or derivatives thereof.

In an embodiment, R4 represents $CH_2OR6$, COOR6 or $CH_2COOR6$; R1, R2 and/or R6 is/are a sugar moiety comprising groups selected from H, angeloyl, acetyl, tigloyl, senecioly, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 represents $CH_2OR6$, COOR6 or $CH_2COOR6$; R1, R2 and/or R6 is/are a sugar moiety comprising at least 2 groups selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 represents $CH_2OR6$, COOR6 or $CH_2COOR6$; R1, R2 and/or R6 is/are a sugar moiety comprising at least 2 groups selected from angeloyl, tigloyl, senecioyl, benzoyl, alkenoyl or a derivative thereof.

In an embodiment, R4 represents $CH_2OR6$, COOR6 or $CH_2COOR6$; R1, R2 and/or R6 is/are a sugar moiety comprising at least 2 groups selected from angeloyl, benzoyl, alkenoyl or a derivative thereof.

In an embodiment, a compound selected from formula (1A) comprising at least 2 groups selected from angeloyl, acetyl, tigloyl, senecioyl, or derivative thereof or a group capable of performing the function of angeloyl.

In a further embodiment, a compound selected from a formula (1A) comprises at least 2 groups selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In a further embodiment, a compound selected from a formula (1A) comprises a sugar moiety or a side chain of performing function of sugar moiety comprising at least 2 groups selected from angeloyl, acetyl, tigloyl, senecioyl, or a derivative thereof or a group capable of performing the function of angeloyl.

In a further embodiment, a compound selected from a formula (1A) comprises a sugar moiety or a side chain capable of performing the function of a sugar moiety comprising at least 2 groups selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In a further embodiment, a compound selected from a formula (1A) wherein R1 and R2 comprises a group selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, acyl, heterocylic or heteroraryl or derivative thereof. R4 is a group comprising $CH_2OCOCH_3$, $CH_2COO$-alkyl, $CH_2OH$, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof. A sugar moiety is a segment of a molecule comprising one or more sugars or their aldironic acids thereof, or a derivative thereof. In a further embodiment, the compounds of this invention can be isolated from natural sources or synthesized.

Substitution, deletion and/or addition of any group in the above-described by other groups will be apparent to one of ordinary skill in the art based on the teachings of this application. In a further embodiment, the substitution, deletion and/or addition of the group(s) in the compound of the invention does not substantially affect the biological function of the compound. A composition comprising an effective amount of the compound of any one of compound selected from the above formula or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention provides uses of a compound selected from a compound with formula (1B):

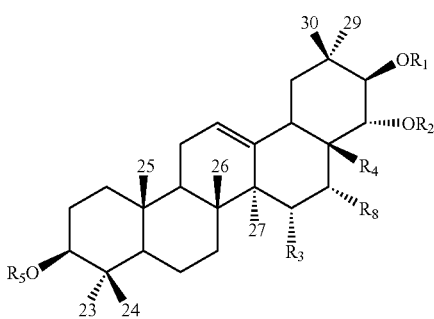

also named as (1B),
or a salt, ester, metabolite or derivative thereof, wherein R1 comprises a group selected from hydrogen, angeloyl, acetyl, tigloyl, senecioyl, alkyl, dibenzoyl, benzoyl, alkanoyl, alkenoyl, benzoyl alkyl substituted alkanoyl, aryl, heterocylic or heteroraryl or derivatives thereof; R2 comprises a group selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof; R4 represents $CH_2OR6$, $COOR6$, wherein R6 is selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof; R3 is H or OH; R5 comprises a sugar moiety, wherein the sugar moiety comprises at least one sugar of, but is not limited to, D-glucose, D-galactose, L-rhamnose, L-arabinose, D-xylose, alduronic acid: D-glucuronic acid, D-galacturonic acid or a derivative thereof, or the combination thereof.

In an embodiment, R1 comprises a sugar moiety wherein at least two groups are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R1 comprises a sugar moiety wherein at least one group is selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R2 comprises a sugar moiety wherein at least one group is selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R2 comprises a sugar moiety or a side chain wherein at least two groups are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 comprises $CH_2OR6$, $COOR6$ wherein R6 is a sugar moiety which comprises at least one group selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 comprises $CH_2OR6$, $COOR6$, wherein R6 is a sugar moiety which comprises at least two groups selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 represents $CH_2OR6$, $COOR6$, wherein R6 is a sugar moiety which comprises at least two groups selected from angeloyl, acetyl, tigloyl, senecioyl, or alkyl.

In an embodiment, R4 comprises $CH_2OR6$, $COOR6$ wherein R6 is a sugar moiety which comprises at least two groups selected from angeloyl, acetyl, tigloyl, senecioyl, alkyl, benzoyl, dibenzoyl, alkanoyl, alkenoyl, dibenzoyl, benzoyl alkyl substituted alkanoyl, aryl, acyl, heterocylic or heteroraryl or a derivative thereof.

In an embodiment, R4 comprises $CH_2OR6$, $COOR6$ of formula (1B), at least two of R1, R2 and R6 comprise the group selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In an embodiment, R4 comprises $CH_2OR6$, $COOR6$ of formula (1B), at least two of R1, R2 and R6 comprise angeloyl, benzoyl, alkenoyl, or a derivative thereof.

In an embodiment, R4 is a side chain comprising $CH_2OCOCH_3$, $CH_2COO$-alkyl, $CH_2OH$, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or a derivative thereof.

In a further embodiment, R5 comprises a sugar moiety, wherein the sugar moiety comprises one or more sugar of, but is not limited to glucose, galactose, rhamnose, arabinose, xylose, fucose, allose, altrose, gulose, idose, lyxose, mannose, psicose, ribose, sorbose, tagatose, talose, fructose, or alduronic acid: glucuronic acid, galacturonic acid, or derivatives thereof, or the combination thereof.

In an embodiment, R5 comprises a sugar moiety or a group capable of performing the function of the sugar moiety.

In an embodiment, the R5 represents H.

In an embodiment, R4 represents H, OH or $CH_3$.

In an embodiment, position C23, C24, C25, C26, C29 and C30 of the compound independently comprise $CH_3$, $CH_2OH$, CHO, COOH, COOa-lkyl, COO-aryl, COO-heterocyclic, COO-heteroaryl, $CH_2Oaryl$, $CH_2O$— heterocyclic, $CH_2O$— heteroaryl, alkyls group, acetyl group or derivatives thereof.

In an embodiment, R1 and R2 independently comprise an angeloyl group.

In an embodiment, R1 is a sugar moiety or a side chain which comprise two angeloyl groups.

In an embodiment, R1 and R2 independently comprises a benzoyl group.

In an embodiment, R1 is a sugar moiety which has two benzoly groups.

In an embodiment, $R_3$ represents H or OH.

In an embodiment, R8 may be OH

Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound. A composition comprising an effective amount of the compound selected from the above formula or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention provides uses of a compound selected from a compound with formula (1C):

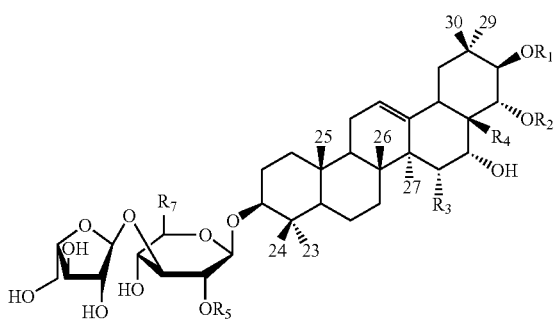

also named as (1C),
or a salt, ester, metabolite or derivative thereof, wherein R1 and R2 independently comprise an angeloyl group; R3 represents H or OH; R4 comprises $CH_2OR6$, wherein R6 is H; R5 comprises a sugar moiety comprising one or more sugars of D-glucose, D-galactose or its derivatives. R7 represents COOH In an embodiment, R1 and R2 independently comprise an angeloyl group; R3 represents H or OH; R4 comprises COOR6 wherein R6 is H; R5 comprises a sugar moiety comprising one or more sugars of D-glucose, D-galactose or its derivatives. R7 represent COOH.

In an embodiment, R1 represents H; R2 comprises angeloyl group; R3 represents H or OH; R4 comprises $CH_2OR6$ or COOR6, wherein R6 comprises an angeloyl group or acetyl group.

In an embodiment, at least two of R1, R2, and R6 comprise an angeloyl group or acid having five carbons; R3 represents H or OH; R4 comprises $CH_2OR6$ or COOR6, wherein R6 is angeloyl group, H, acetyl group, tigloyl group, senecioyl group, or an acid having two to five carbons.

In an embodiment, at least one angeloyl from R1 or R2 is replaced by an acetyl group, tigloyl group, senecioyl group, or an acid having two to five carbons; R3 represents H or OH; R4 represents $CH_2OR6$ or COOR6, wherein R6 is angeloyl group.

In an embodiment, R4 comprises $CH_2OR6$ or COOR6; at least one of R1, R2, and R6 is a sugar moiety comprising at least two angeloyl groups, acetyl group, tigloyl group, senecioyl group, or an acid having two to five carbons or combination thereof. In an embodiment, positions C24 of the compound comprises $CH_3$ or $CH_2OH$.

In a further embodiment, R7 represents $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls group, acetyl group or derivatives thereof.

In an embodiment, positions C24 of the compound comprises $CH_3$ or $CH_2OH$.

In an embodiment, position of C23, C24, C25, C26, C29 and C30 of the compound independently comprises $CH_3$ or $CH_2OH$.

In an embodiment, position of C23, C24, C25, C26, C29 and C30 of the compound respectively comprise $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls group, acetyl group or derivative thereof.

In an embodiment, R5 comprises a sugar moiety comprising one or more sugars of glucose, galactose, rhamnose, arabinose, xylose, fucose, allose, altrose, gulose, idose, lyxose, mannose, psicose, ribose, sorbose, tagatose, talose, fructose, or alternatively alduronic acid or glucuronic acid or galacturonic acid, or derivative thereof, or the combination thereof.

In an embodiment, the R5 represents H.

In an embodiment, R4 comprises H, OH, or $CH_3CH_2OR6$, wherein R6 comprises H or an acetyl group.

In an embodiment, R1 or/and R2 is a functional group capable of performing the function of the angeloyl. R5 represents a side chain capable of performing the function of the sugar moiety.

In an embodiment, R1 and R2 are selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivatives thereof.

In an embodiment, R1 or/and R2 is a sugar moiety comprising two of groups selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivatives thereof.

In an embodiment, R1 and R2 are selected from H, angeloyl, acetyl, tigloyl, senecioyl, alkyl, benzoyl, alkanoyl, alkenoyl, benzoyl alkyl substituted alkanoyl, aryl, acyl, heterocylic or heteroraryl; R4 represents $CH_2OR6$ or COOR6, wherein R6 is selected from H, $COCH_3$, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivatives thereof.

In an embodiment, R4 comprises $CH_2OR6$, COOR6 or $CH_2COOR6$; at least two of R1, R2 and R6 are selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivatives thereof.

In an embodiment, R4 comprises $CH_2OR6$, COOR6 or $CH_2COOR6$; R1, R2 and/or R6 is/are a sugar moiety, which comprises at least 2 groups selected from H, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivatives thereof.

In an embodiment, a compound selected from formula (1C) comprises at least 2 groups selected from angeloyl, acetyl, tigloyl, senecioyl, or derivatives thereof or a group capable of performing the function of angeloyl.

In an embodiment, a compound selected from formula (1C) comprises at least 2 groups selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivatives thereof.

In an embodiment, a compound selected from formula (1C) wherein R1 and R2 comprise groups selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof. R4 is a compound comprising $CH_2OCOCH_3$, $CH_2COO$-alkyl, $CH_2OH$, COOH, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof.

Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides uses of a compound selected from a compound of formula (1D):

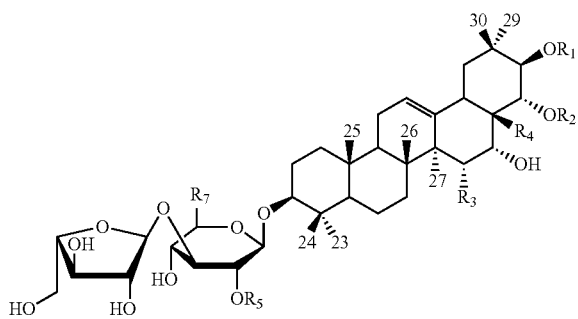

and also named as (1D),
or a salt, ester, metabolite or derivative thereof, wherein R1 comprise a compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof; R2 comprise a compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof; R4 comprises CH$_2$OR6, COOR6 wherein R6 is selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof; R3 is H or OH; R5 comprises a sugar moiety, or D-glucose or D-galactose; R7 represents COOH In an embodiment, R7 comprises CH$_3$, CH$_2$OH, COOH, COOalkyl, In an embodiment, R7 comprises CH$_3$, CH$_2$OH, CHO, COOH, COOalkyl, COOaryl, COO-heterocyclic, COO-heteroaryl, CH$_2$Oaryl, CH$_2$O— heterocyclic, CH$_2$O— heteroaryl, alkyls group, acetyl group or a derivative thereof.

In an embodiment, R1 represents a compound comprising a sugar moiety comprising at least two compounds selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof;

In an embodiment, R1 represents a compound comprising a sugar moiety comprising at least one compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof;

In an embodiment, R2 represents a compound comprising a sugar moiety comprising at least one compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof;

In an embodiment, R2 represents a compound comprising a sugar moiety or a compound which comprises at least two compounds selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof;

In an embodiment, R4 comprises CH$_2$OR6, COOR6 wherein R6 is a sugar moiety which comprises at least one compound selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof;

In an embodiment, R4 comprises CH$_2$OR6, COOR6 wherein R6 is a sugar moiety which comprises at least two compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof;

In an embodiment, R4 comprises CH$_2$OR6, COOR6 wherein R6 is a sugar moiety which comprises at least two compounds selected from angeloyl, acetyl, tigloyl, senecioyl, or alkyl;

In an embodiment, R4 comprises CH$_2$OR6, COOR6 wherein R6 is a sugar moiety which comprises at least two compounds selected from angeloyl, acetyl, tigloyl, senecioyl, alkyl, benzoyl, alkanoyl, alkenoyl, dibenzoyl, benzoyl alkyl substituted alkanoyl, aryl, acyl, heterocylic or heteroraryl or a derivative thereof;

In an embodiment, R4 comprises CH$_2$OR6, COOR6 wherein at least two of R1, R2 and R6 comprise the compound selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 is a compound comprising CH$_2$OCOCH3, CH$_2$COOalkyl, CH$_2$OH, COOH, angeloyl, acetyl, tigloyl, senecioyl, alkyl, benzoyl, alkanoyl, alkenoyl, benzoyl alkyl substituted alkanoyl, aryl, acyl, heterocylic or heteroraryl or a derivative thereof.

In a further embodiment, R5 comprises a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof. In an embodiment, R5 comprises a compound capable of performing the function of the sugar moiety. In a further embodiment, the R5 comprises a H. In a further embodiment, R4 represents H or OH or CH$_3$.

In an embodiment, position 24 of the compound comprise CH$_3$ or CH$_2$OH, In a further embodiment, positions 23, 24, 25, 26, 29, 30 of the compound independently comprise CH$_3$, CH$_2$OH, CHO, COOH, COOalkyl, COOaryl, COO-heterocyclic, COO-heteroaryl, CH$_2$Oaryl, CH$_2$O— heterocyclic, CH$_2$O— heteroaryl, alkyls group, acetyl group or a derivative thereof.

In an embodiment, R5 comprises a sugar moiety comprising L-glucose, D-galactose, L-rhamnose, or/and L-arabinose.

In an embodiment, R1 and R2 independently comprise an angeloyl group; In a embodiment, R1 is a sugar moiety or rhamnose which comprise two angeloyl groups. In an embodiment, R3 represents H or OH; In a further embodiment, the compounds can be isolated from natural sources or synthesized.

A sugar moiety is a segment of a molecule comprising one or more sugar groups. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

Figure 3:
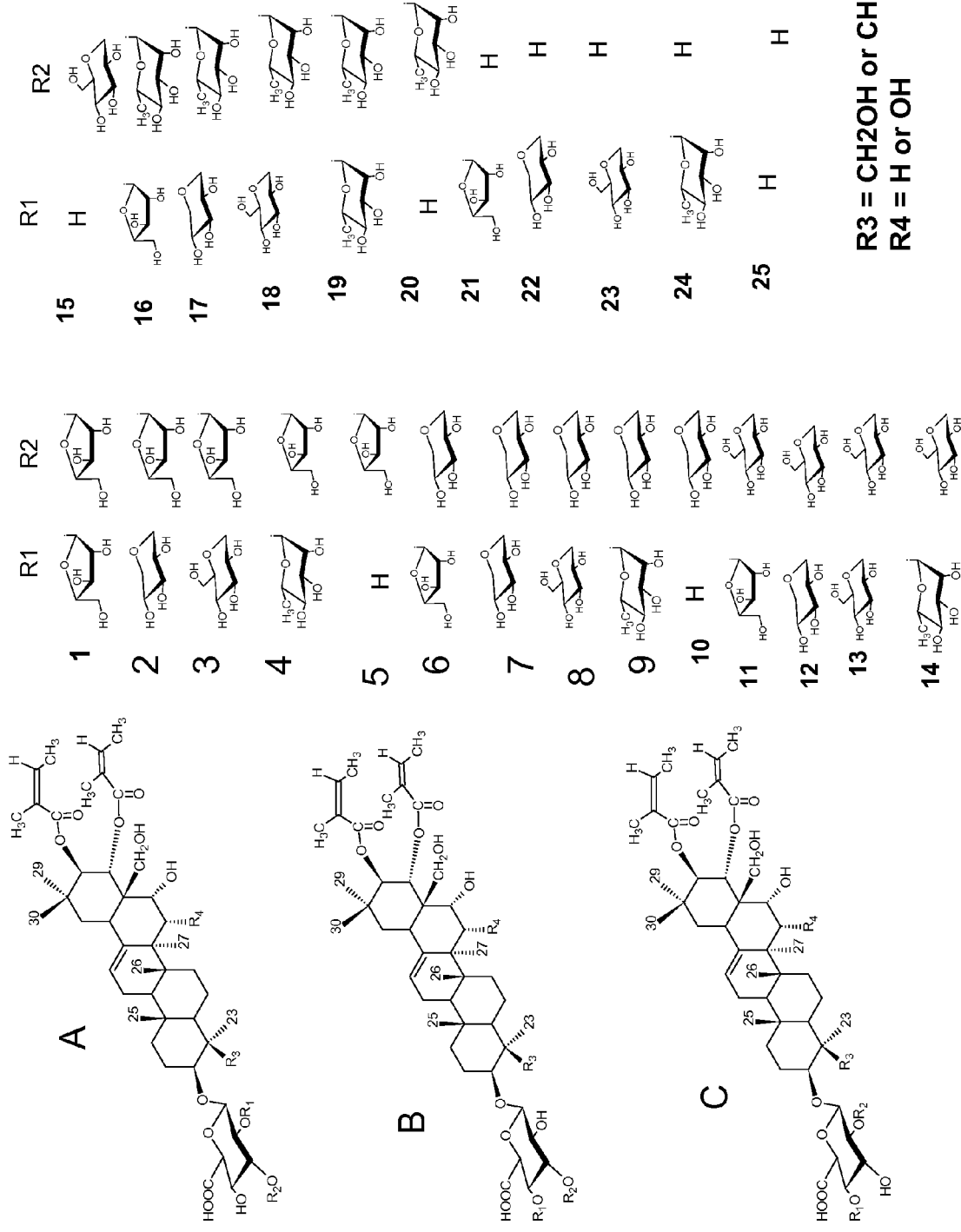

A method of inhibiting venous insufficiency, particularly hemorrhoids or inhibiting leg swelling, or peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, hamonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic comprising administering to a subject, in need thereof, an effective amount of the composition of any one of the above compounds or compounds in FIG. 1 to 3, or a compound comprises a triterpene which comprises any two of angeloyl, tigloyl, senecioyl, preferable two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or the combination thereof, preferable selected from glucuronic acid, galacturonic acid, glucose, galactose and arabinose.

This invention provides a method of inhibiting tumor cell growth comprising administering to a subject, in need thereof, an appropriate amount of triterpenoidal saponins comprising two or more angeloyl groups or comprising the structure of FIGS. 1-3, or a compound comprises a triterpene which comprises any two of angeloyl, tigloyl, senecioyl, preferable two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or the combination thereof, preferably selected from glucuronic acid, galacturonic acid, glucose, galactose and arabinose. This invention provides a composition comprising an effective amount of the compound of any one of compound selected from the above formula or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This invention provides a composition comprising the compounds as described above effective in reducing or inhibiting cancer growth. The cancer includes but is not limited to bladder cancer, bone cancer, skin cancer and ovarian cancer.

This invention also provides a composition comprising the above described compounds or their derivatives for inhibiting and also a method of treating venous insufficiency, particularly hemorrhoids or inhibiting leg swelling, or peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, episiotomies, hemonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic comprising administering to a subject, in need thereof, an effective amount of the composition.

In an embodiment of the above, the uses of compositions comprising any one of triterpenoid saponins with the following formula:

3-O-{[β-D-galactopyranosyl(1→2)]-[α-L-arabinofuranosyl (1→3)]-β-D-glucuronopyranoside butyl ester}-21-O-acetyl-22-O-angeloyl-3β,16α,21β,22α,28-pentahydroxyolean-12-ene.

3-O-[β-D-galactopyranosyl(1→2)]-α-L-arabinofuranosyl (1→3)-β-D-glucuronopyranosyl-21,22-O-diangeloyl-3β, 15α,16α,21β,22α,28-hexahydroxyolean-12-ene, 3-O-[β-D-galactopyranosyl(1→2)]-α-L-arabinofuranosyl (1→3)-β-D-glucuronopyranosyl-21-O-(3,4-diangeloyl)-α-L-rhamnophyranosyl-22-O-acetyl-3β,16α,21β,22α, 28-pentahydroxyolean-12-ene, 3-O-[β-D-glucopyranosyl-(1→2)]-α-L-arabinofuranosyl (1→3)-β-D-glucuronopyranosyl-21,22-O-diangeloyl-3β, 15α,16α,21β,22α,24β,28-heptahydroxyolean-12-ene, 3-O-[β-glucopyranosyl(1→2)]-α-arabinofuranosyl(1→3)-β-glucuronopyranosyl-21,22-O-diangeloyl-3β,16α,21β, 22α,24β,28-hexahydroxyolean-12-ene, 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β,16α,21β,22α,28-pentahydroxyolean-12-ene, 3-O-[β-galactopyranosyl(1→2)]-α-arabinofuranosyl(1→3)-β-glucuronopyranosyl-21,22-O-diangeloyl-3β,16α,21β, 22α,28-pentahydroxyolean-12-ene, 3-O-[β-D-galactopyranosyl(1→2)]-α-L-arabinofuranosyl (1→3)-β-D-glucuronopyranosyl-21-O-angeloyl,22-O-(2-methylpropanoyl)-3β,15α,16α,21β,22α,28-hexahydroxyolean-12-ene, 3-O-[β-D-galactopyranosyl-(1→2)]-α-L-arabinofuranosyl-(1→3)-β-D-glucuronopyranosyl-21-O-angeloyl-28-O-2-methylbutanoyl-3β,15α,16α,21β,22α,28-hexahydroxyolean-12-ene This invention provides a composition comprising the compounds as described above effective in inhibiting venous insufficiency, particularly hemorrhoids or inhibiting of leg swelling, and inhibiting cancer growth. The cancer includes but is not limited to bladder cancer, bone, cancer, skin cancer and ovarian cancer.

This invention also provides a composition for inhibiting venous insufficiency, particularly hemorrhoids or inhibition of leg swelling, or inhibiting cancer growth comprising any of compounds selected from the following compounds:

A) 3-O-[β-D-galactopyranosyl(1→2)]-α-L-arabinofuranosyl(1→3)-β-D-glucuronopyranosyl-21,22-O-diangeloyl-3β,15α,16α,21β,22α,28-hexahydroxyolean-12-ene, B) 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α,21β, 22α,28-pentahydroxyolean-12-ene C) 3-O-[β-D-glucopyranosyl-(1→2)]-α-L-arabinofuranosyl (1→3)-(-D-glucuronopyranosyl-21,22-O-diangeloyl-3β, 15α,16α,21β,22α,24β,28-heptahydroxyolean-12-ene D) 3-O-[β-galactopyranosyl(1→2)]-α-arabinofuranosyl (1→3)-β-glucuronopyranosyl-21,22-O-diangeloyl-3β, 16α,21β,22α,28-pentahydroxyolean-12-ene E) 3-O-[β-galactopyranosyl(1→2)]-α-arabinofuranosyl (1→3)-β-glucuronopyranosyl-21-O-(3,4-diangeloyl)-α-rhamnopyranosyl-28-O-acetyl-3β,16α,21β,22α,28-pentahydroxyolean-12-ene F) 3-O-[β-galactopyranosyl(1→2)]-α-arabinofuranosyl (1→3)-β-glucuronopyranosyl-21,22-O-diangeloyl-3β, 16α,21β,22α,28-pentahydroxyolean-12-ene G) 3-O-[β-D-galactopyranosyl(1→2)]-α-L-arabinofuranosyl(1→3)-β-D-glucuronopyranosyl-21,22-O-dibenzoyl-3β,15α,16α,21β,22α,28-hexahydroxyolean-12-ene, H) 3-O-[β-D-galactopyranosyl(1→2)]-α-L-arabinofuranosyl(1→3)-β-D-glucuronopyranosyl-21-O-(3,4-dibenzoyl)-α-L-rhamnophyranosyl-22-O-acetyl-3β,16α,21β, 22α,28-pentahydroxyolean-12-ene I) 3-O-[β-D-glucopyranosyl-(1→2)]-α-L-arabinofuranosyl (1→3)-(-D-glucuronopyranosyl-21,22-O-dibenzoyl-3β, 15α,16α,21β,22α,24β,28-heptahydroxyolean-12-ene J) 3-O-[β-galactopyranosyl(1→2)]-α-arabinofuranosyl (1→3)-β-glucuronopyranosyl-21,22-O-dibenzoyl-3β, 16α,21β,22α,28-pentahydroxyolean-12-ene K) 3-O-[β-galactopyranosyl(1→2)]-α-arabinofuranosyl(1→3)-β-glucuronopyranosyl-21-O-(3,4-dibenzoyl)-α-rhamnopyranosyl-28-O-acetyl-3β,16α,21β,22α,28-pentahydroxyolean-12-ene L) 3-O-[β-galactopyranosyl(1→2)]-α-arabinofuranosyl(1→3)-β-glucuronopyranosyl-21,22-O-dibenzoyl-3β,16α,21β,22α,28-pentahydroxyolean-12-ene M) 3-O-[β-D-galactopyranosyl(1→2)]-β-D-xyopyranosyl(1→3)-β-D-glucuronopyranosyl-21,22-O-dibenzoyl-3β,15α,16α,21β,22α,28-hexahydroxyolean-12-ene, N) 3-O-[β-D-galactopyranosyl(1→2)]-β-D-xyopyranosyl(1→3)-β-D-glucuronopyranosyl-21-O-(3,4-dibenzoyl)-α-L-rhamnophyranosyl-22-O-acetyl-3β,16α,21β,22α,28-pentahydroxyolean-12-ene O) 3-O-[β-D-glucopyranosyl-(1→2)]-β-D-xyopyranosyl(1→3)-(-D-glucuronopyranosyl-21,22-O-dibenzoyl-3β,15α,16α,21β,22α,24β,28-heptahydroxyolean-12-ene P) 3-O-[β-D-galactopyranosyl(1→2)]-β-D-xyopyranosyl(1→3)-β-D-glucuronopyranosyl-21,22-O-dibenzoyl-3β,16α,21β,22α,28-pentahydroxyolean-12-ene Q) 3-O-[β-galactopyranosyl(1→2)]-β-xyopyranosyl(1→3)-β-glucuronopyranosyl-21-O-(3,4-dibenzoyl)-α-rhamnopyranosyl-28-O-acetyl-3β,16α,21β,22α,28-pentahydroxyolean-12-ene R) 3-O-[β-galactopyranosyl(1→2)]-β-xyopyranosyl(1→3)-β-glucuronopyranosyl-21,22-O-dibenzoyl-3β,16α,21β,22α,28-pentahydroxyolean-12-ene S) 3-O-[β-D-galactopyranosyl(1→2)]-β-D-xyopyranosyl(1→3)-β-D-glucuronopyranosyl-21,22-O-diangeloyl-3β,15α,16α,21β,22α,28-hexahydroxyolean-12-ene, T) 3-O-[β-D-galactopyranosyl(1→2)]-β-D-xyopyranosyl(1→3)-β-D-glucuronopyranosyl-21-O-(3,4-diangeloyl)-α-L-rhamnophyranosyl-22-O-acetyl-3β,16α,21β,22α,28-pentahydroxyolean-12-ene U) 3-O-[β-D-glucopyranosyl-(1→2)]-β-D-xyopyranosyl(1→3)-(-D-glucuronopyranosyl-21,22-O-diangeloyl-3β,15α,16α,21β,22α,24β,28-heptahydroxyolean-12-ene V) 3-O-[β-galactopyranosyl(1→2)]-β-D-xyopyranosyl(1→3)-β-glucuronopyranosyl-21,22-O-diangeloyl-3β,16α,21β,22α,28-pentahydroxyolean-12-ene W) 3-O-[β-galactopyranosyl(1→2)]-β-D-xyopyranosyl(1→3)-β-D-glucuronopyranosyl-21-O— (3,4-diangeloyl)-α-rhamnopyranosyl-28-O-acetyl-3β,16α,21β,22α,28-pentahydroxyolean-12-ene X) 3-O-[β-galactopyranosyl(1→2)]-β-D-xyopyranosyl(1→3)-β-D-glucuronopyranosyl-21,22-O-diangeloyl-3β,16α,21β,22α,28-pentahydroxyolean-12-ene This invention provides a composition for inhibiting venous insufficiency, particularly hemorrhoids or inhibiting leg swelling, inhibiting cancer growth comprising any of the compounds selected from the following:

A1) 3-O-[β-D-galactopyranosyl(1→2)]-α-L-arabinofuranosyl(1→3)-β-D-glucuronopyranosyl-21-O-angeloyl,22-O-benzoyl-3β,15α,16α,21β,22α,28-hexahydroxyolean-12-ene, B1) 3-O-[β-D-galactopyranosyl(1→2)]-α-L-arabinofuranosyl(1→3)-β-D-glucuronopyranosyl-21-O-(3-angeloyl,4-benzoyl)-α-L-rhamnophyranosyl-22-O-acetyl-3β,16α,21β,22α,28-pentahydroxyolean-12-ene C1) 3-O-[β-D-glucopyranosyl-(1→2)]-α-L-arabinofuranosyl(1→3)-(-D-glucuronopyranosyl-21-O-angeloyl,22-O-benzoyl-3β,15α,16α,21β,22α,24β,28-heptahydroxyolean-12-ene D1) 3-O-[β-galactopyranosyl(1→2)]-α-arabinofuranosyl(1→3)-β-glucuronopyranosyl-21-O-angeloyl,22-benzoyl-3β,16α,21β,22α,28-pentahydroxyolean-12-ene E1) 3-O-[β-galactopyranosyl(1→2)]-α-arabinofuranosyl(1→3)-β-glucuronopyranosyl-21-O—F)(3-angeloyl,4-benzoyl)-α-rhamnopyranosyl-28-O-acetyl-3β,16α,21β,22α,28-pentahydroxyolean-12-ene F1) 3-O-[β-galactopyranosyl(1→2)]-α-arabinofuranosyl(1→3)-β-glucuronopyranosyl-21-O-angeloyl,22-O-benzoyl-3β,16α,21β,22α,28-pentahydroxyolean-12-ene G1) 3-O-[β-D-galactopyranosyl(1→2)]-α-L-arabinofuranosyl(1→3)-β-D-glucuronopyranosyl-21-O-benzoyl,22-O-angeloyl-3β,15α,16α,21β,22α,28-hexahydroxyolean-12-ene, H1) 3-O-[β-D-galactopyranosyl(1→2)]-α-L-arabinofuranosyl(1→3)-β-D-glucuronopyranosyl-21-O-(3-benzoyl,4-angeloyl)-α-L-rhamnophyranosyl-22-O-acetyl-3β,16α,21β,22α,28-pentahydroxyolean-12-ene I1) 3-O-[β-D-glucopyranosyl-(1→2)]-α-L-arabinofuranosyl(1→3)-(-D-glucuronopyranosyl-21-O-benzoyl,22-O-angeloyl-3β,15α,16α,21β,22α,24β,28-heptahydroxyolean-12-ene J 1) 3-O-[β-galactopyranosyl(1→2)]-α-arabinofuranosyl(1→3)-β-glucuronopyranosyl-21-O-benzoyl,22-O-angeloyl-3β,16α,21β,22α,28-pentahydroxyolean-12-ene K1) 3-O-[β-galactopyranosyl(1→2)]-α-arabinofuranosyl(1→3)-β-glucuronopyranosyl-21-O-(3-benzoyl, 4-angeloyl)-α-rhamnopyranosyl-28-O-acetyl-3β,16α,21β,22α,28-pentahydroxyolean-12-ene L1) 3-O-[β-galactopyranosyl(1→2)]-α-arabinofuranosyl(1→3)-β-glucuronopyranosyl-21-O-benzoyl,22-O-angeloyl-3β,16α,21β,22α,28-pentahydroxyolean-12-ene M1) 3-O-[β-D-galactopyranosyl(1→2)]-β-D-xyopyranosyl(1→3)-β-D-glucuronopyranosyl-21-O-angeloyl,22-O-benzoyl-3β,15α,16α,21β,22α,28-hexahydroxyolean-12-ene, N1) 3-O-[β-D-galactopyranosyl(1→2)]-β-D-xyopyranosyl(1→3)-β-D-glucuronopyranosyl-21-O-(3-angeloyl,4-dibenzoyl)-α-L-rhamnophyranosyl-22-O-acetyl-3β,16α,21β,22α,28-pentahydroxyolean-12-ene O1) 3-O-[β-D-glucopyranosyl-(1→2)]-β-D-xyopyranosyl(1→3)-(-D-glucuronopyranosyl-21-O-21-O-angeloyl,22-O-benzoyl-3β,15α,16α,21β,22α,24β,28-heptahydroxyolean-12-ene, P1) 3-O-[β-D-galactopyranosyl(1→2)]-β-D-xyopyranosyl(1→3)-β-D-glucuronopyranosyl-2121-O-angeloyl,22-O-benzoyl-3β,16α,21β,22α,28-pentahydroxyolean-12-ene Q1) 3-O-[β-galactopyranosyl(1→2)]-β-xyopyranosyl(1→3)-β-glucuronopyranosyl-21-O-(3-angeloyl,4-dibenzoyl)-α-rhamnopyranosyl-28-O-acetyl-3β,16α,21β,22α,28-pentahydroxyolean-12-ene, R1) 3-O-[β-galactopyranosyl(1→2)]-β-xyopyranosyl(1→3)-β-glucuronopyranosyl-angeloyl,22-O-benzoyl-3β,16α,21β,22α,28-pentahydroxyolean-12-ene, S1) 3-O-[β-D-galactopyranosyl(1→2)]-β-D-xyopyranosyl(1→3)-β-D-glucuronopyranosyl-21-O-benzoyl,22-O-angeloyl-3β,15α,16α,21β,22α,28-hexahydroxyolean-12-ene, T1) 3-O-[β-D-galactopyranosyl(1→2)]-β-D-xyopyranosyl(1→3)-β-D-glucuronopyranosyl-21-O-(3-benzoyl, 4-angeloyl)-α-L-rhamnophyranosyl-22-O-acetyl-3β,16α,21β,22α,28-pentahydroxyolean-12-ene, U1) 3-O-[β-D-glucopyranosyl-(1→2)]-β-D-xyopyranosyl(1→3)-(-D-glucuronopyranosyl-21-O-benzoyl,22-O-angeloyl-3β,15α,16α,21β,22α,24β,28-heptahydroxyolean-12-ene V1) 3-O-[β-galactopyranosyl(1→2)]-β-D-xyopyranosyl(1→3)-β-glucuronopyranosyl-21-O-benzoyl,22-O-angeloyl-3β,16α,21β,22α,28-pentahydroxyolean-12-ene W1) 3-O-[β-galactopyranosyl(1→2)]-β-D-xyopyranosyl (1→3)-β-glucuronopyranosyl-21-O— (3-benzoyl, 4-angeloyl)-α-rhamnopyranosyl-28-O-acetyl-3β,16α,21β,22α,28-pentahydroxyolean-12-ene X1) 3-O-[β-D-galactopyranosyl(1→2)]-β-D-xyopyranosyl (1→3)-β-D-glucuronopyranosyl-21-O-benzoyl,22-O-angeloyl-3β,16α,21β,22α,28-pentahydroxyolean-12-ene.

Triterpenoid saponins with the characteristic structures mentioned above in this invention can be used to inhibit venous insufficiency, particularly hemorrhoids or inhibit leg swelling, Triterpenoid saponins with the characteristic structures mentioned above in this invention can be used to reduce or inhibit cancer growth. The cancers are included but not limited to Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. Triterpenoid saponins with the characteristic structures mentioned above in this invention can be used to affect cell membrane structure and adhesion process. In an embodiment, it provides a method of binding with and adhesion proteins to blocks the migration, metastasis of cancer cells, growth of cancers.

In an embodiment, the compound is a triterpenoidal saponin or sapongenin, wherein the triterpenoidal saponin comprises at least any one or two of an angeloyl group, tigloyl group, or senecioyl group, or their combinations thereof at carbon 21 and/or 22, or 28, directly attached to the sapogenin or attached to a sugar moiety can be used to treat varicose vein disease, inhibit venous insufficiency, particularly hemorrhoids or inhibit leg swelling, reduce or inhibit cancer growth. In an embodiment, the compound is a five ring triterpene saponin comprising at least two angeloyl groups, tigloyl group, or senecioyl group, or their combinations thereof and a sugar moiety. The angeloyl groups are attached to a side chain at the end of the five rings and a sugar moiety is attached to a side chain of the ring at the other end of the five rings.

In an embodiment, the compound comprises at least two angeloyl groups, a tigloyl group, or a senecioyl group, or combinations thereof and a sugar moiety. The angeloyl groups and the sugar moiety are attached to the side chains of the backbone of the compound respectively. In an embodiment, the angeloyl can be replaced by a functional group which functions as an angeloyl group. In an embodiment, a sugar moiety or chain is at C3 or other positions, comprising one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof preferably D-glucose, D-galactose, L-rhamnose, L-arabinose, alduronic acids of D-glucuronic acid or D-galacturonic acid, or their combinations thereof, or their derivatives thereof. In a further embodiment, $CH_3$ or $CH_2OH$ or COOH or acetyl group may attach at C 23-30 independently. The activities of a saponin compound for regulating or inhibiting tumor cell growth are based on or attributed to its structure that has the functional group(s) such as angeloyl group, tigloyl group, senecioyl group or acetyl group, or their combinations thereof.

Both compound Y1 and Compound Y2 have two angeloyl groups and therefore, strongly inhibited the growth of cancer cells (See FIG. 4).

The compounds Y, Y1, Y2, Y8, Y9 and Y10 which all have two angeloyl groups and, therefore, inhibited the growth of ovarian cancer cells (See FIG. 5).

The compound (X) and Escin with single angeloyl groups showed weaker anticancer activity and hemolytic activity compared with the compounds with two angeloyl groups (See FIGS. 5, 6 and 7).

The compound without angeloyl groups has no anticancer and hemolytic activies (See FIGS. 4, 5, 6 and 7).

The compound with two angeloyl groups have stronger potency than the one with one angeloyl for reducing leg swelling, symptoms of chronic venous insufficiency, peripheral edema, antilipemic, chronic venous disease, varicose vein disease, varicose syndrome, venous stasis, expectorant and peripheral vascular disorders. This invention provides a composition comprising the compounds with the structure of:

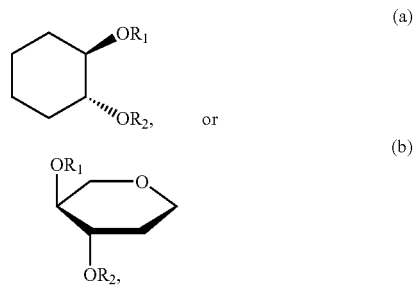

wherein R1 and R2 comprise angeloyl groups, tigloyl groups, senecioyl groups or acetyl group or their combinations, preferable wherein the R1 and R2 comprise angeloyl groups. In an embodiment, R1 and R2 comprise compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

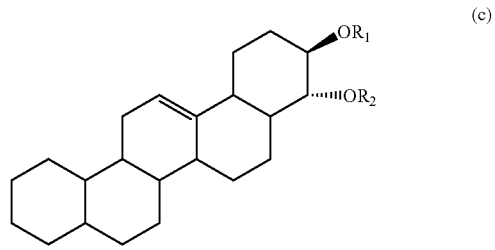

wherein R1 and R2 comprise angeloyl groups, tigloyl groups, senecioyl groups or acetyl group or their combinations, preferable wherein the R1 and R2 comprise angeloyl groups.

In an embodiment, R1 and R2 comprise compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound further comprises a sugar moiety.

In a further embodiment, the sugar moiety comprises glucose, galactose or arabinose or combination thereof.

In an embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In an embodiment, the R1 or R2 may be attached in other position of the structure.

(d)

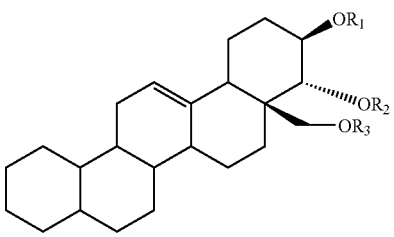

wherein R1, R2 or R3 comprise angeloyl groups, tigloyl groups, senecioyl groups or acetyl group or their combinations, preferable wherein at least two of the R1, R2 and R3 comprise angeloyl groups. In embodiment, at least two of R1, R2 and R3 comprise compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, at least one of R1, R2 and R3 comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound comprises a sugar moiety. In an embodiment, the sugar moiety is attached at one end of structure (d), opposite to R1, R2 and R3. In a further embodiment, the sugar moiety comprises glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof. In an embodiment, the R1, R2 and R3 may be attached in other position of the structure.

In an embodiment, the compound is triterpenoid saponin comprise comprises at least two angeloyl groups, tigloyl groups, senecioyl groups or acetyl group or their combinations, preferable wherein at least two angeloyl groups.

In an embodiment, at least two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, at least one of the side bonds comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound comprises a sugar moiety. In a further embodiment, the sugar moiety comprises glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof.

In an embodiment, a triterpene comprise the following structure has anti-cancer or inhibiting virus activities.

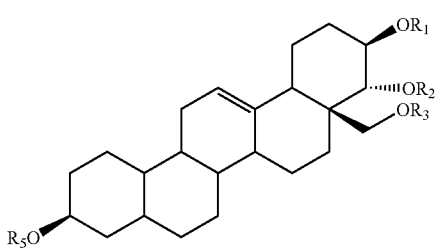

wherein R1, R2 or R3 comprise angeloyl groups, tigloyl groups, senecioyl groups or acetyl group or their combinations, preferable wherein at least two of the R1, R2 and R3 comprise angeloyl groups. In embodiment, at least two of R1, R2 and R3 comprise compounds selected from angeloyl, acetyl, tigloyl, senecioyl, alkyl, benzoyl, dibenzoyl, alkanoyl, alkenoyl, benzoyl alkyl substituted alkanoyl, aryl, heterocylic, heteroraryl, or acid with 2 to 5 carbon or derivative thereof.

In an embodiment, at least one of R1, R2 and R3 comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, R5 comprises a sugar moiety. In an embodiment, wherein the sugar moiety comprise glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof. In an embodiment, the R1, R2 and R3 may be attached in other position of the structure.

In an embodiment, the compound is triterpenoid saponin comprise comprises at least two angeloyl groups, tigloyl groups, senecioyl groups or acetyl group or their combinations, preferable wherein at least two angeloyl groups.

In an embodiment, at least two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, at least one of the side bonds comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, or acid with 2 to 5 carbon or derivative thereof.

In an embodiment, the compound comprises a sugar moiety. In a further embodiment, the sugar moiety comprises glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof.

In a further embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof.

A composition comprising an effective amount of compound selected from the above formula or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. In a further embodiment, a compound or sapongenin comprises the structure (d) or (e) has anti-cancer or inhibiting virus activities.

A composition for treating cancers or inhibiting virus, comprising a compound, wherein the compound is a triterpene, which comprises at least two side chains which comprise angeloyl groups, wherein the side chains are at adjacent carbon in trans position. In an embodiment, the side chains are at alternative carbon in cis position. In an embodiment, the side chains are at alternative carbon in trans position. In an embodiment, the side chains are in non-adjacent carbon cis or trans position. In an embodiment, the side chains comprise a functional group capable of performing the function of angeloyl group.

The above compounds can be used for inhibiting tumor cell growth, reducing leg swelling, symptoms of chronic venous insufficiency, peripheral edema, antilipemic, chronic venous disease, varicose vein disease, varicose syndrome, venous stasis, expectorant, peripheral vascular disorders, by administering to a subject in need thereof, an effective amount of the above described compounds.

This invention provides a method for inhibiting tumor cell growth, regulating cell growth, reducing inflammation, in a subject, comprising administering to a subject, in need thereof, an effective amount of the compound which comprises any of the above structures to said subject. The cancers are included but not limited to Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer.

This invention also provides a method for reducing swelling, reducing symptoms of chronic venous insufficiency, peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of leg pain; for treating pruritis, lower leg volume, for reducing symptoms of pain; thrombosis, thromophlebitis; for preventing gastric ulcers antispasmotic, comprising administering to a subject, in need thereof, an effective amount of the composition of this invention.

This invention provides a composition regulating the protein at the surface of the cell and the ions that pass through the cell.

This invention provides a composition comprising the compounds provided in the invention for treating bedwetting, enuresis and frequency micturition, and for improving the functions of the central nervous system including signaling the bladder to wake up from deep sleep or relaxing the bladder so that it can store more urine. The compounds provided in the invention also can be used to relax the detrusor tension caused by aging, stress, nervousness, over-activity, instability, hyperreflexia, and uninhibited bladder. In another embodiment, the compounds may be used for relaxing the contracted bladder tissue induced by acetylcholine (Ach). The compounds provided in this invention may be used as acetylcolinesterase, an AChE inhibitor, for regulating Antidiuretic hormone (ADH), which reduces the volume of urine, and as an anti-inflammatory agent.

The compounds provided in the invention can be used for accelerating the growth of bladder, suppressing deep sleep, increasing alertness in a sleeping subject, modulating the release, breakdown and uptake of antidieuretic hormone (ADH) and its receptors; modulating the secretion, breakdown and uptake of adrenocorticotropic hormone (ACTH) and its receptors, modulating the release, breakdown and uptake of 5-hydroxytryptamine, acetylcholine (Ach), adrenaline (AD), dopamine (DA), norepinephrine (NE) and their receptors; for preventing sleep paralysis, for modulating the formation, release, breakdown and activity of neuropeptides and their receptors.

This invention provides a method comprising compounds in this invention modulating the secretion, breakdown or uptake of adrenocorticotropic hormone (ACTH) or its receptors, This invention provides a composition regulating the protein on the surface of the cell or alters the functional properties of intracellular membranes. The compounds and compositions provided in this invention can regulate the water passing through the cell wall to soften the skin or improve the skin structure.

This invention provides a composition comprising the compounds provided in the invention for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, sever acute respiratory syndrome, respiratory viral diseases, chronic venous insufficiency, hypertension, chronic venous disease, anti-oedematous, anti inflammatory, hemonhoids, peripheral edema formation, varicose vein disease, flu, post traumatic edema and postoperative swelling; for inhibiting blood clot, for inhibiting ethanol absorption; for lowering blood sugar; for regulating the adrenocorticotropin and corticosterone level; and for treating impotence or premature ejaculation or diabetes (See PCT/US05/31900, filed Sep. 7,2006; U.S. Ser. No. 10/906,303, filed Feb. 14, 2005; International Application No. PCT/US04/43465, filed Dec. 23, 2004; International Application No.

PCT/US04/33359, filed Oct. 8, 2004 and U.S. Ser. No. 11/131,551, filed May 17, 2005, the contents of which are incorporated herein by reference).

This invention provides a composition for AntiMS, antianeurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, and venotonic treatment.

A composition comprising an effective amount of the compound of any one of Y0, Y1, Y2, Y(Y3), Y7, Y8, Y9, Y10, or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This composition can be administered orally or in a particular embodiment, it can be administered through intraperitoneal (I.P.), intravenous (I.V.) injection or intravenous drip.

In an embodiment, the medicine can be administered with glucose solution or NaCl solution. The administration of the medicine can be as intravenous injection or intravenous drip.

Example 1

Intravenous drip: 0.05-0.2 mg/kg medicine dissolved in 250 ml of 10% glucose solution or in 250 ml of 0.9% NaCl solution.

Example 2

Intravenous injection: 0.05-0.2 mg/kg/day medicine dissolved in 10-20 ml of 10% glucose solution or of 0.9% NaCl solution. Course of treatment: 7-10 days.

Example 3

Intravenous drip: 0.1-0.2 mg/kg/day medicine dissolved in 250 ml of 10% glucose solution or in 250 ml of 0.9% NaCl solution. Course of treatment: 7-10 days.

Example 4

Intravenous injection: 0.1-0.2 mg/kg/day medicine dissolved in 10-20 ml of 10% glucose solution or of 0.9% NaCl solution. Course of treatment: 7-10 days.

Example 5

Intraperitoneal (I.P.): 2.5 mg/kg/day medicine dissolved in 10% glucose solution or of 0.9% NaCl solution. Course of treatment: 7-10 days.

The composition can be administered orally wherein the dosage of mammal is 1-10 mg/Kg.

The composition can be administered orally wherein the dosage is 10-30 mg/Kg.

The composition can be administered orally wherein the dosage is 30-60 mg/Kg.

The composition can be administered orally wherein the dosage is 60-90 mg/Kg.

The composition can be administered intravenous injection or intravenous drip wherein the dosage of mammal is 0.01-0.1 mg/Kg.

The composition can be administered intravenous injection or intravenous drip wherein the dosage is 0.1-0.2 mg/Kg.

The composition can be administered intravenous injection or intravenous drip wherein the dosage is 0.2-0.4 mg/Kg, The composition can be administered intravenous injection or intravenous drip wherein the dosage is 0.4-0.6 mg/Kg.

The composition can be administered intraperitoneal (I.P.) wherein the dosage of mammal is 1-3 mg/Kg.

The composition can be administered intraperitoneal (I.P.) wherein the dosage is 3-5 mg/Kg.

The composition can be administered intraperitoneal (I.P.) wherein the dosage is 4-6 mg/Kg.

The composition can be administered intraperitoneal (I.P.) wherein the dosage is 6-10 mg/Kg.

This invention provides a method of treating a mammal for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, sever acute respiratory syndrome, respiratory viral diseases, chronic venous insufficiency, hypertension, chronic venous disease, anti-oedematous, anti inflammatory, hemonhoids, peripheral edema formation, varicose vein disease, flu, post traumatic edema and postoperative swelling; for inhibiting ethanol absorption; for lowering blood sugar; for regulating the adrenocorticotropin and corticosterone level comprising administering to said mammal a therapeutically effective amount of a pharmaceutical composition comprising a composition comprises the molecular formula or compound in this invention.

This invention provides a method of treating a mammal for treating cancers comprising administering to said mammal a therapeutically effective amount of a pharmaceutical composition comprising a composition comprises the molecular formula or compound in this invention. The cancers are included but not limited to: Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof.

See experiments results in FIG. 4-6 and FIG. 12-30

This invention provides a method comprising the compounds interacting with cancer cells and increases the static charge of the cells, which increase water flow into the cells. The cancer cells are collapsed. The compounds comprise Xanifolia Y0, Y1, Y2, Y, Y7, Y8, Y9, Y10, X or a salt, ester, metabolite or derivative thereof.

This invention also provides a method for treating cancers comprising administering to said mammal a therapeutically effective amount of a pharmaceutical composition comprising a composition comprises the molecular formula or compound in this invention. The cancers comprise Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof.

This invention describes a method interacting or regulating the protein on the surface of a cell or altering the functional properties of intracellular membranes or regulating the fluid passage through the cell wall to kill the cancer cells. The method comprising administering contacting an effective amount of compound selected from formula (1), (1A), (1B), (1C), (1D) preferable Xanifolia Y0, Y, Y1, Y2, Y7, Y8, Y9, Y10. In an embodiment the compound select from Xanifolia Y0, Y, Y1, Y2, Y7, Y8, Y9, and Y10 interact with the protein in the membrane and open up the channel for water or solute particle. The cell takes in water or solute particle and bursts.

In an embodiment the components of the compound select from Xanifolia Y0, Y, Y1, Y2, Y7, Y8, Y9, and Y10 combine with the protein in the membrane and open up the channel for water or solute particle. The cell takes in water or solute particle and bursts.

One or more aquaporin AQPs 1, 2, 3, 4, 5, 6, 7, 8, 9, 10 in the cancer cell membrane is overexpressed. So as providing more chance react with Xanifolia compound. Water or ion particle pass through the cell membrane the cancer cells The compound select from Xanifolia Y0, Y, Y1, Y2, Y7, Y8, Y9, and Y10 dilute the solution outside the cancer to make more water pass in the cell. The overexpress of Aquaporin of AQPs 1, 2, 3, 4, 5, 6, 7, 8, 9 or 10 provide more channel for water or ion particle which causes cancer cell die.

This invention provides a method of inhibiting cancer growth by destroys the cancer cell wherein aquaporin is overexpressed; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. In an embodiment, the cancer is ovarian cancer.

This invention provides a method of treating a mammal for treating cancers comprising administering to said mammal a therapeutically effective amount of a pharmaceutical composition comprising a composition comprises the molecular formula or compound in this invention. The cancers are included but not limited to Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof.

Alkenyl means unsaturated linear or branched structures and combinations thereof, having 1-7 carbon atoms, one or more double bonds therein. Non-limiting examples of alkenyl groups include vinyl, propenyl, isopropenyl, butenyl, s- and t-butenyl, pentenyl, hexenyl, butadienyl, pentadienyl, and hexadienyl.

An aryl is a functional group of organic molecule derived from an aromatic compound such as benzene, a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substitutes independently selected from halogen, alkyl or alkoxy.

Acyl is a functional group obtained from an organic acid by the removal of the carboxyl. Acyl groups can be written as having the general formula —COR, where there is a double bond between the carbon and oxygen. The names of acyl groups typically end in -yl, such as formyl, acetyl, propionyl, butyryl and benzoyl.

Benzoyl is one of acyls, $C_6H_5COR$, obtained from benzoic acid by the removal of the carboxyl.

Heterocyclic compound—a compound containing a heterocyclic ring which refers to a non-aromatic ring having 1-4 heteroatoms said ring being isolated or fused to a second ring selected from 3- to 7-membered alicyclic ring containing 0-4 heteroatoms, aryl and heteroaryl, wherein said heterocyclic comprises pyrrolidinyl, pipyrazinyl, morpholinyl, trahydrofuranyl, imidazolinyl, thiomorpholinyl, and the like.

Heterocyclyl groups derived from heteroarenes by removal of a hydrogen atom from any ring atom.

Alkanoyl is the general name for an organic functional group RCO—, where R represents hydrogen or an alkyl group. Preferably alkanoyl is selected from acetyl, propionoyl, butyryl, isobutyryl, pentanoyl and hexanoyl.

Alkenoyl is alkenylcarbonyl in which alkenyl is defined above. Examples are pentenoyl(tigloyl) and hexenoyl(angeloyl).

Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl.

Benzoyl alkyl substituted alkanoyl is refer to straight or branched $C_1$-$C_6$ alkanoyl substituted with at least one benzoyl and at least one alkyl, wherein the benzoyl is attached to a straight or branched $C_1$-$C_6$ alkyl. Preferably a benzoyl alkyl substituted alkanoyl is benzoyl methyl isobutanoyl.

A sugar moiety is a segment of molecule comprising one or more sugars or derivatives thereof or alduronic acid thereof.

Isobutyryl is Synonym of 2-Methylpropanoyl

Y and Y3 represent the same compound.

To investigate the anti-tumor activity of *Xanthoceras sorbifolia*, we employed cancer cell lines derived from different human organs and tested the effect on growth activity. In these preliminary studies, we found that the plant extract inhibits the growth of certain cell lines. We studied 10-15 cell-lines (derived from different human organs) with a MTT cell-growth assay, and found that OVCAR3 cells (from ovary) to be the most sensitive (with IC50=14.5 ug/ml). Int'l App'l No. PCT/US04/33359 and U.S. Ser. No. 10/906,303

The active compound was then purified and named Xanifolia-Y. Its chemical structure was determined by 2D NMR and MS analysis. Xanifolia-Y is a novel triterpenoid saponin with a diangeloyl group attached at one end and carbohydrates or sugar moieties at another end of the triterpene structure. In an embodiment, the diangeloyl attached at C21, C22 positions and carbohydrates or sugar moieties at C3 position of a triterpene structure. The diangeloyl group is important for its activity.

The purified compound has been tested with 60 cancer cell lines. Test results show inhibition towards most cell lines tested with GI50 values ranging from 0.1-1 uM. OVCAR3 cells, cancer cells derived from ovary, are the most sensitive to Xanifolia-Y among cell lines tested in our early studies. We subsequently tested 10 additional human ovarian cancer cell lines and found all of them to be susceptible to inhibition by Xanifolia-Y with IC50 values ranging from 2-12 uM. See experiment 10

In vivo studies employing human ovarian carcinoma xenografts in nude mice were performed. The human ovarian cancer cells (ES2) were inoculated into the peritoneal cavity of nude mice and subsequently received Xanifolia-Y. (Experiment 7, 8, 9). The tumor bearing mice received the drug (by i.p. route) for 10 days starting from either day 1, day 4, or day 10 after inoculations. The results show that the median survival time for tumor bearing mice without drug-treatment is approximately 20-24 days. However, there was no death for tumor bearing mice with drug-treatment starting on day 1 after tumor inoculation. The median survival time for tumor bearing mice with drug-treatment starting on day 4 after tumor inoculation is no death in 50 days; and tumor bearing mice with drug-treatment started on day 10 after tumor inoculation is half of the mice survive in 50 days. These results indicate that the compounds of this invention are capable of increasing the survival rate of mammal.

The median survival time for tumor bearing mice with drug-treatment starting on day 4 after tumor inoculation is 58 days (extension of life span of 141%); and tumor bearing mice with drug-treatment started on day 10 after tumor inoculation is 31 days (extension of life span of 29%). These results indicate that Xanifolia-Y is capable of extending the life span of mammal bearing tumors. It is useful in treating ovarian cancer in humans.

These results indicate that Xanifolia-Y is capable of extending the life span of mammal bearing tumors. It is useful in treating ovarian cancer in humans.

Among gynecological malignancies, ovarian cancer has the highest rate of mortality in women in the United States with an estimated 22,220 new cases in 2005 and over 16,000 deaths (NIH web info). The disease is often missed in diagnosis in the early stage due to asymptomatic and the lack of reliable diagnostic marker. As a result, most of the ovarian cancer patients being diagnosed are already at advanced stages. The standard treatment of ovarian cancer is a combination of a platinum analogue with paclitaxel (McGuire et al., 1996; Ozols et al., 2003). Improved patients survival time was observed in patients with intraperitoneal administration of these agents (Armstrong et al., 2006). The peritoneal cavity is the principal site of disease in ovarian cancer. The improved efficacy of these agents could be due to a more direct interaction with cancer cells. However, the increase of median survival from 49.7 to 65.6 months is still far from satisfactory.

As mentioned above, our in vivo animal experiments mimicking the human situation showed that Xanifolia-Y is effective in prolonging mammal life span. Mice were inoculated with human ovarian carcinoma (ES2) in the peritoneal cavity. Starting from the mid-way (time to mortality) point of tumor progression (considered as a late stage of disease in human), drug was then administered into the peritoneal cavity. It was found that Xanifolia-Y treatment is beneficial to tumor bearing mice by prolonging their life span. Depending on the stage of the disease progression, the sooner the start of the drug-treatment, the better the results are.

Based on our results, it can prolonged the life-span of tumor bearing mice after Xanifolia-Y-treatment is due to blockage of the migration or metastasis of inoculated cancer cells into the mesothelium lining in the peritoneal cavity. In vitro studies show that Xanifolia-Y inhibits cell adhesion to culture flasks (See Experiment 13). It is known that adhesive molecules play an important role in the migration and metastasis of ovarian cancer (Skubitz, 2002, Schaller, 1996; Zetter, 1993). A major route for the spread of ovarian cancer is by the attachment of tumor cells to the mesothelium lining in the peritoneal cavity (Gardner et al., 1995). Xanifolia-Y blocks the function of these adhesive molecules on cells. In an embodiment, Xanifolia-Y blocks the function of these adhesive molecules on carcinoma cells. In an embodiment, Xanifolia-Y blocks the function of these adhesive molecules on ovarian carcinoma cells. In an embodiment, Xanifolia-Y blocks the function of these adhesive molecules on the mesothelial cells. In an embodiment, Xanifolia-Y binds to the adhesive proteins (by masking) on the membrane and inhibits the interaction of adhesion proteins with their receptors. In an embodiment, Xanifolia-Y action on membrane affects adhesion proteins' function in membrane. The lost of adhesion activity of cancer cells is result from direct or indirect action of Xanifolia-Y on membrane proteins.

Most of the adhesion proteins are glycoproteins. The carbohydrate moiety in adhesion proteins interact with carbohydrates from other molecules, such as saponin or Xanifolia-Y. Xanifolia-Y has a trisaccharide at the C3 position and it was found that a loss of carbohydrates reduces its activity (FIGS. 4D and 5C). Our EM studies show that Xanifolia-Y affects membrane structure and makes holes. Damage to the membrane structure could alter adhesion protein's conformation and interfere with their binding with other molecules or even cause them to lose their anchorage on membrane.

Our studies of Xanifolia-Y indicate it can be used in cancer therapy, especially as a benefit to patients with late stage ovarian cancer. They indicate that our determined saponins and formulas are useful in cancer therapy by demonstrating its inhibition of tumor growth in mammal systems.

We labeled Xanifolia-Y as ligands and used it to confirm its bindings, such as its location on cells, binding to adhesion proteins or other target protein with RIA, investigate its associated proteins with co-IP and verify them with competition assay. We confirm Xanifolia-Y as an anticancer agent. Specifically we determine tumor nodule growth in peritoneal cavity during Xanifolia-Y treatment.

Xanifolia-Y blocks cancer migration and metastasis. In an embodiment, it blocks ovarian cancer migration and metastasis. Xanifolia-Y has effect on membrane and adhesion proteins.

To study the effect of Xanifolia-Y on membrane structure, the morphology of cell membrane treated with Xanifolia-Y was examined with EM. In this experiment, K562 cells were treated with 5 uM of Xanifolia-Y for 60 min. Solvent DMSO and AKOH—Y (a derivative of Xanifolia-Y without the angeloyl group and it has no activity) served as controls. Cells were negative stained with 1% UAc and subsequently examined with EM. FIG. 34 show that patches of pits were found in the membrane of Xanifolia-Y treated cells (FIG. 34B) but not in cells treated with the DMSO (FIG. 34A) or AKOH—Y (FIG. 34C) controls. These pits have the size from 80 A to 500 A (in diameter). The pits represent holes formed in the membrane. The pits are arranged in a characteristic pattern with smaller pits (80 A in diameter) located in the periphery and the bigger ones (500 A in diameter) in the center. The bigger holes are resulted from fusing of the smaller holes (FIG. 34D). Membrane image of cells treated with A: DMSO solvent control, 60 min (magnification: ×60,000); B: Xanifolia-Y 5 uM, 60 min. (×60000); C: AKOH—Y, 20 uM, 60 min. (×60000); D: Xanifolia-Y 5 uM, 60 min. (×20000). This experiments results show that the Xanifolia-Y alters the membrane of cell. In an embodiment, it damage the membrane of cancer cell.

See FIG. 34

Xanifolia-Y can be used for inhibiting cancers cell growth or treating cancers wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the cancer is preferably ovarian cancer. Among the different cell lines tested in our studies, carcinoma cells derived from ovary proved to be the most sensitive, a finding which is substantiated with more human ovarian cancer cell lines. The results of animal studies with human tumor xenograft in mice show that it can extend the life span of mice bearing tumors. The compounds of this application can extend the life span of mammal bearing human cancer.

Cancer drugs that target on membrane or membrane constituents are not explored. Xanifolia-Y is a new drug. It has effects on cell membrane, a target that differs from current anticancer drugs.

This invention provides a method of altering the characteristic of cancer cell membrane to block the migration, metastasis of cancer cells or inhibit the growth of cancers or anti-angiogenesis.

This invention provides a method of inhibiting the growth, migration, metastasis of cancer by altering the characteristic of membrane of cancer cell, wherein the characteristic comprise adhesion protein; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting Xanifolia Y0, Y1, Y2, Y, Y7, Y8, Y9, Y10, or a salt, ester, metabolite thereof.

This invention provides a method of inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting Xanifolia Y0, Y1, Y2, Y, Y7, Y8, Y9, Y10, or a salt, ester, metabolite thereof. In an embodiment the method is administering contacting the compound selected from formula in this application. This invention provides a composition for inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This application shows Xanifolia-Y is an alternate or supplemental agent to DNA-inhibition or microtubule-targeting drugs. It could be beneficial if it is used singly or in combination with other drugs of different mechanisms (block M-phase progression or DNA synthesis). Our inventions show combined effect of Xanifolia-Y and paclitaxel on inhibition of ES2 cells' growth (Detail in Experiment 14)

Identify the binding target of Xanifolia-Y of adhesion proteins and signaling proteins in ovarian cancer cells.

In our animal studies, it was shown that Xanifolia-Y extended the life span of tumor bearing mice. (See Experiments 7, 8, 9). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion is blocking of the protein accessibility due to direct binding to Xanifolia-Y, In an embodiment, the interaction of Xanifolia-Y with membrane alter indirectly the adhesion protein's binding site(s).

We have shown that Xanifolia-Y are cytotoxic to tumor cells, In an embodiment it kills ovarian cancer cells. Our inventions show that Xanifolia-Y inhibits cancer cell growth and prolongs life-span of tumor bearing mice. Our studies also indicate that the sooner the drug-treatment, the longer the life-span of the tumor bearing animals is extended. Xanifolia-Y also has an effect in blocking or inhibiting migration or metastasis. The delay of Xanifolia-Y-treatment allows more chances for cancer cells to metastasize to the mesothelium lining in the peritoneal cavity which resulted in more tumor growth and shorter life span. Adhesive molecules play an important role in cell migration and metastasis. It was shown in our studies that Xanifolia-Y inhibits cell attachment to culture flasks. Xanifolia-Y interferes with the function of the adhesive molecules. In embodiment Xanifolia-Y blocks the function of the adhesive molecules. In an embodiment, Xanifolia-Y binds directly to adhesive proteins. It is masking the adhesive proteins. In an embodiment, Xanifolia-Y indirectly alters membrane structure that cause changes in protein conformation, or locations and result in loss of adhesion process.

Experimental Details

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure are disclosed in PCT/US05/31900, U.S. Ser. No. 11/289,142, U.S. Serial 10/906,303, and U.S. Ser. No. 11/131,551, the contents of which are incorporated herein by reference.

Experiment 1

Determination of the Hemolytic Activities of Compound Y from *Xanthoceras sorbifolia*

Methods:
  Human whole blood was obtained from the Houston Gulf Coast Blood Center.
  Red blood cells were isolated by the following method: Human blood (in EDTA) was diluted 1:1 with PBS, underlay with 4 mL of Histopaque-1077 (SIGMA) and was centrifuged at 400 g for 30 min.
  Red blood cells (RBC) were collected and washed three times with PBS.
  10% suspensions of RBC were prepared with PBS before use.
  50 μL of RBC suspension was added to 2 mL of saponins with different concentration.
  The suspension was mixed by vortexing then left to sit at room temperature for 60 minutes.
  The suspension was centrifuged at 3000 rpm for 5 min.
    Absorbance of the supernatant was measured at 540 nm.

Results:

In this experiment, hemolytic activities of human red blood cells by Xanifolia-Y (#63Y), Escin and SIGMA saponin standard were compared. Y contains two angeloyl groups, Escin has one angeloyl group and SIGMA saponin standard is a mixture of saponins from *Quillaia* bark. The results show that #63Y (compound Y) has higher hemolytic activity (IC50=1 μg/mL) than Escin or SIGMA saponin standard (IC50=5 μg/mL). See FIG. 6 A.

Experiment 2

Determination the Hemolytic and MTT Activities of Compound Y After Removal of the Angeloly Group or the Sugar Moiety by Alkaline or Acid Hydrolysis, Respectively Methods:

(A) Alkaline Hydrolysis of Xanifolia-Y: 20 mg of Xanifolia-Y was dissolved in 0.5 mL of 1 M NaOH. The solution was incubated in an 80° C. water bath for 4 hours. It was cooled to room temperature before being neutralized with 0.5 mL 1 N HCl (adjusted pH to about 3). The mixture was extracted with 2 mL 1-butanol 3 times. The butanol fractions were collected and lyophilized. The hydrolyzed saponin was further purified with HPLC in a C-18 column eluted with 25% acetonitrile.

(B) Acid Hydrolysis of Xanifolia-Y: 15 mg Xanifolia-Y was dissolved in 1 mL of Methanol. 1 mL of 2N HCl was then added. The mixture was refluxed in an 80° C. water bath for 5 hours. The solution was then neutralized by adding 2 mL of 1 N NaOH (to a final pH 3-4). The aglycone was then extracted with ethylacetate 3 mL×3. The extracts were collected and pooled. Further isolation of aglycone (sugar-removed Xanifolia-Y) was achieved by HPLC with isocratic elution of 80% acetonitrile.

Results:

The angeloly groups or the sugar moiety of the compound Y were removed by alkaline or acid hydrolysis respectively. The hemolytic activities of the hydrolysed products were then analyzed. Results of these studies indicate that removing sugars from the compound Y reduced hemolytic activity, but removing the angeloyl groups from the compound Y destroyed the hemolytic activity. It also suggested that sugars are helpful but not essential for hemolytic activity. See FIG. 4D. The experiment results show that compound-Y lost MTT activities if the angeloyl groups were removed. However, the MTT activities became very weak when the sugar moiety of the compound was removed. See FIG. 5 C, 5 D. Results of comparison of hemoyltic activities between Compound Y, Escin from SIGMA are shown in FIG. 7. Results of the comparison of hemolytic activities between compound Y, compound Y without sugar moiety or angeloly groups are shown in FIG. 6 A, 6B. Chemical structures of compound Y without sugar moiety (ACH—Y) or angeloly groups (AKOH—Y) are shown in FIG. 7 respectively.

Experiment 3

Effects of Xanifolia-Y on Reduction of Venous Insufficiency, Particularly Hemorrhoids Methods:

SD rats, male, age-matched 7-8 weeks old weighing 163±18 g were in the experiment. The tested animals were allowed to acclimate for a week.

A cotton swab with a diameter of 4 mm soaked with 0.16 mL of inducer (deionized water: pyridine: ethyl ether: 6% croton oil/ethyl ether, 1:4:5:10) was applied to the rat's anus for 12 seconds. The final concentration of croton oil was 3%. The edema developed linearly until 7-8 hours after application and the severity of the edema was sustained for more than 24 hours. Twenty-four hours later, recto-anus tissue (approx. 10 mm long) was isolated after the rats were euthanized. The weights of rat body and recto-anus were measured. The recto-anus coefficient (RAC) was calculated using the formula: weight of recto-anus (mg)/body weight (g).

RAC=weight of recto-anus (mg)/body weight (g)×100%

The rates were randomly divided into 5 groups: control, positive control and 3 test groups, and each group had 8 rats. The dose for 3 groups of rats are 10, 20 and 40 mg/kg. The dose of 0.5% CMC—Na for control group is the same as the each test group. The tested drug was fed into the stomach on the morning, once a day before the animal modeling for 5 days. The anus suppository was applied to positive control once after the animal modeling (1 mL/100 g). The weights of recto-anus and RACs were calculated, compared with the controls and subject to a student t-test.

Results

The edema formed 30 minutes after the treatment. The rats were euthanized 22 hours after the last administration. The results showed that Xanifolia Y significantly reduced the swelling of the recto-anus of rats (Table 1).

TABLE 1

Effects of Xanifolia Y on reduction of swelling of the recto-anus of rats

| Group | Weight of recto-anus (g) | RAC | Reduction rate % |
|---|---|---|---|
| Modeling | 6.20 ± 0.77 | 2.33 ± 0.36 | |
| 10 mg/Kg | 4.68 ± 0.77* | 1.83 ± 0.36* | 21.5 |
| 20 mg/Kg | 4.28 ± 0.60** | 1.61 ± 0.24** | 30.9 |
| 40 mg/Kg | 3.97 ± 0.65** | 1.51 ± 0.23** | 35.1 |
| Anus suppository | 3.90 ± 0.80 | 1.54 ± 0.36 | 33.9 | n = 8, X ± SD,
*p < 0.05,
**p < 0.01

Experiment 4

Effects of Xanifolia Y on Reduction of the Swelling of Rats' Feet in the Carrageenin-Induced Swollen Feet Model in Rats Method:

SD rats, male, weighing 163±18 g were used in the experiment. The tested animals are allowed to acclimate for a week. The rats drink water freely. The rats were randomly divided into 5 groups: control, positive control and 3 test groups, and each group had 8 rats. The dose for 3 groups of rats are 10, 20 and 40 mg/kg. Indometacin for the positive control is 10 mg/kg and fed once after modeling. The dose of CMC—Na for the control group is the same as each test group and fed into the stomach once a day before modeling for 5 days. The tested drug was fed into the stomach 10 minutes before the animal modeling (1 mL/100 g). The volumes of right foot of each rat were measured 0.5, 1, 2 and 4 hours before and after modeling. The volumes of the right hind feet were measured at a different time, 10 minutes after inflammation induced by subcutaneous injection (with syringe needle 7) of 0.05 mL of the 1% of Carrageenin/normal saline mixture into the feet.

The Rate of swelling of the feet was calculated, compared with the controls and subject to a student t-test.

Rate of swelling (E) (%)=$L_{tn}-L_{t0}/L_{t0}\times100\%$ $L_{tn}$: volume of foot after the inflammation
$L_{t0}$: volume of foot before the inflammation Results:

The results of this experiment showed Xanifolia Y significantly reduced swelling of the feet and the effect was related to the dosages. (Table 2).

TABLE 2

Effects of Xanifolia Y on reduction of swelling of rats' feet induced by Carrageenin

| Group | Dosage(mg/kg) | Swelling rate after administration (%) | | | |
|---|---|---|---|---|---|
| | | 0.5 hour | 1 hour | 2 hours | 4 hours |
| Modeling | | 22.6 ± 8.1 | 27.6 ± 8.2 | 23.0 ± 10.1 | 12.9 ± 6.1 |
| Test | 10 | 16.7 ± 3.8 | 18.5 ± 6.2 | 16.0 ± 5.9 | 10.5 ± 7.2 |
| Test | 20 | 10.5 ± 4.1** | 13.6 ± 4.2** | 12.4 ± 5.3* | 8.5 ± 5.4 |
| Test | 40 | 10.3 ± 3.3** | 12.6 ± 4.7** | 12.5 ± 6.2* | 6.5 ± 5.4 |
| Indometacin | 10.0 | 11.8 ± 4.3** | 14.7 ± 6.5* | 12.8 ± 7.0** | 10.7 ± 8.8 | n = 8, X ± SD,
*p < 0.05,
**p < 0.01 Student-t

Experiment 5

Purification of the Inhibition Components in the *Xanthoceras Sorbifolia* Extract (A) Fractionation of Plant Extracts with FPLC Methods Column. Octadecyl functionalized silica gel. Column dimension: 2 cm×28 cm; equilibrated with 10% acetonitrile-0.005% TFA before use.

Sample loading: 1-2 ml, concentration: 100 mg/ml in 10% acetonitrile/TFA.

Gradient elution condition: 10-80% acetonitrile in a total volume of 500 ml.

Monitor absorption wavelength: at 254 nm.

Fraction Collector: 5 ml/fractions (collect from 10% to 72% acetonitrile)

Instrument: AKTA-FPLC, P920 pump; Monitor UPC-900; Frac-900.

Results

The elution profile of the chromatography shows 4-5 broad fractions. These fractions were analyzed with HPLC. Specific components, corresponding to a-z in these FPLC fractions. FPLC fractions are then grouped into 7 pools and analyzed for cell growth activity with MTT assay. The fractions contain inhibition activity can be found. (See PCT/US05/31900, filed Sep. 7, 2006; U.S. Ser. No. 10/906,303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, the contents of which are incorporated herein by reference).

(B) Isolation of Component Ys with Preparative HPLC

Methods

Column: A preparative HPLC column (Waters Delta Pak C18-300A);

Elution conditions: 45% acetonitrile isocratic elution with flow rate of 1 ml/min.

Fractions are monitored at 207 nm and were collected and lyophilized.

Results

Final separation of Y fractions was achieved by HPLC with a preparative column. These fractions, which include compound Y0, Y1, Y2, Y (Y3) and Y4, were collected. Re-chromatography of compound Y showed a single peak in HPLC with a C18 reverse phase column. Re-chromatography of the compound Y8, Y9 and Y10 showed a single peak in HPLC with a C18 reverse phase column.

(C) Appearance and Solubility

The pure compound Ys is an amorphous white powder, soluble in aqueous alcohol, i.e., methanol or ethanol, 50% acetonitrile and 100% pyridine.

(D) Inhibition Analysis of Compound Ys with Mtt Assay

Inhibition analysis of compound Y was determined with MTT assay. FIG. 5A shows the inhibition activities of compound Y, Y8, Y9 and Y10 on the growth of ovarian cancer cells (OCAR-3). FIG. 28 shows the inhibition activities of compound Y(Y3), Y0, Y1 and Y2 on the growth of ovarian cancer cells (OCAR-3)

Experiment 6

Determination of the Chemical Structure

Methods

NMR analysis. The pure compound Y of *Xanthoceras sorbifolia* was dissolved in pyridine-D5 with 0.05% v/v TMS. All NMR spectra were acquired using a Bruker Avance 600 MHz NMR spectrometer with a QXI probe (1H/13C/15N/31P) at 298 K. The numbers of scans for 1D 1H spectra were 16 to 128, depending on the sample concentration. 2D HMQC spectra were recorded with spectral widths of 6000× 24,000 Hz and data points of 2024×256 for t2 and t1 dimensions, respectively. The number of scans was 4 to 128. 2D HMBC were acquired with spectral widths of 6000×30,000 Hz and data points of 2024×512 for t2 and t1 dimensions, respectively. The number of scans was 64. The 2D data were zero-filled in t1 dimension to double the data points, multiplied by cosine-square-bell window functions in both t1 and t2 dimensions, and Fourier-transformed using software XWIN-NMR. The final real matrix sizes of these 2D spectra are 2048×256 and 2048×512 data points (F2×F1) for HMQC and HMBC, respectively.

Mass spectral analysis. The mass of samples was analyzed by (A) MALDI-TOF Mass Spectrometry and by (B) ESI-MS Mass spectrometry. (A) Samples for MALDI-TOF were first dissolved in acetonitrile, and then mixed with the matrix CHCA, i.e., Alpha-cyano-4-hydroxycinnamic acid, 10 mg CHCA/mL in 50:50 water/acetonitrile and 0.1% TFA in final concentration. The molecular weight was determined by the high resolution mass spectroscope analysis with standards. (B) For ESI, the sample was analyzed with LCQ DECA XP Plus machine made by Thermo Finnigan. It is ionized with ESI source and the solvent for the compound is acetonitrile.

Results

Figure 11:
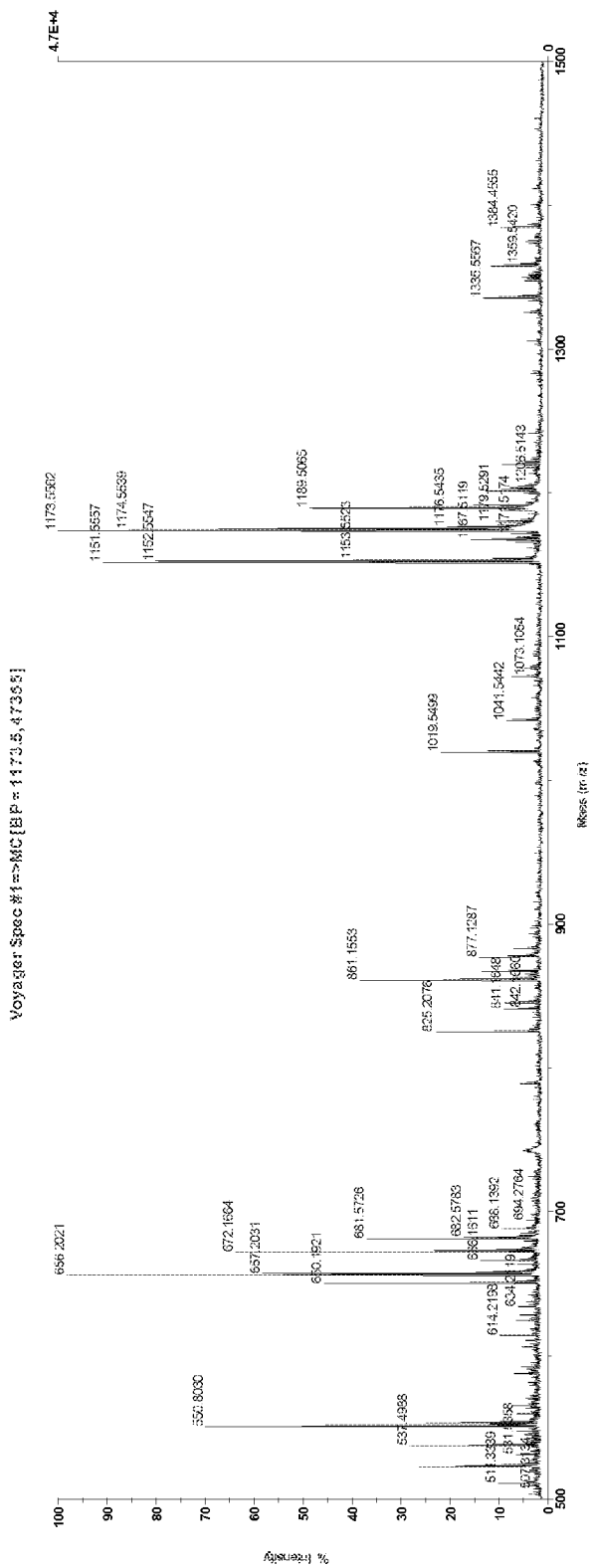
Figure 12:
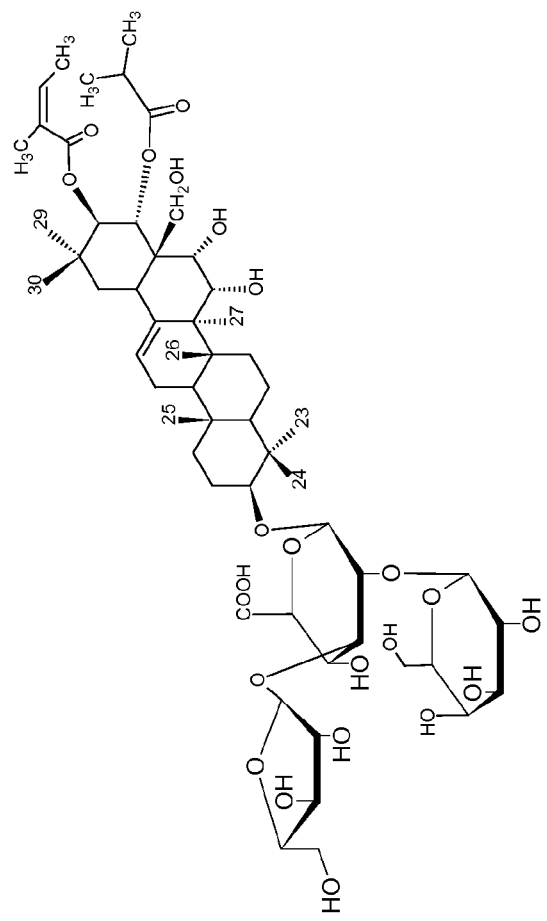
Figure 15:
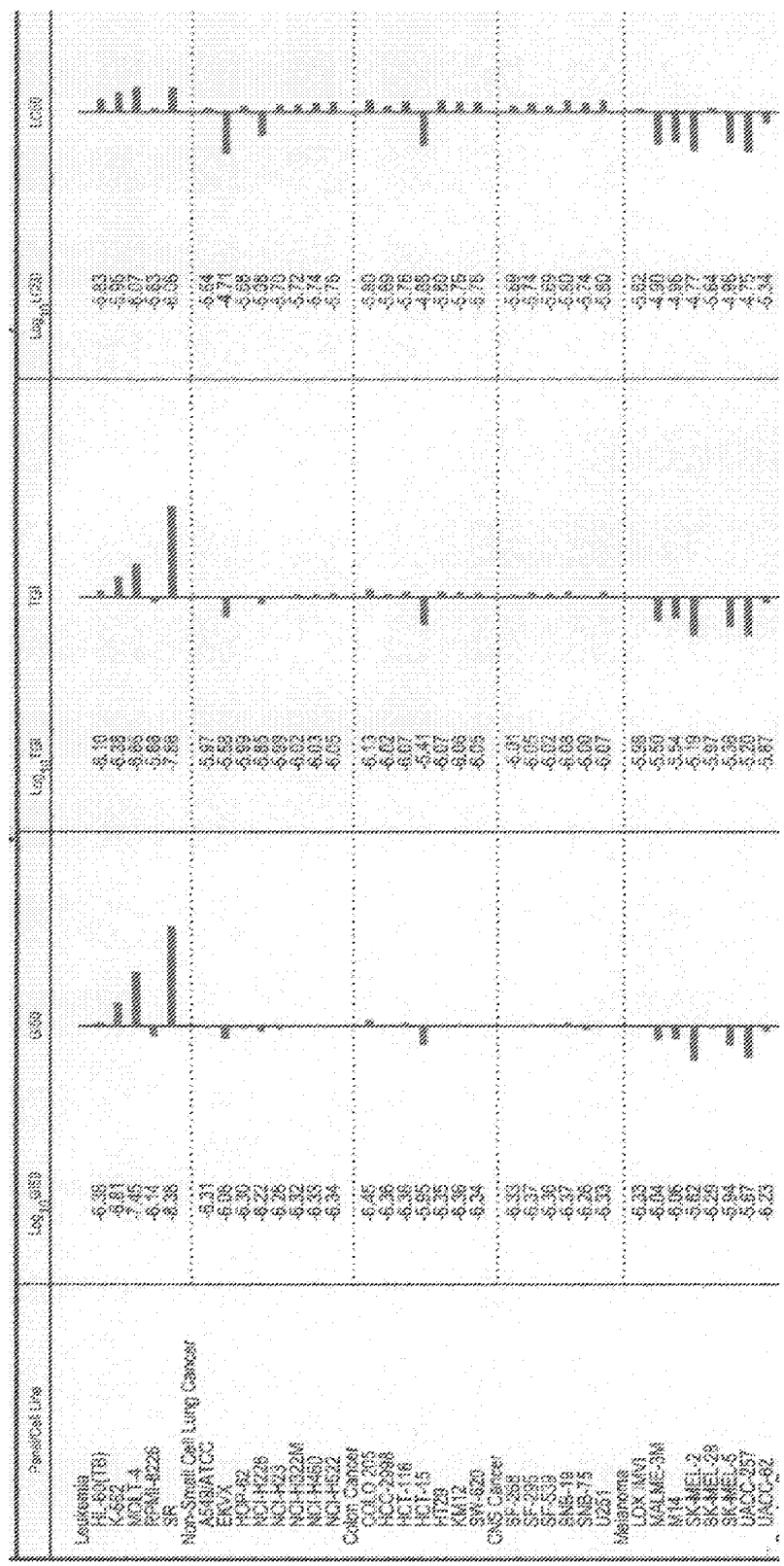
Figure 16:
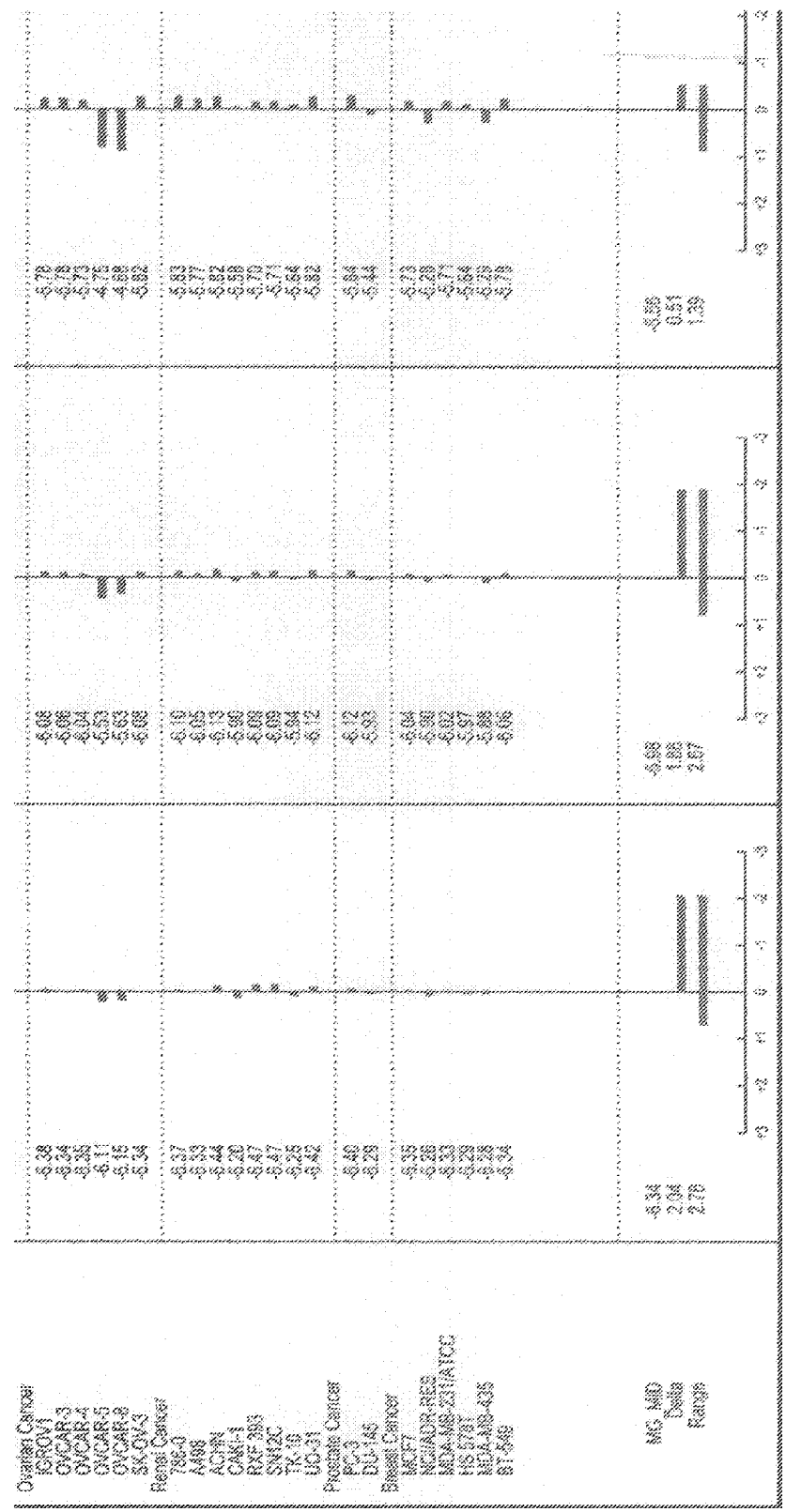
Figure 17:
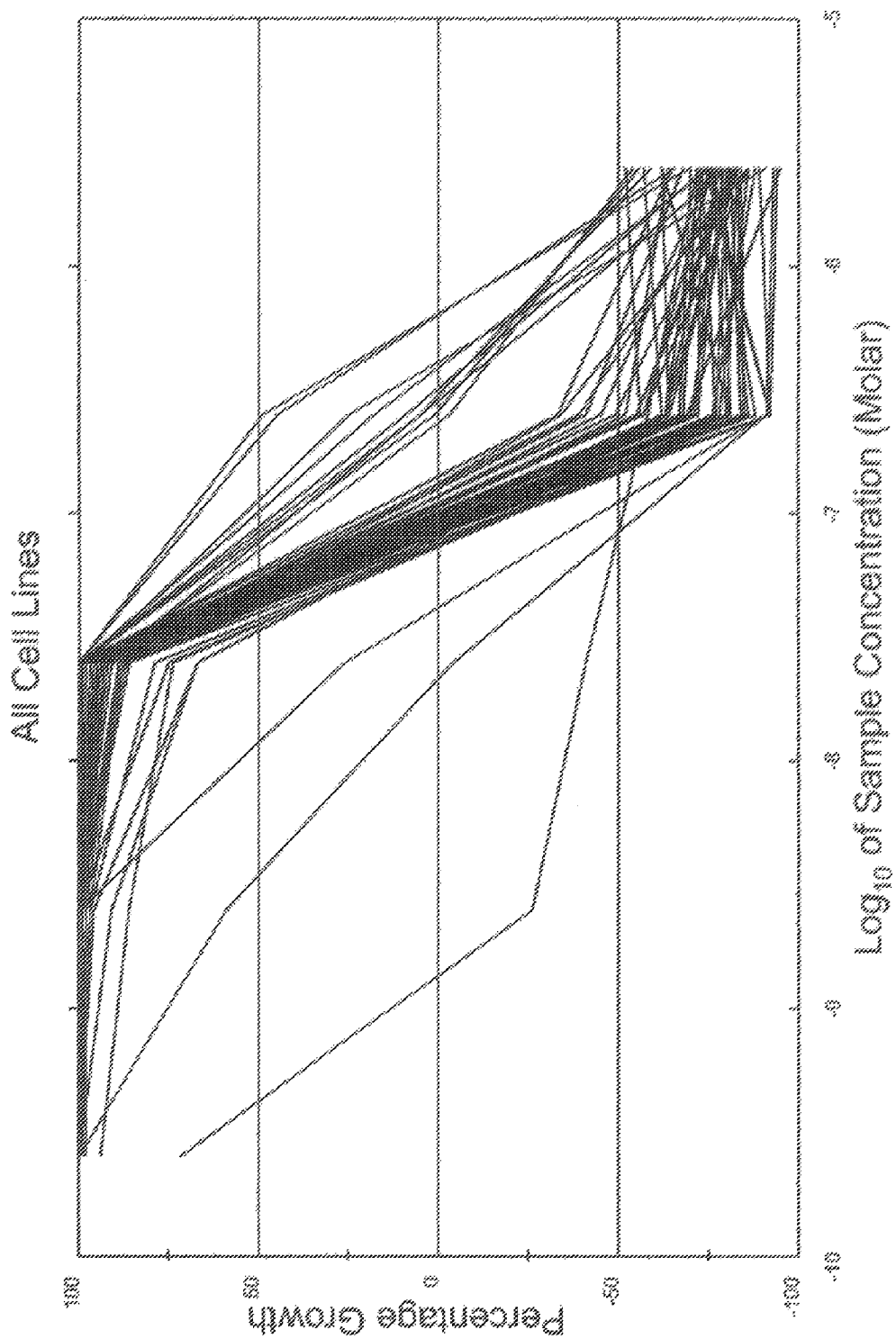
Figure 18:
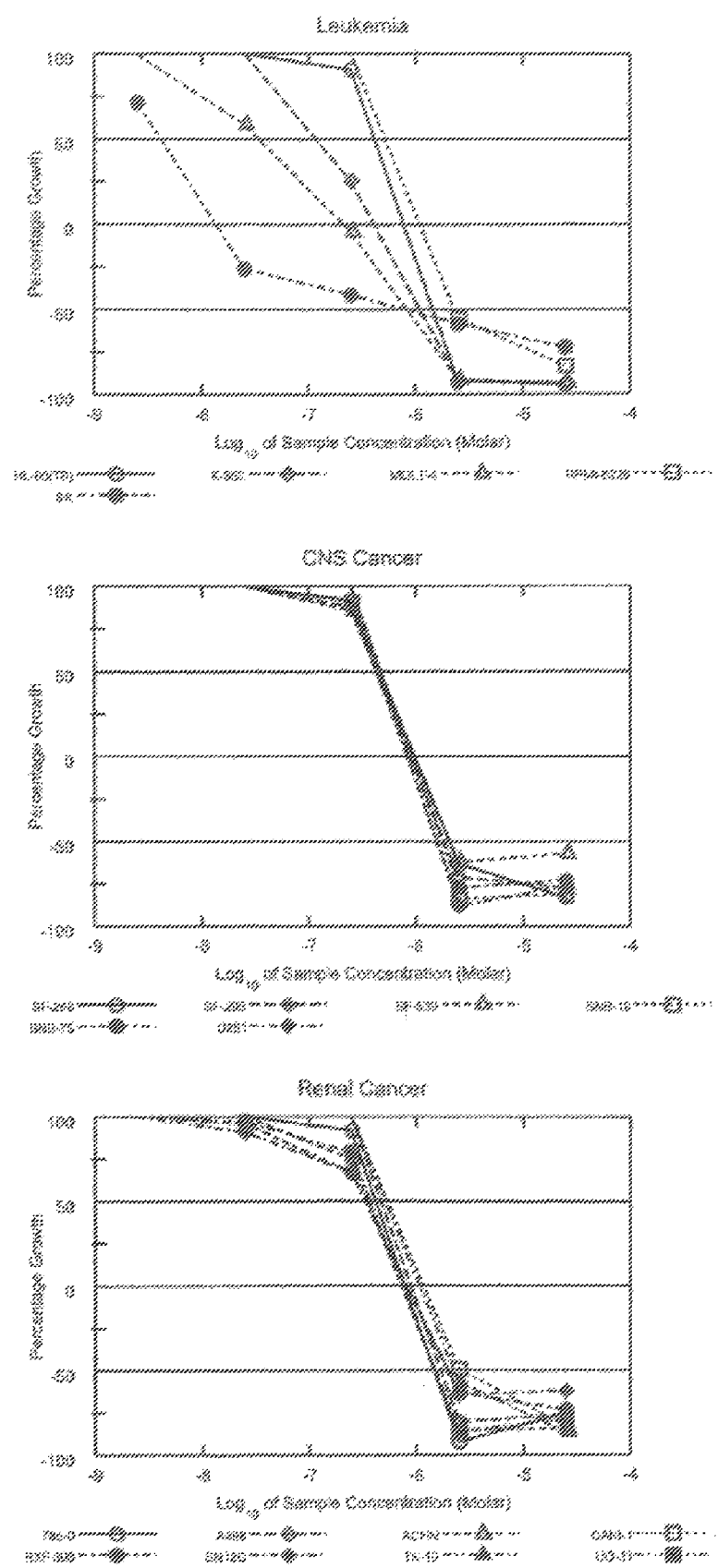
Figure 19:
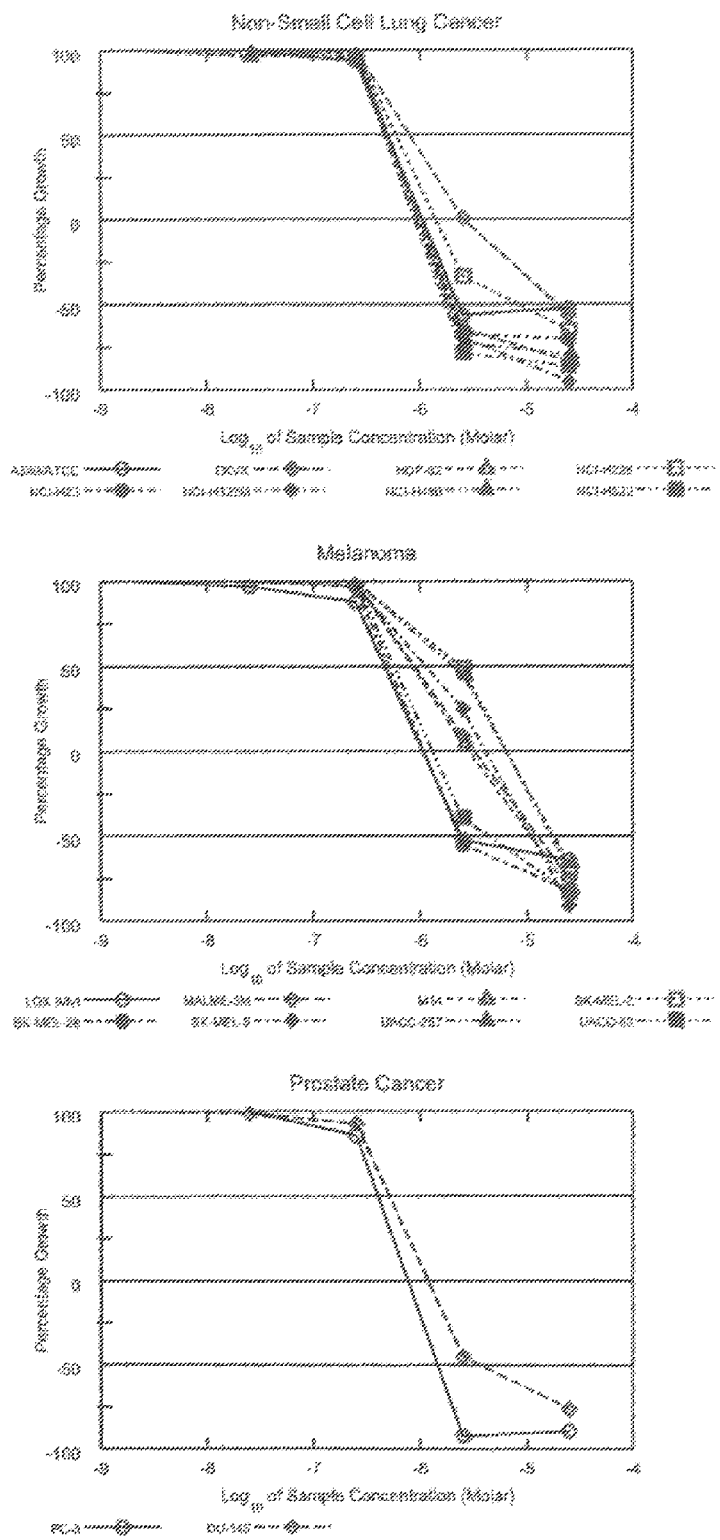
Figure 20:
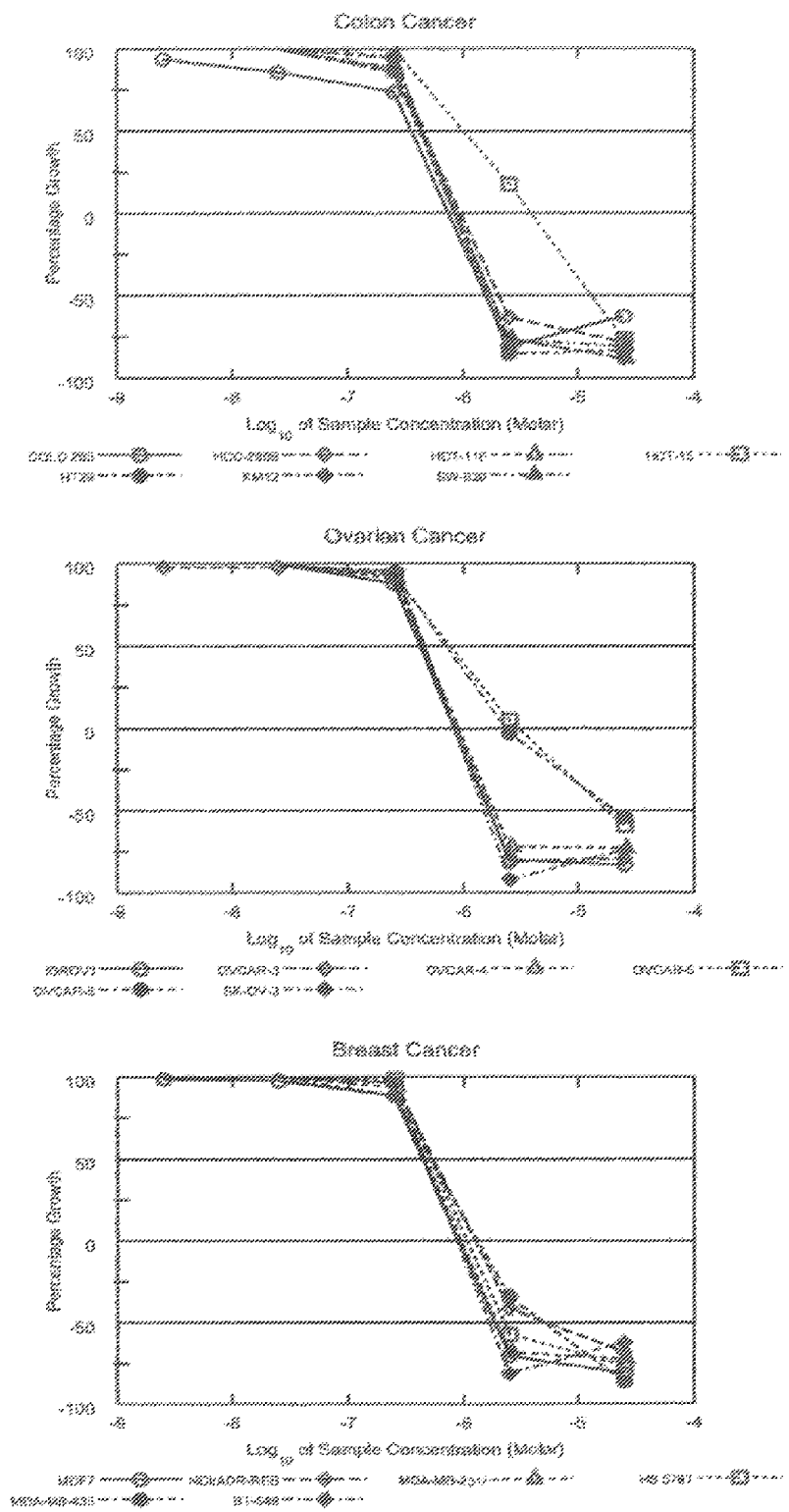
Figure 23:
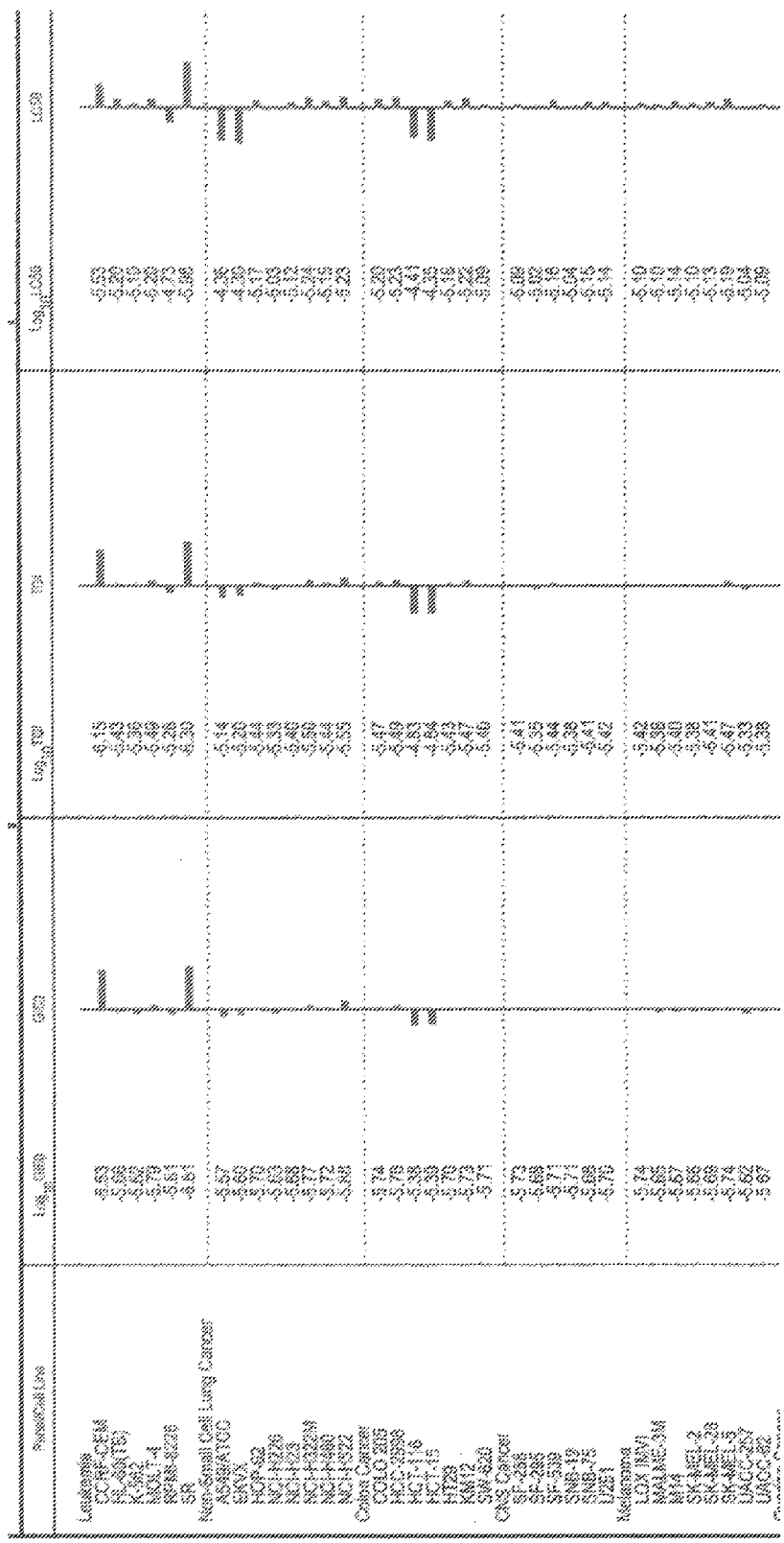
Figure 24:
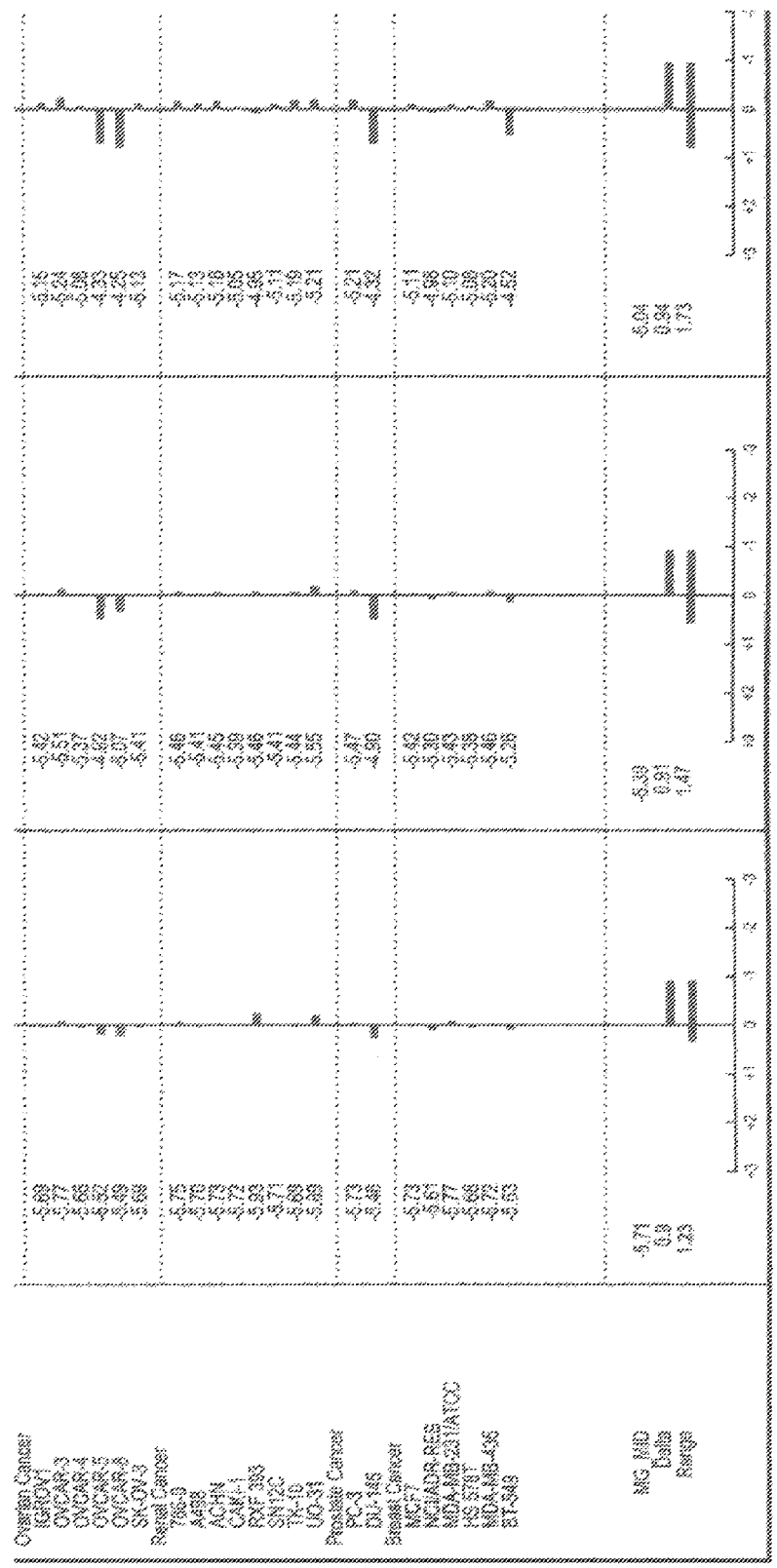
Figure 25:
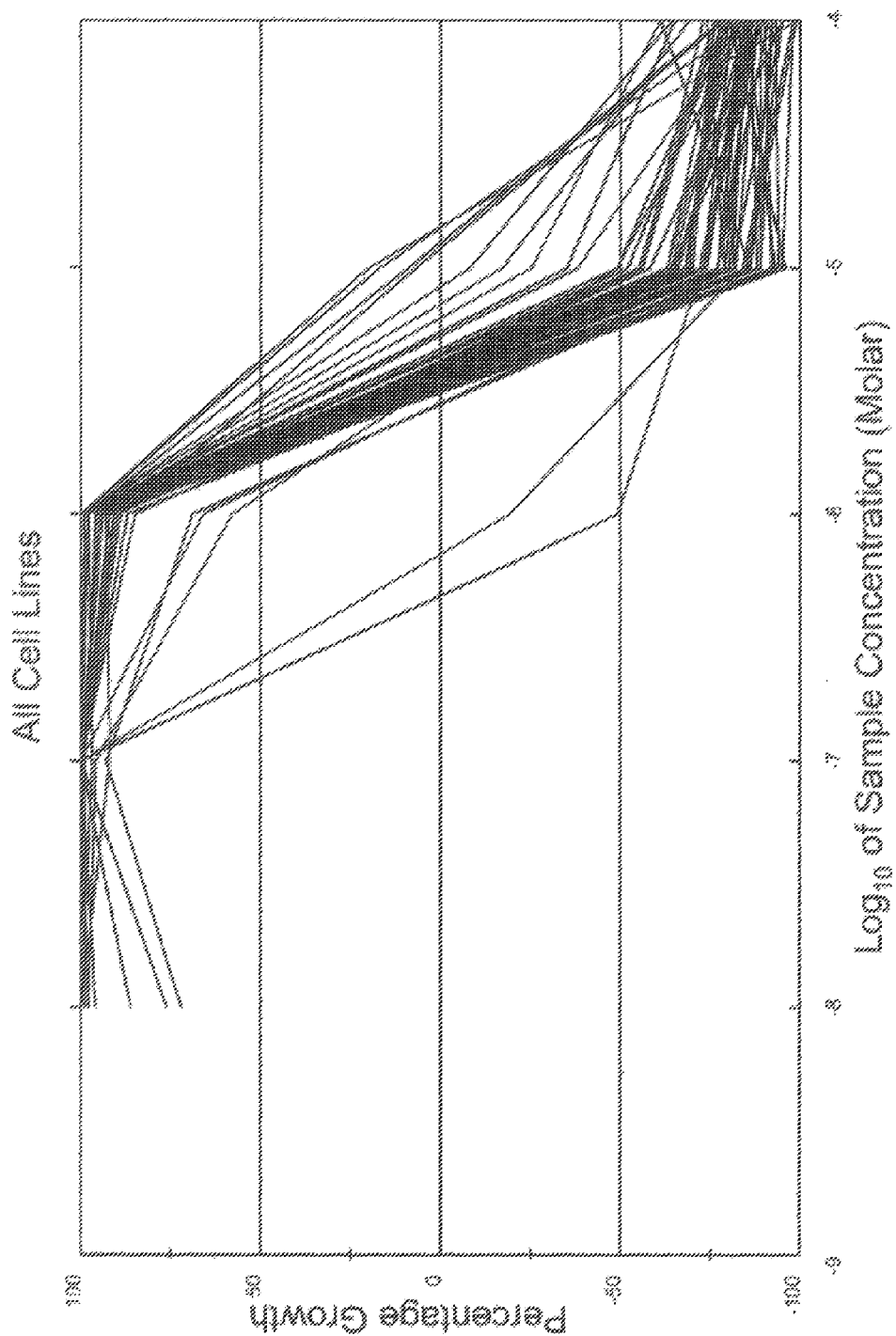
Figure 26:
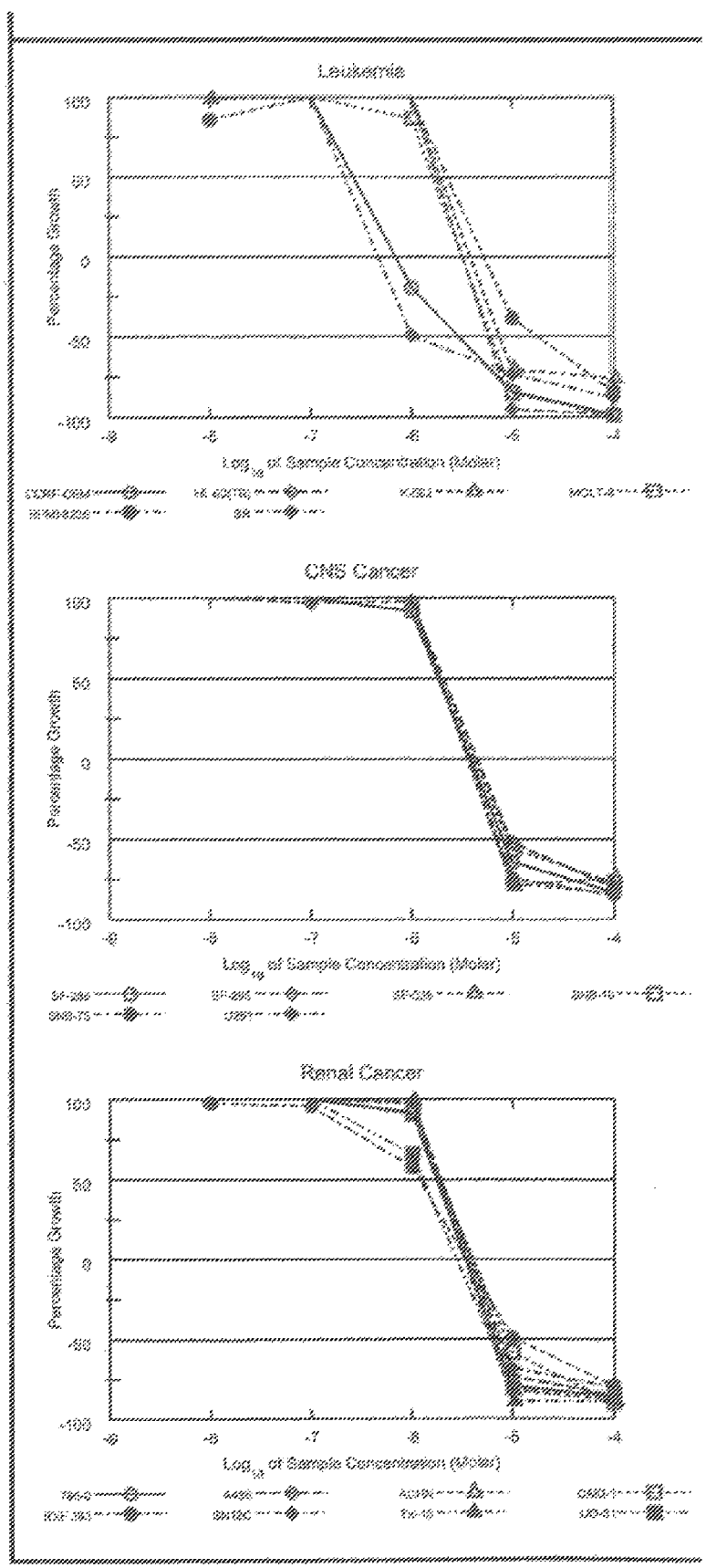
Figure 27:
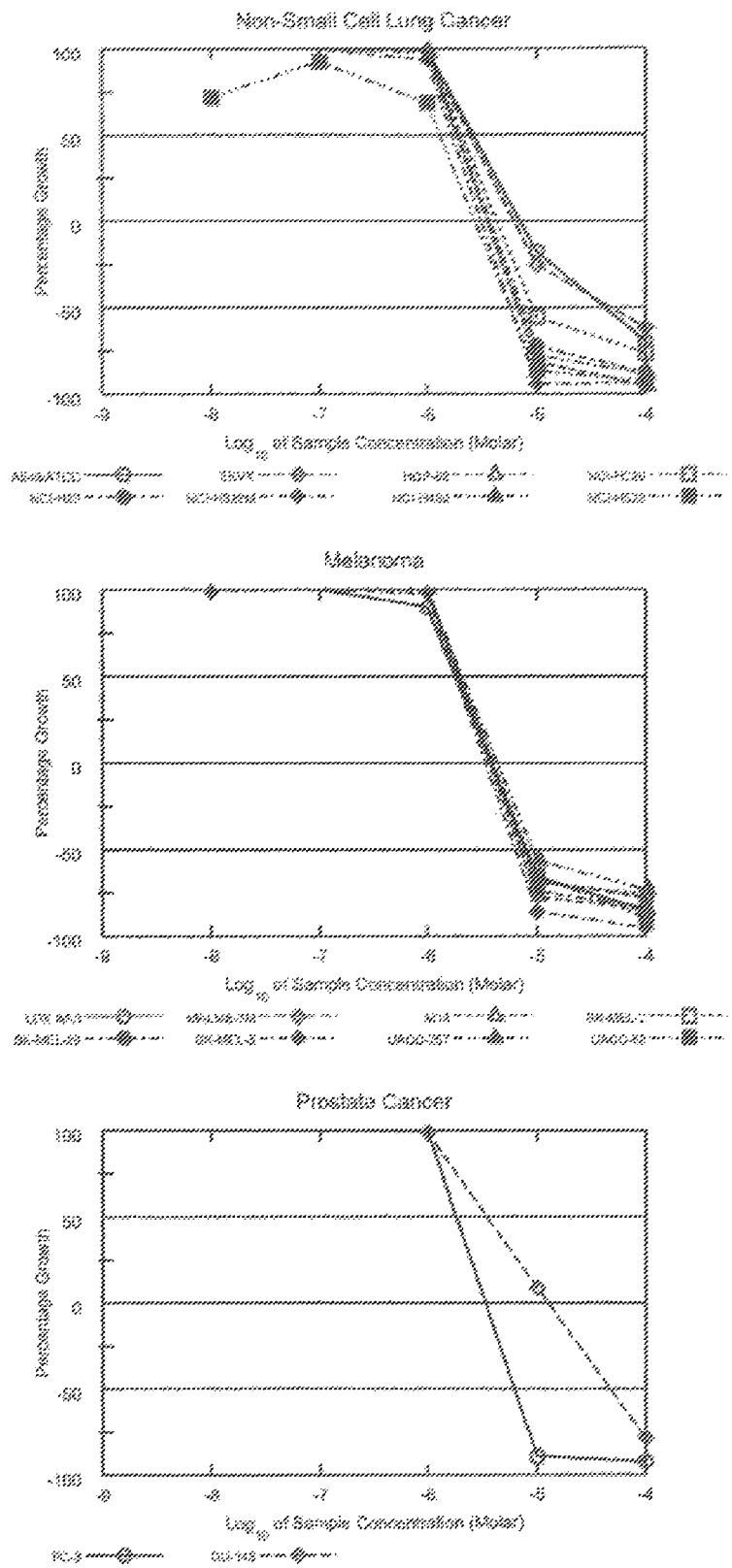

The profile of the proton NMR is presented in FIG. 8A, 8B, 9A, 9B, 10A, 10B and. The NMR profiles of 1H, 13C, TOCSY, HMQC, HMBC and NOESY are shown respectively. FIG. 11 shows the MS of Y0. Based on these data and analysis, the structure of compound Y0 is assigned as shown below.

Structure of Compound Y0

This invention provides a bioactive compound Y0 and the chemical name is:
3-O-[β-D-galactopyranosyl(1→2)]-α-L-arabinofuranosyl (1→3)-β-D-glucuronopyranosyl-21-O-angeloyl,22-O-(2-methylpropanoyl)-3β,15α,16α,21β,22α,28-hexahydroxyolean-12-ene,

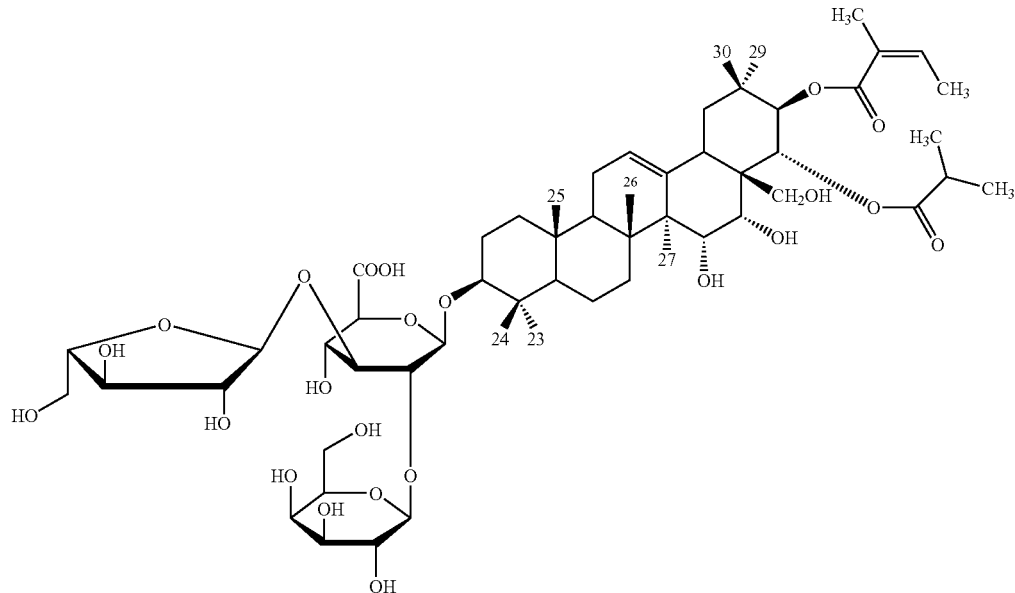

Experiment 7

Animal Study

Methods

Athymic Nu/Nu mice are divided into three groups (A, B and C) with four animals in each group.

On day 0, mice of group A and B were transplanted intra-peritoneally with ES2 (human ovarian cancer) cells.

On day 1, mice from B and C groups received drug (Xanifolia-Y, by i.p. route at dose of 5 mg/kg)

On days 2 to 4, and 7 to 11, B and C groups animals received daily drug administration of Xanifolia-Y, by i.p. route at dose of 2.5 mg/kg.

Group A mice have no drug-treatment.

Results:

Group A Mice—Died on day 19-22
Group B Mice—Survived over 50 days
Group C Mice—Survived over 50 days
Also See FIG. 30

Experiment 8

Animal Study

Methods

Athymic Nu/Nu mice were divided into three groups (A, D and E) with four animals in each group.

On day 0, all mice were transplanted intra-peritoneally with ES2 (human ovarian cancer) cells.

Group A mice received no drug-treatment.

Group D: From day 4, mice received a daily drug administration of Xanifolia-Y, via i.p. route for 9 days at dose of 2.5 mg/kg.

Group E: From day 10, mice received daily drug administration of Xanifolia-Y, via i.p. route for 10 days at dose of 2.5 mg/kg.

Result:

Group A, Mice implanted with tumor and no drug. All died within 24 days

Group D, Mice implanted with tumor and were given drug 9 times from 4th day. All survived Group E Mice implanted with tumor and were given drug 10 times from 10th day. Half the number of mice survived Also See FIG. 31

Experiment 9

Animal Study

Athymic Nu/Nu mice (2-3 months old) were transplanted sc with ES2 (human ovarian cancer) cells.

Five days after the transplant (day one), mice were divided into two groups (H and J) with two animals in each group.

Group H: On days 1-5, and 8-10 mice received daily drug administration of Xanifolia-Y, by i.p. route at dose of 2.5 mg/kg.

Group J mice received no drug-treatment.

Result:

Group H: Mice received drug-treatment, tumor size is 10 mm in 10 days

Group J: Mice received no drug-treatment, tumor size is 18 mm in 10 days The tumor size is 45% smaller in mice with drug than the mice with no drug in 10 days period.
See FIG. 32

Experiment 10

Animal Study

Methods
Athymic Nu/Nu mice (5-6 weeks old) are divided into three groups (0, P and Q) with 5-6 animals in each group.
On day 0, all mice were transplanted intra-peritoneally with ES2 (human ovarian cancer) cells.
Group 0: animals received no drug-treatment.
Group P: On days 4-8, 11-15, 18-22, 25-29, 32-36, 39-43, animals received daily drug administration of Xanifolia-Y, by i.p. route at dosage of 2.5 mg/kg
Group Q: On days 10-15, 18-22, 25-29, 32-36, 39-43, animals received daily drug administration of Xanifolia-Y, by i.p. route at dosage of 2.5 mg/kg.

The median survival time of tumor bearing mice with drug-treatment starting on day 4 after tumor inoculation is 58 days (extension of life span of 141%); and The median survival time of tumor bearing mice with drug-treatment started on day 10 after tumor inoculation is 31 days (extension of life span of 29%).
See FIG. 37

Experiment 11

Studies of Effect on Human Ovarian Cancer Cell Lines

Since we found that ovarian carcinoma cell lines are among the sensitive cells studied, we further investigated if other ovarian carcinoma cell lines are also susceptible to Xanifolia-Y.

Majority of ovarian cancers arise from the surface epithelium of ovary, most of them belong to the histological sub-types of clear cell and serous carcinoma. We obtained 10 more human ovarian carcinoma cell-lines of these histological subtypes for these studies. The inhibition activity exerted by Xanifolia-Y was determined with MTT assay. The following table shows the IC50 values of Xanifolia-Y on these cell lines.
Results:

TABLE 2

IC50 values of human ovarian carcinoma determined by MTT assay.

| Cell lines | Types | IC50 (uM) |
|---|---|---|
| OVCAR3 | Serous | 2.2 |
| TOV-21G | Clear cell | 2.2 |
| ES2 | Clear cell | 4.4 |
| RMG2 | Clear cell | 8.8 |
| OVCA 429 | Serous | 7 |
| OVCA 432 | Serous | 4.4 |
| OVCA 433 | Serous | 8.8 |
| Caov 3 | Serous | 7 |
| SKOV 3 | Serous | 10.5 |
| Hey 8A | Serous | 10.5 |

The IC50 values of Xanifolia-Y in these cell-lines are ranging from 2 to 10 uM. These studies show that the effective concentration of Xanifolia-Y is in the micro-molar range which is comparable to those of other anti-cancer drugs.

Experiment 12

Study Apoptosis Induced by Xanifolia-Y

Experiment of apoptosis of OVCAR3 cells after treatment with Xanifolia-Y was assessed with flow cytometry of GFP-Annexin-V and propidium iodide.

Results were shown in FIG. 33 which indicates that induction of the early apoptosis (the lower right quadrant) and late apoptotic/necrosis (the upper right quadrant) were found in cells 24 h after exposure to Xanifolia-Y. By comparing the distribution of apoptotic/necrotic cells after the drug-treatment, a higher number of early apoptotic cells were observed as compare to those of the late apoptotic/necrosis cells. These results indicate that apoptosis is a major form of cell death induced by Xanifolia-Y. See FIG. 33.

Experiment 13

Effect of Xanifolia-Y on Membrane Structure (EM Studies)

Xanifolia-Y has a potent hemolytic activity in red blood cells (FIG. 34). To study the effect of Xanifolia-Y on membrane structure, the morphology of cell membrane treated with Xanifolia-Y was examined with EM. In this experiment, K562 cells were treated with 5 uM of Xanifolia-Y for 60 min. Solvent DMSO and AKOH—Y (a derivative of Xanifolia-Y without the angeloyl group and it has no activity) served as controls. Cells were negative stained with 1% UAc and subsequently examined with EM.

FIG. 34 show that patches of pits were found in the membrane of Xanifolia-Y treated cells (FIG. 34B) but not in cells treated with the DMSO (FIG. 34A) or AKOH—Y (FIG. 34C) controls. These pits have the size from 80 A to 500 A (in diameter). The pits represent holes formed in the membrane. The pits are arranged in a characteristic pattern with smaller pits (80 A in diameter) located in the periphery and the bigger ones (500 A in diameter) in the center. The bigger holes are resulted from fusing of the smaller holes (FIG. 34D).

Membrane image of cells treated with A: DMSO solvent control, 60 min (magnification: ×60,000); B: Xanifolia-Y 5 uM, 60 min. (×60000); C: AKOH—Y, 20 uM, 60 min. (×60000); D: Xanifolia-Y 5 uM, 60 min. (×20000)

This experiments results show that the Xanifolia-Y alters the membrane of cell.
See FIG. 34

Experiment 14

Inhibition of Cell Adhesion by Xanifolia-Y

Methods and Results. ES2 or Hey8A cells were plated in T25 flasks with medium containing 5 ug/ml of Xanifolia-Y. Cultures were incubated for 5 hours. Attached cells were removed from flasks by trypsinization and the amounts were counted.

Compare to no drug controls, 86±4% of ES2 cells and 67±8% of Hey8A cells were found attached to flasks under this condition. At 5 ug/ml Xanifolia-Y, over 90% of unattached cells are alive as determined by the trypan Blue exclusion assay and by their ability to re-attach to flasks when plating in medium without Xanifolia-Y. However, with 10 ug/ml Xanifolia-Y, less than 40% of cells attached to flasks and many of them are dead cells. This experiment shows that Xanifolia-Y inhibits cells adhesion process.

Experiment 15

Combined Inhibition Effect of Xanifolia-Y and Paclitaxel

Methods: ES2 cells were exposed to (i) Xaniffolia-Y with concentrations of 40, 20, 10, 5, 2.5, and 1.25 ug/ml; or (ii) Paclitaxel with concentrations of 10, 5, 2.5, 1.25, 0.62 and 0.031 ng/ml; or (iii) Combined Xanifolia-Y and Paclitaxel with concentrations of each drug in same order (for example, 40 ug/ml Y plus 10 ng/ml T; 20 ug/ml Y plus 5 ng/ml T, etc. please see FIG. 9). Cells growth under these conditions was determined by the MTT assay.

Results: As shown in FIG. 9, The IC50 for Xanifolia-Y and Paclitaxel, is 5 ug/ml and 1.25 ng/ml, respectively. Additive effect was observed when both drugs were used, because in this case, the IC50 value for Paclitaxel (0.625 ng/ml) and for Xanifolia-Y (2.5 ug/ml) is less than those when they are used singly.

See FIG. 35.

Experiment 16

Identify the Binding Target of Xanifolia-Y of Adhesion Proteins and Signaling Proteins in Ovarian Cancer Cells In our animal studies, it was shown that Xanifolia-Y extended the life span of tumor bearing mice (FIGS. 30 and 31). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion is blocking of the protein accessibility due to direct binding to Xanifolia-Y, the interaction of Xanifolia-Y with membrane alter indirectly the adhesion protein's binding site(s).

A. We label Xanifolia-Y and use it as ligand to find the target molecules bind to it. Xanifolia-Y has carbohydrates (Galactose, arabinose and glucoronic acids). These carbohydrates can be $^3$H-labeled with peridodate-tritiated Borohydride (Cahmberg and Andersson, 1977). For the control, the non-reactive derivative of Xanifolia-Y (AKOH—Y) also is labeled. Labeled Xanifolia-Y is purified by HPLC and verified that it retains activity before use. Our studies indicate that the carbohydrates of Xanifolia-Y do not contribute a major role in its activity. Therefore, $^3$H-labeling of carbohydrate in Xanifolia-Y should not affect its activity.

B. We employ the following methods to study the direct binding between the labeled Xanifolia-Y and its target.

I. Detect binding of Xanifolia-Y on cell surface (by autoradiography): This autoradiographic method employs labeled Xanifolia-Y adding to culture cells (K562 suspension cells, or ES2 monolayer cells) and determine cells pick up label on cells surface. Cells are incubated in medium with labeled Xanifolia-Y with a concentration equal to the IC50 value (e.g. 4.4 ug/ml for ES2 cells). At this concentration, cells are alive. After incubation (30 min to 1 hour), cells are washed, fixed, dried and emulsified. Radioactive Xanifolia-Y is detected with autoradiography and microscopic analysis. Radioactive AKOH—Y (not active) serves as a negative control. This experiment shows that Xanifolia-Y binds to membrane.

II. Determine binding between selected protein and Xanifolia-Y by RIA: This experiment determines the known adhesion proteins bind to Xanifolia-Y. Binding of Xanifolia-Y to known purified adhesion proteins (or other signaling proteins) can be determined with RIA (Radio-Immuno Assay). Antibodies of many of these adhesion proteins (and protein itself) are available and can be employed in RIA assay. Binding of radioactive Xanifolia-Y (which compete with non-radioactive Xanifolia-Y) with specific protein is immuno-precipitated by specific antibodies. Affinity binding constant for these known proteins is determined by this method.

III. Immuno-precipitation (IP) analysis: Xanifolia-Y binds to molecules that associated with adhesion proteins. Many of known signaling proteins or adhesion protein form complex (spheroids). Spheroids are immuno-precipitated with the specific antibody to one of the adhesion protein. Cells are cultured with radioactive Xanifolia-Y. Membrane proteins or spheroids are isolated. Alternatively, isolated spheroids from cells are incubated with radioactive Xanifolia-Y in a cell-free system. Co-IP of the radioactive Xanifolia-Y in the spheroid indicates its association of Xanifolia-Y-binding protein. After the spheroid is identified, the contents of the spheroid are analyzed with biochemical methods, such as 2D gel electrophoresis.

IV. Purification and identification of Xanifolia-Y-binding protein: We employ the radioactive Xanifolia-Y as a tracer to identify and purify its target. The effective concentration for Xaniflolia-Y in vitro assay is in the micro-molar range, suggesting that the binding to its target is relatively tight (or with high affinity). Therefore, it does able to detect its binding target in cell-free system. Membrane is isolated and proteins will be fractionated with ion-exchanger and gel filtration chromatography. Fractions from chromatography will be analyzed (by radioactive counting) for their association of Xanifolia-Y. Alternatively, proteins isolated from cancer cells or the membrane fraction are separated by 2D gel, blot the proteins in NC membrane and incubate with radioactive labeled Xanifolia-Y and determine the target protein that pick up radioactive Xanifolia-Y (tagged by the labeled-Xanifolia-Y). The tagged target is detected by autoradiography (beta-imager). The identity of protein is determined by Peptide Mapping and MALDI-TOF technique.

Our compounds interacting with target protein comprise integrins family, CD44, fibronectin, Myosin VI, collagen, laminin, Glycosylation cell surface proteins, polyglycans and FAK Adhesive molecules play an important role in migration and metastasis of ovarian cancer (Skubitz, 2002, Schaller, 1996; Zetter, 1993). A major route for the spread of ovarian cancer is by the attachment of tumor cells to the mesothelium lining in the peritoneal cavity (Gardner et al., 1995). For example, serous ovarian cancer cells invade through their membrane and released proteolytic enzymes or EMC molecules for attachment to mesothelial cells (Skubitz, 2002).

The integrins family and CD44—These proteins are detected on all mesothelial cells and ovarian cancer cells and play an important role in tumor/mesothelial interaction (Gardner et al., 1995).

Ovarian carcinoma cells form multicellular spheroids, in the peritoneal cavity of patients with advanced disease (Burleson et al., 2004). It was shown that adhesive proteins in ovarian carcinoma multicellular spheroids were involved in the adhesion process (Casey et al., 2001). The adhesive proteins are: integrins, CD44 and fibronectin.

Myosin VI, a motor protein that regulates border cell migration, is abundantly expressed in high-grade ovarian carcinomas including ES2 cells. Yoshida et al., (2004) reported that inhibition of myosin VI expression in ES2 cells impeded ovarian cells spreading and migration.

Casey et al., (2003) reported that Glycosylation cell surface proteins and polyglycans mediate the adhesion, migration and invasion of ovarian carcinoma cells. The major ligand for CD44 is the extra-cellular matrix glycosaminoglycan and hyaluronic acid (HA). Mesothelial cells contain large amount of HA (Catterall et al., 1997). These surface proteins also include: fibronectin, collagen and laminin.

FAK (focal-adhesion-associated kinase). FAK is a protein tyrosine kinase which involves in the regulation of cell cycle progression, cell survival and cell migration (Schaller, 2001). It was reported that FAK promote cell motility and invasion of ovarian cancer through distinct signaling pathway (Hsia et al., 2003). The role of integrins for adhesion is to activate intracellular signaling pathways (Schaller and Parsons, 1993). One of the affected kinase is (FAK). FAK expression inhibited by Xanifolia-Y-treatment.

Experiment 17

The Effect of Xanifolia-Y in Preventing Nodule Formation in Peritoneal Cavity

This experiment shows Xanifolia-Y blocks migration, invasion or growth of ovarian cancer in peritoneal cavity.

Our animal experiments indicate that the life span of the tumor bearing mice is extended after the Xanifolia-Y-treatment. The results show that a sooner treatment provides a better protection. The results show that Xanifolia-Y inhibits tumor cell's growth and reduce their attachments to mesothelium linings. We use Hey8A cells inoculated in peritoneal cavity produce tumor nodules (solid tumor mass) and the numbers of nodules increase during the tumor progression (Lander Jr., et al., 2005). The numbers of tumor nodules are determined by laparotomy. The growth of nodules (number and mass) before and after Xanifolia-Y-treatment is determined. The results show that Xanifolia-Y inhibits the growth number of nodule; and inhibits tumor growth after the Xanifolia-Y-treatment.

(A) Animal Model: Hey8A Cells are Inoculated into Peritoneal Cavity.

The relationship between the nodule formation and timelines during tumor progression are established. Usually, 4 to 6 nodules are formed during the entire period of tumor progression in this system (Lander Jr., et al., 2005). We start the drug-treatment at times equivalent to 20% and 50% of full tumor progression. At these times, the number of nodule is less and the size (weight) of the nodules is smaller. At the end of the drug-treatment, animals are euthanized and number of tumor nodules is determined and the tumor size (mass) is weighted.

Animals: 40 nu/nu mice are used per experiment.

2 groups of mice (20 each) (i) Drug-treatment start at time equivalent to 20% of full tumor progression (or on 4 days after tumor inoculation) (ii) Drug-treatment starts at time equivalent to 50% of full tumor progression (or on 10 days after tumor inoculation). On the day of starting drug-treatment, half of the animals (10) will be scarified and the number and weight of nodules will measured.

Drug-treatments: Animals are administered daily for 5 days per week for two-three weeks. Dose: 0.25 mg/kg, through i.p. route.

Result: The numbers of tumor nodules are less in mice with drug treatment compare to mice without drug treatment. The size of tumor in drug treatment mice is smaller than tumor in no-drug treatment mice.

(B) Animal Model: ES2 Cells are Inoculated into Peritoneal Cavity.

The relationship between the nodule formation and timelines during tumor progression are established. Usually, 4 to 6 nodules are formed during the entire period of tumor progression in this system (Lander Jr., et al., 2005). We start the drug-treatment at times equivalent to 20% and 50% of full tumor progression. At these times, the number of nodule is less and the size (weight) of the nodules is smaller. At the end of the drug-treatment, animals are euthanized and number of tumor nodules is determined and the tumor size (mass) is weighted.

Animals: 40 nu/nu mice are used per experiment.

2 groups of mice (20 each) (i) Drug-treatment start at time equivalent to 20% of full tumor progression (or on 4 days after tumor inoculation) (ii) Drug-treatment starts at time equivalent to 50% of full tumor progression (or on 10 days after tumor inoculation). On the day of starting drug-treatment, half of the animals (10) will be scarified and the number and weight of nodules will measured.

Drug-treatments: Animals are administered daily for 5 days per week for two-three weeks. Dose: 0.25 mg/kg, through i.p. route.

Result: The numbers of tumor nodules are less in mice with drug treatment compare to mice without drug treatment. The size of tumor in drug treatment mice is smaller than tumor in no-drug treatment mice.

We use two histological types of human ovarian cancer ES2 and Hey8A. These two are most common ovarian cancer types: clear cells carcinoma (ES2) and serous carcinoma (Hey8A). Hey and ES2 show high expression of integrins and other adhesion proteins (Ahmed et al., 2005).

Ovarian cancer cells that are resistant to drugs are chosen in this study. ES2 cells express low levels of P-glycoprotein and have multi-drug chemotherapy resistant character (resistant to doxorubicin, cisplatin, carmustine, etoposide and cyanomorpholinodoxorubicin).

Experiment 18

Determination of Aquaporin in HeLa and OVCAR3 Cells

Methods:
1. Hela or OVCAR3 cells were cultured in RPMI 1640 medium at 37C in an incubator with 5% CO2.
2. Cells were harvested, washed with PBS.
3. Cellular protein was dissolved in SDS sample buffer with protease inhibitors (PMSF and Leupeptin) and was incubated at 70° C. for 20 min before use.
4. Equal amounts of protein from Hela or OVCAR3 cells were separated with 12% SDS gel and subsequently blotted on nitrocellulose paper.
5. Western blot was performed with anti-AQ1 antibody (Chemicon/SIGMA) and second antibody which was conjugated with Alkaline phosphatase.

Results:
The following figure shows the results of Western blot.
Aquaporin-1 (indicated with an arrow) was observed in OVCAR3 cells but was minimally detected in HeLa cells.
Based on same amounts of protein loading into gel, it was found that OVCAR3 cells have higher concentration of Aquaporin-1 than in Hela cells.
Since OVCAR3 cells are more sensitive to Xanifolia-Y and it has a higher concentration of Aquaporin-1, these results show Xanifolia-Y is potent to inhibit the cancer cell growth wherein the Aquaporin is overexpressed.

Figure 40:
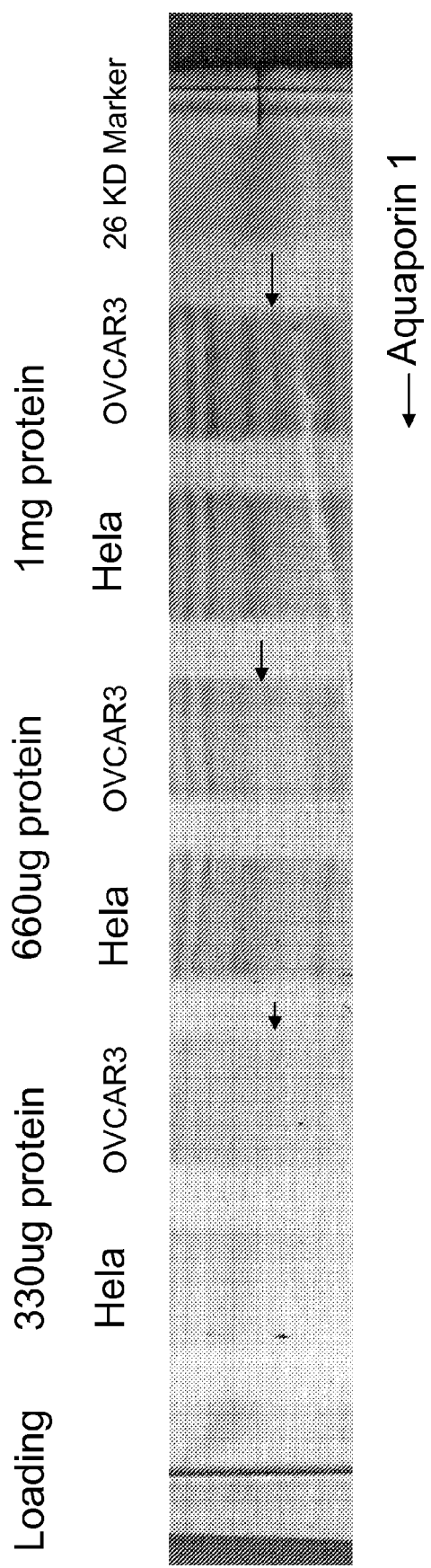
Figure 41:
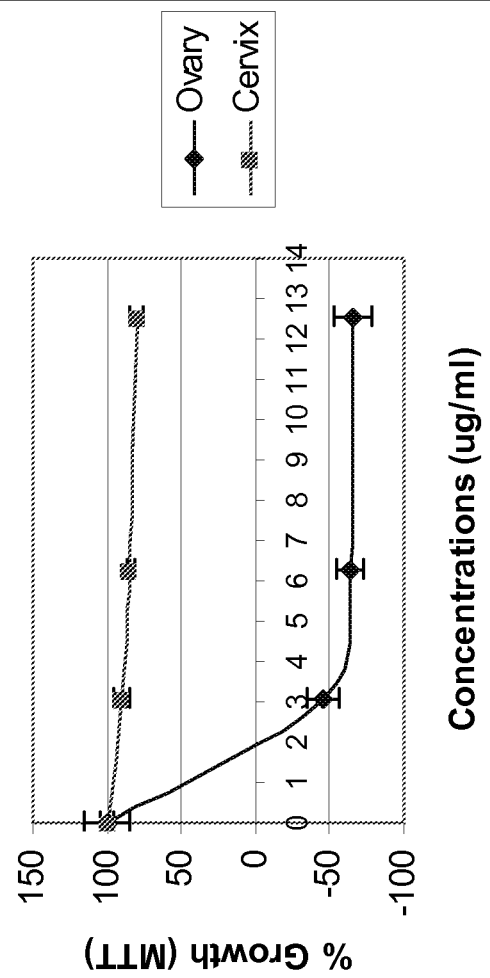

See FIG. 40

REFERENCES

1. Voutquenne, L., Cecile Kokougan. Catherine Lavaud, Isabelle Pouny, Marc Litaudon. Triterpenoid saponins and Acylated prosapogenins from *Harpullia austro-calcdonica*." Phytochemistry 59 (2002) 825-832.
2. Zhong Jaing, Jean-francois Gallard, Marie-Therese Adeline, Vincent Dumontet, Mai Van Tri, Thierry Sevenet, and Mary Pais "Six Triterpennoid Saponins from *Maesa laxiflora*."J. Nat. Prod. (1999), 62, 873-876.
3. Young Seo, John M. Berger, Jennine Hoch, Kim M Neddermann, Isia Bursuker, Steven W. Mamber and David G. Kingston. "A new Triterpene Saponin from *Pittosporum viridiflorum* from the Madagascar Rainforest". J. Nat. Prod. 2002, 65, 65-68.
4. Xiu-Wei Yang, Jing Zhao, Xue-Hui Lui, Chao-Mei Ma, Masao Hattori, and Li He Zhang "Anti-HIV-1 Protease Triterpenoid Saponins from the Seeds of *Aesculus chinensis*." J. Nat. Prod. (1999), 62, 1510-1513.
5. Yi Lu, Tatsuya Umeda, Akihito Yagi, Kanzo Sakata, Tirthankar Chaudhuri, D. K. Ganguly, Secion Sarma. "Triterpenoid Saponins from the roots of the tea plant (*Camellia sinensis* var. *Assamica*)." Phytochchemistry 53 (2000) 941-946.
6. Sandra Apers, Tess E. De Bruyne, Magda Claeys, Arnold J. Viletinck, Luc A. C. Pieters. "New acylated triterpenoid saponins from *Maesa laceceolata*." Phytochemistry 52 (1999) 1121-1131.
7. Ilaria D'Acquarica, Maria Cristina, Di Giovanni, Francesco Gasparrini, Domenico Misiti, Claudio D'Arrigo, Nicolina Fagnano, Decimo Guarnieri, Giovanni Iacono, Giuseppe Bifulco and Raffaele Riccio. "Isolation and structure elucidation of four new triterpenoid estersaponins from fruits of the *Pittosporumtobira AIT*." Tetrahedron 58 (2002) 10127-10136.
8. Method for prevention and treatment of chronic venous insufficiency, Jia et al., U.S. Pat. No. 6,210,680
9. Novel analgestic compounds, extracts containing same and methods of preparation. Quinn Ronald, WO 2005/051969

What is claimed is:

1. A compound selected from the following:

a) An isolated or purified compound having structure Xanifolia (Y),

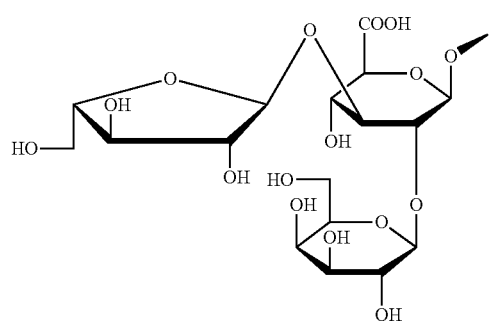

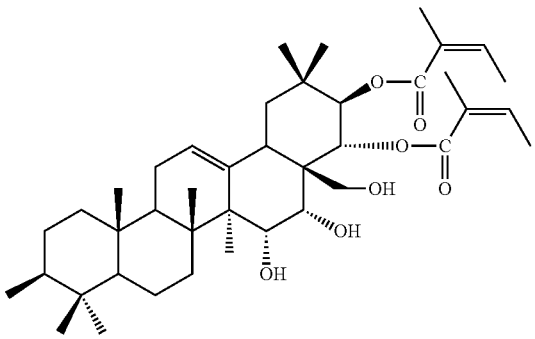

or chemical name: 3-O-[β-D-galactopyranosyl(1→2)]-α-L-arabinofuranosy (1→3)-β-D-glucuronopyranosyl-21,22-O-diangeloyl-3β,15α,16α,21β,22α,28-hexahydroxyolean-12-ene;

b) An isolated or purified compound having structure Xanifolia (Y1),

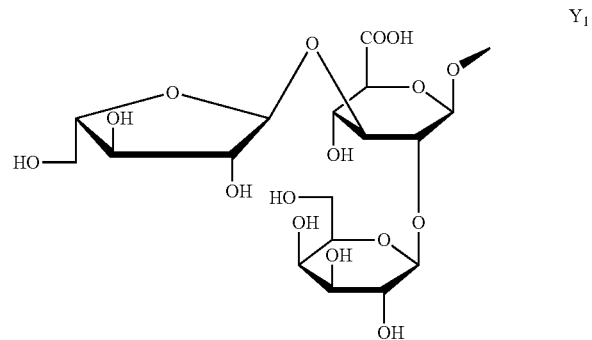

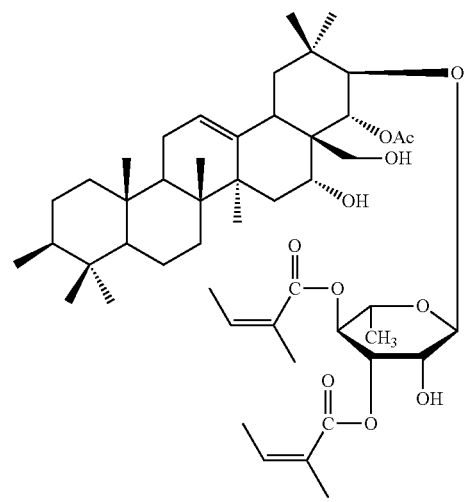

or chemical name: 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α,21β,22α,28-pentahydroxyolean-12-ene;

c) An isolated or purified compound having structure Xanifolia (Y2),

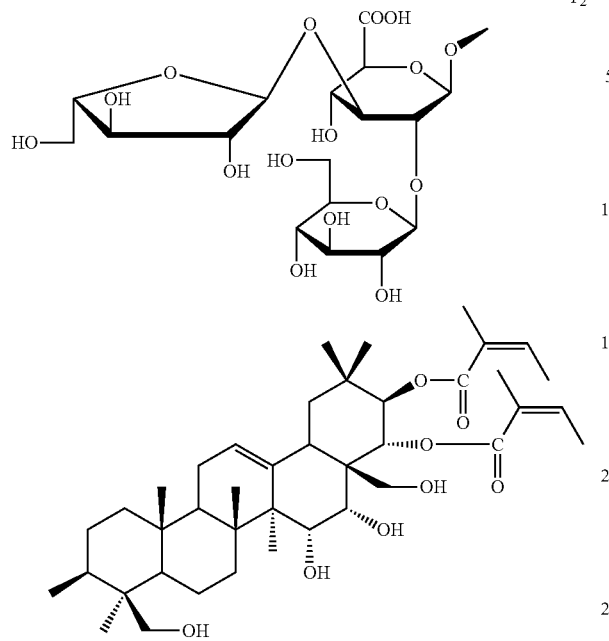

Y2 or chemical name: 3-O-[β-D-glucopyranosyl-(1→2)]-α-L-arabinofuranosy (1→3)-β-D-glucuronopyranosyl-21,22-O-diangeloyl-3β,15α,16α,21β,22α,24β,28-heptahydroxy-olean-12-ene;

d) An isolated or purified compound having structure Xanifolia (Y8),

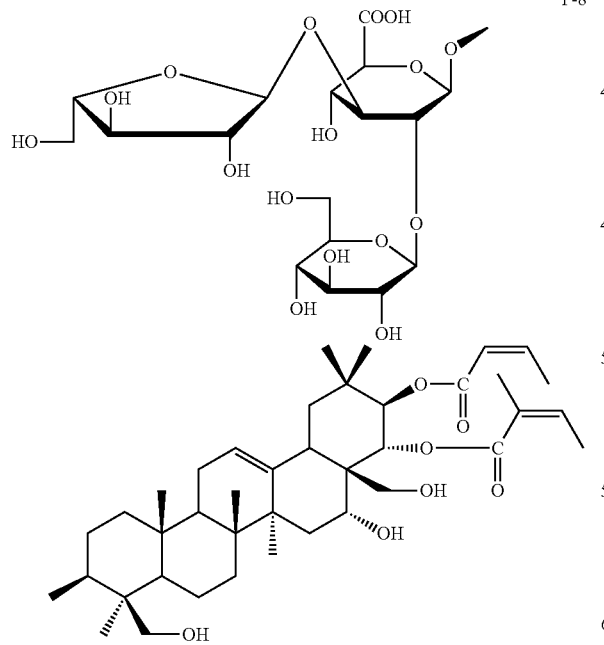

Y-8 or chemical name: 3-O-[β-glucopyranosyl (1→2)]-α-arabinofuranosyl(1→3)-β-glucuronopyranosyl-21,22-O-diangeloyl-3β,16α,21β,22α,24β,28-hexahydroxyolean-12-ene;

e) An isolated or purified compound having structure Xanifolia (Y9),

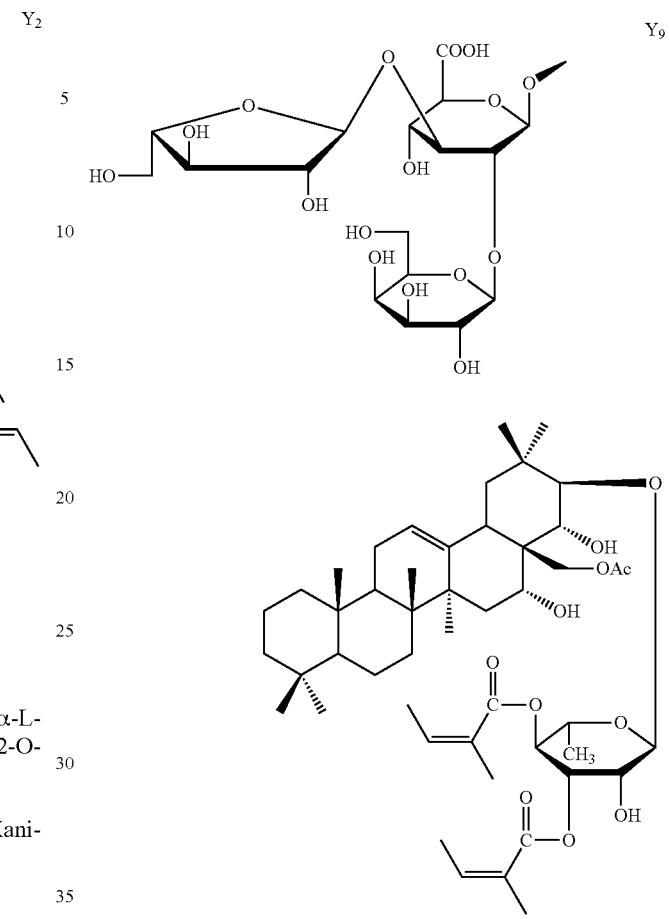

Y9 or chemical name: 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β,16α,21β,22α,28-pentahydroxyolean-12-ene; and f) An isolated or purified compound having structure Xanifolia (Y10),

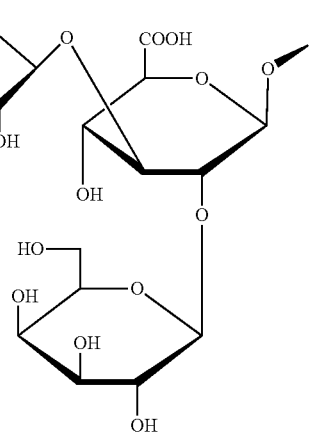

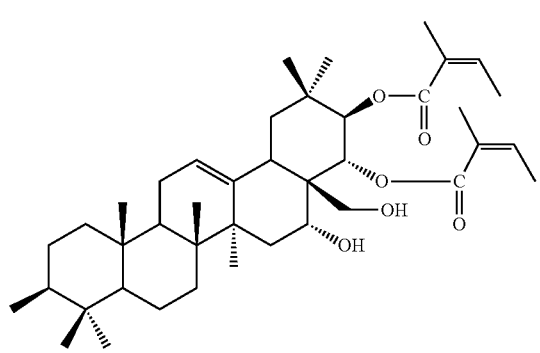

or chemical name: 3-O-[β-galactopyranosyl(1→2)]-α-arabinofuranosyl(1→3)-β-glucuronopyranosyl-21,22-O-diangeloyl-3β,16α,21β,22α,28-pentahydroxyolean-12-ene.

g) An isolated or purified compound having structure Xanifolia (Y0),

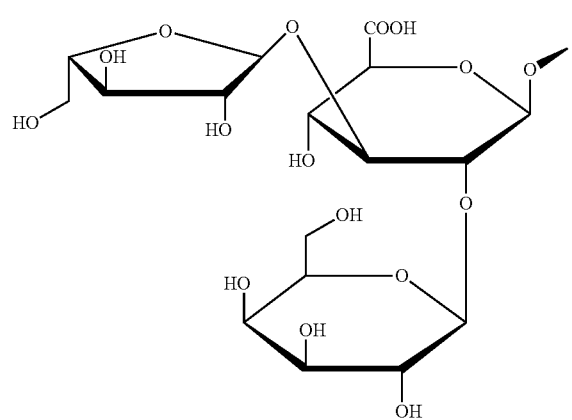

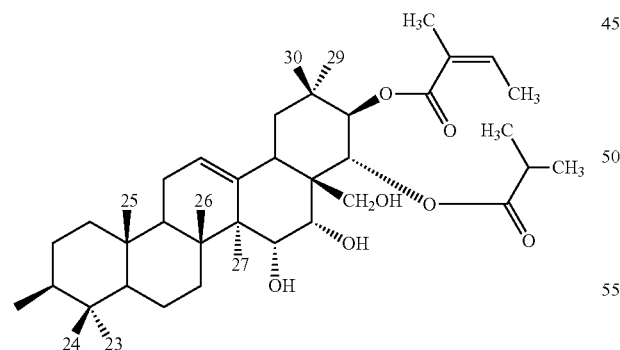

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β,15α,16α,21β,22α,28-hexahydroxyolean-12-ene, h) An isolated or purified compound having structure Xanifolia (X),

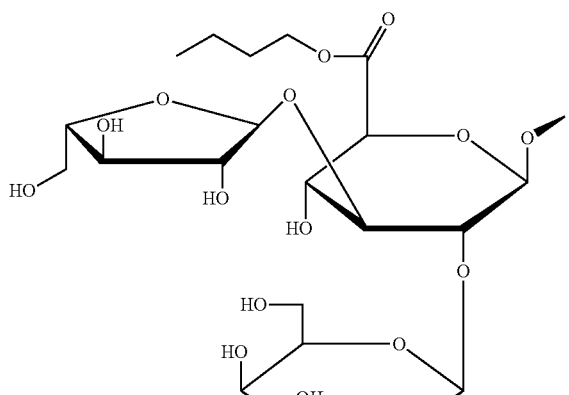

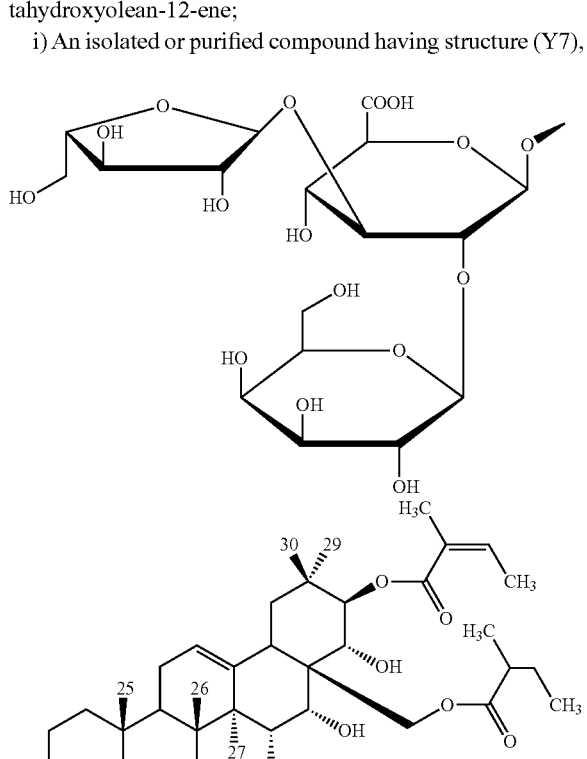

or chemical name: 3-O-{[β-D-galactopyranosyl(1→2)]-[α-L-arabinofuranosyl (1→3)]-β-D-glucuronopyranoside butyl ester}-21-O-acetyl-22-O-angeloyl-3β,16α,21β,22α,28-pentahydroxyolean-12-ene;

i) An isolated or purified compound having structure (Y7), or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β,15α,16α,21β,22α,28-hexahydroxyolean-12-ene;

k) An isolated or purified compound having a structure:

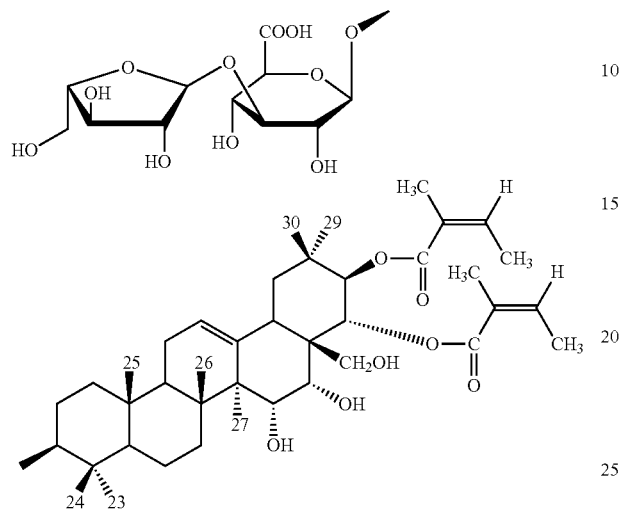

l) An isolated or purified compound having a structure:

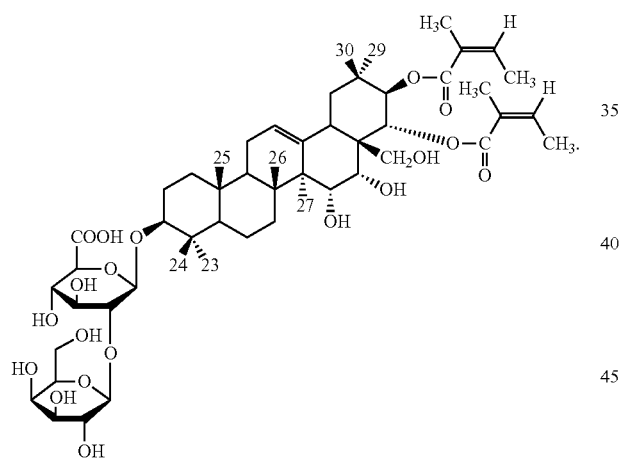

2. A composition for use as a medicament or health food consisting of an amount of the compound of claim 1.

3. The compound of claim 1 for inhibiting cancer growth wherein the cancer is selected from the group consisting of breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, and renal cancer.

4. A composition comprising an effective amount of the compound of claim 1 effective for inhibiting cancer growth, wherein the cancer is selected from the group consisting of breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, and renal cancer.

5. A composition comprising an effective amount of the compound selected from claim 1 effective for extending the life span of a subject which is bearing cancer or reducing the size of a solid tumor in a subject, wherein the subject comprises a mammal.

6. A method for inhibiting cancer growth or extending the life span of a subject which is bearing cancer or reducing the size of a solid tumor in a subject or altering the adhesion characteristic of membrane of cancer cells or inducing apoptosis of cancer cells comprising contacting said cells or administering to said subject with an effective amount of a compound, wherein the compound is selected from the formula of

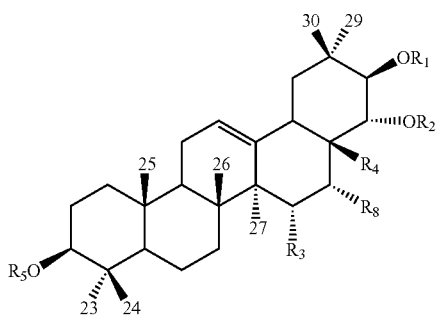

also named (1B), or a salt, ester, wherein

R1 is selected from a group consisting of alkanoyl, alkenoyl, acyl, and sugar moiety;

R2 is selected from a group consisting of hydrogen, alkanoyl, alkenoyl, and acyl;

R4 represents $CH_2OR6$ or $COOR6$, wherein R6 is selected from a group consisting of hydrogen, alkanoyl, alkenoyl, and acyl;

R3, R8 is H or OH;

R5 is a hydrogen or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or combination thereof; wherein position C23, C24, C25, C26, C29 and C30 of the compound is independently attached a group selecting from $CH_3$, and $CH_2OH$; wherein at least two of R1, R2, and R6 are independently selected from a group consisting of alkanoyl, alkenoyl, acyl, heterocylic; or at least one of R1, R2, and R6 is a sugar moiety substituted with at least two alkenoyl groups in trans configuration;

wherein the acyl is angeloyl group, acetyl, tigloyl, senecioyl, methylpropanoyl or methylbutanoyl; wherein the alkanoyl is methylpropanoyl, acetyl or methylbutanoyl; wherein the alkenoyl is angeloyl, tigloyl or senecioyl; wherein the number of sugar moieties; at R5 is/are 0, 1, 2, 3, or more than 4; wherein the cancer is selected from the group consisting of breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, and renal cancer.

7. The method of claim 6, wherein the compound is selected from the following:

a) A compound having the structure Xanifolia (Y),

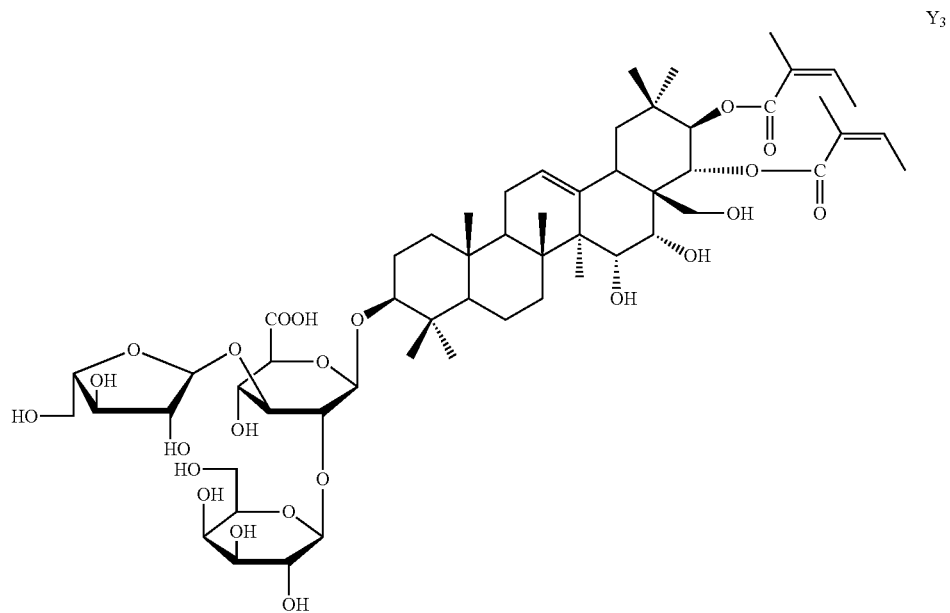

or chemical name: 3-O-[β-D-galactopyranosyl (1→2)]-α-L-arabinofuranosy (1→3)-β-D-glucuronopyranosyl-21,22-O-diangeloyl-3β,15α,16α,21β,22α,28-hexahydroxyolean-12-ene;

b) A compound having the structure Xanifolia (Y1),

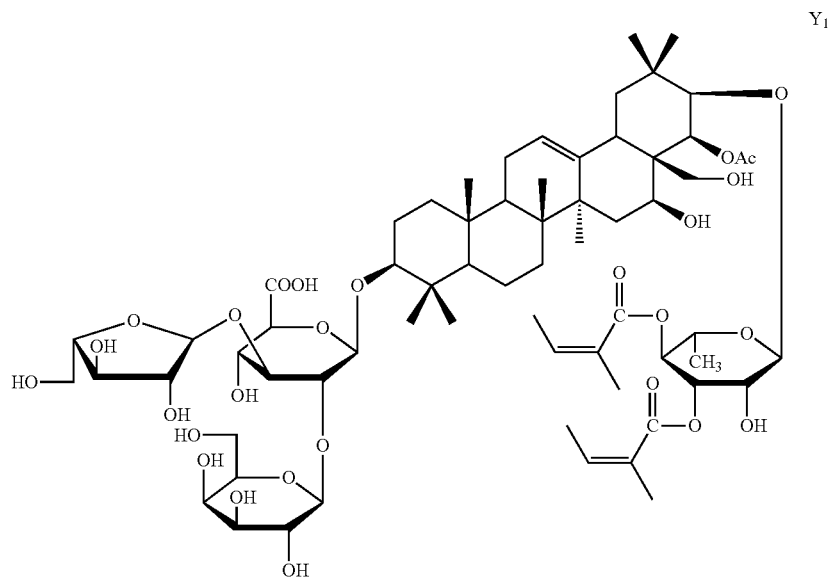

or chemical name: 3-O-[β-D-galactopyranosyl(1→2)]-α-L-arabinofuranosyl (1→3)-β-D-glucuronopyranosyl-21-O-(3, 4-diangeloyl)-α-L-rhamnophyranosyl-22-O-acetyl-3β,16α, 21β,22α,28-pentahydroxyolean-12-ene;

c) A compound having the structure Xanifolia (Y2),
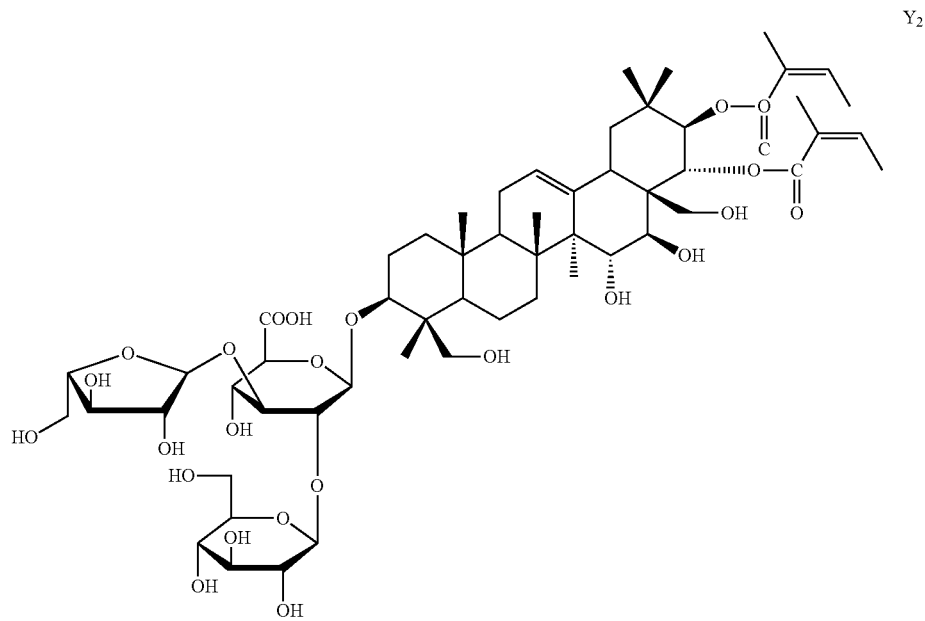
or chemical name: 3-O-[β-D-glucopyranosyl-(1→2)]-α-L-arabinofuranosy (1→3)-3-D-glucuronopyranosyl-21,22-O-diangeloyl-3β,15α,16α,21β,22α,24β,28-heptahydroxy-olean-12-ene;
d) A compound having the structure Xanifolia (Y8),
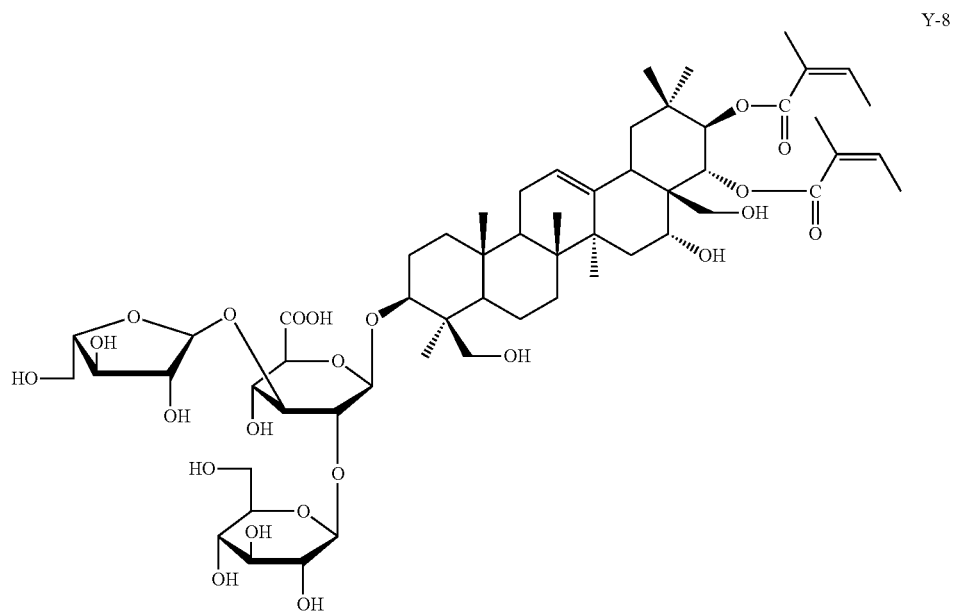
or chemical name: 3-O-[β-glucopyranosyl(1→2)]-α-arabinofuranosyl (1→3)-β-glucuronopyranosyl-21,22-O-diangeloyl-3β,16α,21β,22α,24β,28-hexahydroxyolean-12-ene;

e) A compound having the structure Xanifolia (Y9),

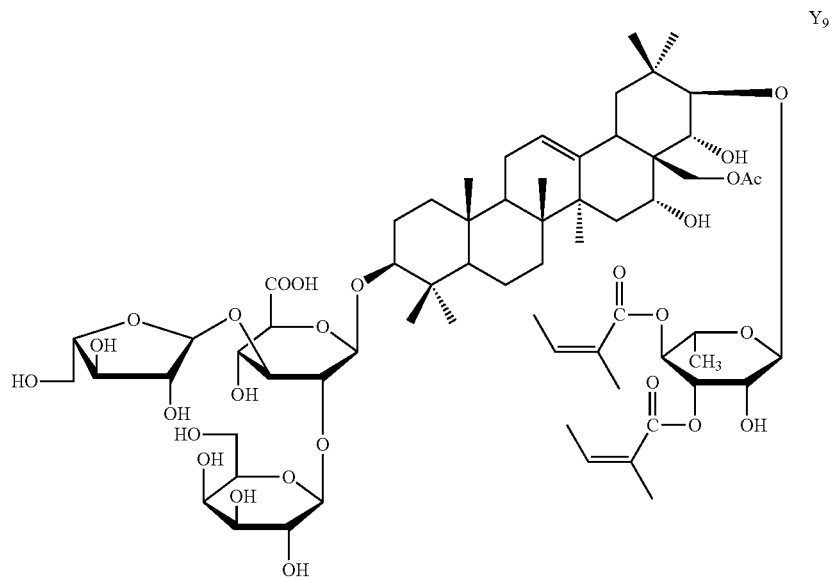

or chemical name: 3-O-[β-galactopyranosyl (1→2)]-α-arabinofuranosyl(1→3)-β-glucuronopyranosyl-21-O-(3,4-diangeloyl)-α-rhamnopyranosyl-28-O-acetyl-3β,16α,21β,22α,28-pentahydroxyolean-12-ene; and f) A compound having the structure Xanifolia (Y10),

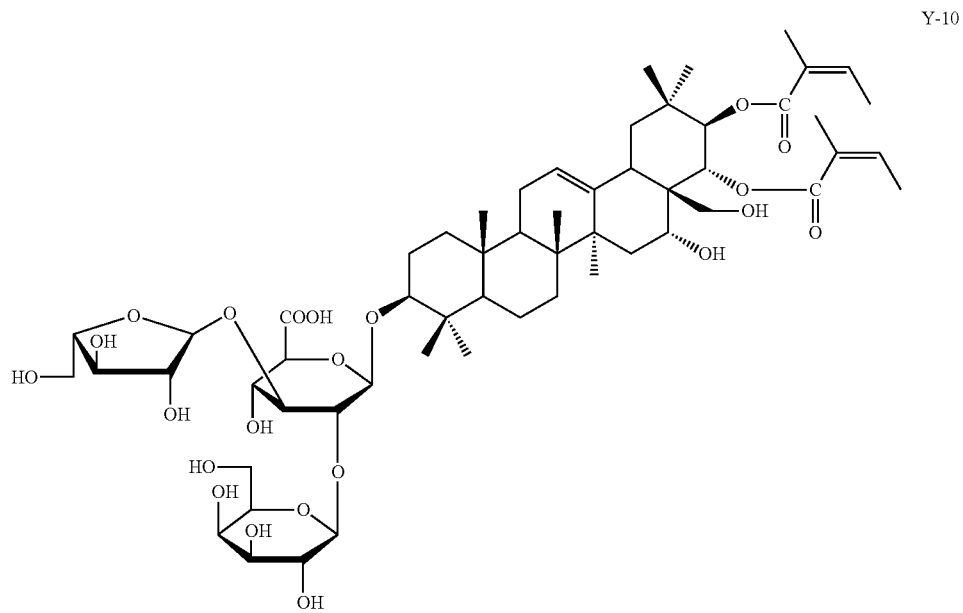

or chemical name: 3-O-[β-galactopyranosyl (1→2)]-α-arabinofuranosyl (1→3)-β-glucuronopyranosyl-21,22-O-diangeloyl-3β,16α,21β,22α,28-pentahydroxyolean-12-ene;

g) A compound having the structure Xanifolia (Y0),

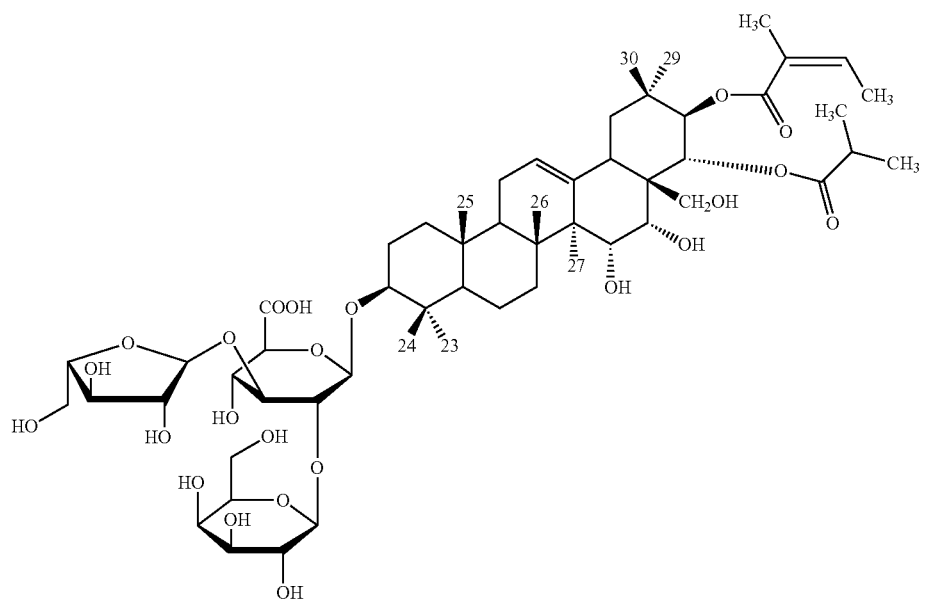

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β,15α,16α,21β,22α,28-hexahydroxyolean-12-ene, h) A compound having the structure Xanifolia (X),

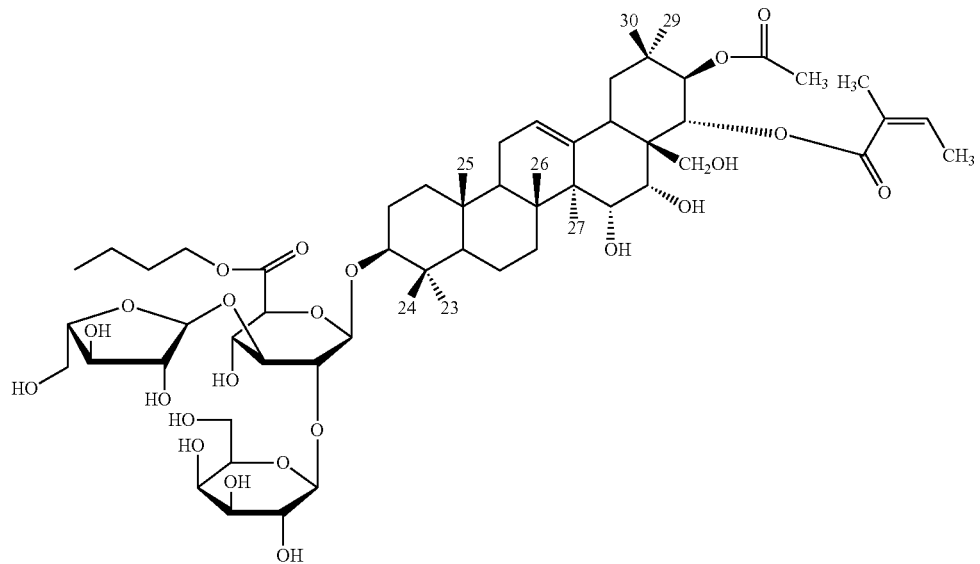

or chemical name: 3-O-{[β-D-galactopyranosyl (1→2)]-[α-L-arabinofuranosyl(1→3)]-β-D-glucuronopyranoside butyl ester}-21-O-acetyl-22-O-angeloyl-3β,16α,21β,22α,28-pentahydroxyolean-12-ene;

i) A compound having the structure (Y7),
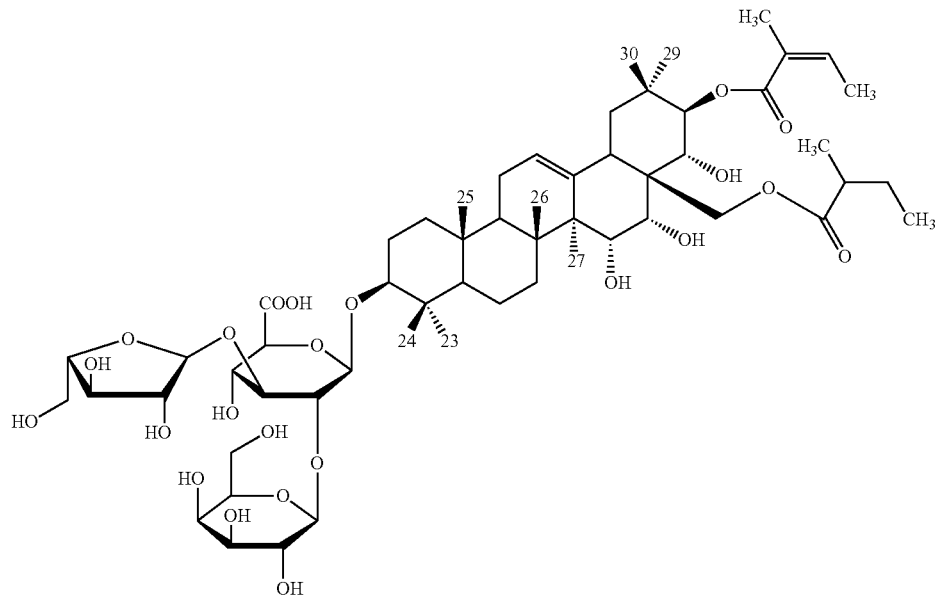
or chemical name: 3-O-[β-D-galactopyranosyl-(1→2)]-α-L-arabinofuranosyl-(1→3)-β-D-glucuronopyranosyl-21-angeloyl-28-O-2-methylbutanoyl-3β,15α,16α,21β,22α,28-hexahydroxyolean-12-ene;
j) A compound having the structure (ACH—Y):
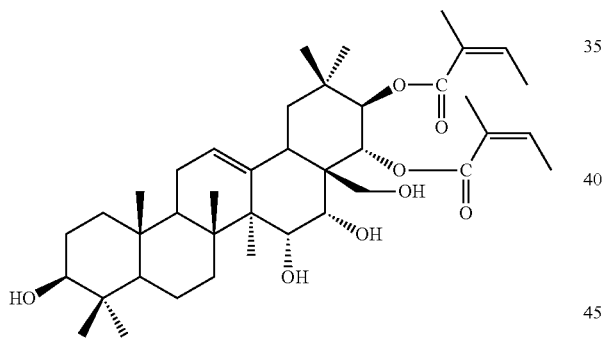
k) A compound having the structure:
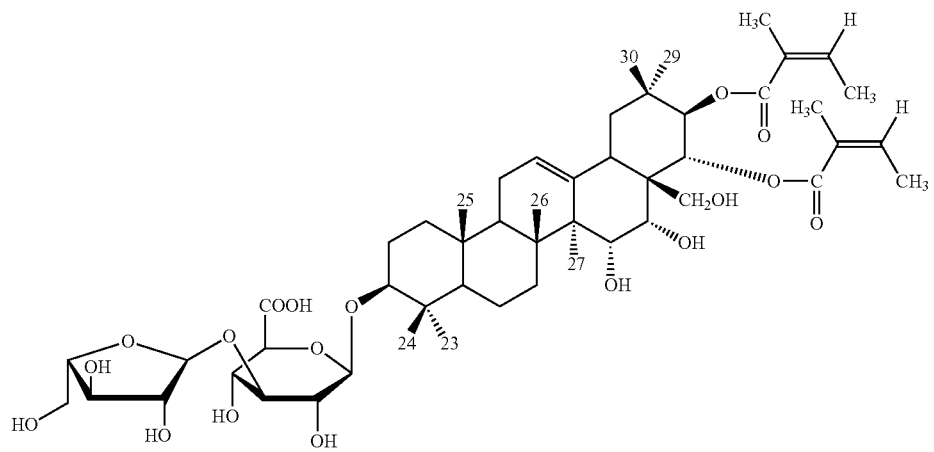

1) A compound having the structure:

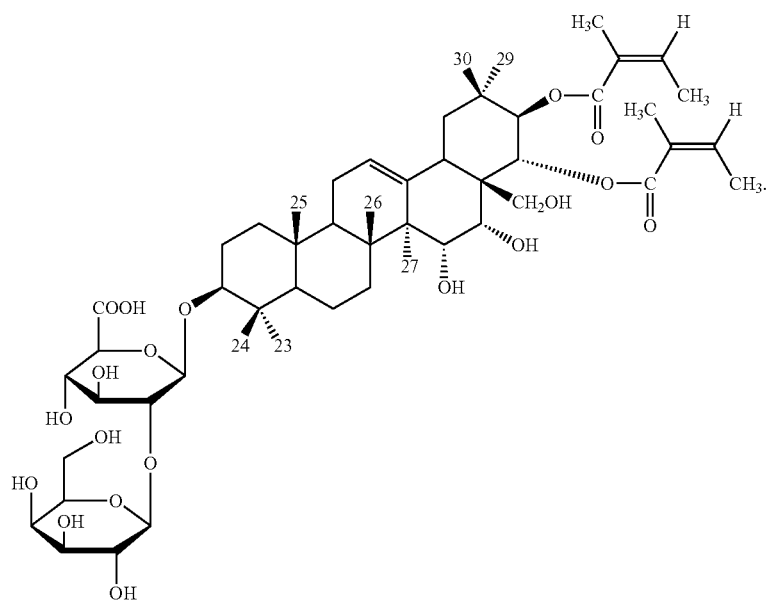

8. A method of claim 6, wherein the method is inhibiting cancer growth by destroying cancer cells that over express aquaporin.

9. The method of claim 6, wherein the method comprises altering the functional properties of intracellular membranes, regulating the fluid passage through the cell wall, opening the channel protein of the cell for charged molecules or ions passing through the membrane, opening the ion gates of the cell for ion passing through the membrane, increasing the ions or charged particles flowing into the cancer cell, increasing the water diffusion into the cell, increasing the static charges of the cells, increasing water flowing into the cells, regulating the ions flowing into the cells or destroying the cell with inflow water.

10. A composition comprising an effective amount of the compound of claim 1 for inhibiting varicose veins disease, chronic venous insufficiency, hemorrhoids or inhibiting leg swelling.

11. A method for inhibiting varicose veins disease, chronic venous insufficiency, hemorrhoids or inhibiting leg swelling in a subject, comprising administering to said subject an effective amount of compound selected from claim 1.

12. The method of claim 6, wherein the method comprises extending the life span of a subject which bearing cancer, or reducing the size of a solid tumor in a subject.

13. The method of 6, wherein the method comprises altering the adhesion characteristic of membrane to block the migration and metastasis of cancer cells.

14. A composition for inducing apoptosis of cancer cell or altering the adhesion characteristic of membrane to block the migration and metastasis of cancer cells or inhibit the growth of cancers or inhibit angiogenesis of cancers in a subject, comprising contacting an effective amount of the compound of claim 1 wherein the cancer is selected from the group consisting of breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer, and cervical cancer.

15. The method of inducing apoptosis of cancer cell or altering the adhesion characteristic of membrane to block the migration and metastasis of cancer cells or inhibit the growth of cancers or inhibit angiogenesis of cancers comprising contacting the subject with an effective amount of the compound selected from claim 1, wherein the cancer is selected from the group consisting of breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer, and cervical cancer.

16. The method of claim 6, wherein administration of the medicament is by intravenous injection, intravenous drip, intraperitoneal injection or oral administration; wherein a medicament is intravenous drip: 0.05-0.2 mg/kg medicine dissolved in 250 ml of 10% glucose solution or in 250 ml of 0.9% NaCl solution, or a medicament is intravenous injection: 0.05-0.2 mg/kg/day medicine dissolved in 10-20 ml of 10% glucose solution or of 0.9% NaCl solution, or a medicament is intravenous drip: 0.1-0.2 mg/kg/day medicine dissolved in 250 ml of 10% glucose solution or in 250 ml of 0.9% NaCl solution, or a medicament is intravenous injection: 0.1-0.2 mg/kg/day medicine dissolved in 10-20 ml of 10% glucose solution or of 0.9% NaCl solution, or a medicament is intraperitoneal (I.P.): 2.5 mg/kg/day medicine dissolved in 10% glucose solution or of 0.9% NaCl solution, or a medicament is administered orally wherein the dosage of mammal is 1-10 mg/Kg, or a medicament is administered orally wherein the dosage is 10-30 mg/Kg, or a medicament is administered orally wherein the dosage is 30-60 mg/Kg, or a medicament is administered orally wherein the dosage is 60-90 mg/Kg, or a medicament is administered by intravenous injection or intravenous drip wherein the dosage of mammal is 0.01-0.1 mg/Kg, or a medicament is administered by intravenous injection or intravenous drip wherein the dosage is 0.1-0.2 mg/Kg, or a medicament is administered by intravenous injection or intravenous drip wherein the dosage is 0.2-0.4 mg/Kg, or a medicament is administered by intravenous injection or intravenous drip wherein the dosage is 0.4-0.6 mg/Kg, or a medicament is administered by intraperitoneal (I.P.) wherein the dosage of mammal is 1-3 mg/Kg, or a medicament is administered by intraperitoneal (I.P.) wherein the dosage is 3-5 mg/Kg, or a medicament is administered by intraperitoneal (I.P.) wherein the dosage is 4-6 mg/Kg, or a medicament is administered by intraperitoneal (I.P.) wherein the dosage is 6-10 mg/Kg.

17. The method of claim 6, wherein the method comprises administering to said subject an effective amount of compound, wherein R4 is CH$_2$OR6; wherein at least two of R1, R2, and R6 are independently selected from a group consisting of alkanoyl, alkenoyl, acyl, or at least one of R1, R2, and R6 is a sugar moiety substituted with at least two acyl; wherein the acyl is angeloyl group; wherein the alkanoyl is methylpropanoyl, acetyl, or methylbutanoyl; wherein the alkenoyl is angeloyl.

18. A method for inhibiting angiogenesis of cancers in a subject, comprising administering to said subject an effective amount of the compound of claim 1.

19. The method of claim 6, wherein the compound is a triterpenoid saponin having at least two side chains; wherein the side chains are at any of carbon 21, 22 and 28; wherein the side chains are at adjacent carbon trans configuration, or wherein the side chains are at alternate carbons in cis configuration, wherein the side chains is attached to a group selected from alkanoyl, alkenoyl, acyl; wherein the acyl is angeloyl group, acetyl, methylpropanoyl or methylbutanoyl; wherein the alkanoyl is methylpropanoyl, acetyl or methylbutanoyl; wherein the alkenoyl is angeloyl.

20. The method of claim 6, wherein R5 is hydrogen.
21. The method of claim 6, wherein the method is inducing apoptosis of cancers.
22. The method of claim 6, wherein the method is inhibiting angiogenesis of cancers.
23. The method of claim 6, wherein the method is extending the life span of a subject which is bearing cancer.
24. The method of claim 6, wherein the method is reducing the size of a solid tumor in a subject.
25. The method of claim 6, wherein the method is altering the adhesion characteristic of membrane of cancer cells.
26. The method of claim 6, wherein the number of sugar moieties at R5 is 1.
27. The method of claim 6, wherein the number of sugar moieties at R5 is 2.
28. The method of claim 6, wherein the number of sugar moieties at R5 is 3.
29. The method of claim 6, wherein the number of sugar moieties at R5 is more than 4.
30. The method of claim 6, wherein the compound is a compound having the structure Xanifolia (Y),

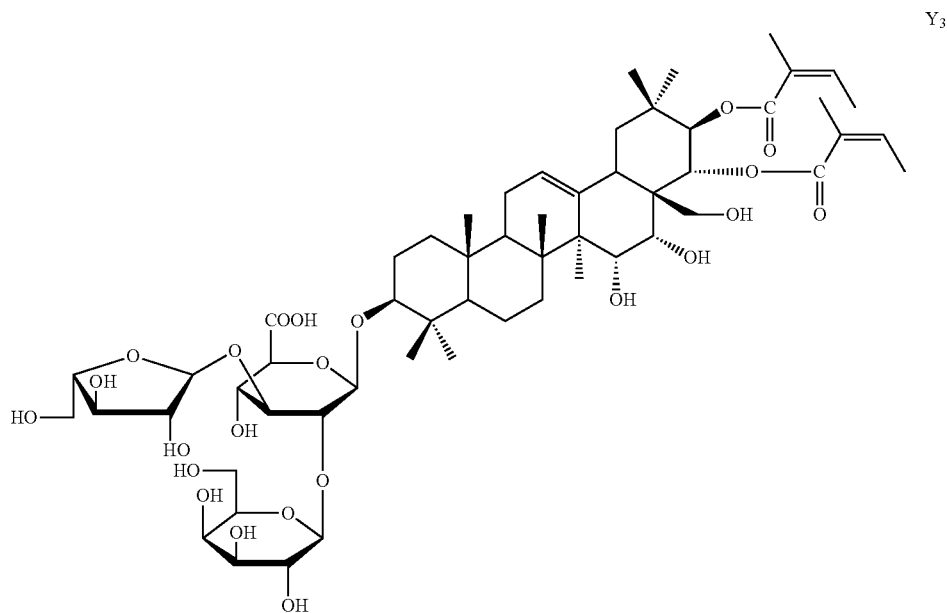

or chemical name: 3-O-[β-D-galactopyranosyl (1→2)]-α-L-arabinofuranosy (1→3)-β-D-glucuronopyranosyl-21,22-O-diangeloyl-3β,15α,16α,21β,22α,28-hexahydroxyolean-12-ene.

31. The method of claim 6, wherein the compound is a compound having the structure Xanifolia (Y1),

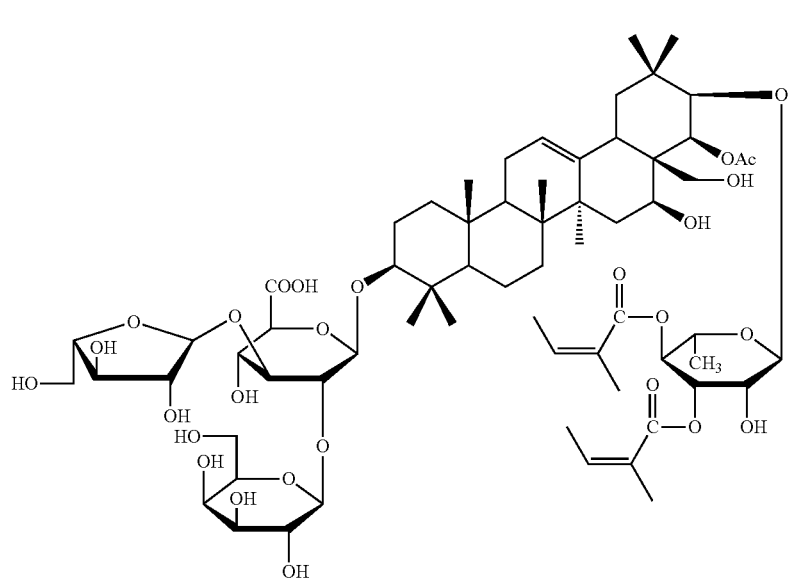

or chemical name: 3-O-[β-D-galactopyranosyl (1→2)]-α-L-arabinofuranosyl (1→3)-β-D-glucuronopyranosyl-21-O-(3,4-diangeloyl)-α-L-rhamnophyranosyl-22-O-acetyl-3β,16α,21β,22α,28-pentahydroxyolean-12-ene.

32. The method of claim 6, wherein the compound is a compound having the structure Xanifolia (Y2),

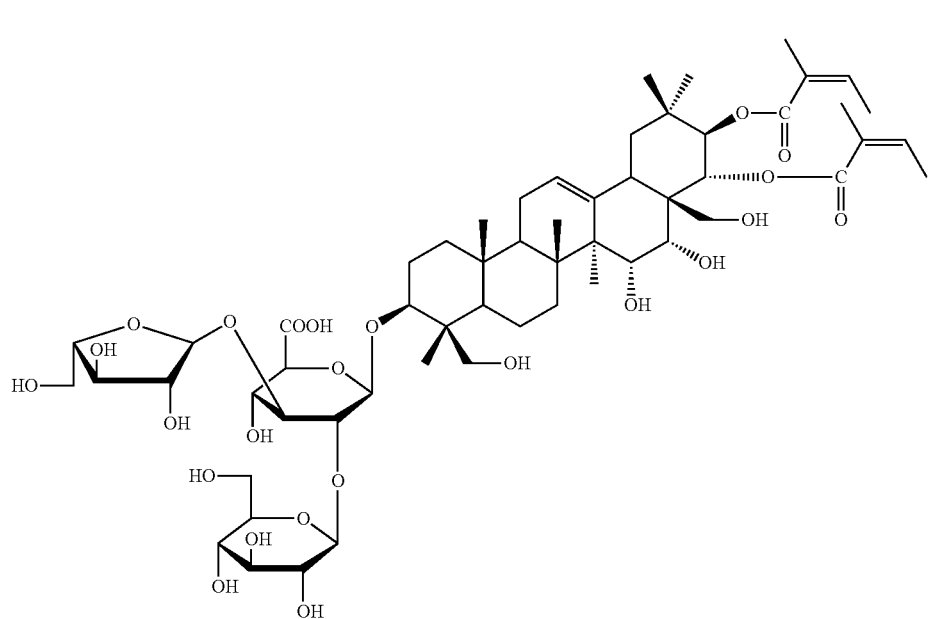

or chemical name: 3-O-[β-D-glucopyranosyl-(1→2)]-α-L-arabinofuranosy (1→3)-β-D-glucuronopyranosyl-21,22-O-diangeloyl-3β,15α,16α,21β,22α,24β,28-heptahydroxy-olean-12-ene.

33. The method of claim 6, wherein the compound is a compound having the structure Xanifolia (Y8),

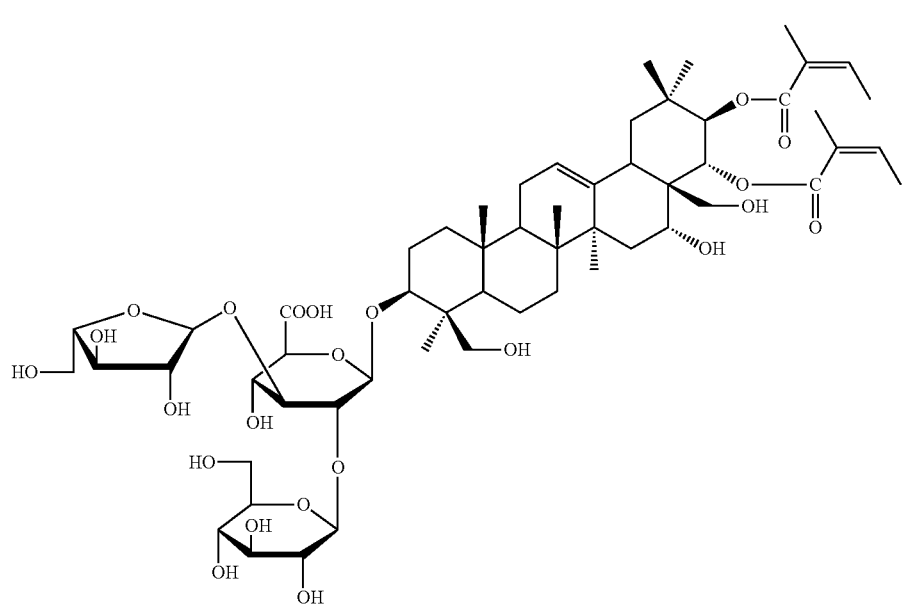

Y-8 or chemical name: 3-O-[β-glucopyranosyl (1→2)]-α-arabinofuranosyl(1→3)-β-glucuronopyranosyl-21,22-O-diangeloyl-3β,16α,21β,22α,24β,28-hexahydroxyolean-12-ene.

34. The method of claim 6, wherein the compound is a compound having the structure Xanifolia (Y9),

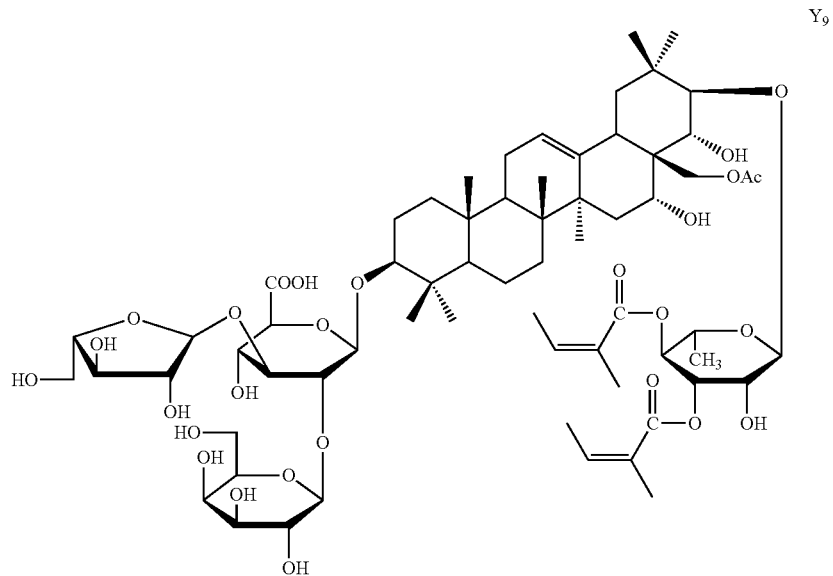

Y9 or chemical name: 3-O-[β-galactopyranosyl(1→2)]-α-arabinofuranosyl(1→3)-βglucuronopyranosyl-21-O-(3,4-diangeloyl)-α-rhamnopyranosyl-28-O-acetyl-3β,16α,21β,22α,28-pentahydroxyolean-12-ene.

35. The method of claim 6, wherein the compound is a compound having the structure Xanifolia (Y10),

Y-10

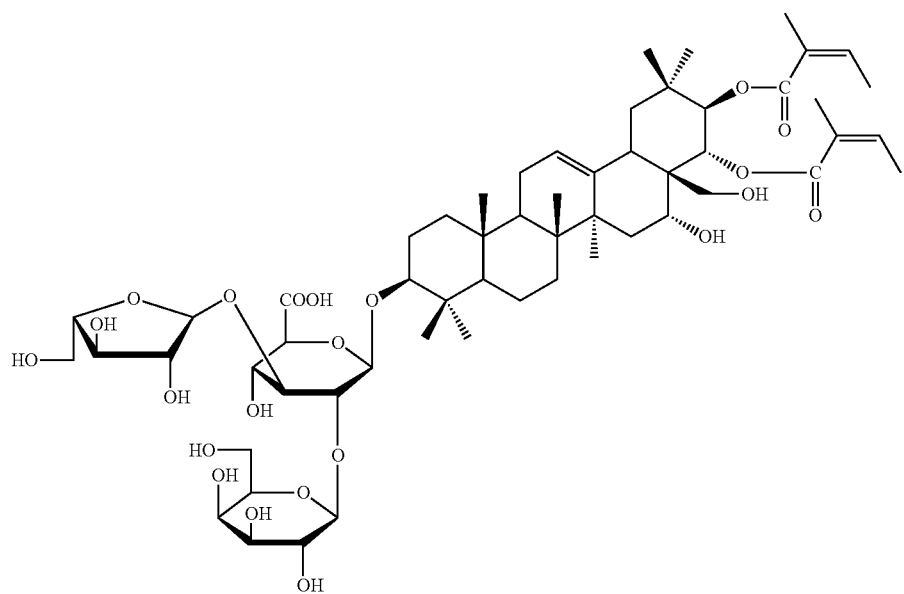

or chemical name: 3-O-[β-galactopyranosyl(1→2)]-α-arabinofuranosyl(1→3)-β-glucuronopyranosyl-21,22-O-diangeloyl-3β,16α,21β,22α,28-pentahydroxyolean-12-ene.

36. The method of claim 6, wherein the compound is a compound having the structure Xanifolia (Y0),

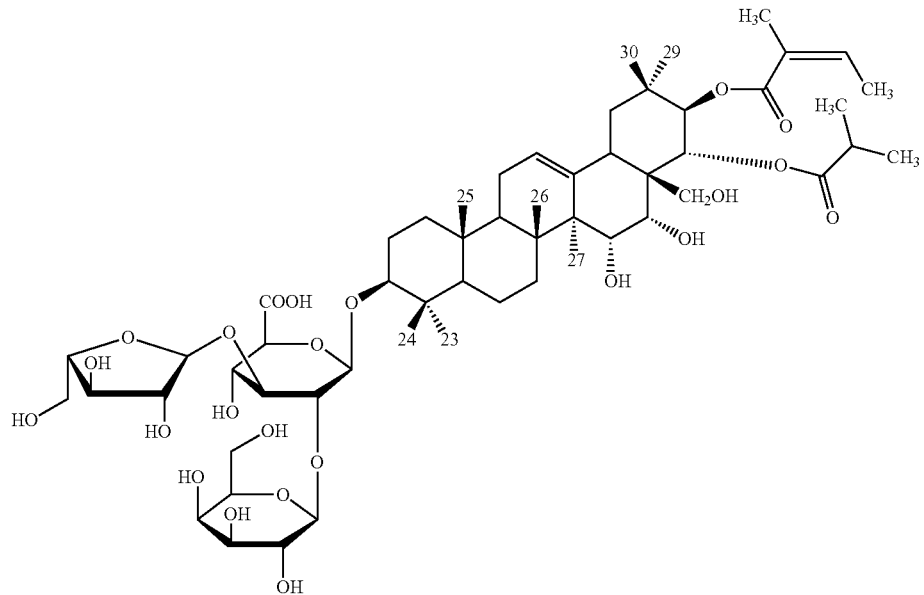

or chemical name: 3-O-[β-D-galactopyranosyl(1→2)]-α-L-arabinofuranosyl(1→3)-β-D-glucuronopyranosyl-21-O-angeloyl,22-O-(2-methylpropanoyl)-3β,15α,16α,21β,22α,28-hexahydroxyolean-12-ene.

37. The method of claim 6, wherein the compound is a compound having the structure Xanifolia (X),

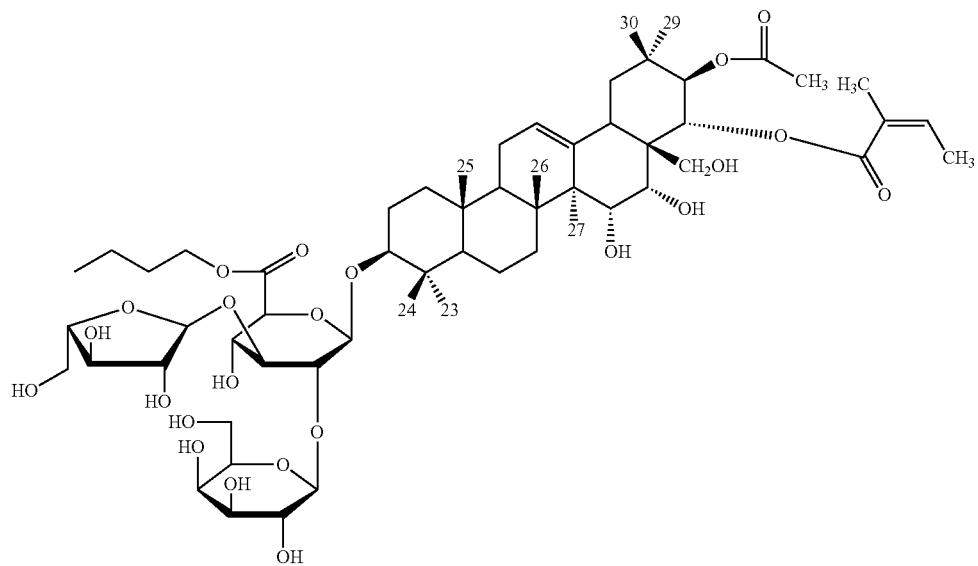

or chemical name: 3-O-{[β-D-galactopyranosyl(1→2)]-[α-L-arabinofuranosyl(1→3)]-β-D-glucuronopyranoside butyl ester}-21-O-acetyl-22-O-angeloyl-3β,16α,21β,22α,28-pentahydroxyolean-12-ene.

38. The method of claim 6, wherein the compound is a compound having the structure (Y7),

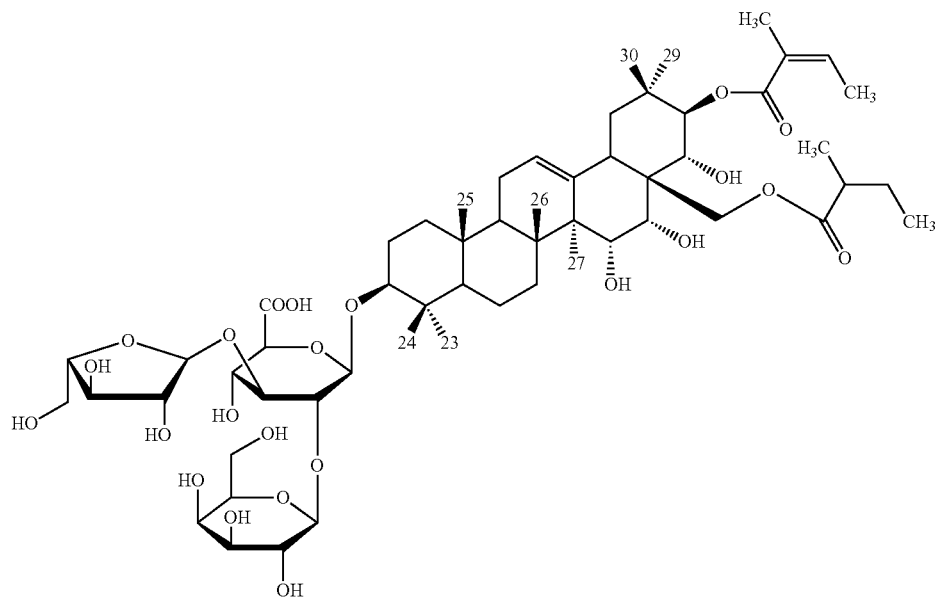

or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β,15α,16α,21β,22α,28-hexahydroxyolean-12-ene.

39. The method of claim 6, wherein the compound is a compound having the structure (ACH—Y):

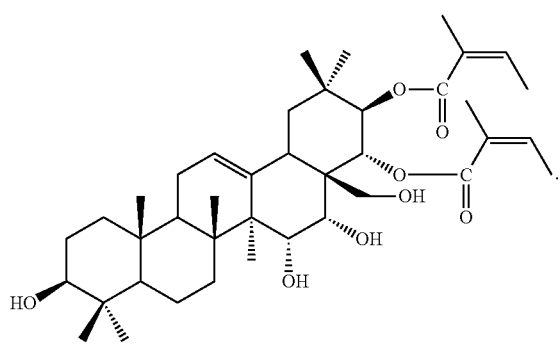

40. The method of claim 6, wherein the R4 represents CH$_2$OR6, wherein R6 is selected from a group consisting of hydrogen, alkanoyl, alkenoyl, and acyl; wherein the acyl is angeloyl group, acetyl, tigloyl, senecioyl, methylpropanoyl or methylbutanoyl; wherein the alkanoyl is methylpropanoyl, acetyl or methylbutanoyl; wherein the alkenoyl is angeloyl, tigloyl or senecioyl.

41. The method of claim 6, wherein the R4 represents CH$_2$OR6 or COOR6, wherein R6 is H.

42. The method of claim 6, wherein the compound is a compound having the structure:

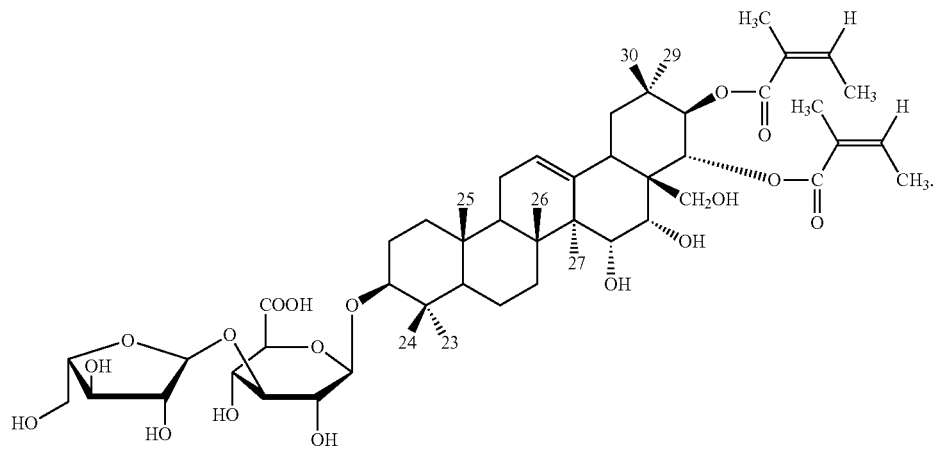

43. The method of claim 6, wherein the compound is a compound having the structure:

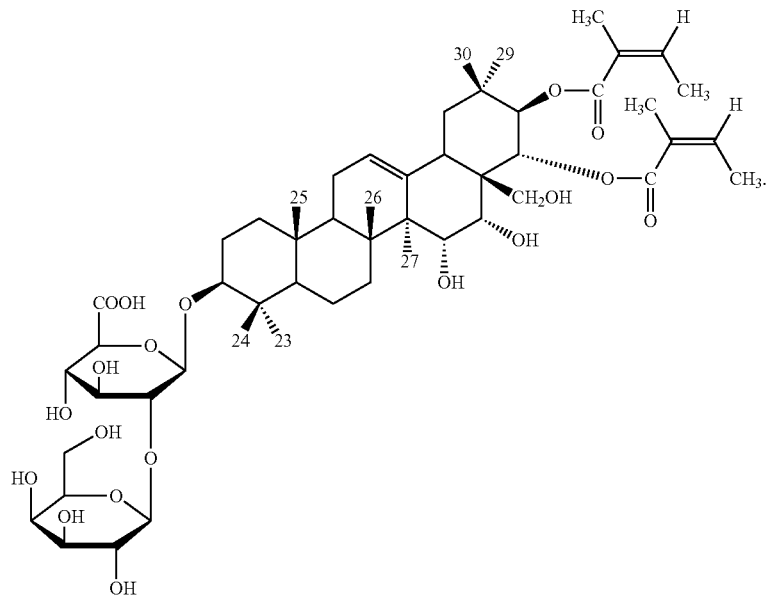

44. The method of claim 11, wherein the cancer is breast cancer.

45. The method of claim 11, wherein the cancer is leukocyte cancer.

46. The method of claim 11, wherein the cancer is liver cancer.

47. The method of claim 11, wherein the cancer is ovarian cancer.

48. The method of claim 11, wherein the cancer is bladder cancer.

49. The method of claim 11, wherein the cancer is prostate cancer.

50. The method of claim 11, wherein the cancer is skin cancer.

51. The method of claim 11, wherein the cancer is bone cancer.

52. The method of claim 11, wherein the cancer is brain cancer.

53. The method of claim 11, wherein the cancer is leukemia cancer.

54. The method of claim 11, wherein the cancer is lung cancer.

55. The method of claim 11, wherein the cancer is colon cancer.

56. The method of claim 11, wherein the cancer is CNS cancer.

57. The method of claim 11, wherein the cancer is melanoma cancer.

58. The method of claim 11, wherein the cancer is renal cancer.

59. The method of claim 11, wherein the cancer is cervical cancer.

* * * * *